US012365693B2

(12) United States Patent
Ostrem et al.

(10) Patent No.: US 12,365,693 B2
(45) Date of Patent: *Jul. 22, 2025

(54) COMPOSITIONS AND METHODS FOR TREATING CANCER

(71) Applicant: The Regents of the University of California, Oakland, CA (US)

(72) Inventors: Jonathan Ostrem, San Francisco, CA (US); Ulf Peters, San Francisco, CA (US); Kevan M. Shokat, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/956,941

(22) Filed: Nov. 22, 2024

(65) Prior Publication Data

US 2025/0101036 A1    Mar. 27, 2025

Related U.S. Application Data

(63) Continuation of application No. 18/821,460, filed on Aug. 30, 2024, which is a continuation of application No. 18/490,700, filed on Oct. 19, 2023, now Pat. No. 12,116,375, which is a continuation of application No. 18/058,655, filed on Nov. 23, 2022, now Pat. No. 11,891,402, which is a continuation of application No. 17/212,737, filed on Mar. 25, 2021, now Pat. No. 11,603,376, which is a continuation of application No. 16/720,526, filed on Dec. 19, 2019, now Pat. No. 11,008,334, which is a continuation of application No. 16/013,271, filed on Jun. 20, 2018, now abandoned, which is a continuation of application No. 14/934,184, filed on Nov. 6, 2015, now Pat. No. 10,023,588, which is a continuation of application No. 14/391,369, filed as application No.
(Continued)

(51) Int. Cl.
| | |
|---|---|
| C07D 495/04 | (2006.01) |
| A61K 38/17 | (2006.01) |
| C07C 235/20 | (2006.01) |
| C07C 317/08 | (2006.01) |
| C07D 207/14 | (2006.01) |
| C07D 211/58 | (2006.01) |
| C07D 211/62 | (2006.01) |
| C07D 231/40 | (2006.01) |
| C07D 295/185 | (2006.01) |
| C07D 295/26 | (2006.01) |
| C07D 401/04 | (2006.01) |
| C07D 401/06 | (2006.01) |
| C07D 401/12 | (2006.01) |
| C07D 405/12 | (2006.01) |
| C07D 409/04 | (2006.01) |
| C07D 413/12 | (2006.01) |
| C07D 417/12 | (2006.01) |
| C07D 471/10 | (2006.01) |
| C07D 487/04 | (2006.01) |
| C07D 487/10 | (2006.01) |
| C12N 9/14 | (2006.01) |
| C12Q 1/6886 | (2018.01) |

(52) U.S. Cl.
CPC ........ *C07D 495/04* (2013.01); *A61K 38/1709* (2013.01); *C07C 235/20* (2013.01); *C07C 317/08* (2013.01); *C07D 207/14* (2013.01); *C07D 211/58* (2013.01); *C07D 211/62* (2013.01); *C07D 231/40* (2013.01); *C07D 295/185* (2013.01); *C07D 295/26* (2013.01); *C07D 401/04* (2013.01); *C07D 401/06* (2013.01); *C07D 401/12* (2013.01); *C07D 405/12* (2013.01); *C07D 409/04* (2013.01); *C07D 413/12* (2013.01); *C07D 417/12* (2013.01); *C07D 471/10* (2013.01); *C07D 487/04* (2013.01); *C07D 487/10* (2013.01); *C12N 9/14* (2013.01); *C12Q 1/6886* (2013.01); *C12Q 2600/156* (2013.01); *C12Q 2600/158* (2013.01); *C12Y 306/05002* (2013.01); *G01N 2500/04* (2013.01)

(58) Field of Classification Search
CPC .................................................. A61K 38/1709
See application file for complete search history.

(56) References Cited

U.S. PATENT DOCUMENTS

| | | | |
|---|---|---|---|
| 3,752,660 | A | 8/1973 | Little et al. |
| 10,023,588 | B2 | 6/2018 | Ostrem et al. |

(Continued)

FOREIGN PATENT DOCUMENTS

| | | |
|---|---|---|
| EP | 1736465 A1 | 12/2006 |
| EP | 0094498 A2 | 11/2023 |

(Continued)

OTHER PUBLICATIONS

Hall et al., "The structural basis for the transition from Ras-GTP to Ras-GDP", PNAS, vol. 99, pp. 12138-12142 (Year: 1986).*

(Continued)

*Primary Examiner* — Andrew D Kosar
*Assistant Examiner* — Gillian A Hutter
(74) *Attorney, Agent, or Firm* — Todd Esker; Bozicevic, Field & Francis LLP

(57) ABSTRACT

K-Ras is the most frequently mutated oncogene in human cancer. Disclosed herein are compositions and methods for modulating K-Ras and treating cancer.

30 Claims, 53 Drawing Sheets

Specification includes a Sequence Listing.

Related U.S. Application Data

PCT/US2013/036031 on Apr. 10, 2013, now abandoned.

(60) Provisional application No. 61/794,956, filed on Mar. 15, 2013, provisional application No. 61/728,145, filed on Nov. 19, 2012, provisional application No. 61/622,507, filed on Apr. 10, 2012.

(56) References Cited

U.S. PATENT DOCUMENTS

| | | | |
|---|---|---|---|
| 10,857,140 | B2 | 12/2020 | McCormick et al. |
| 11,008,334 | B2 * | 5/2021 | Ostrem ............... A61P 35/02 |
| 11,136,297 | B2 | 10/2021 | Shokat et al. |
| 11,603,376 | B2 * | 3/2023 | Ostrem ............... A61P 35/00 |
| 11,718,630 | B2 * | 8/2023 | Ostrem ............... C07D 487/10 544/387 |
| 11,891,402 | B2 | 2/2024 | Ostrem et al. |
| 12,166,375 | B2 | 10/2024 | Ostrem et al. |
| 2008/0261821 | A1 | 10/2008 | Maly et al. |
| 2015/0087628 | A1 | 3/2015 | Ostrem et al. |
| 2020/0255446 | A1 | 8/2020 | Ostrem et al. |
| 2021/0230183 | A1 | 7/2021 | Ostrem et al. |
| 2023/0135350 | A1 | 5/2023 | Ostrem et al. |
| 2023/0242548 | A1 | 8/2023 | Ostrem et al. |
| 2024/0067656 | A1 | 2/2024 | Ostrem et al. |

FOREIGN PATENT DOCUMENTS

| | | |
|---|---|---|
| JP | S58203966 A | 11/1983 |
| JP | S59163372 A | 9/1984 |
| JP | 2005502623 A | 1/2005 |
| JP | 2008524154 A | 7/2008 |
| JP | 4775259 B2 | 9/2011 |
| WO | WO9833496 A1 | 8/1998 |
| WO | WO03004480 A2 | 1/2003 |
| WO | WO2003004480 A3 | 1/2003 |
| WO | WO2003088908 A2 | 10/2003 |
| WO | WO2004074283 A1 | 9/2004 |
| WO | WO2006066948 A1 | 6/2006 |
| WO | WO2007144394 A2 | 12/2007 |
| WO | WO2007144394 A3 | 12/2007 |
| WO | WO2008050821 A1 | 5/2008 |
| WO | WO2008112440 A1 | 9/2008 |
| WO | WO2010087399 A1 | 8/2010 |
| WO | WO2010121918 A1 | 10/2010 |
| WO | WO-2011031896 A2 * | 3/2011 ........... A61K 31/517 |
| WO | WO2011031896 A3 | 3/2011 |
| WO | WO2013155223 A1 | 10/2013 |
| WO | WO2014152588 A1 | 9/2014 |
| WO | WO-2015054572 A1 * | 4/2015 ........... A61K 31/454 |
| WO | WO2016049524 A1 | 3/2016 |
| WO | WO2022245857 A1 | 11/2022 |

OTHER PUBLICATIONS

American Chemical Society, STN Database RN 5530-21-23, Entered STN Nov. 16, 1984, 1 page.
Arkin, M.R. et al. (Feb. 18, 2003, e-published Feb. 11, 2003). "Binding of small molecules to an adaptive protein-protein interface," PNAS 100(4):1603-1608.
Chemocare.com "Taxol" (2016), located at <http:www.chemocare.com/chemotherapy/drug-info/taxol.aspx>> last accessed Sep. 20, 2016, 6 pages.
Choong, I.C. et al. (Nov. 7, 2002). "Identification of potent and selective small-molecule inhibitors of caspase-3 through the use of extended tethering and structure-based drug design," J Med Chem 45(23):5005-5022.
Erlanson, D.A. et al. (Aug. 15, 2000). "Site-directed ligand discovery," PNAS USA 97(17):9367-9372.
European Search Report dated Nov. 6, 2015, for EP Patent Application No. 13775551.8, 10 pages.

Forbes, S. et al. (Jan. 30, 2006). "COSMIC 2005," Br J Cancer 94(2):318-322.
Garske, A.L. et al. (Sep. 13, 2011, e-published Aug. 18, 2011). "Chemical genetic strategy for targeting protein kinases based on covalent complementarity," PNAS USA 108(37):15046-15052.
Gorfe, A.A. et al. (Jun. 2008). "Mapping the nucleotide and isoform-dependent structural and dynamical features of Ras proteins," Structure 16(6);885-896.
Hall, A. et al. (Aug. 25, 1986). "The effect of Mg2+ on the guanine nucleotide exchange rate of p21N-ras," The Journal of Biological Chemistry 261(24):10963-10965.
Hall, B.E. et al. (Sep. 17, 2002, e-published Sep. 4, 2002). "The structural basis for the transition from Ras-GTP to Ras-GDP," PNAS USA 99(19):12138-12142.
Hara M. et al. (May 1988). "Guanine nucleotide binding properties of purified v-Ki-ras p21 protein produced in *Escherichia coli*," Oncogene Res 2(4):325-333.
Hardy, J.A. et al. (Aug. 24, 2004, e-published Aug. 16, 2004). "Discovery of an allosteric site in the caspases," PNAS USA 101(34): 12461-12466.
Hattori, S. et al. (May 1987). "Neutralizing monoclonal antibody against ras oncogene product p21 which impairs guanine nucleotide exchange," Mol Cell Biol 7(5):1999-2002.
Ito, Y. et al. (Jul. 29, 1997). "Regional polysterism in the GTP bound form of the human c-Ha-Ras protein," Biochemistry 36(30):9109-9119.
International Search Report dated Jul. 22, 2013, for PCT Application No. PCT/US2013/036031, filed on Apr. 10, 2013, 5 pages.
Kelly, J. et al., (Jun. 1998). "Synthesis of isomeric 3-piperidinyl and 3-pyrrolidinyl benzo[5,6]cyclohepta [1,2-b]pyridines: sulfonamido derivatives as inhibitors of Ras prenylation," Bioorg Med Chem 6(6):673-686.
Kraulis, P.J. et al. (Mar. 29, 1994). "Solution structure and dynamics of ras p21.GDP determined by heteronuclear three- and four dimensional NMR spectroscopy," Biochemistry 33(12):3515-3531.
Lee, W. et al. (May 27, 2010). "The mutation spectrum revealed by paired genome sequences from a lung cancer patient," Nature 465(7297):473-477.
Lenzen, C. et al. (1995). "Analysis of intrinsic and CDC25-stimulated guanine nucleotide exchange of p21ras-nucleotide complexes by fluorescence measurements," Methods Enzymol. 255:95-109.
Long, D.M. (2011). "Taxol: An important compound with an impressive structure," located at https://longscience.com/2011/09/10/taxol-an-organic-compund-you-should-know-about/ > last accessed Sep. 20, 2016, 4 pages.
Margarit, S.M. et al. (Mar. 7, 2003). "Structural evidence for feedback activation by Ras.GTP of the Ras-specific nucleotide exchange factor SOS," Cell 112(5):685-695.
Milburn, M.V. et al. (Feb. 23, 1990). "Molecular switch for signal transduction: structural differences between active and inactive forms of protooncogenic ras proteins," Science 247(4945):939-945.
"Nitrogen Mustard H N-2: Blister Agent." National Institute for Occupational Safety and Health (NIOSH). (May 12, 2011). Accessed Jun. 20, 2019. Available from: <https://www.cdc.gov/niosh/ershdb/emergencyresponsecard 29750011.html >. (Year: 2011).
Ostrem, J.M. et al. (Nov. 20, 2013). "K-Ras (G12C) inhibitors allosterically control GTP affinity and effector interactions," Nature 503(7477), 14 pages.
Pacold, M.E. et al. (Dec. 2000). "Crystal structure and functional analysis of Ras binding to its effector phosphoinositide 3-kinase gamma," Cell 103(6):931-943.
Palmioli, A. et al. (Sep. 4, 2009, e-published Jun. 8, 2009). "Selective cytotoxicity of a bicyclic Ras inhibitor in cancer cells expressing K-Ras(G13D)," Biochem Biophys Res Commun 386(4):593-597.
Palmioli, A. et al. (Aug. 1, 2009, e-published May 30, 2009). "First experimental identification of Ras-inhibitor binding interface using a water-soluble Ras ligand," Bioorg Med Chem Lett 19(15):4217-4222.
Pardin, C. et al. (Dec. 15, 2006, e-published Sep. 27, 2006). "Synthesis and evaluation of peptidic irreversible inhibitors of tissue transglutaminase," Bioorg Med Chem 14(24):8379-8385.

(56) References Cited

OTHER PUBLICATIONS

PubChem Database Accession No. SID 22405303 (Mar. 5, 2007). located at <https://pubchem.ncbi.nlm.nih.gov/substance/22405303/version/1>, last visited Oct. 16, 2015, 8 pages.

Rensland, H. et al. (Jan. 17, 1995). "Substrate and product structural requirements for binding of nucleotides to H-ras p21: the mechanism of discrimination between guanosine and adenosine nucleotides," Biochemistry 34(2):593-599.

Stefanachi, A. et al. (Mar. 15, 2008, e-published Jan. 10, 2008). "1-, 3- and 8- substituted-9-deazaxanthines as potent and selective antagonists at the human A2B adenosine receptor," Bioorg Med Chem 16(6):2852-2869.

Sydor, J.R. et al. (Oct. 1998). "Transient kinetic studies on the interaction of Ras and the Ras-binding domain of c-Raf-1 reveal rapid equilibration of the complex," Biochemistry 37(40):14292-14299.

Taveras, A.G. et al. (Jan. 1997). "Ras oncoprotein inhibitors: the discovery of potent, ras nucleotide exchange inhibitors and the structural determination of a drug-protein complex," Bioorg Med Chem 5(1):125-133.

Vetter, I.R. et al. (Nov. 9, 2001). "The guanine nucleotide-binding switch in three dimensions," Science 294(5545):1299-1304.

Written Opinion mailed Jul. 22, 2013, for PCT Application No. PCT/US2013/036031, filed on Apr. 10, 2013, 7 pages.

Yang, W. et al. (Jun. 2, 2009). "Fragment-based discovery of nonpeptidic BACE-1 inhibitors using tethering," Biochemistry 48(21):4488-4496.

\* cited by examiner

FIG. 2A
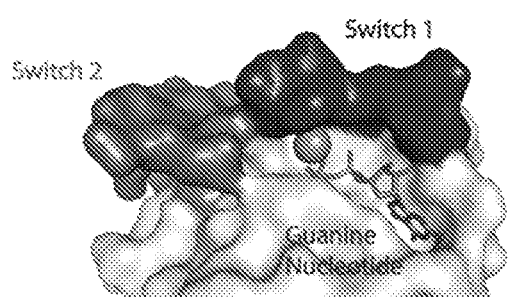
inactive, GDP bound Ras
FIG. 2B
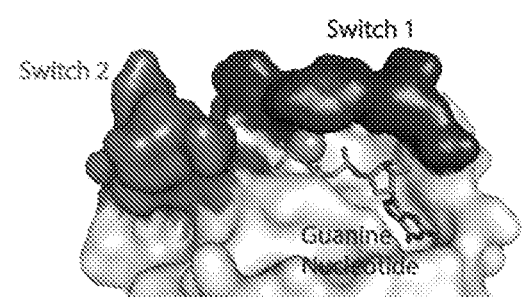
active, GTP-analog bound Ras
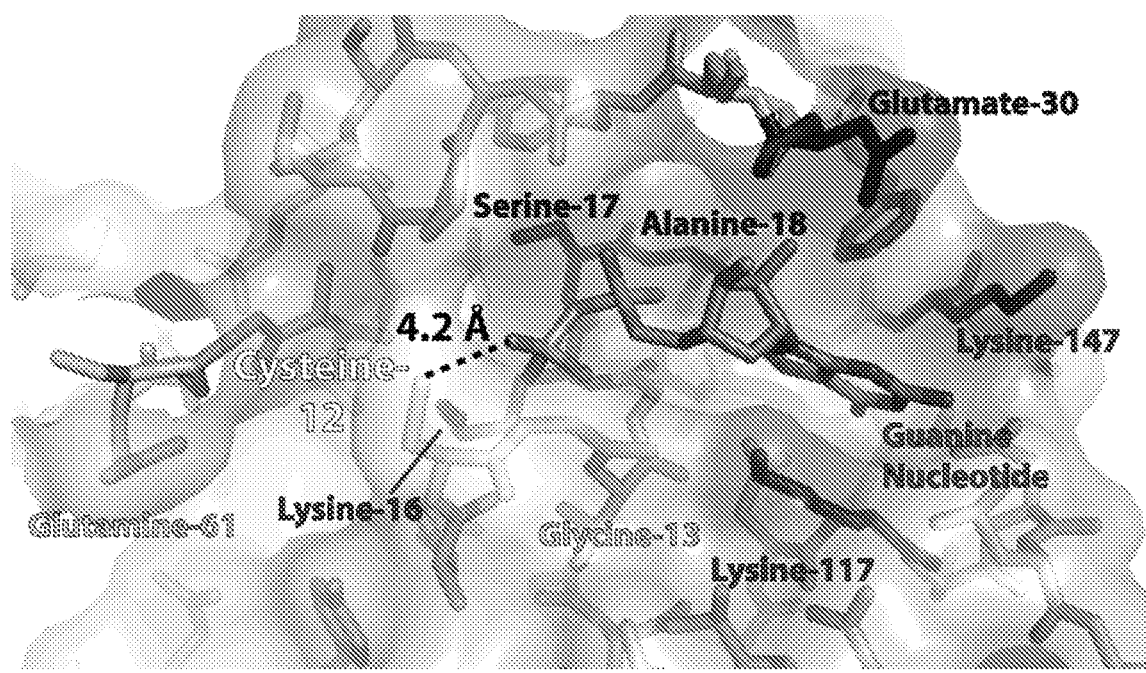
FIG. 2C inactive, GDP bound Ras active, GTP-analog bound Ras JO-01-189cbut and GDP bound Ras H-RasWT: (SEQ ID NO:1)
```
MTEYKLVVVG AGGVGKSALT IQLIQNHFVD EYDPTIEDSY RKQVVIDGET CLLDILDTAG
QEEYSAMRDQ YMRTGEGFLC VFAINNTKSF EDIHQYREQI KRVKDSDDVP MVLVGNKCDL
AARTVESRQA QDLARSYGIP YIETSAKTRQ GVEDAFYTLV REIRQHKLRK LNPPDESGPG
CMSCKCVLS)
```

H-RasWT truncated: (SEQ ID NO:2)
```
MTEYKLVVVG AGGVGKSALT IQLIQNHFVD EYDPTIEDSY RKQVVIDGET CLLDILDTAG
QEEYSAMRDQ YMRTGEGFLC VFAINNTKSF EDIHQYREQI KRVKDSDDVP MVLVGNKCDL
AARTVESRQA QDLARSYGIP YIETSAKTRQ GVEDAFYTLV REIRQH
```

H-Ras G12C truncated: (SEQ ID NO:3)
```
1    MTEYKLVVVG  ACGVGKSALT  IQLIQNHFVD  EYDPTIEDSY  RKQVVIDGET
51   CLLDILDTAG  QEEYSAMRDQ  YMRTGEGFLC  VFAINNTKSF  EDIHQYREQI
101  KRVKDSDDVP  MVLVGNKCDL  AARTVESRQA  QDLARSYGIP  YIETSAKTRQ
151  GVEDAFYTLV  REIRQH
```

K-Ras G12C truncated cysteine-light: (SEQ ID NO:4)
```
  1 mteyklvvvg acgvgksalt iqliqnhfvd eydptiedsy rkqvvidget slldildtag
 60 qeeysamrdq ymrtgegfll vfainntksf edihhyreqi krvkdsedvp mvlvgnksdl
120 psrtvdtkqa qdlarsygip fietsaktrq gvddafytlv reirkhkek
```

K-Ras4A: (SEQ ID NO:5)
```
  1 mteyklvvvg aggvgksalt iqliqnhfvd eydptiedsy rkqvvidget clldildtag
 61 qeeysamrdq ymrtgegflc vfainntksf edihhyreqi krvkdsedvp mvlvgnkcdl
121 psrtvdtkqa qdlarsygip fietsaktrq rvedafytlv reirqyrlkk iskeektpgc
181 vkikkciim
```

K-Ras4A G12C: (SEQ ID NO:6)
```
  1 mteyklvvvg acgvgksalt iqliqnhfvd eydptiedsy rkqvvidget clldildtag
 61 qeeysamrdq ymrtgegflc vfainntksf edihhyreqi krvkdsedvp mvlvgnkcdl
121 psrtvdtkqa qdlarsygip fietsaktrq rvedafytlv reirqyrlkk iskeektpgc
181 vkikkciim
```

K-Ras4A G12D: (SEQ ID NO:7)
```
  1 mteyklvvvg adgvgksalt iqliqnhfvd eydptiedsy rkqvvidget clldildtag
 61 qeeysamrdq ymrtgegflc vfainntksf edihhyreqi krvkdsedvp mvlvgnkcdl
121 psrtvdtkqa qdlarsygip fietsaktrq rvedafytlv reirqyrlkk iskeektpgc
181 vkikkciim
```

K-Ras4A G13C: (SEQ ID NO:8)
```
  1 mteyklvvvg agcvgksalt iqliqnhfvd eydptiedsy rkqvvidget clldildtag
 61 qeeysamrdq ymrtgegflc vfainntksf edihhyreqi krvkdsedvp mvlvgnkcdl
121 psrtvdtkqa qdlarsygip fietsaktrq rvedafytlv reirqyrlkk iskeektpgc
181 vkikkciim
```

K-Ras4A G13D: (SEQ ID NO:9)
```
  1 mteyklvvvg agdvgksalt iqliqnhfvd eydptiedsy rkqvvidget clldildtag
 61 qeeysamrdq ymrtgegflc vfainntksf edihhyreqi krvkdsedvp mvlvgnkcdl
121 psrtvdtkqa qdlarsygip fietsaktrq rvedafytlv reirqyrlkk iskeektpgc
181 vkikkciim
```

*FIG. 9A*

K-Ras4B: (SEQ ID NO:10)
```
  1 mteyklvvvg aggvgksalt iqliqnhfvd eydptiedsy rkqvvidget clldildtag
 61 qeeysamrdq ymrtgegflc vfainntksf edihhyreqi krvkdsedvp mvlvgnkcdl
121 psrtvdtkqa qdlarsygip fietsaktrq gvddafytlv reirkhkekm skdgkkkkkk
181 sktkcvim
```

K-Ras4B G12C: (SEQ ID NO:11)
```
  1 mteyklvvvg acgvgksalt iqliqnhfvd eydptiedsy rkqvvidget clldildtag
 61 qeeysamrdq ymrtgegflc vfainntksf edihhyreqi krvkdsedvp mvlvgnkcdl
121 psrtvdtkqa qdlarsygip fietsaktrq gvddafytlv reirkhkekm skdgkkkkkk
181 sktkcvim
```

K-Ras4B G12D: (SEQ ID NO:12)
```
  1 mteyklvvvg adgvgksalt iqliqnhfvd eydptiedsy rkqvvidget clldildtag
 61 qeeysamrdq ymrtgegflc vfainntksf edihhyreqi krvkdsedvp mvlvgnkcdl
121 psrtvdtkqa qdlarsygip fietsaktrq gvddafytlv reirkhkekm skdgkkkkkk
181 sktkcvim
```

K-Ras4B G13C: (SEQ ID NO:13)
```
  1 mteyklvvvg agcvgksalt iqliqnhfvd eydptiedsy rkqvvidget clldildtag
 61 qeeysamrdq ymrtgegflc vfainntksf edihhyreqi krvkdsedvp mvlvgnkcdl
121 psrtvdtkqa qdlarsygip fietsaktrq gvddafytlv reirkhkekm skdgkkkkkk
181 sktkcvim
```

K-Ras4B G13D: (SEQ ID NO:14)
```
  1 mteyklvvvg agdvgksalt iqliqnhfvd eydptiedsy rkqvvidget clldildtag
 61 qeeysamrdq ymrtgegflc vfainntksf edihhyreqi krvkdsedvp mvlvgnkcdl
121 psrtvdtkqa qdlarsygip fietsaktrq gvddafytlv reirkhkekm skdgkkkkkk
181 sktkcvim
```

K-Ras G12C truncated: (SEQ ID NO:15)
```
  1 mteyklvvvg acgvgksalt iqliqnhfvd eydptiedsy rkqvvidget clldildtag
 61 qeeysamrdq ymrtgegflc vfainntksf edihhyreqi krvkdsedvp mvlvgnkcdl
121 psrtvdtkqa qdlarsygip fietsaktrq gvddafytlv reirkhkek
```

K-Ras wild-type truncated: (SEQ ID NO:16)
```
  1 mteyklvvvg aggvgksalt iqliqnhfvd eydptiedsy rkqvvidget clldildtag
 61 qeeysamrdq ymrtgegflc vfainntksf edihhyreqi krvkdsedvp mvlvgnkcdl
121 psrtvdtkqa qdlarsygip fietsaktrq gvddafytlv reirkhkek
```

K-Ras wild-type cysteine-free truncated: (SEQ ID NO:17)
```
  1 mteyklvvvg aggvgksalt iqliqnhfvd eydptiedsy rkqvvidget slldildtag
 60 qeeysamrdq ymrtgegfll vfainntksf edihhyreqi krvkdsedvp mvlvgnksdl
120 psrtvdtkqa qdlarsygip fietsaktrq gvddafytlv reirkhkek
```

*FIG. 9B*

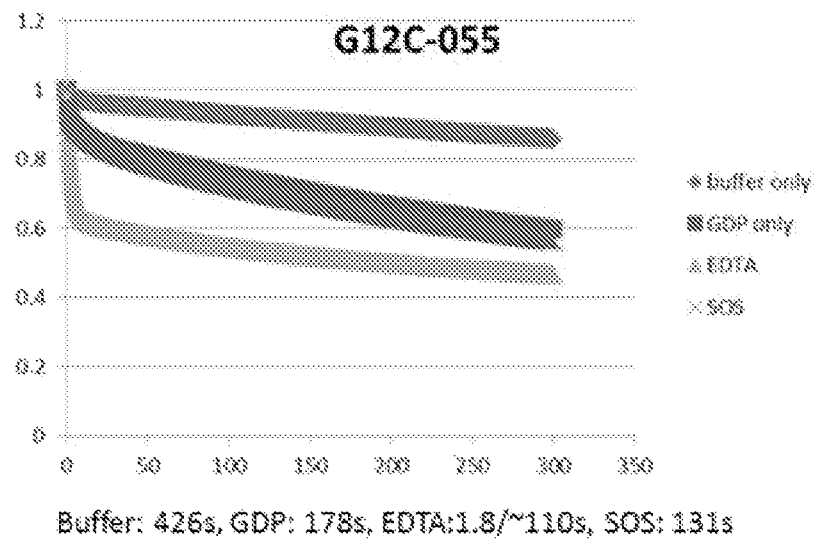
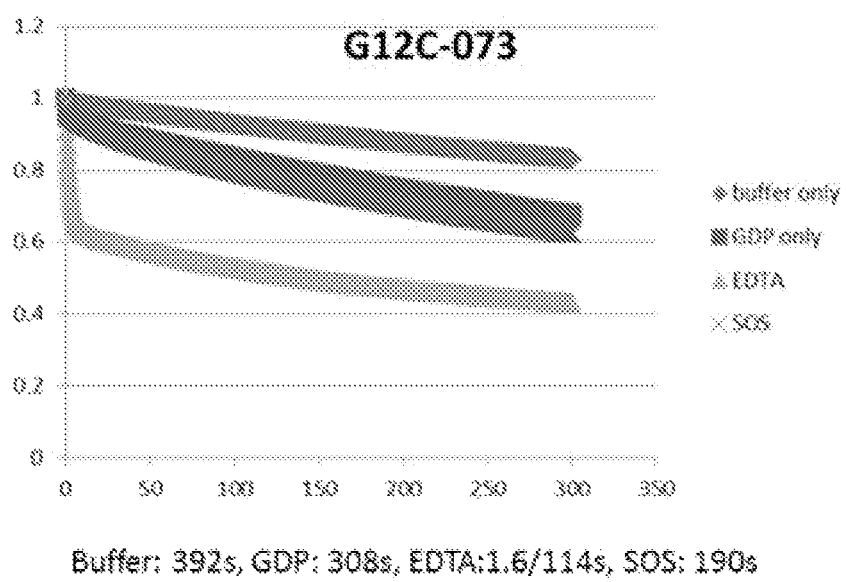
*FIG. 10B*

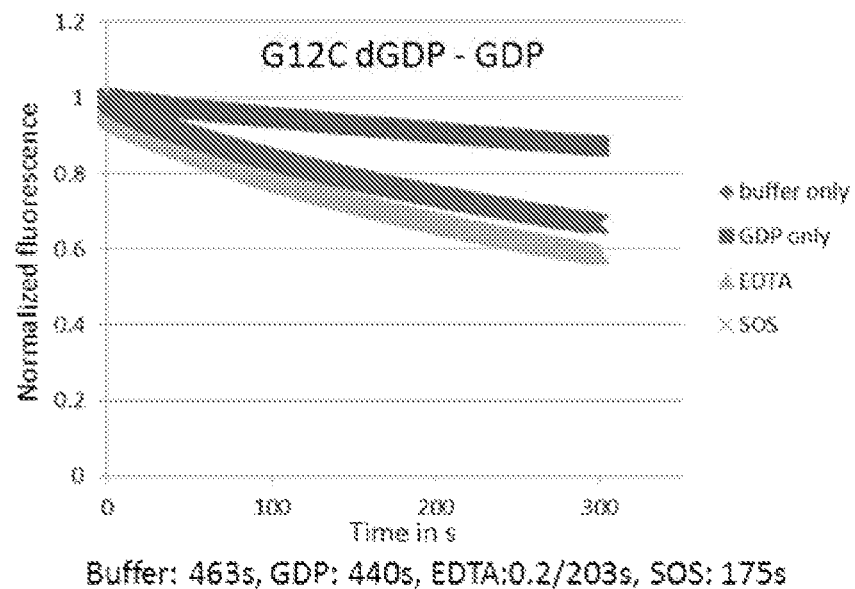
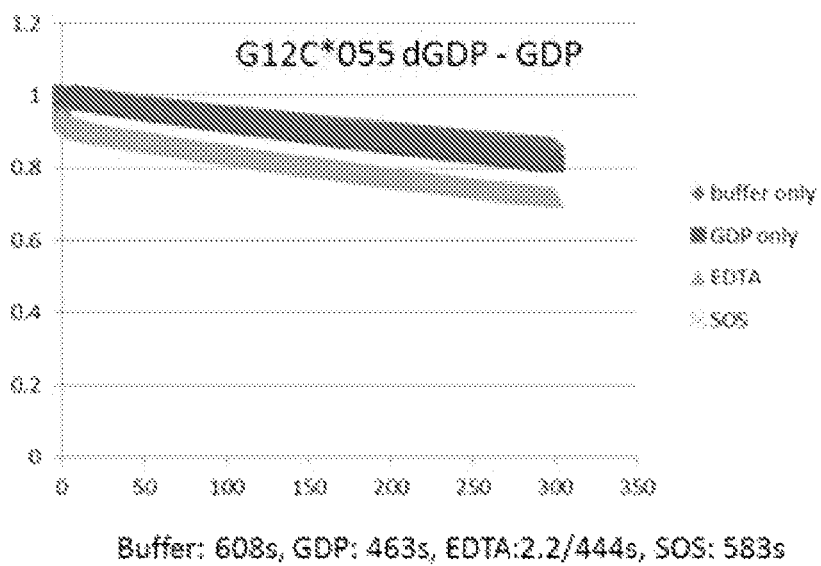
FIG. 11A

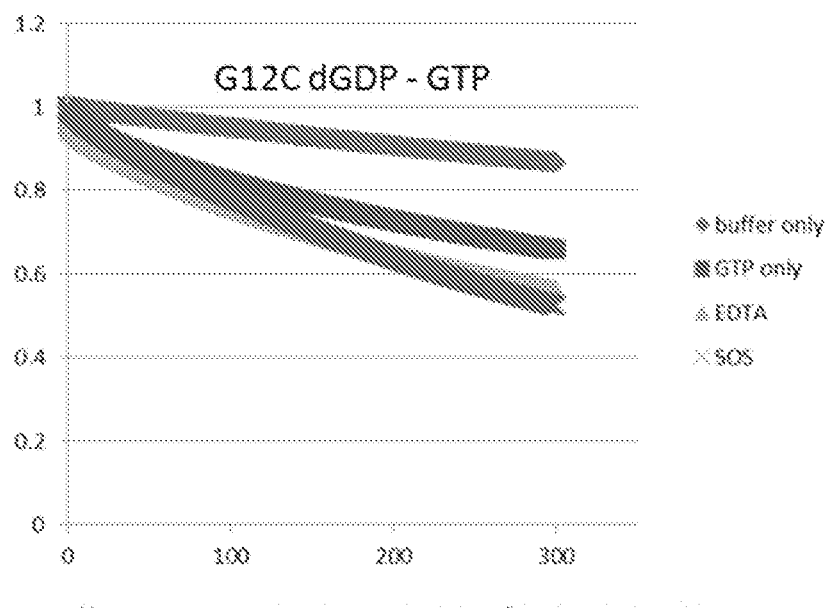
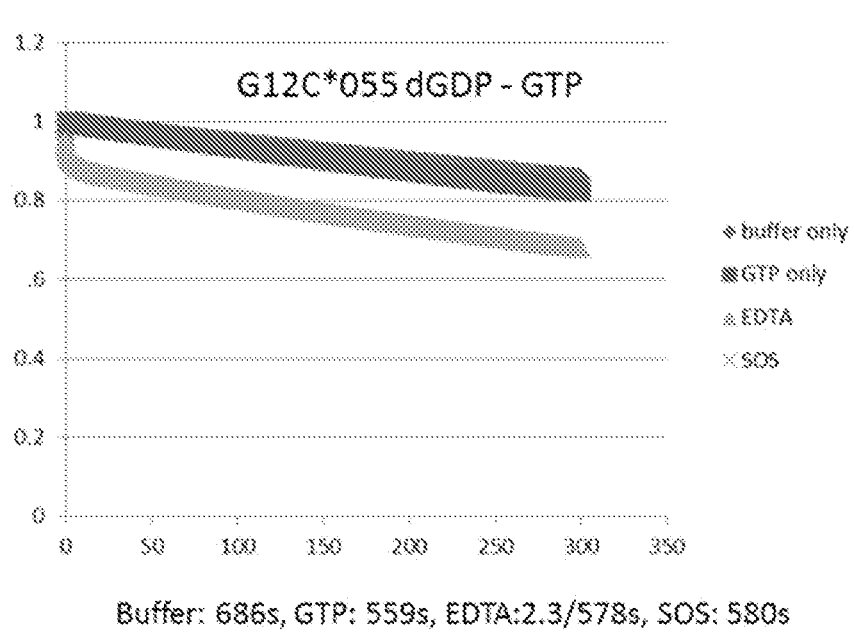
FIG. 11B

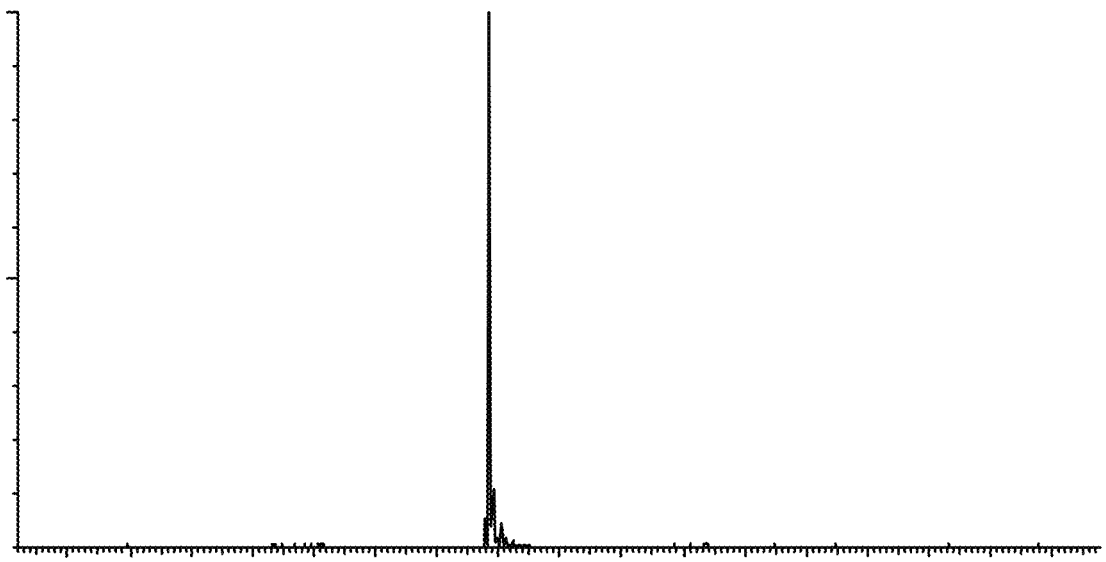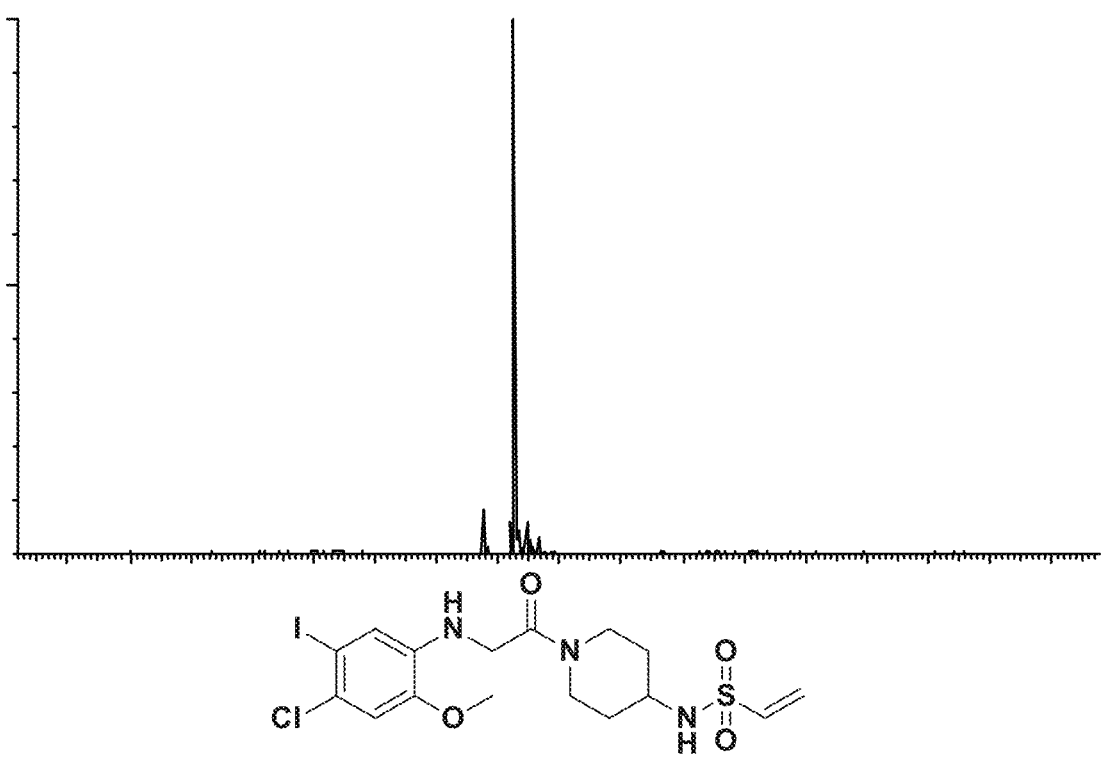
*FIG. 14A*

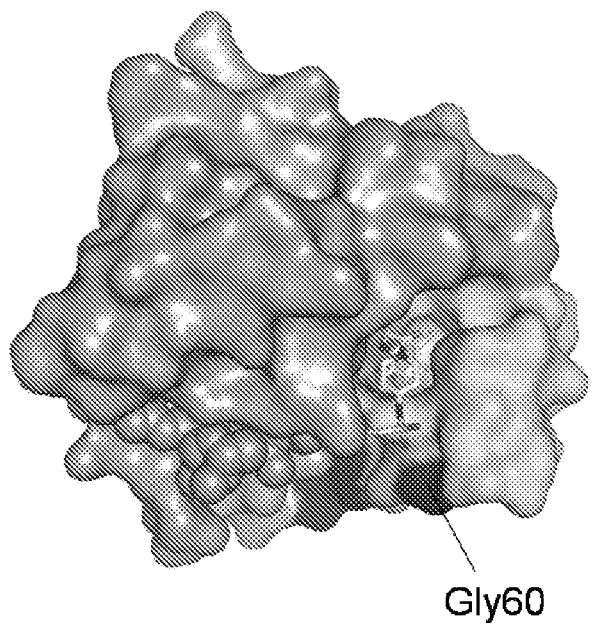
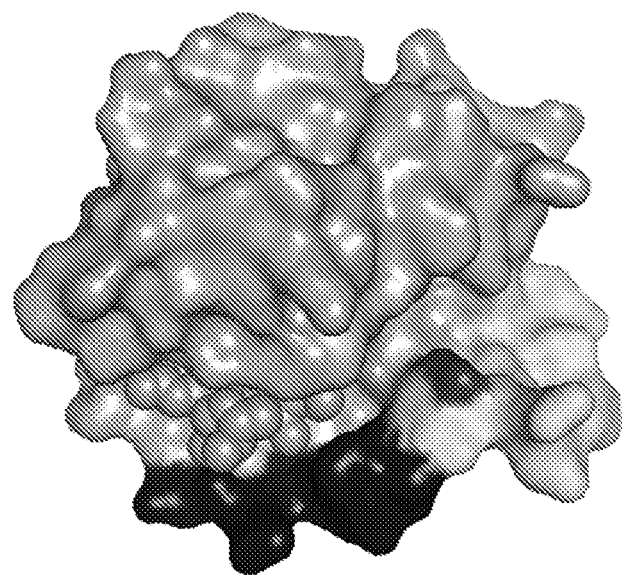
FIG. 19

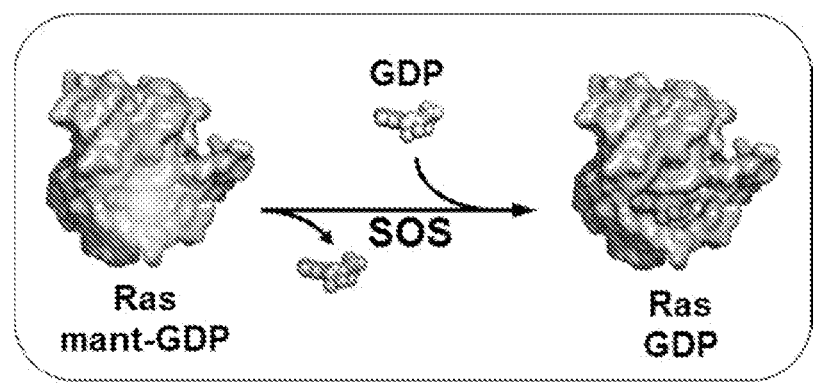
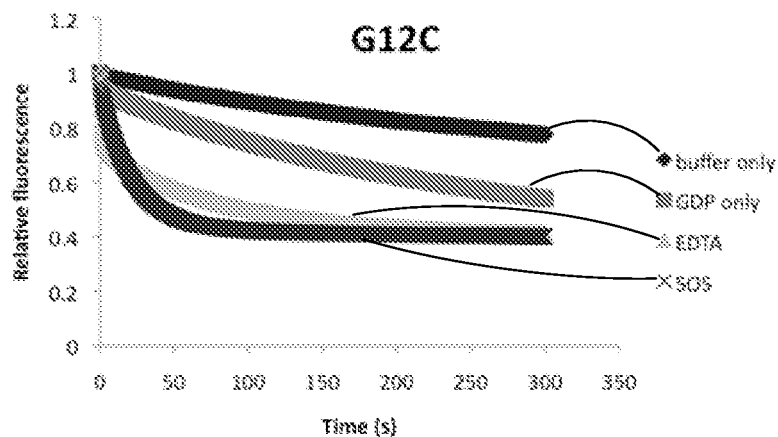
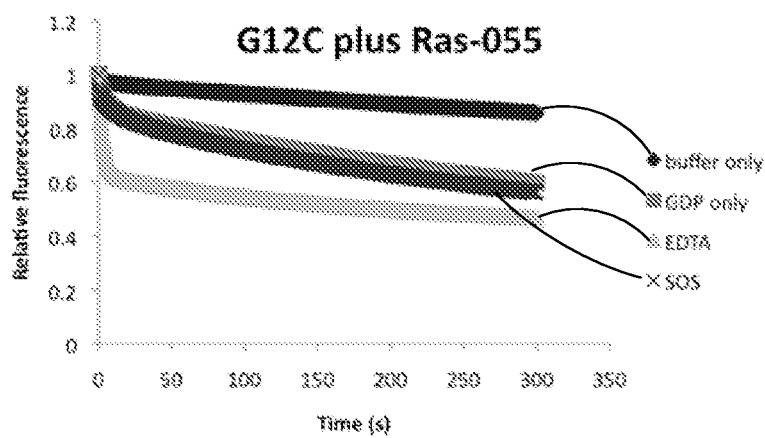
*FIG. 21*

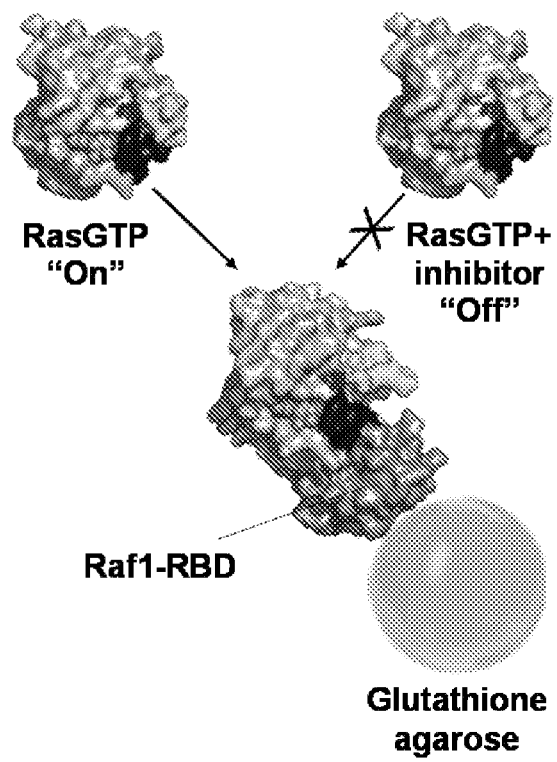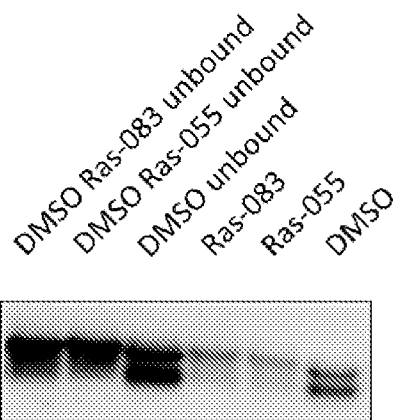
*FIG. 23*

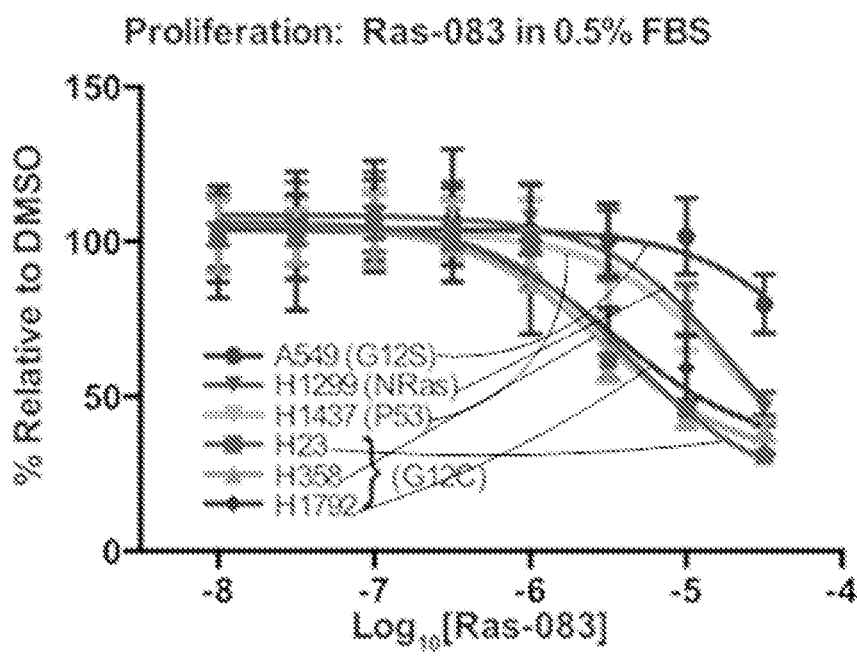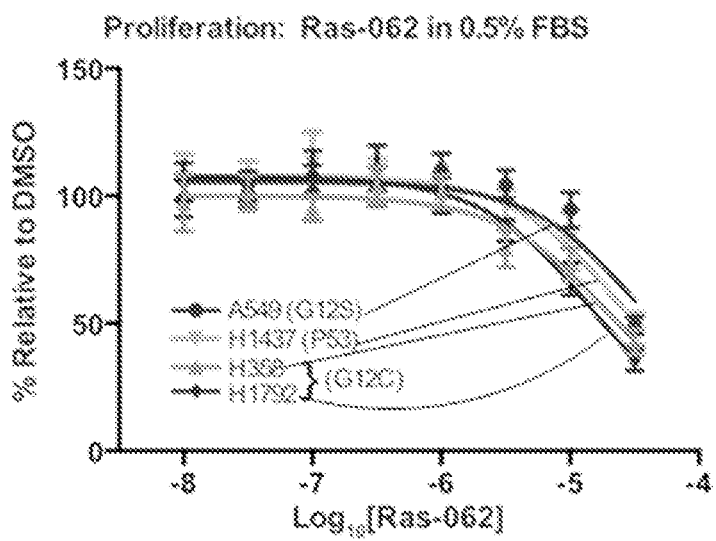
FIG. 25

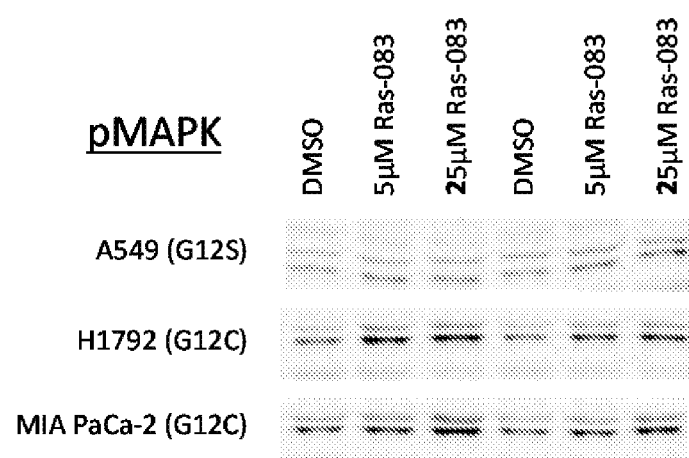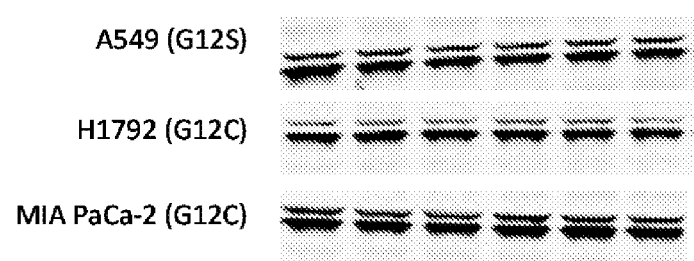
*FIG. 27A*

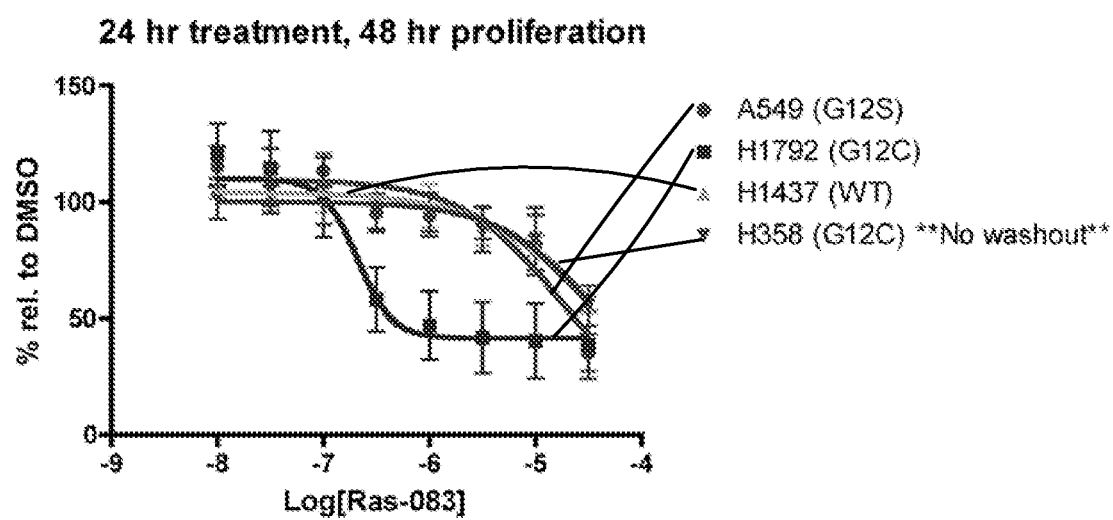
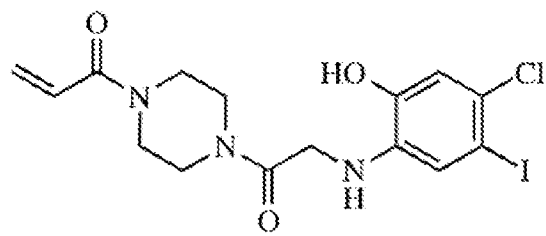
Ras-083
FIG. 28

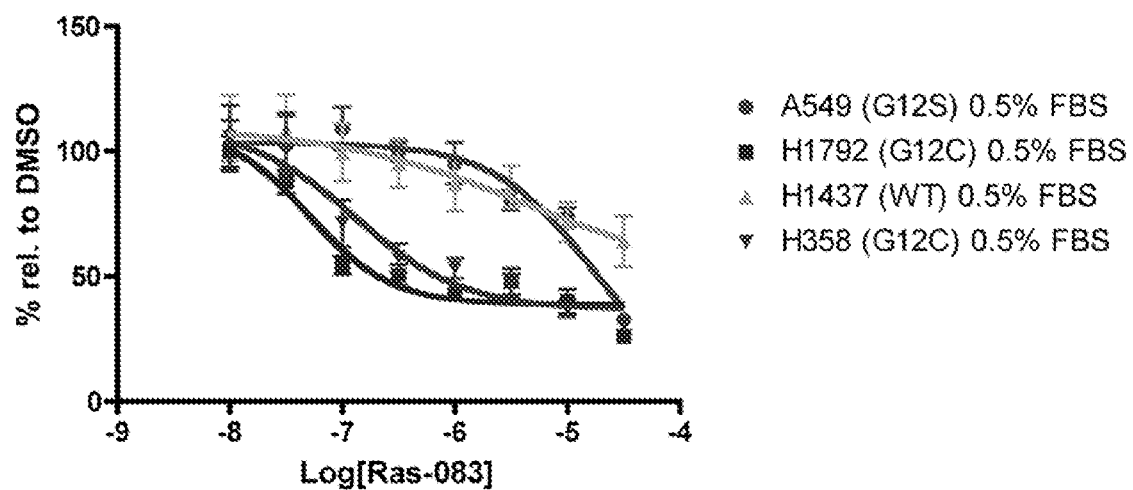
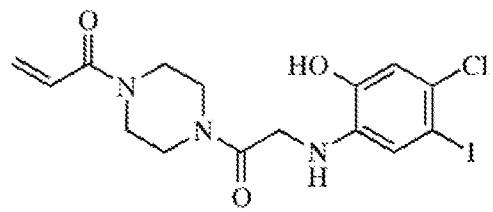
Ras-083
*FIG. 29*

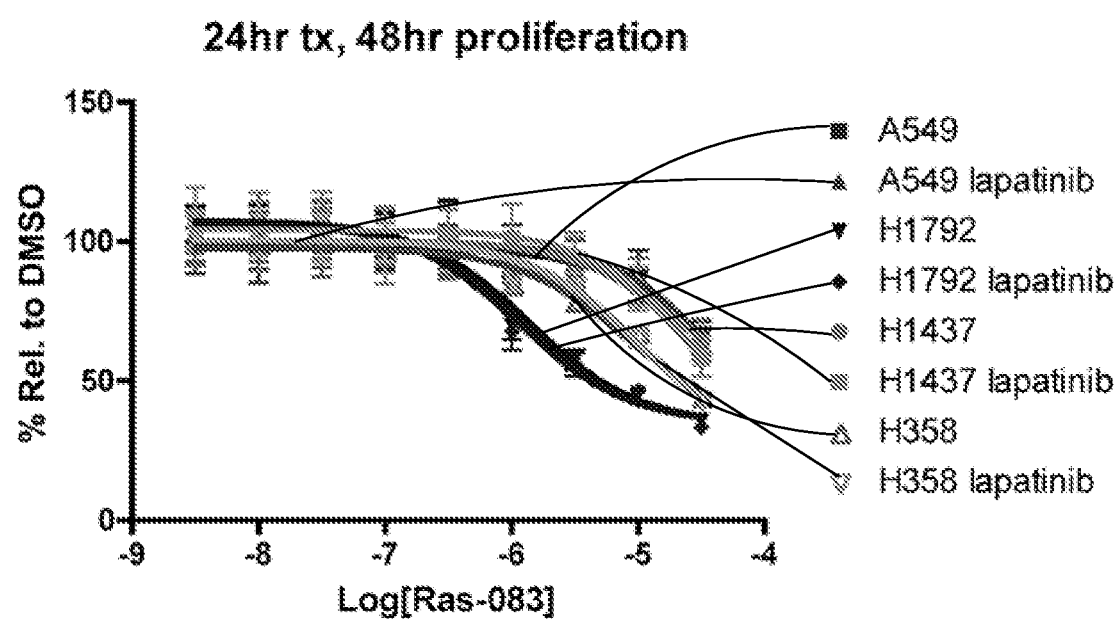
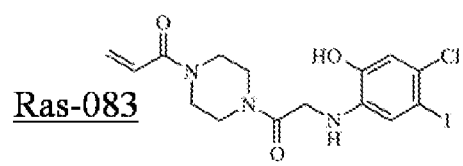
FIG. 30

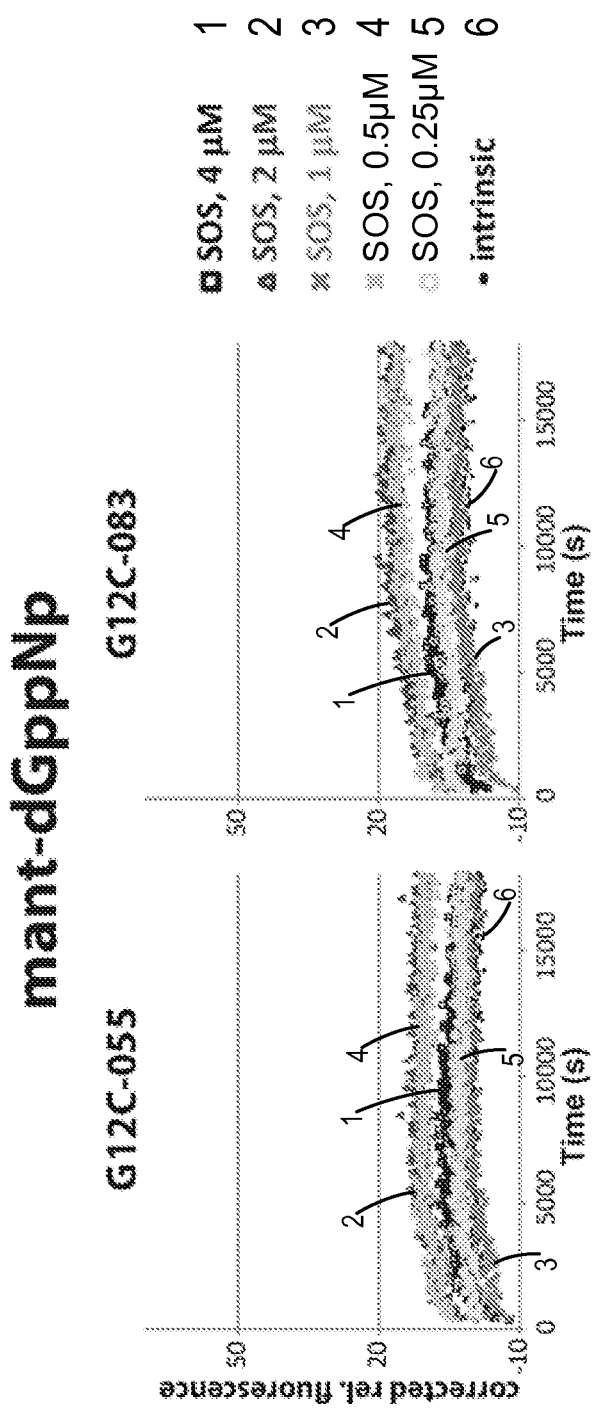
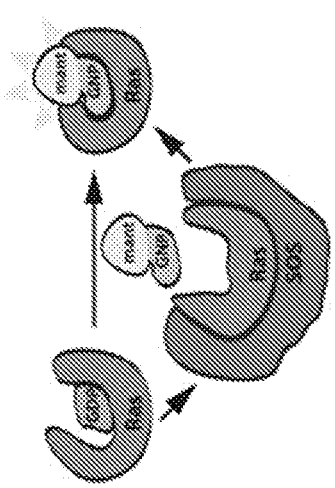
FIG. 35B

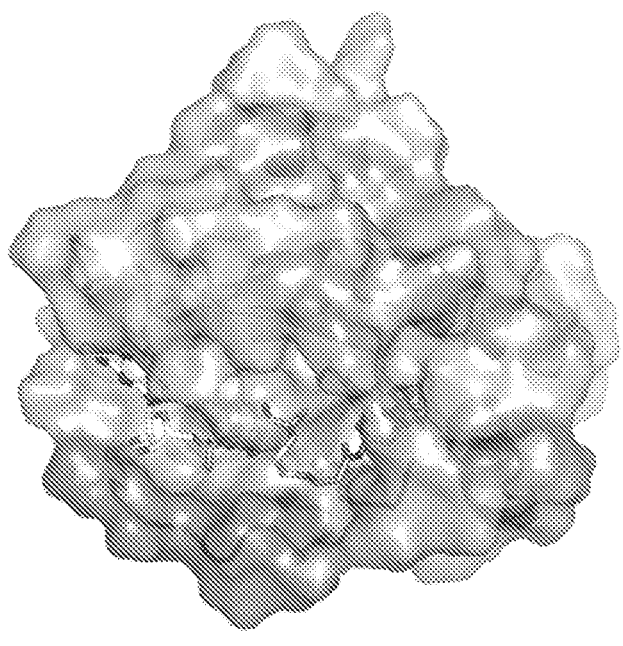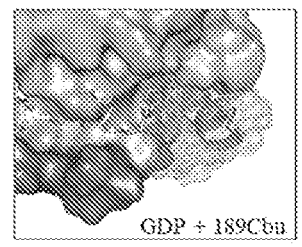
*FIG. 40*

SEQUENCE LISTING

```
Sequence total quantity: 17
SEQ ID NO: 1            moltype = AA  length = 189
FEATURE                 Location/Qualifiers
source                  1..189
                        mol_type = protein
                        organism = Homo sapiens
SEQUENCE: 1
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSDDVP MVLVGNKCDL 120
AARTVESRQA QDLARSYGIP YIETSAKTRQ GVEDAFYTLV REIRQHKLRK LNPPDESGPG 180
CMSCKCVLS                                                        189

SEQ ID NO: 2            moltype = AA  length = 166
FEATURE                 Location/Qualifiers
REGION                  1..166
                        note = Synthetic polypeptide of truncated H-Ras WT
source                  1..166
                        mol_type = protein
                        organism = synthetic construct
SEQUENCE: 2
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSDDVP MVLVGNKCDL 120
```

```
AARTVESRQA QDLARSYGIP YIETSAKTRQ GVEDAFYTLV REIRQH         166

SEQ ID NO: 3            moltype = AA  length = 166
FEATURE                 Location/Qualifiers
REGION                  1..166
                        note = Synthetic polypeptide of truncated H-Ras G12C
source                  1..166
                        mol_type = protein
                        organism = synthetic construct
SEQUENCE: 3
MTEYKLVVVG ACGVGKSALT IQLIQNHFVD EYDPTIEDSY RKQVVIDGET CLLDILDTAG  60
QEEYSAMRDQ YMRTEGFLC VFAINNTKSF EDIHQYREQI KRVKDSDDVP MVLVGNKCDL  120
AARTVESRQA QDLARSYGIP YIETSAKTRQ GVEDAFYTLV REIRQH                166

SEQ ID NO: 4            moltype = AA  length = 169
FEATURE                 Location/Qualifiers
REGION                  1..169
                        note = Synthetic polypeptide of truncated K-Ras G12C
source                  1..169
                        mol_type = protein
                        organism = synthetic construct
SEQUENCE: 4
MTEYKLVVVG ACGVGKSALT IQLIQNHFVD EYDPTIEDSY RKQVVIDGET SLLDILDTAG  60
QEEYSAMRDQ YMRTEGFLL VFAINNTKSF EDIHHYREQI KRVKDSEDVP MVLVGNKSDL  120
PSRTVDTKQA QDLARSYGIP FIETSAKTRQ GVDDAFYTLV REIRKHKEK            169

SEQ ID NO: 5            moltype = AA  length = 189
FEATURE                 Location/Qualifiers
source                  1..189
                        mol_type = protein
                        organism = Homo sapiens
SEQUENCE: 5
MTEYKLVVVG AGGVGKSALT IQLIQNHFVD EYDPTIEDSY RKQVVIDGET CLLDILDTAG  60
QEEYSAMRDQ YMRTEGFLC VFAINNTKSF EDIHHYREQI KRVKDSEDVP MVLVGNKCDL  120
PSRTVDTKQA QDLARSYGIP FIETSAKTRQ RVEDAFYTLV REIRQYRLKK ISKEEKTPGC  180
VKIKKCIIM                                                         189

SEQ ID NO: 6            moltype = AA  length = 189
FEATURE                 Location/Qualifiers
REGION                  1..189
                        note = Synthetic polypeptide
source                  1..189
                        mol_type = protein
                        organism = synthetic construct
SEQUENCE: 6
MTEYKLVVVG ACGVGKSALT IQLIQNHFVD EYDPTIEDSY RKQVVIDGET CLLDILDTAG  60
QEEYSAMRDQ YMRTEGFLC VFAINNTKSF EDIHHYREQI KRVKDSEDVP MVLVGNKCDL  120
PSRTVDTKQA QDLARSYGIP FIETSAKTRQ RVEDAFYTLV REIRQYRLKK ISKEEKTPGC  180
VKIKKCIIM                                                         189

SEQ ID NO: 7            moltype = AA  length = 189
FEATURE                 Location/Qualifiers
REGION                  1..189
                        note = Synthetic polypeptide
source                  1..189
                        mol_type = protein
                        organism = synthetic construct
SEQUENCE: 7
MTEYKLVVVG ADGVGKSALT IQLIQNHFVD EYDPTIEDSY RKQVVIDGET CLLDILDTAG  60
QEEYSAMRDQ YMRTEGFLC VFAINNTKSF EDIHHYREQI KRVKDSEDVP MVLVGNKCDL  120
PSRTVDTKQA QDLARSYGIP FIETSAKTRQ RVEDAFYTLV REIRQYRLKK ISKEEKTPGC  180
VKIKKCIIM                                                         189

SEQ ID NO: 8            moltype = AA  length = 189
FEATURE                 Location/Qualifiers
REGION                  1..189
                        note = Synthetic polypeptide
source                  1..189
                        mol_type = protein
                        organism = synthetic construct
SEQUENCE: 8
MTEYKLVVVG AGCVGKSALT IQLIQNHFVD EYDPTIEDSY RKQVVIDGET CLLDILDTAG  60
QEEYSAMRDQ YMRTEGFLC VFAINNTKSF EDIHHYREQI KRVKDSEDVP MVLVGNKCDL  120
PSRTVDTKQA QDLARSYGIP FIETSAKTRQ RVEDAFYTLV REIRQYRLKK ISKEEKTPGC  180
VKIKKCIIM                                                         189

SEQ ID NO: 9            moltype = AA  length = 189
FEATURE                 Location/Qualifiers
REGION                  1..189
```

```
                             note = Synthetic polypeptide
source                       1..189
                             mol_type = protein
                             organism = synthetic construct
SEQUENCE: 9
MTEYKLVVVG AGDVGKSALT IQLIQNHFVD EYDPTIEDSY RKQVVIDGET CLLDILDTAG    60
QEEYSAMRDQ YMRTGEGFLC VFAINNTKSF EDIHHYREQI KRVKDSEDVP MVLVGNKCDL   120
PSRTVDTKQA QDLARSYGIP FIETSAKTRQ RVEDAFYTLV REIRQYRLKK ISKEEKTPGC   180
VKIKKCIIM                                                          189

SEQ ID NO: 10                moltype = AA  length = 188
FEATURE                      Location/Qualifiers
source                       1..188
                             mol_type = protein
                             organism = Homo sapiens
SEQUENCE: 10
MTEYKLVVVG AGGVGKSALT IQLIQNHFVD EYDPTIEDSY RKQVVIDGET CLLDILDTAG    60
QEEYSAMRDQ YMRTGEGFLC VFAINNTKSF EDIHHYREQI KRVKDSEDVP MVLVGNKCDL   120
PSRTVDTKQA QDLARSYGIP FIETSAKTRQ GVDDAFYTLV REIRKHKEKM SKDGKKKKKK   180
SKTKCVIM                                                           188

SEQ ID NO: 11                moltype = AA  length = 188
FEATURE                      Location/Qualifiers
REGION                       1..188
                             note = Synthetic polypeptide
source                       1..188
                             mol_type = protein
                             organism = synthetic construct
SEQUENCE: 11
MTEYKLVVVG ACGVGKSALT IQLIQNHFVD EYDPTIEDSY RKQVVIDGET CLLDILDTAG    60
QEEYSAMRDQ YMRTGEGFLC VFAINNTKSF EDIHHYREQI KRVKDSEDVP MVLVGNKCDL   120
PSRTVDTKQA QDLARSYGIP FIETSAKTRQ GVDDAFYTLV REIRKHKEKM SKDGKKKKKK   180
SKTKCVIM                                                           188

SEQ ID NO: 12                moltype = AA  length = 188
FEATURE                      Location/Qualifiers
REGION                       1..188
                             note = Synthetic polypeptide
source                       1..188
                             mol_type = protein
                             organism = synthetic construct
SEQUENCE: 12
MTEYKLVVVG ADGVGKSALT IQLIQNHFVD EYDPTIEDSY RKQVVIDGET CLLDILDTAG    60
QEEYSAMRDQ YMRTGEGFLC VFAINNTKSF EDIHHYREQI KRVKDSEDVP MVLVGNKCDL   120
PSRTVDTKQA QDLARSYGIP FIETSAKTRQ GVDDAFYTLV REIRKHKEKM SKDGKKKKKK   180
SKTKCVIM                                                           188

SEQ ID NO: 13                moltype = AA  length = 188
FEATURE                      Location/Qualifiers
REGION                       1..188
                             note = Synthetic polypeptide
source                       1..188
                             mol_type = protein
                             organism = synthetic construct
SEQUENCE: 13
MTEYKLVVVG AGCVGKSALT IQLIQNHFVD EYDPTIEDSY RKQVVIDGET CLLDILDTAG    60
QEEYSAMRDQ YMRTGEGFLC VFAINNTKSF EDIHHYREQI KRVKDSEDVP MVLVGNKCDL   120
PSRTVDTKQA QDLARSYGIP FIETSAKTRQ GVDDAFYTLV REIRKHKEKM SKDGKKKKKK   180
SKTKCVIM                                                           188

SEQ ID NO: 14                moltype = AA  length = 188
FEATURE                      Location/Qualifiers
REGION                       1..188
                             note = Synthetic polypeptide
source                       1..188
                             mol_type = protein
                             organism = synthetic construct
SEQUENCE: 14
MTEYKLVVVG AGDVGKSALT IQLIQNHFVD EYDPTIEDSY RKQVVIDGET CLLDILDTAG    60
QEEYSAMRDQ YMRTGEGFLC VFAINNTKSF EDIHHYREQI KRVKDSEDVP MVLVGNKCDL   120
PSRTVDTKQA QDLARSYGIP FIETSAKTRQ GVDDAFYTLV REIRKHKEKM SKDGKKKKKK   180
SKTKCVIM                                                           188

SEQ ID NO: 15                moltype = AA  length = 169
FEATURE                      Location/Qualifiers
REGION                       1..169
                             note = Synthetic polypeptide
source                       1..169
                             mol_type = protein
```

```
                         organism = synthetic construct
SEQUENCE: 15
MTEYKLVVVG ACGVGKSALT IQLIQNHFVD EYDPTIEDSY RKQVVIDGET CLLDILDTAG    60
QEEYSAMRDQ YMRTGEGFLC VFAINNTKSF EDIHHYREQI KRVKDSEDVP MVLVGNKCDL   120
PSRTVDTKQA QDLARSYGIP FIETSAKTRQ GVDDAFYTLV REIRKHKEK               169

SEQ ID NO: 16            moltype = AA   length = 169
FEATURE                  Location/Qualifiers
REGION                   1..169
                         note = Synthetic polypeptide
source                   1..169
                         mol_type = protein
                         organism = synthetic construct
SEQUENCE: 16
MTEYKLVVVG AGGVGKSALT IQLIQNHFVD EYDPTIEDSY RKQVVIDGET CLLDILDTAG    60
QEEYSAMRDQ YMRTGEGFLC VFAINNTKSF EDIHHYREQI KRVKDSEDVP MVLVGNKCDL   120
PSRTVDTKQA QDLARSYGIP FIETSAKTRQ GVDDAFYTLV REIRKHKEK               169

SEQ ID NO: 17            moltype = AA   length = 169
FEATURE                  Location/Qualifiers
REGION                   1..169
                         note = Synthetic polypeptide
source                   1..169
                         mol_type = protein
                         organism = synthetic construct
SEQUENCE: 17
MTEYKLVVVG AGGVGKSALT IQLIQNHFVD EYDPTIEDSY RKQVVIDGET SLLDILDTAG    60
QEEYSAMRDQ YMRTGEGFLL VFAINNTKSF EDIHHYREQI KRVKDSEDVP MVLVGNKSDL   120
PSRTVDTKQA QDLARSYGIP FIETSAKTRQ GVDDAFYTLV REIRKHKEK               169
```

COMPOSITIONS AND METHODS FOR TREATING CANCER

CROSS-REFERENCE TO RELATED APPLICATIONS

This application is a continuation of U.S. application Ser. No. 18/821,460 filed Aug. 30, 2024, which is a continuation of U.S. application Ser. No. 18/490,700 filed Oct. 19, 2023, which is a continuation of U.S. application Ser. No. 18/058,655 filed Nov. 23, 2022, issued as U.S. Pat. No. 11,891,402, which is a continuation of U.S. application Ser. No. 17/212,737 filed Mar. 25, 2021, issued as U.S. Pat. No. 11,603,376, which is a continuation of U.S. application Ser. No. 16/720,526 filed Dec. 19, 2019, issued as U.S. Pat. No. 11,008,334, which is a continuation of U.S. application Ser. No. 16/013,271 filed Jun. 20, 2018, abandoned, which is a continuation of U.S. application Ser. No. 14/934,184 filed Nov. 6, 2015, issued as U.S. Pat. No. 10,023,588, which is a continuation of U.S. application Ser. No. 14/391,369 filed Oct. 8, 2014, abandoned, which is a Section 371 of PCT/US2013/036031 filed Apr. 10, 2013, which claims priority to U.S. Application No. 61/622,507 filed Apr. 10, 2012; U.S. Application No. 61/728,145 filed Nov. 19, 2012; and U.S. Application No. 61/794,956 filed Mar. 15, 2013, which are all incorporated herein by reference in their entirety and for all purposes.

INCORPORATION BY REFERENCE OF SEQUENCE LISTING PROVIDED AS A SEQUENCE LISTING XML FILE

A Sequence Listing is provided herewith as a Sequence Listing XML, UCSF-847CON9-ST26, created on Nov. 21, 2024 and having a size of 24,086 bytes. The contents of the Sequence Listing XML are incorporated herein by reference in their entirety.

BACKGROUND OF THE INVENTION

K-Ras is the most frequently mutated oncogene in human cancer. However, past attempts to directly target this enzyme with reversible inhibitors have been almost entirely unsuccessful.

Ras proteins are small guanine nucleotide-binding proteins that act as molecular switches by cycling between active GTP-bound and inactive GDP-bound conformations. Ras signaling is regulated through a balance between activation by guanine nucleotide exchange factors (GEFs), most commonly son of sevenless (SOS), and inactivation by GTPase-activating proteins (GAPs) such as neurofibromin or p120GAP (see FIG. 1). The Ras proteins play a critical role in the regulation of cell proliferation, differentiation, and survival. Dysregulation of the Ras signaling pathway is almost invariably associated with disease. Hyper-activating somatic mutations in Ras are among the most common lesions found in human cancer. Most of these mutations have been shown to decrease the sensitivity of Ras to GAP stimulation and decrease its intrinsic GTPase activity, leading to an increase in the active GTP-bound population. Although mutation of any one of the three Ras isoforms (K-Ras, N-Ras, or H-Ras) has been shown to lead to oncogenic transformation, K-Ras mutations are by far the most common in human cancer. For example, K-Ras mutations are known to be often associated with pancreatic, colorectal and non-small-cell lung carcinomas. Similarly, H-Ras mutations are common in cancers such as papillary thyroid cancer, lung cancers and skin cancers. Finally, N-Ras mutations occur frequently in hepatocellular carcinoma.

The structural basis for the Ras cycle and Ras hyperactivation are well understood. Over 40 crystal structures of H-Ras have been solved, including both wild-type and mutants bound to GDP or analogs of GTP. Likewise, the structures of H-Ras in complex with many of its binding partners are known. The nucleotide-binding pocket is bordered by four main regions: the phosphate-binding loop (P-loop, residues 10-17), Switch 1 (residues 30-40), Switch 2 (residues 60-76), and the base-binding loops (residues 116-120 and 145-147), (Hall et al. PNAS, 2002, 19, 12138-12142 and Vetter 2001 *Science*). The Switch regions govern interactions between Ras and its binding partners by adopting different conformations when bound to GTP or GDP. Threonine-35 and glycine-60 make key hydrogen bonds with the γ-phosphate of GTP, holding the Switch 1 and Switch 2 regions in the active conformation, respectively. Upon hydrolysis of GTP and release of phosphate, these two regions are free to relax into the inactive GDP conformation.

The regions bordering the nucleotide pocket also contain the most common sites of Ras mutation in cancer. The vast majority of oncogenic mutations occur at residues 12 or 13 in the P-loop, or residue 61 in Switch 2. Structural data suggest that mutation of glycine-12 or glycine-13 would sterically occlude the critical arginine residue of the GAP and thus prohibit inactivation of Ras signaling. Mutation of glutamine-61 similarly impairs GAP-mediated Ras inactivation.

Thus, there is a need in the art for effective Ras inhibitors and anticancer compounds. The present invention provides solutions to these and other problems in the art.

BRIEF SUMMARY OF THE INVENTION

Described herein, inter alia, is the use of covalent (e.g. reversible or irreversible) chemistry to target a Ras protein, including but not limited to chemically tractable oncogenic mutants such as K-RasG12C. Also described herein, inter alia, are the first small molecules which specifically target the human oncogene (K-RasG12C) and do not bind to the proto-oncogenic form of the protein (K-Ras).

In a first aspect, a compound having the formula $R^1$-$L^1$-$L^2$-$L^3$-E is provided. $R^1$ is a Switch 2-Binding Pocket binding moiety. $L^1$ is a bond or a divalent radical chemical linker. $L^2$ is a bond or a divalent radical chemical linker. $L^3$ is a bond or a divalent radical chemical linker. E is an electrophilic chemical moiety capable of forming a covalent bond with a Ras (e.g. K-Ras) cysteine residue or a Ras (e.g. K-Ras) aspartate residue.

In a second aspect, a pharmaceutical composition including a pharmaceutically acceptable excipient and a compound described herein (including embodiments, examples, and in Table 1, 2, 3, 4, or 5) is provided.

In a third aspect, a method of treating a disease in a patient in need of such treatment is provided. The method including administering a therapeutically effective amount of a compound described herein (including embodiments, examples, and in Table 1, 2, 3, 4, or 5) to the patient.

In a fourth aspect, a method of modulating the activity of a K-Ras protein is provided. The method including contacting the K-Ras protein with an effective amount of a compound described herein (including embodiments, examples, and in Table 1, 2, 3, 4, or 5).

In a fifth aspect, a method of modulating a K-Ras protein is provided. The method including contacting the K-Ras protein with an effective amount of a compound described herein (including embodiments, examples, and in Table 1, 2, 3, 4, or 5).

In a sixth aspect, a K-Ras protein covalently bonded to a compound, such as, for example, a compound described herein (including modulators, inhibitors, embodiments, examples, and in Table 1, 2, 3, 4, or 5) is provided. The compound is covalently bonded to a cysteine residue of the K-Ras protein.

In a seventh aspect, a K-Ras protein covalently bonded to a compound, such as, for example, a compound described herein ((including modulators, inhibitors, embodiments, examples, and in Table 1, 2, 3, 4, or 5) is provided. The compound is covalently bonded to an aspartate residue of the K-Ras protein.

In an eighth aspect, a method of identifying a covalent inhibitor of K-Ras protein is provided. The method including contacting a K-Ras protein with a K-Ras inhibitor test compound, allowing the K-Ras inhibitor test compound to covalently inhibit the K-Ras protein, and detecting the level of covalent inhibition of the K-Ras protein, thereby identifying a covalent inhibitor of K-Ras protein.

In some embodiments, provided is a compound having the formula:

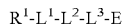

wherein, $R^1$ is a Switch 2-Binding Pocket binding moiety; $L^1$ is a bond or a divalent radical chemical linker; $L^2$ is a bond or a divalent radical chemical linker; $L^3$ is a bond or a divalent radical chemical linker; and E is an electrophilic chemical moiety capable of forming a covalent bond with a K-Ras cysteine residue or a K-Ras aspartate residue. In some embodiments, $R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. For example, $R^1$ is substituted or unsubstituted cycloalkyl, substituted or unsubstituted heterocycloalkyl, substituted or unsubstituted aryl, or substituted or unsubstituted heteroaryl; or $R^1$ is substituted or unsubstituted aryl or substituted or unsubstituted heteroaryl, such as substituted or unsubstituted fused ring aryl or substituted or unsubstituted fused ring heteroaryl. In some embodiments, $R^1$ is $R^3$-substituted or unsubstituted aryl or $R^3$-substituted or unsubstituted heteroaryl, wherein $R^3$ is independently hydrogen, oxo, halogen, $-CX_3$, $-CN$, $-SO_2Cl$, $-SO_2R^{10}$, $-SO_nNR^7R^8$, $-NHNH_2$, $-ONR^7R^8$, $-NHC(O)NHNH_2$, $-NHC(O)NR^7R^8$, $-N(O)_m$, $-NR^7R^8$, $-C(O)R^9$, $-C(O)OR^9$, $-C(O)NR^7R^8$, $-OR^{10}$, $-NR^7SO_2R^{10}$, $-NR^{7c}=(O)R^9$, $-NR^{7c}(O)-OR^9$, $-NR^7OR^9$, $-OCX_3$, $-OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl. Two $R^3$ substituents bonded to the same atom may optionally be joined to form a substituted or unsubstituted cycloalkyl or substituted or unsubstituted heterocycloalkyl; $R^7$, $R^8$, $R^9$, and $R^{10}$ are independently hydrogen, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC(O)H$, $-NHC(O)-OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; m and v are independently 1 or 2; n is independently an integer from 0 to 4; and X is independently $-Cl$, $-Br$, $-I$, or $-F$.

In some embodiments, $R^1$ is:

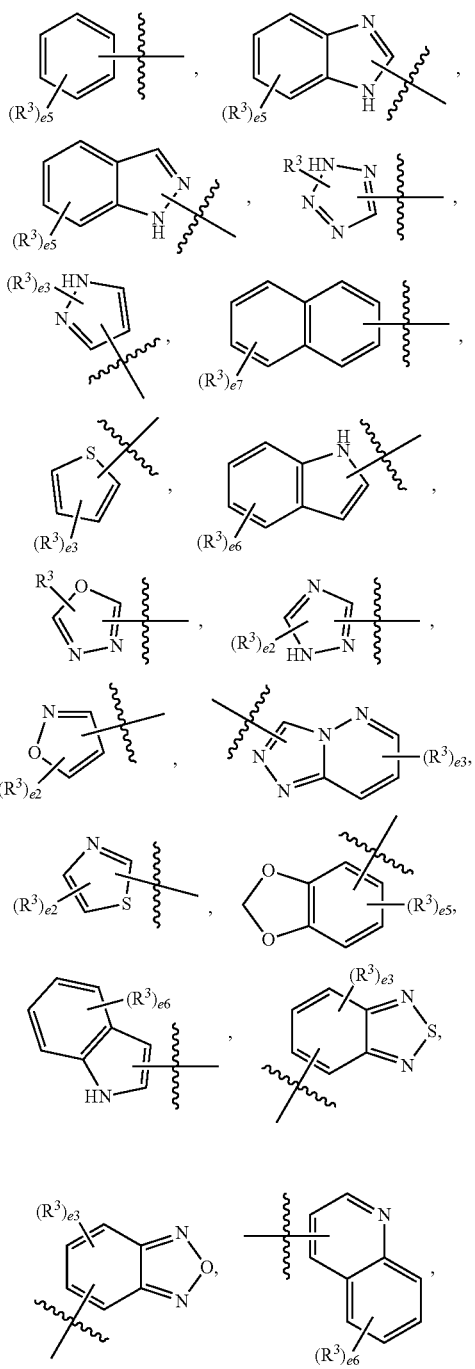

-continued

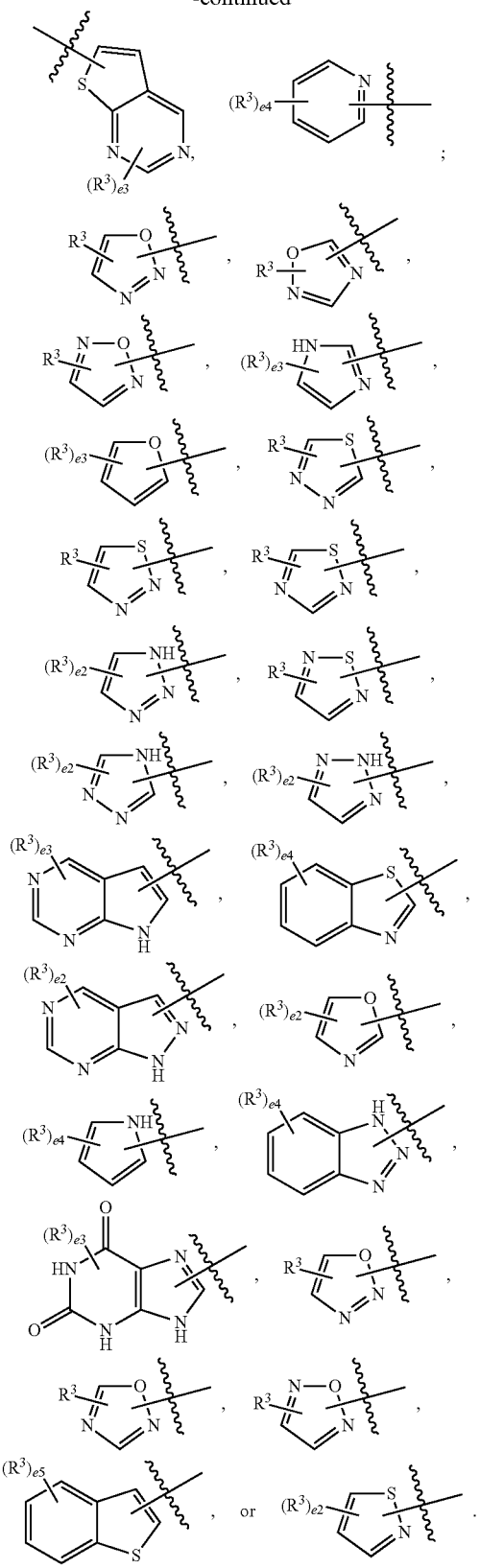

wherein, R³ is independently hydrogen, oxo, halogen, —CX₃, —CN, —SO₂Cl, —SO_nR¹⁰, —SO_vNR⁷R⁸, —NHNH₂, —ONR⁷R⁸, —NHC=(O)NHNH₂, —NHC=(O)NR⁷R⁸, —N(O)_m, —NR⁷R⁸, —C(O)R⁹, —C(O)—OR⁹, —C(O)NR⁷R⁸, —OR¹⁰, —NR⁷SO₂R¹⁰, —NR⁷ᶜ=(O) R⁹, —NR⁷ᶜ (O)—OR⁹, —NR⁷OR⁹, —OCX₃, —OCHX₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R³ substituents may optionally be joined to form a substituted or unsubstituted cycloalkyl, substituted or unsubstituted heterocycloalkyl, substituted or unsubstituted aryl, or substituted or unsubstituted heteroaryl; two R³ substituents bonded to the same atom may optionally be joined to form a substituted or unsubstituted cycloalkyl or substituted or unsubstituted heterocycloalkyl; R⁷, R⁸, R⁹, and R¹⁰ are independently hydrogen, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R⁷ and R⁸ substituents bonded to the same nitrogen atom may optionally be joined to form a substituted or unsubstituted heterocycloalkyl or substituted or unsubstituted heteroaryl; m and v are independently 1 or 2; n is independently an integer from 0 to 4; X is independently —Cl, —Br, —I, or —F; e2 is independently an integer from 0 to 2; e3 is independently an integer from 0 to 3; e4 is independently an integer from 0 to 4; e5 is independently an integer from 0 to 5; e6 is independently an integer from 0 to 6; and e7 is independently an integer from 0 to 7.

In some embodiments, R¹ is R³-substituted pyridinyl, R³-substituted pyrimidinyl, R³-substituted thiophenyl, R³-substituted furanyl, R³-substituted indolyl, R³-substituted benzoxadiazolyl, R³-substituted benzodioxolyl, R³-substituted benzodioxanyl, R³-substituted thianaphthanyl, R³-substituted pyrrolopyridinyl, R³-substituted indazolyl, R³-substituted quinolinyl, R³-substituted quinoxalinyl, R³-substituted pyridopyrazinyl, R³-substituted quinazolinonyl, R³-substituted benzoisoxazolyl, R³-substituted imidazopyridinyl, R³-substituted benzofuranyl, R³-substituted benzothiophenyl, R³-substituted phenyl, R³-substituted naphthyl, R³-substituted biphenyl, R³-substituted pyrrolyl, R³-substituted pyrazolyl, R³-substituted imidazolyl, R³-substituted pyrazinyl, R³-substituted oxazolyl, R³-substituted isoxazolyl, R³-substituted thiazolyl, R³-substituted furylthienyl, R³-substituted pyridyl, R³-substituted pyrimidyl, R³-substituted benzothiazolyl, R³-substituted purinyl, R³-substituted benzimidazolyl, R³-substituted isoquinolyl, R³-substituted thiadiazolyl, R³-substituted oxadiazolyl, R³-substituted pyrrolyl, R³-substituted diazolyl, R³-substituted triazolyl, R³-substituted tetrazolyl, R³-substituted benzothiadiazolyl, R³-substituted isothiazolyl, R³-substituted pyrazolopyrimidinyl, R³-substituted pyrrolopyrimidinyl, R³-substituted benzotriazolyl, or R³-substituted quinolyl; where R³ is independently hydrogen, oxo, halogen, —CX₃, —CN, —SO₂Cl, —SO_nR¹⁰, —SO_nNR⁷R⁸, —NHNH₂, —ONR⁷R⁸, —NHC—(O)NHNH₂, —NHC=(O)NR⁷R⁸, —N(O)_m, —NR⁷R⁸, —C(O)R⁹, —C(O)—OR⁹, —C(O)NR⁷R⁸, —OR¹⁰, —NR⁷SO₂R¹⁰, —NR⁷ᶜ=(O) R⁹, —NR⁷ᶜ (O)—OR⁹, —NR⁷OR⁹, —OCX₃, —OCHX₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl; two $R^3$ substituents bonded to the same atom may optionally be joined to form a substituted or unsubstituted cycloalkyl or substituted or unsubstituted heterocycloalkyl; $R^7$, $R^8$, $R^9$, and $R^{10}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC—(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; m and v are independently 1 or 2; n is independently an integer from 0 to 4; and X is independently —Cl, —Br, —I, or —F.

In other embodiments, $R^1$ is unsubstituted pyridinyl, unsubstituted pyrimidinyl, unsubstituted thiophenyl, unsubstituted furanyl, unsubstituted indolyl, unsubstituted benzoxadiazolyl, unsubstituted benzodioxolyl, unsubstituted benzodioxanyl, unsubstituted thianaphthanyl, unsubstituted pyrrolopyridinyl, unsubstituted indazolyl, unsubstituted quinolinyl, unsubstituted quinoxalinyl, unsubstituted pyridopyrazinyl, unsubstituted quinazolinonyl, unsubstituted benzoisoxazolyl, unsubstituted imidazopyridinyl, unsubstituted benzofuranyl, unsubstituted benzothiophenyl, unsubstituted phenyl, unsubstituted naphthyl, unsubstituted biphenyl, unsubstituted pyrrolyl, unsubstituted pyrazolyl, unsubstituted imidazolyl, unsubstituted pyrazinyl, unsubstituted oxazolyl, unsubstituted isoxazolyl, unsubstituted thiazolyl, unsubstituted furylthienyl, unsubstituted pyridyl, unsubstituted pyrimidyl, unsubstituted benzothiazolyl, unsubstituted purinyl, unsubstituted benzimidazolyl, unsubstituted isoquinolyl, unsubstituted thiadiazolyl, unsubstituted oxadiazolyl, unsubstituted pyrrolyl, unsubstituted diazolyl, unsubstituted triazolyl, unsubstituted tetrazolyl, unsubstituted benzothiadiazolyl, unsubstituted isothiazolyl, unsubstituted pyrazolopyrimidinyl, unsubstituted pyrrolopyrimidinyl, unsubstituted benzotriazolyl, or unsubstituted quinolyl.

In some embodiments, $L^1$, $L^2$ and $L^3$ are independently a bond, —$NR^{2C}$—, —O—, —S—, —C(O)—, —S(O)—, —$S(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker; $R^{2C}$ is independently hydrogen, oxo, halogen, —$CX^c_3$, —CN, —$SO_2Cl$, —$SO_{n3}R^{10c}$, —$SO_{v3}NR^{7c}R^{8c}$, —$NHNH_2$, —$ONR^{7c}R^{8c}$, —NHC=(O)$NHNH_2$, —NHC=(O)$NR^{7c}R^{8c}$, —$N(O)_{m3}$, —$NR^{7c}R^{8c}$, —$C(O)R^{9c}$, —C(O)—$OR^{9c}$, —$C(O)NR^{7c}R^{8c}$, —$OR^{10c}$, —$NR^{7c}SO_2R^{10c}$, —$NR^{7c}$=(O)$R^{9c}$, —$NR^{7c}$(O)—$OR^{10c}$, —$NR^{7c}OR^c$, —$OCX^c_3$, —$OCHX^c_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; Two adjacent $R^{2C}$ substituents may optionally be joined to form a substituted or unsubstituted cycloalkyl or unsubstituted heterocycloalkyl, substituted or unsubstituted aryl, or substituted or unsubstituted heteroaryl; Two $R^{2C}$ substituents bonded to the same atom may optionally be joined to form a substituted or unsubstituted cycloalkyl or substituted or unsubstituted heterocycloalkyl; $R^{7c}$, $R^{8c}$, $R^{9c}$, and $R^{10c}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{7c}$ and $R^{8c}$. substituents bonded to the same nitrogen atom may optionally be joined to form a substituted or unsubstituted heterocycloalkyl or substituted or unsubstituted heteroaryl; m1, m3, v1, and v3 are independently an integer from 1 to 2; n1 and n3 are independently an integer from 0 to 4; and $X^c$ is independently —Cl, —Br, —I, or —F.

In some embodiments, $L^1$, $L^2$ and $L^3$ are indepedently —$CR^{2A}R^{2B}$—,

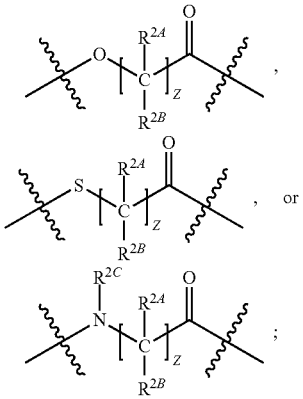

$R^{2A}$ and $R^{2B}$ are independently hydrogen, oxo, halogen, —$CX^a_3$, —CN, —$SO_2Cl$, —$SO_{n1}R^{10a}$, —$SO_{v1}NR^{7a}R^{8a}$, —$NHNH_2$, —$ONR^{7a}R^{8a}$, —NHC=(O)$NHNH_2$, —NHC=(O)$NR^{7a}R^{8a}$, —$N(O)_{m1}$, —$NR^{7a}R^{8a}$, —$C(O)R^{9a}$, —C(O)—$OR^{9a}$, —$C(O)NR^{7a}R^{8a}$, —$OR^{10a}$, —$NR^{7a}SO_2R^{10a}$, —$NR^{7a}C$=(O) $R^{9a}$, —$NR^{7a}C(O)$—$OR^{9a}$, —$NR^{7a}OR^{9a}$, —$OCX^a_3$, —$OCHX^a_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituent bonded to the same atom may optionally be joined to form a substituted or unsubstituted cycloalkyl or substituted or unsubstituted heterocycloalkyl; $R^{2C}$ is independently hydrogen, oxo, halogen, —$CX^c_3$, —CN, —$SO_2Cl$, —$SO_{n3}R^{10c}$, —$SO_{v3}NR^{7c}R^{8c}$, —$NHNH_2$, —$ONR^{7c}R^{8c}$, —NHC=(O)$NHNH_2$, —NHC=(O)$NR^{7c}R^{8c}$, —$N(O)_{m3}$, —$NR^{7c}R^{8c}$, —$C(O)R^9$, —C(O)—$OR^{9c}$, —$C(O)NR^7R^{8c}$, —$OR^{10c}$, —$NR^{7c}CSO_2R^{10c}$, —$NR^{7a}C$=(O)$R^{8a}$, —$NR^{7a}(O)$—$OR^{9a}$, —$NR^{7a}OR^{9a}$, —$OCX^a_3$, —$OCHX^a_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{7a}$, $R^{8a}$, $R^{9a}$ and $R^{10a}$ are independently hydrogen, halogen, —$CF_3$, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O)NH₂, —NHSO₂H, —NHC—(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{7a}$ and $R^{8a}$ substituents bonded to the same nitrogen atom may optionally be joined to form a substituted or unsubstituted heterocycloalkyl or substituted or unsubstituted heteroaryl; $R^{7c}$, $R^{8c}$, $R^{9c}$, and $R^{10c}$ are independently hydrogen, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{7c}$ and $R^{8c}$ substituents bonded to the same nitrogen atom may optionally be joined to form a substituted or unsubstituted heterocycloalkyl or substituted or unsubstituted heteroaryl; z is independently an integer from 0 to 10; m1, m3, v1, and v3 are independently an integer from 1 to 2; n1 and n3 are independently an integer from 0 to 4; and $X^a$ and $X^c$ are independently —Cl, —Br, —I, or —F.

In some embodiments, $L^1$ is independently substituted or unsubstituted cycloalkylene, substituted or unsubstituted heterocycloalkylene, substituted or unsubstituted arylene, substituted or unsubstituted heteroarylene, or substituted or unsubstituted spirocyclic linker; or $L^2$ is independently substituted or unsubstituted cycloalkylene, substituted or unsubstituted heterocycloalkylene, substituted or unsubstituted arylene, substituted or unsubstituted heteroarylene, or substituted or unsubstituted spirocyclic linker; or $L^3$ is independently substituted or unsubstituted cycloalkylene, substituted or unsubstituted heterocycloalkylene, substituted or unsubstituted arylene, substituted or unsubstituted heteroarylene, or substituted or unsubstituted spirocyclic linker.

In some embodiments, $L^1$ is independently $R^{2C}$-substituted or unsubstituted cycloalkylene, $R^{2C}$-substituted or unsubstituted heterocycloalkylene, $R^{2C}$-substituted or unsubstituted arylene, $R^{2C}$-substituted or unsubstituted heteroarylene, or $R^{2C}$-substituted or unsubstituted spirocyclic linker; or $L^2$ is independently $R^{2C}$-substituted or unsubstituted cycloalkylene, $R^{2C}$-substituted or unsubstituted heterocycloalkylene, $R^{2C}$-substituted or unsubstituted arylene, $R^{2C}$-substituted or unsubstituted heteroarylene, or $R^{2C}$-substituted or unsubstituted spirocyclic linker; or $L^3$ is independently $R^{2C}$, substituted or unsubstituted cycloalkylene, $R^{2C}$-substituted or unsubstituted heterocycloalkylene, $R^{2C}$-substituted or unsubstituted arylene, $R^{2C}$-substituted or unsubstituted heteroarylene, or $R^{2C}$-substituted or unsubstituted spirocyclic linker.

In some embodiments, $L^1$ is independently

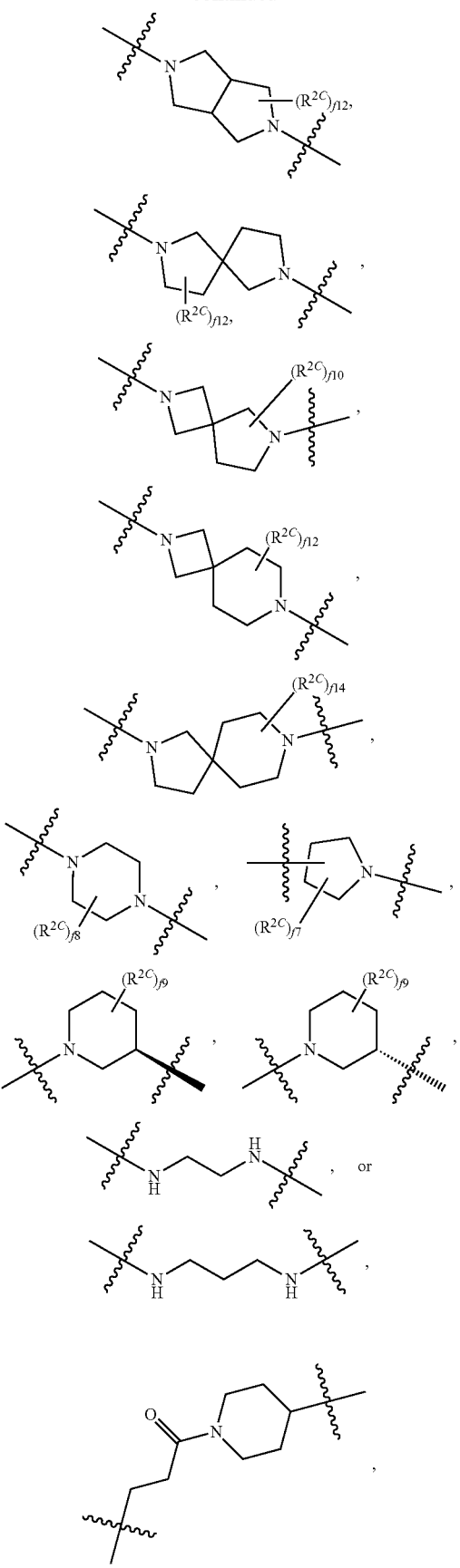

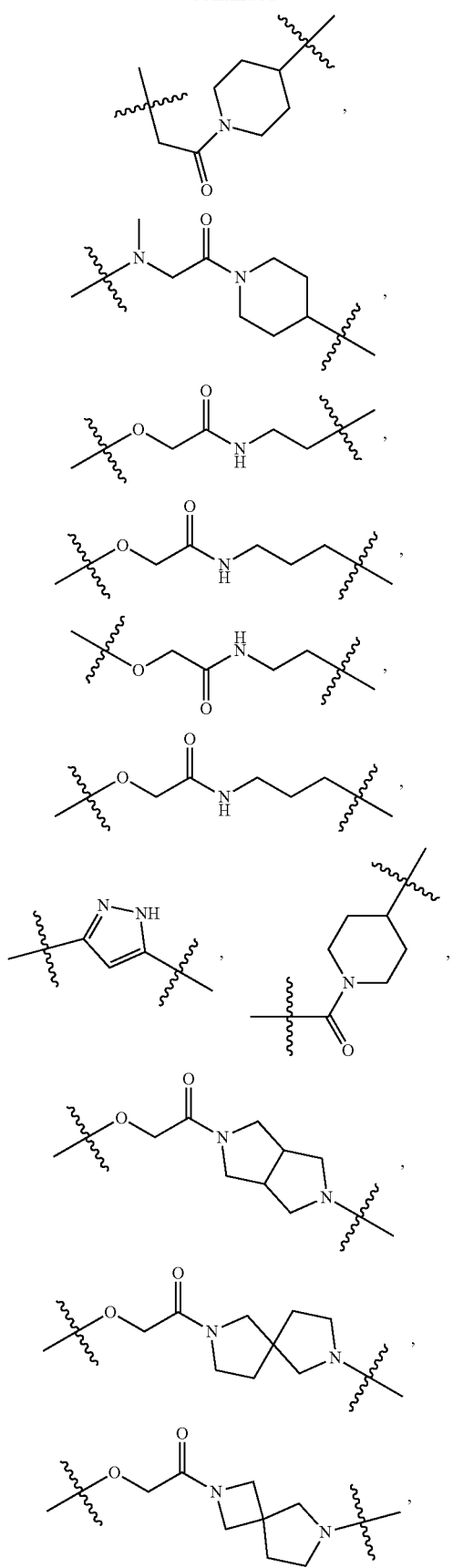
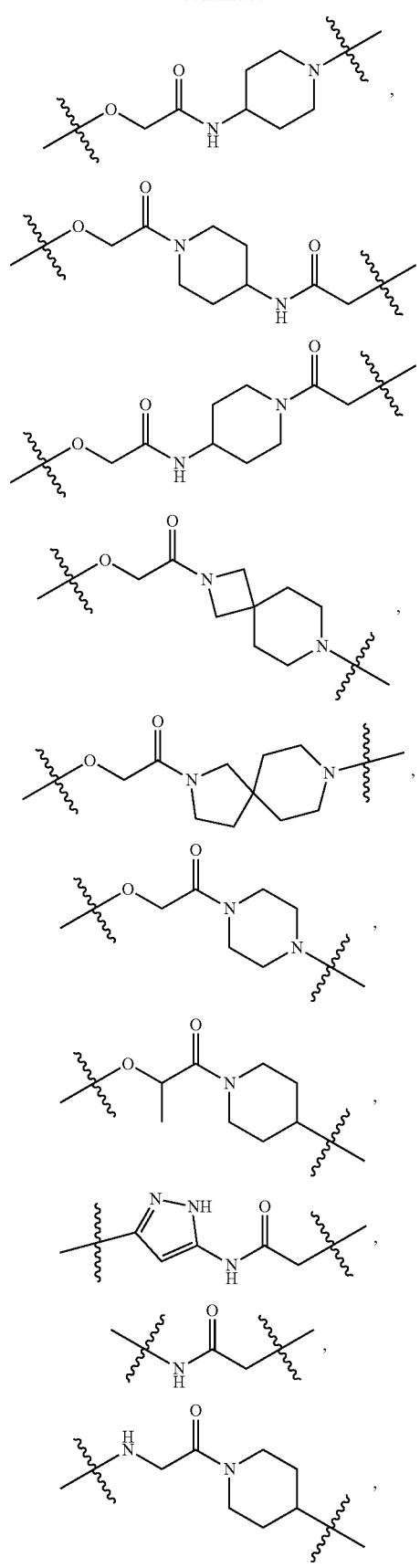

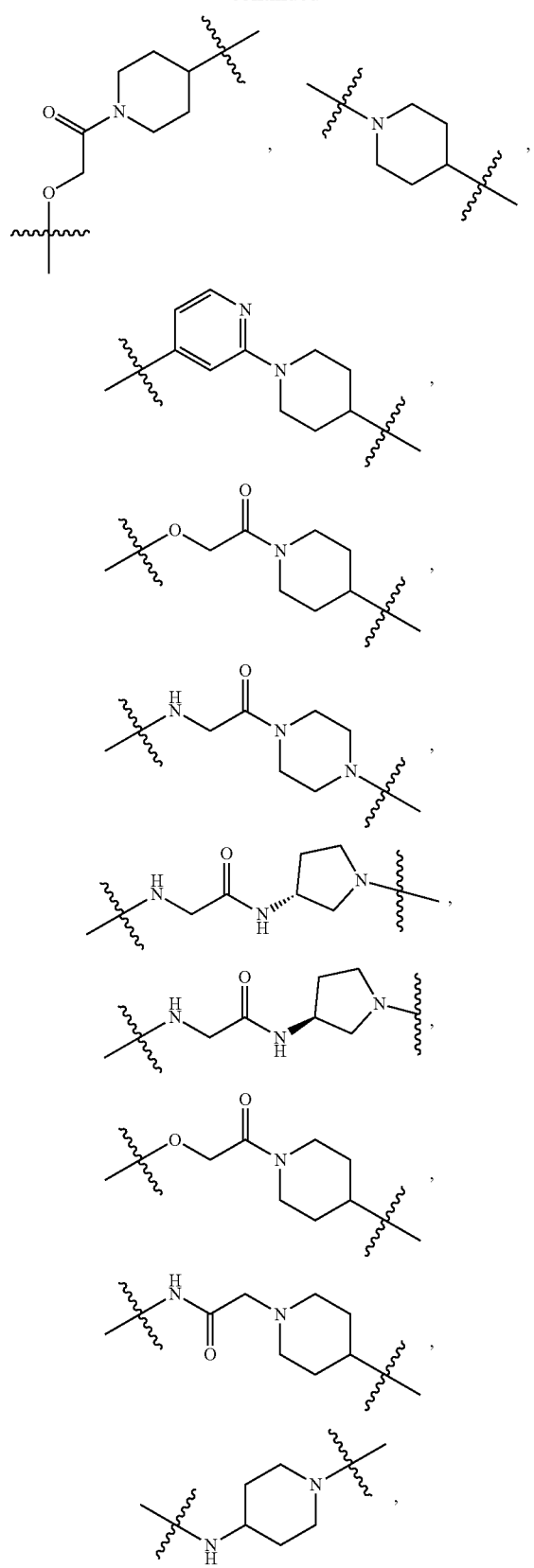
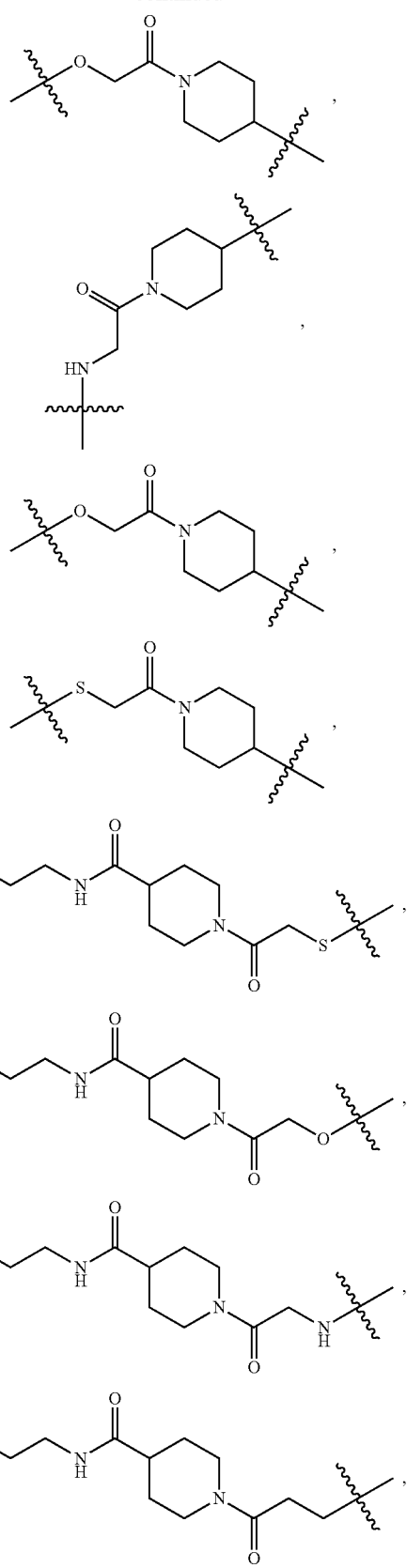

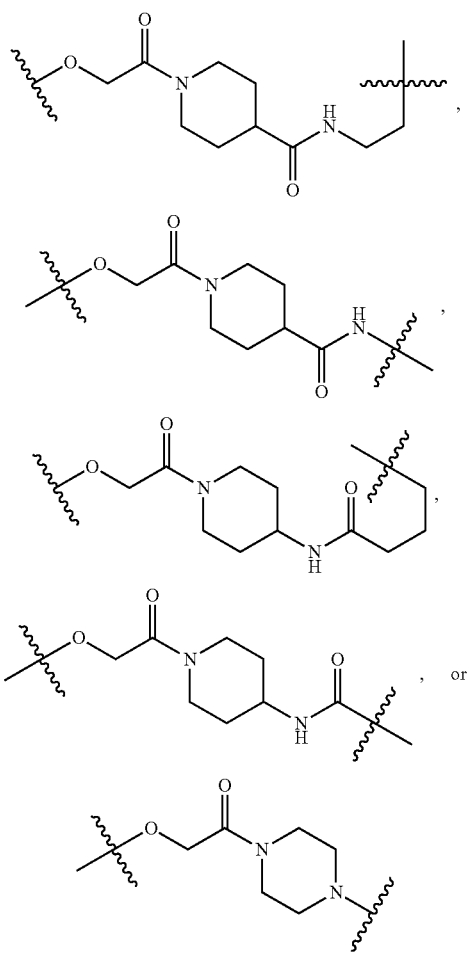
or
$L^2$ is independently
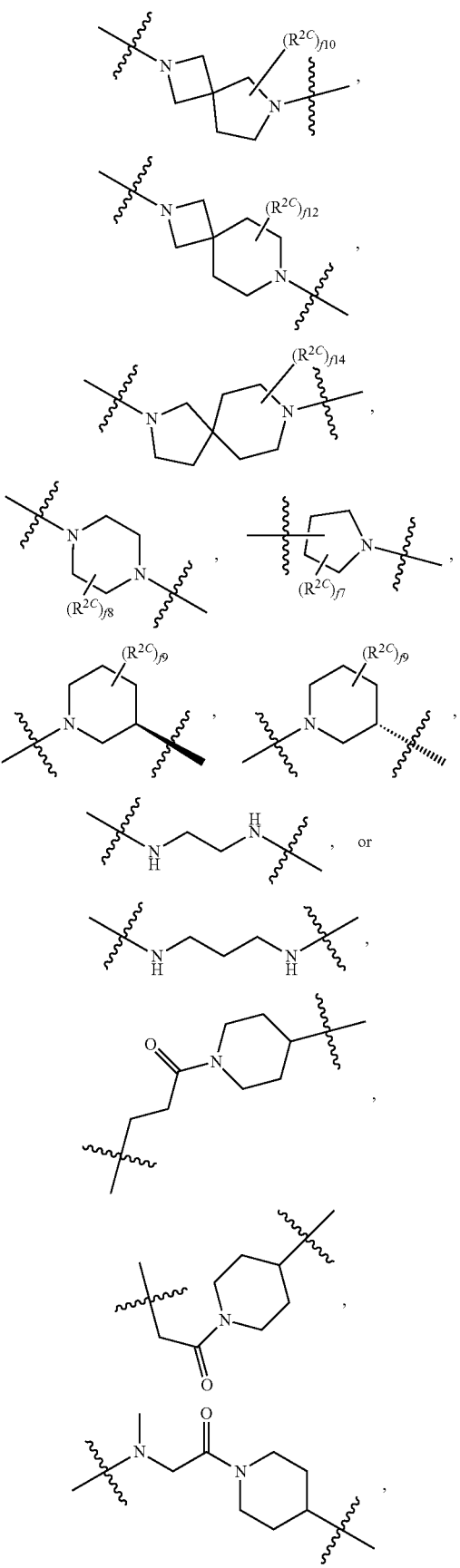

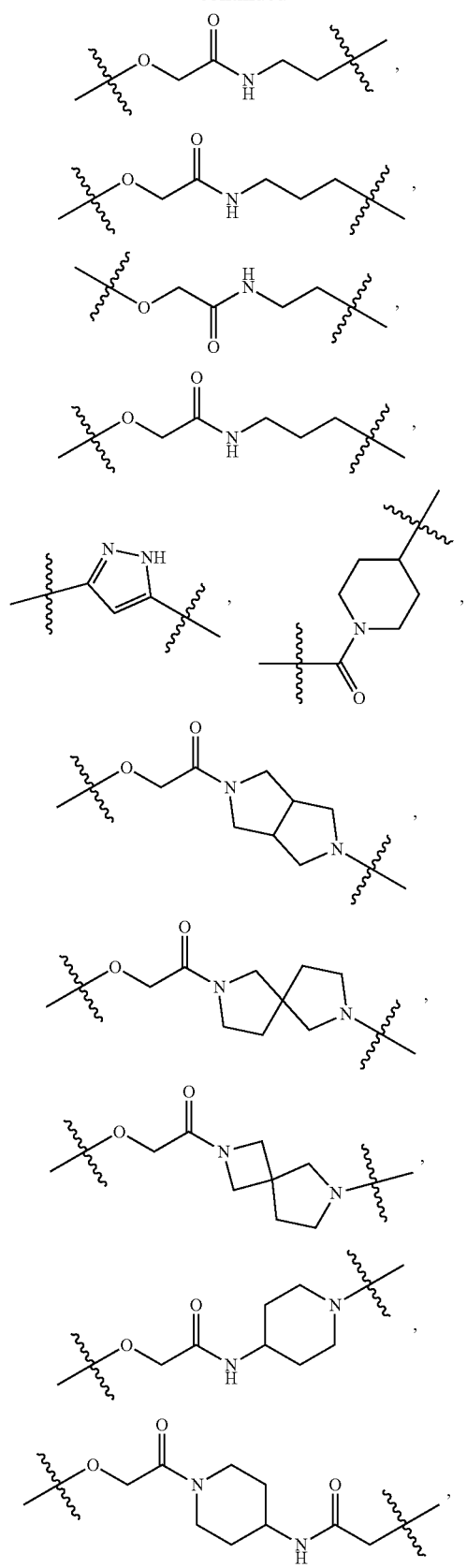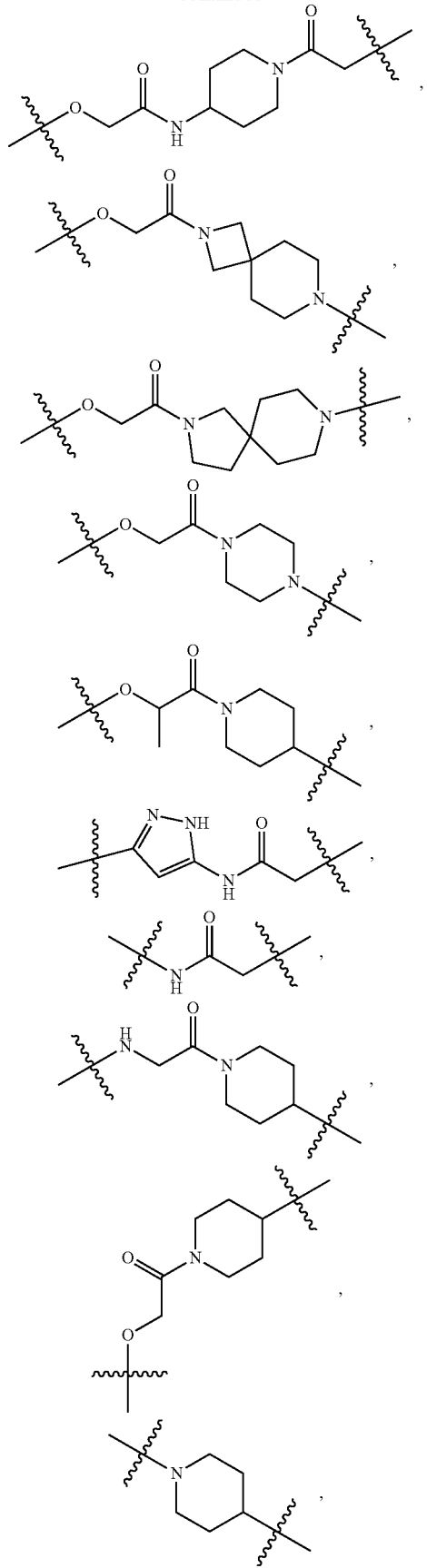

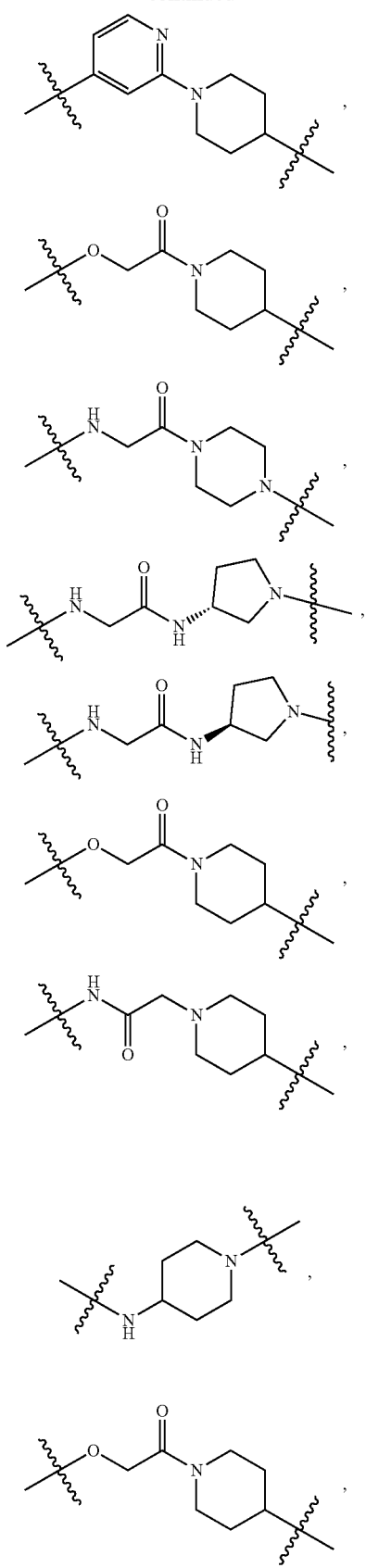
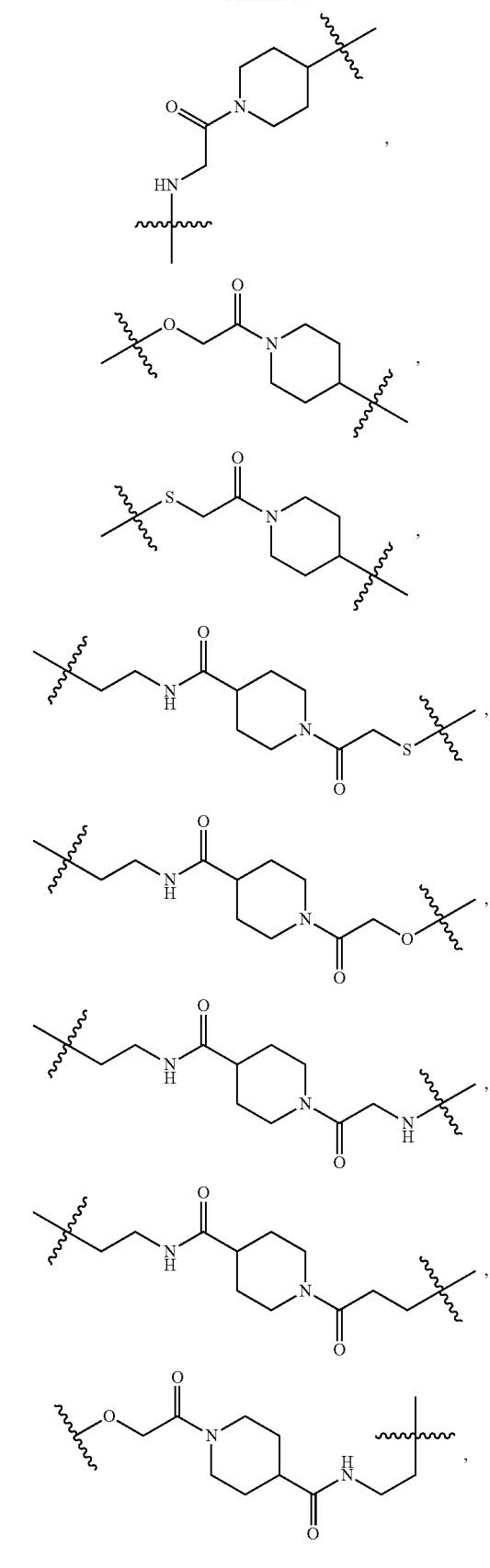

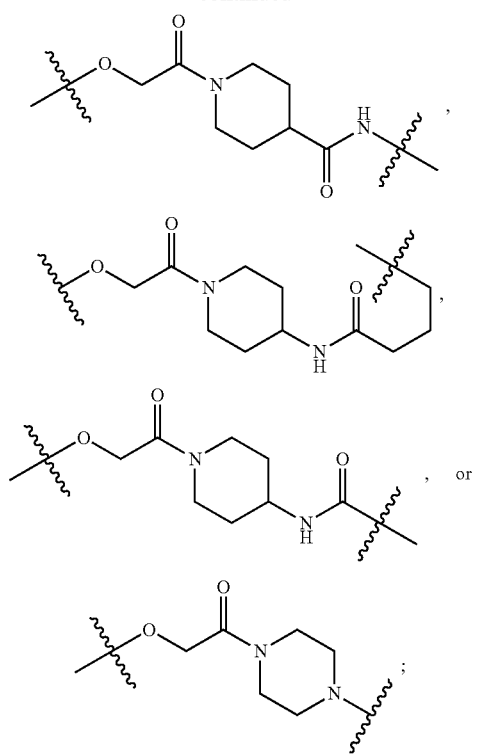
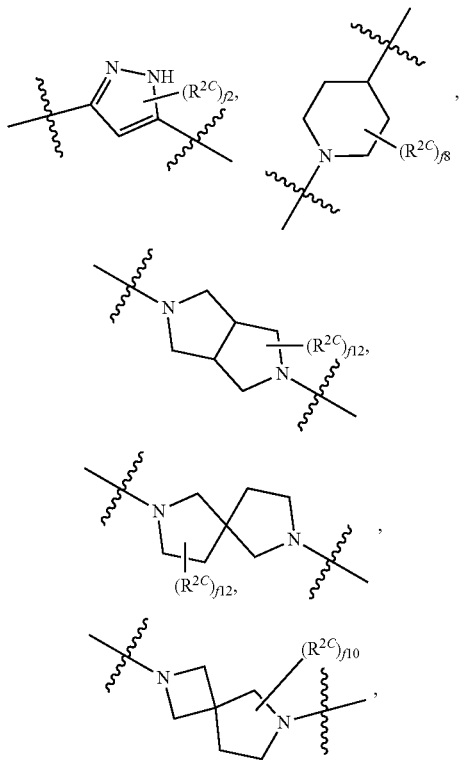
or
L³ is independently
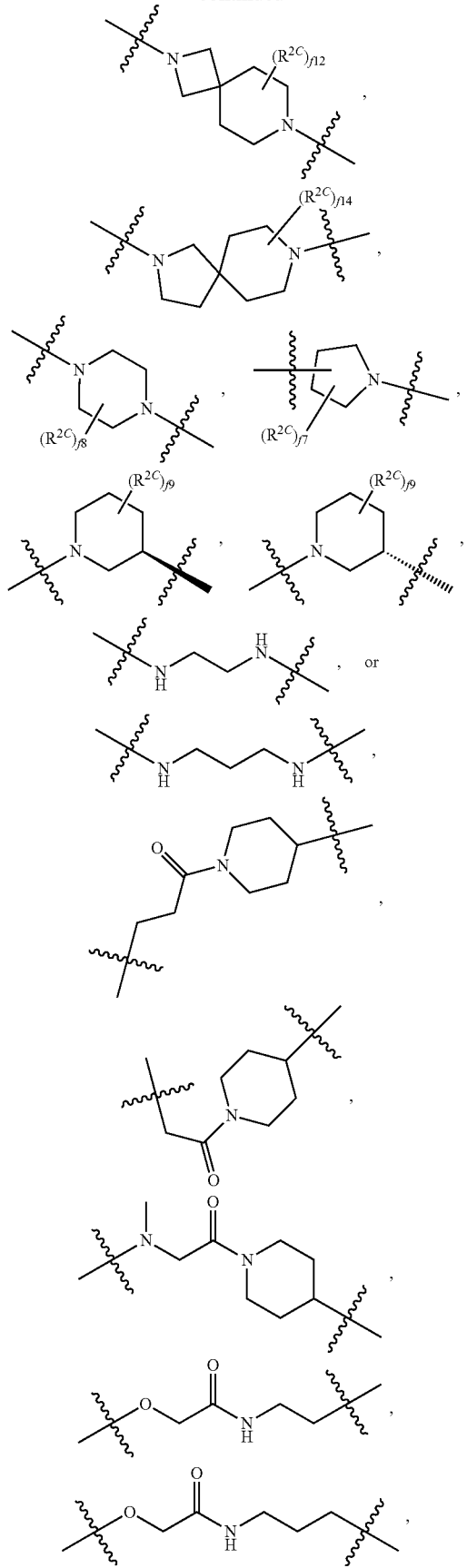

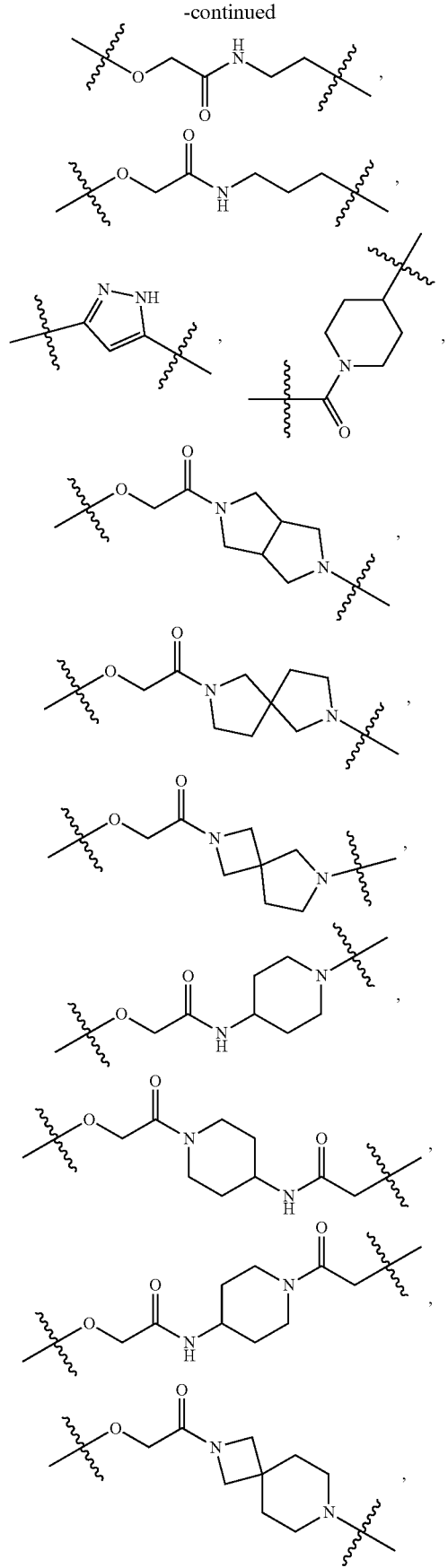
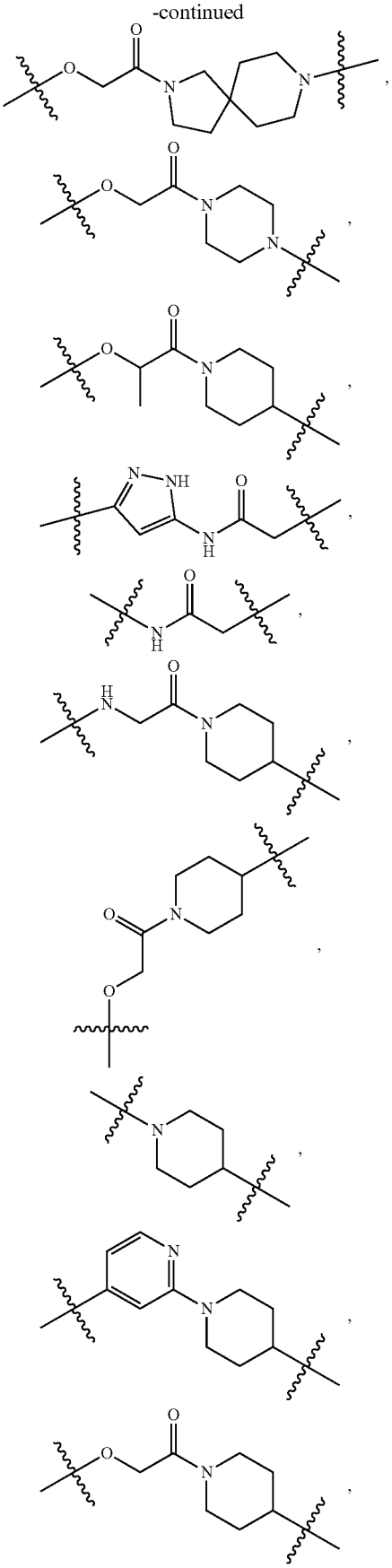

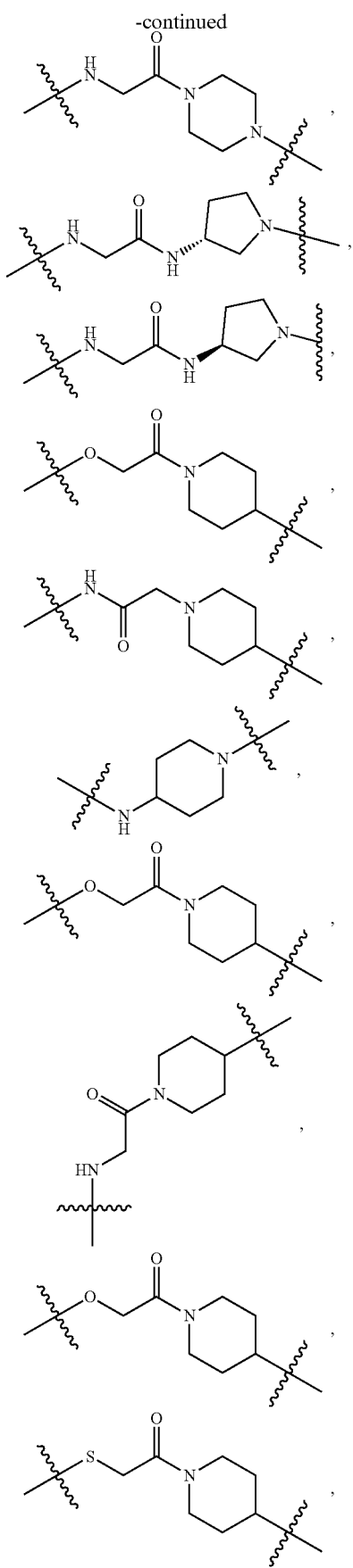
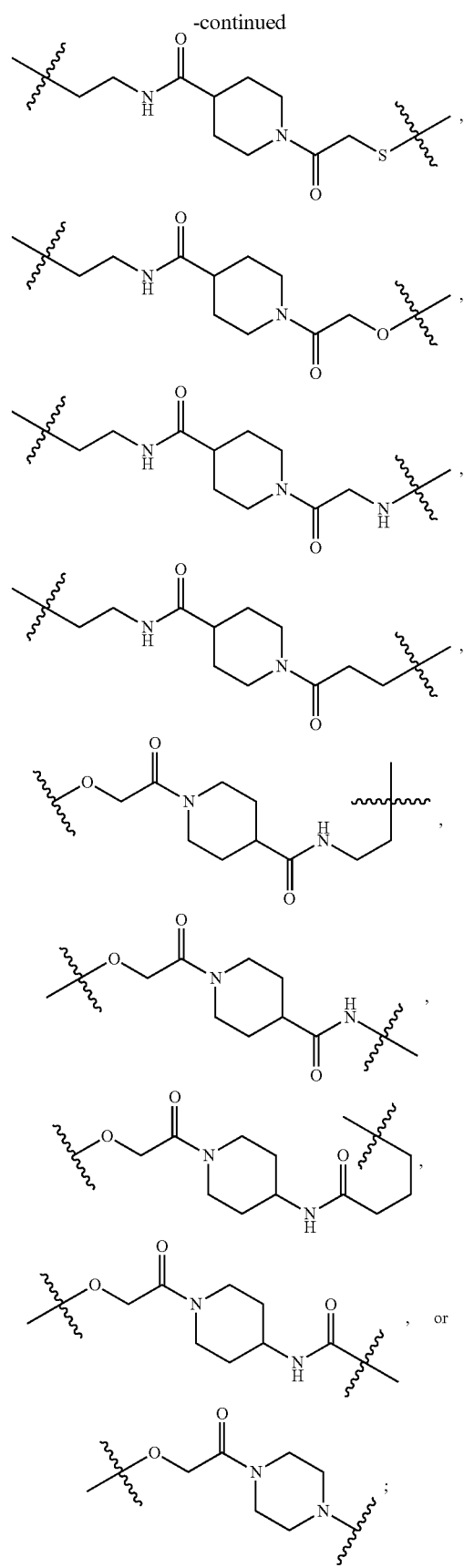

and
wherein f2 is independently an integer from 0 to 2; f6 is independently an integer from 0 to 6; f7 is independently an integer from 0 to 7; f8 is independently an integer from 0 to 8; f9 is independently an integer from 0 to 9; f10 is independently an integer from 0 to 10; f12 is independently an integer from 0 to 12; f14 is independently an integer from 0 to 14.
In some embodiments, E comprises
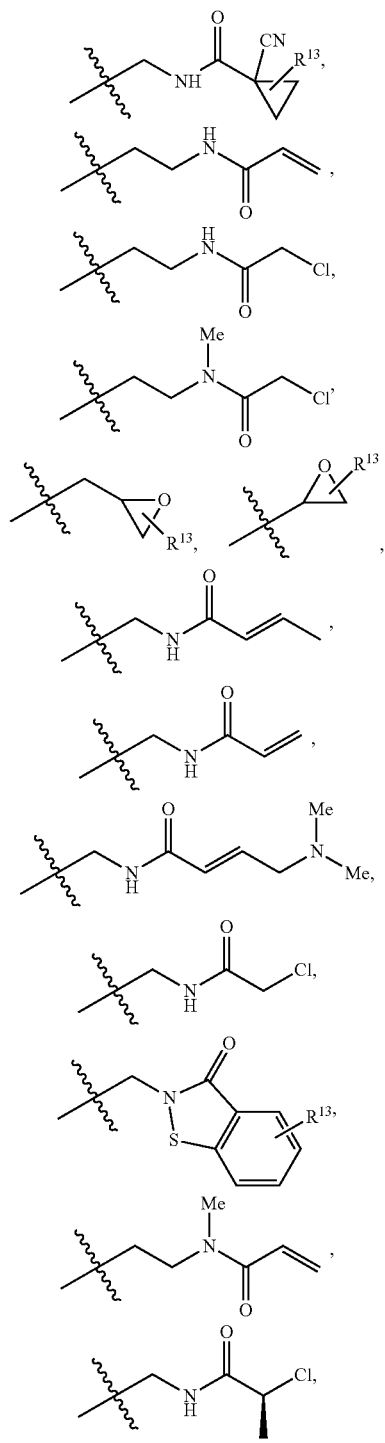
-continued
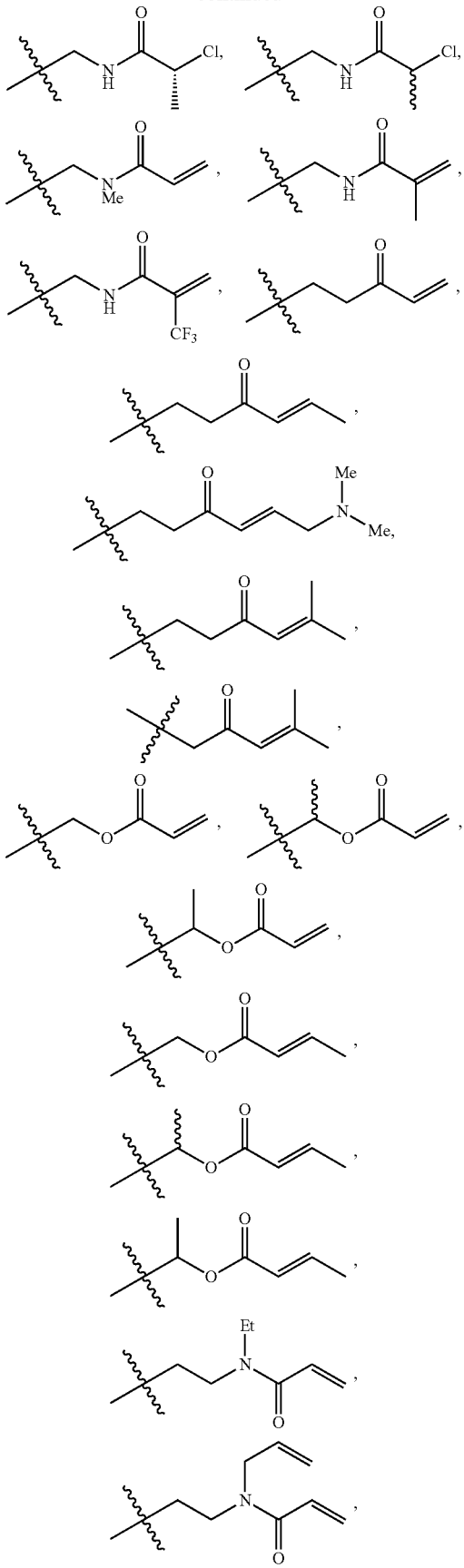

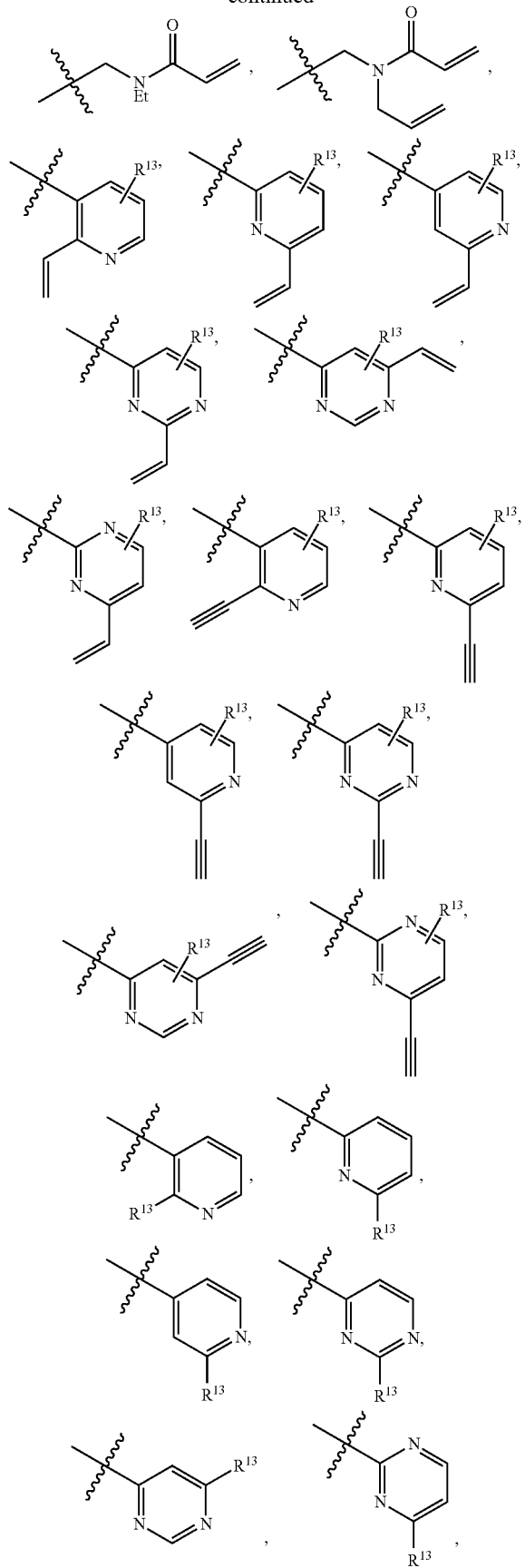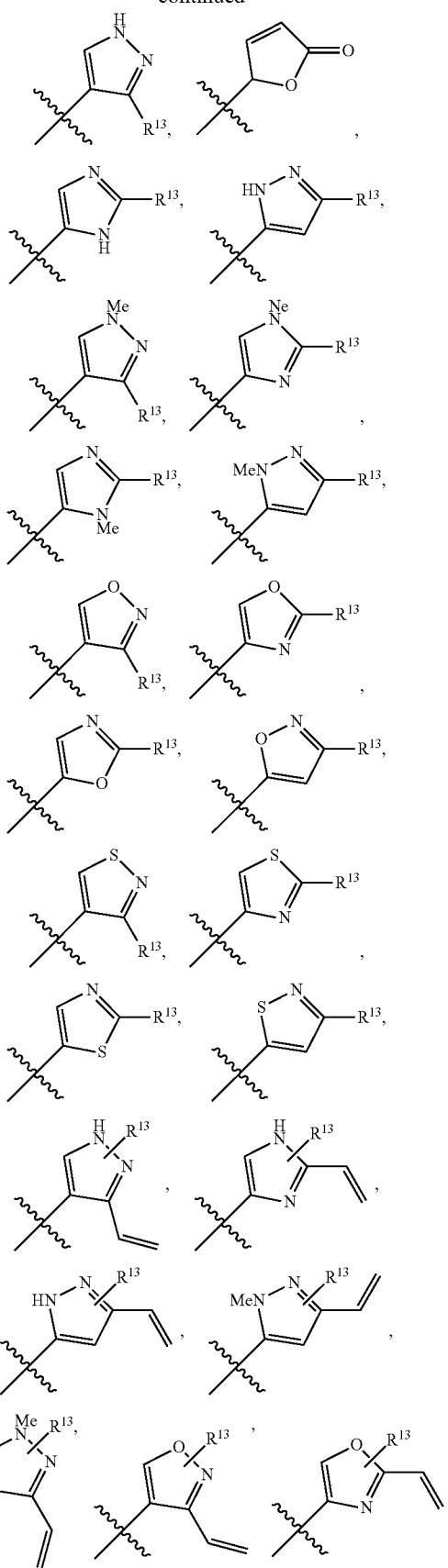

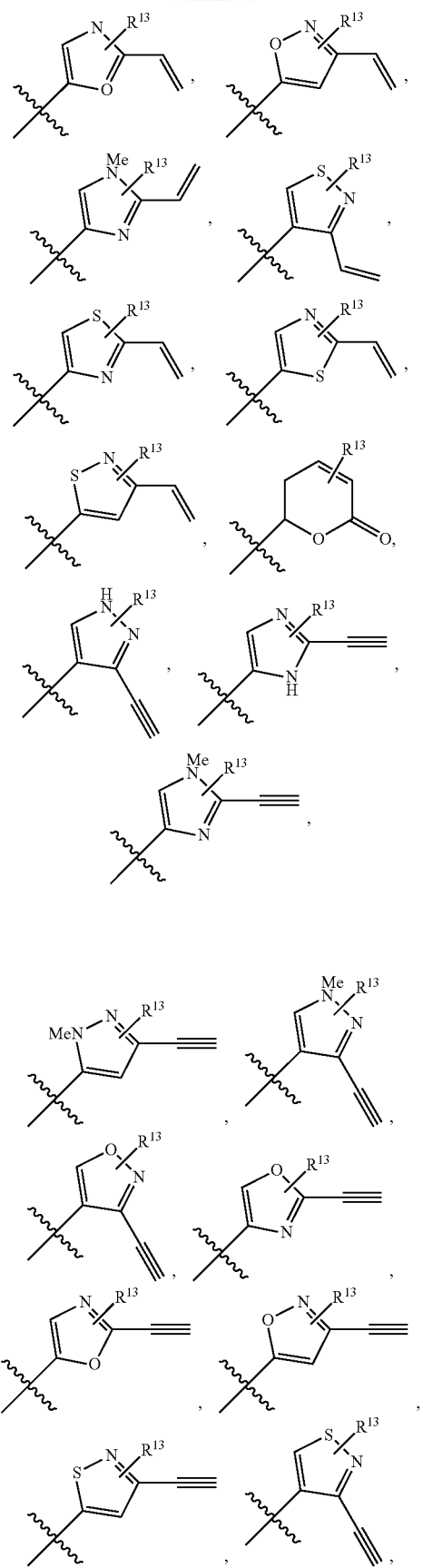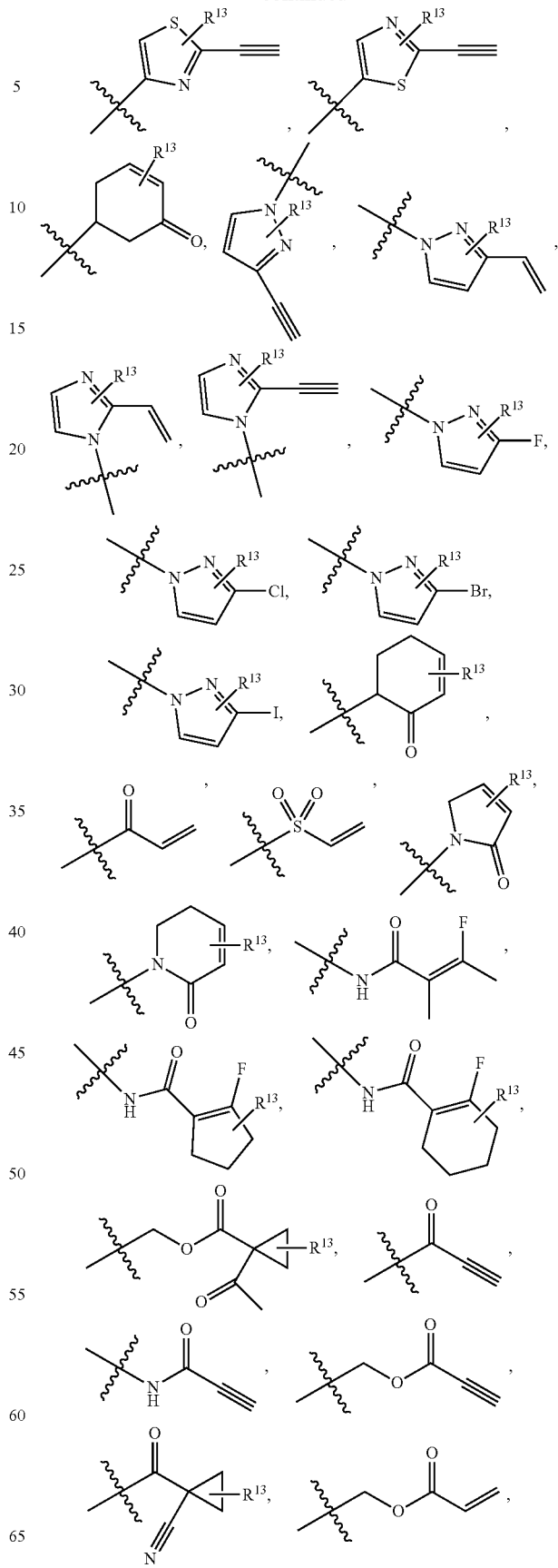

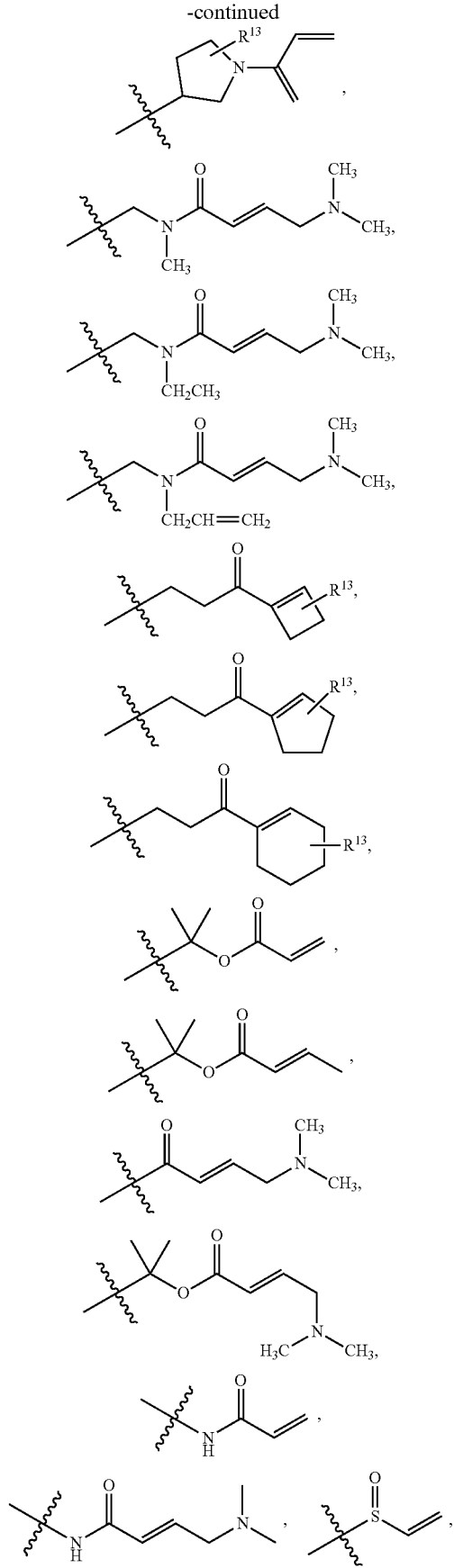
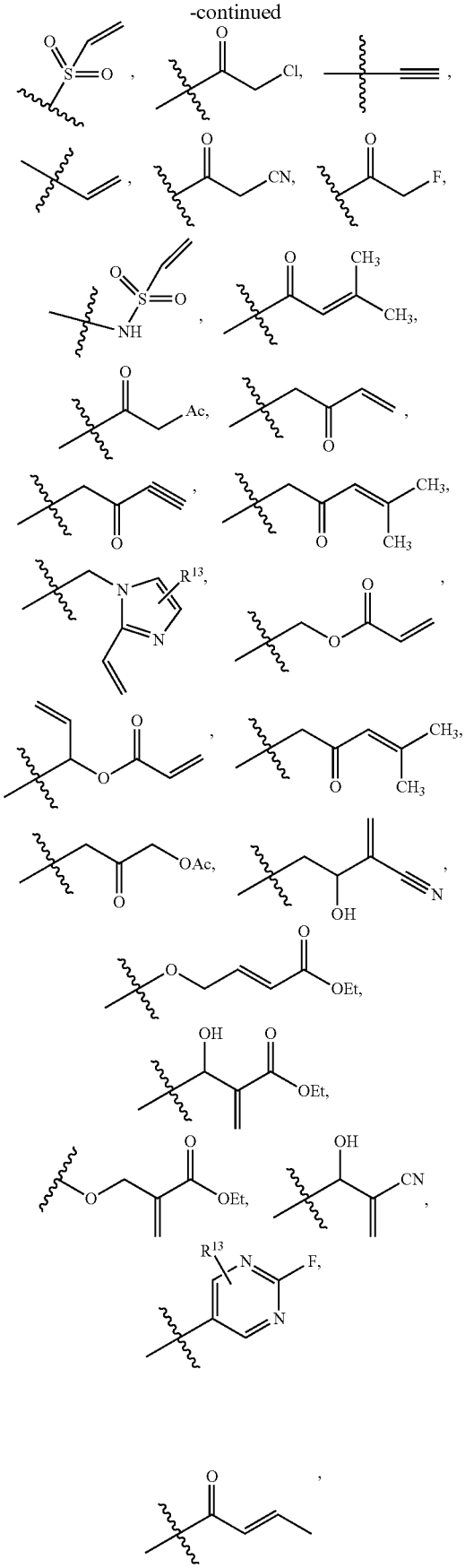

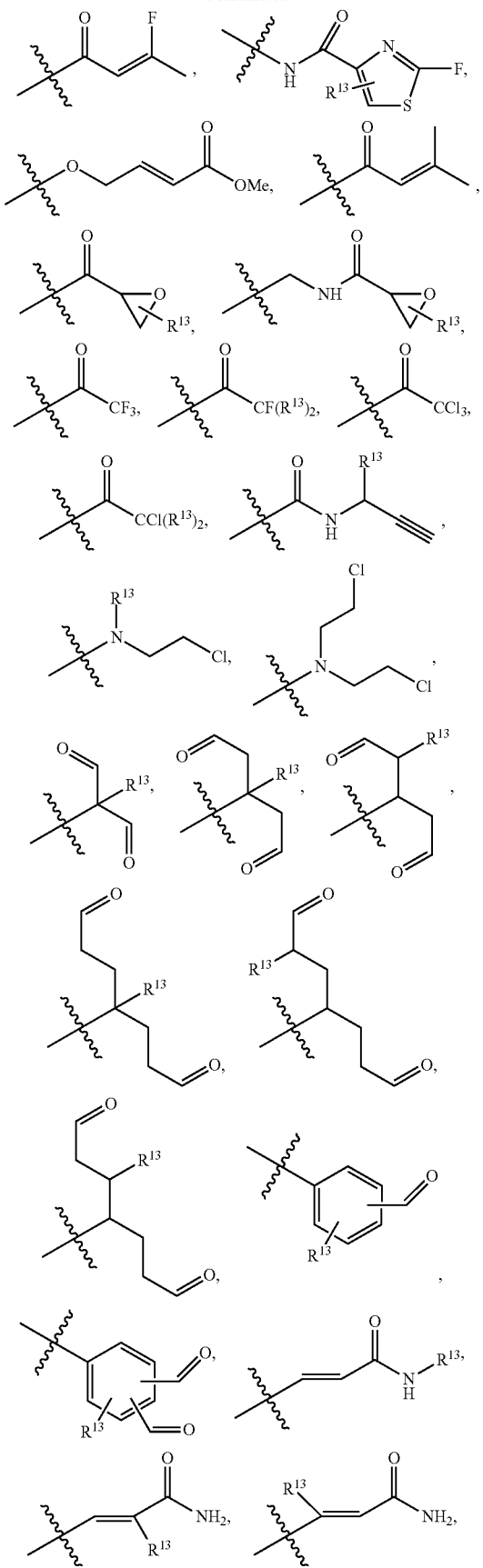
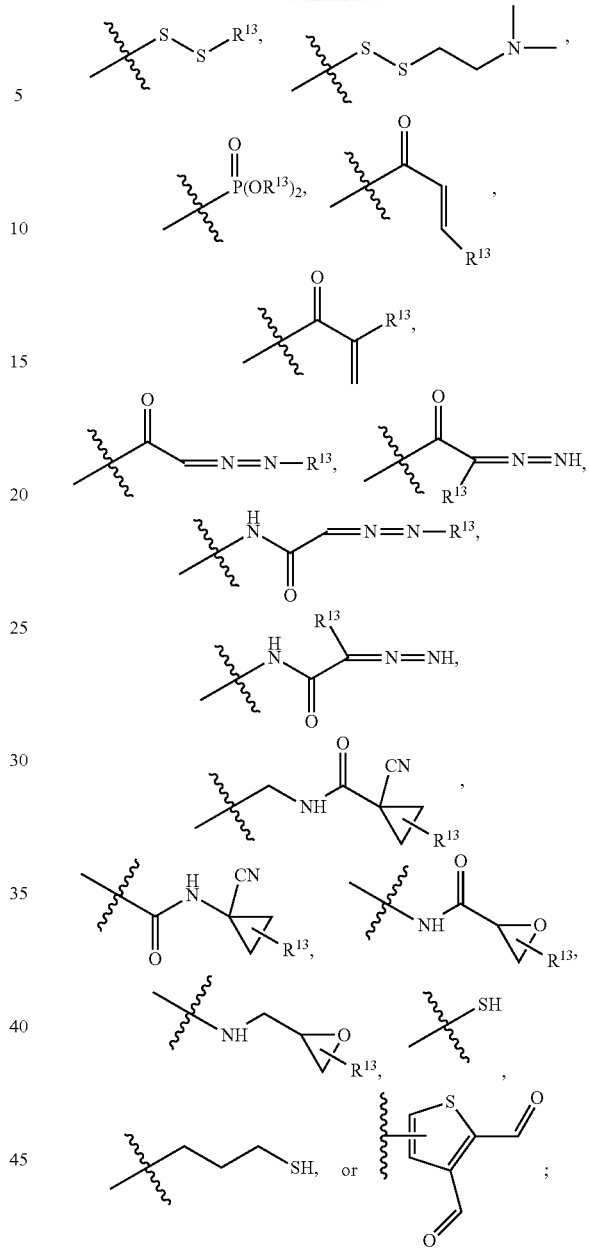

wherein $R^{13}$ is independently hydrogen, oxo, halogen, $-CX^b{}_3$, $-CN$, $-SO_2Cl$, $-SO_rR^{17}$, $-SO_pNR^{14}R^{15}$, $-NHNH_2$, $-ONR^{14}R^{15}$, $-NHC=(O)NHNH_2$, $-NHC=(O)NR^{14}R^{15}$, $-N(O)_2$, $-NR^{14}R^{15}$, $-C(O)R^{16}$, $-C(O)OR^{16}$, $-C(O)NR^{14}R^{15}$, $-OR^{17}$, $-NR^{14}SO_2R^{17}$, $-NR^{14}C=(O)$ $R^{16}$, $-NR^{14}C(O)OR^{16}$, $-NR^{14}OR^{16}$, $-OCX^b{}_3$, $-OCHX^b{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^{13}$ substituents may optionally be joined to form a substituted or unsubstituted cycloalkyl, substituted or unsubstituted heterocycloalkyl, substituted or unsubstituted aryl, or substituted or unsubstituted heteroaryl; Two $R^{13}$ substituents bonded to the same atom may optionally be joined to form a substituted or unsubstituted cycloalkyl or substituted or unsubstituted heterocycloalkyl; $R^{14}$, $R^{15}$, $R^{16}$, and $R^{17}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{14}$ and $R^{15}$ substituents bonded to the same nitrogen atom may optionally be joined to form a substituted or unsubstituted heterocycloalkyl or substituted or unsubstituted heteroaryl; p is independently 1 or 2; q is independently an integer from 1 to 2; r is independently an integer from 0 to 4; and $X^b$ is independently —Cl, —Br, —I, or —F.

In some embodiments, E may comprise a substituted or unsubstituted vinyl sulfone moiety, substituted or unsubstituted vinyl sulfonamide moiety, substituted or unsubstituted fluoro ($C_1$-$C_4$)alkylketone moiety, substituted or unsubstituted chloro($C_1$-$C_4$)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety.

In some embodiments, E comprises an unsubstituted vinyl sulfone moiety, unsubstituted vinyl sulfonamide moiety, unsubstituted fluoro ($C_1$-$C_4$)alkylketone moiety, unsubstituted chloro($C_1$-$C_4$)alkylketone moiety, unsubstituted acrylamide moiety, unsubstituted disulfide moiety, unsubstituted thiol moiety, unsubstituted phosphonate moiety, unsubstituted aldehyde moiety, unsubstituted enone moiety, unsubstituted diazomethylketone moiety, unsubstituted diazomethylamide moiety, unsubstituted cyanocyclopropyl carboxamide moiety, unsubstituted epoxide moiety, unsubstituted epoxyketone moiety, unsubstituted epoxyamide moiety, unsubstituted aryl aldehyde moiety, unsubstituted aryl dialdehyde moiety, unsubstituted dialdehyde moiety, unsubstituted nitrogen mustard moiety, unsubstituted propargyl moiety, or unsubstituted propargylamide moiety.

In some embodiments, the compound is a compound of Formula:

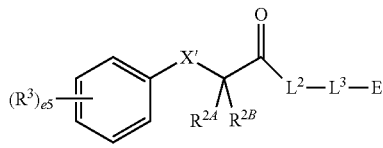

or a pharmaceutically acceptable salt thereof, wherein: e5 is an integer from 0 to 5; X' is —O—, —NH—, or —S—; $R^{2A}$ and $R^{2B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituent bonded to the same atom may optionally be joined to form a substituted or unsubstituted cycloalkyl or substituted or unsubstituted heterocycloalkyl; $R^3$ is independently hydrogen, oxo, halogen, —$CX_3$, —CN, —$SO_2Cl$, —$SO_nR^{10}$, —$SO_vNR^7R^8$, —$NHNH_2$, —$ONR^7R^8$, —NHC=(O)$NHNH_2$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, —$NR^7SO_2R^{10}$, —$NR^{7c}$=(O) $R^9$, —$NR^{7c}$ (O)—$OR^9$, —$NR^7OR^9$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^2$ is independently $R^{2C}$-substituted or unsubstituted cycloalkylene, $R^{2C}$-substituted or unsubstituted heterocycloalkylene, $R^{2C}$-substituted or unsubstituted arylene, $R^{2C}$-substituted or unsubstituted heteroarylene, or $R^{2C}$-substituted or unsubstituted spirocyclic linker; $L^3$ is independently $R^{2C}$-substituted or unsubstituted cycloalkylene, $R^{2C}$-substituted or unsubstituted heterocycloalkylene, $R^{2C}$-substituted or unsubstituted arylene, $R^{2C}$-substituted or unsubstituted heteroarylene, or $R^{2C}$-substituted or unsubstituted spirocyclic linker; E is an electrophilic chemical moiety capable of forming a covalent bond with a cysteine or aspartate residue; $R^{2C}$ is independently hydrogen, oxo, halogen, —$CX_{c3}$, —CN, —$SO_2Cl$, —$SO_{n3}R^{10c}$, —$SO_{v3}NR^{7c}R^{8c}$, —$NHNH_2$, —$ONR^7R^{8c}$, —NHC=(O)$NHNH_2$, —NHC=(O)$NR^{7c}R^{8c}$, —N(O)$_{m3}$, —$NR^{7c}R^{8c}$, —C(O)$R^{9c}$, —C(O)—$OR^{9c}$, C(O)$NR^{7c}R^{8c}$, —$OR^{10c}$, —$NR^{7c}SO_2R^{10c}$, —$NR^{7c}$=(O) $R^{9c}$, —$NR^{7c}$ (O)—$OR^{9c}$, —$NR^7OR^{9c}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^{2C}$ substituents may optionally be joined to form a substituted or unsubstituted cycloalkyl, substituted or unsubstituted heterocycloalkyl, substituted or unsubstituted aryl, or substituted or unsubstituted heteroaryl; two $R^{2C}$ substituents bonded to the same atom may optionally be joined to form a substituted or unsubstituted cycloalkyl or substituted or unsubstituted heterocycloalkyl; $R^7$, $R^8$, $R^9$, and $R^{10}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC =(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{7a}$, $R^{8a}$, $R^{9a}$ and $R^{10a}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC (O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{7a}$ and $R^{8a}$ substituents bonded to the same nitrogen atom may optionally be joined to form a substituted or unsubstituted heterocycloalkyl or substituted or unsubstituted heteroaryl; $R^{7c}$, $R^{8c}$, $R^{9c}$, and $R^{10c}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; m, m1, m3, v, v1, and v3 are independently 1 or 2; n, n1, and n3 are independently an integer from 0 to 4; X, $X^a$ and Xe are independently —Cl, —Br, —I, or —F.

In some embodiments, E comprises a substituted or unsubstituted vinyl sulfone moiety, substituted or unsubstituted vinyl sulfonamide moiety, substituted or unsubstituted peroxide moiety, substituted or unsubstituted fluoro (C$_1$-C$_4$) alkylketone moiety, substituted or unsubstituted chloro(C$_1$-C$_4$)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety.

In some embodiments, $L^2$ is independently $R^{2C}$-substituted or unsubstituted heterocycloalkylene or $R^{2C}$-substituted or unsubstituted spirocyclic linker and $L^3$ is a bond. For example, $L^2$ is monocyclic 4, 5, or 6-membered heterocycloalkylene; or $L^2$ is unsubstituted piperazino or unsubstituted piperidino; or $L^2$ is bicyclic fused heterocycloalkylene; or $L^2$ is an unsubstituted spirocyclic linker.

In some embodiments, E is a substituted or unsubstituted vinyl sulfone moiety, substituted or unsubstituted vinyl sulfonamide moiety, or a substituted or unsubstituted acrylamide moiety.

Further provided herein are pharmaceutical compositions comprising a pharmaceutically acceptable excipient and a compound of the invention.

Also provided is a method of treating a disease in a patient in need of such treatment, said method comprising administering a therapeutically effective amount of a compound of any one of the compounds disclosed herein. In some embodiments, the disease is cancer, including but not limited to colon cancer, colorectal cancer, pancreatic cancer, breast cancer, leukemia, or lung cancer (including non-small cell lung cancer).

Also provided are methods of modulating the activity of a Ras protein, including a H-Ras, N-Ras, or K-Ras protein, comprising contacting said Ras protein with an effective amount of a compound disclosed herein. The activity is, for example, GTPase activity, nucleotide exchange, effector protein binding, effector protein activation, guanine exchange factor (GEF) binding, GEF-facilitated nucleotide exchange, phosphate release, nucleotide release, nucleotide binding, Ras (e.g. K-Ras) subcellular localization, Ras (e.g. K-Ras) post-translational processing, or Ras (e.g. K-Ras) post-translational modifications. Said modulating can be increasing the activity of said Ras (e.g. K-Ras) protein or reducing it. Said Ras (e.g. K-Ras) protein can be a human K-Ras protein. For example, a human K-Ras protein contains a G12C, G12D, G13C, or G13D mutation.

In some embodiments, a method of modulating a K-Ras protein is provided, said method comprising contacting said K-Ras protein with an effective amount of a compound described herein. Said modulating is, for example, modulation of K-Ras subcellular localization, K-Ras post-translational processing, or a K-Ras post-translational modification. Said K-Ras protein is, for example, a human K-Ras protein. In some embodiments, said human K-Ras protein contains a G12C, G12D, G13C, or G13D mutation.

In some embodiments, said Ras (e.g. K-Ras) protein is within a biological cell, for example a biological cell which forms part of an organism.

Provided herein is also a Ras (e.g. K-Ras) protein covalently bound to a compound as disclosed herein, wherein said compound is covalently bound to a cysteine residue of said Ras (e.g. K-Ras) protein. Said covalently modified Ras protein may have a modulated activity relative to a control, wherein said activity is selected from GTPase activity, nucleotide exchange, effector protein binding, effector protein activation, guanine exchange factor (GEF) binding, GEF-facilitated nucleotide exchange, phosphate release, nucleotide release, nucleotide binding, Ras subcellular localization, Ras post-translational processing, and Ras post-translational modifications. In some embodiments, said Ras protein is a K-Ras protein which contains a G12C mutation. The covalently bonded compound can be bonded to cysteine residue 12. In other embodiments, the covalently modified Ras protein is a K-Ras protein which contains a G13C mutation. The covalently bonded compound can be bonded to cysteine residue 13.

In other embodiments, a Ras (e.g. K-Ras) protein is provided which is covalently bound to a compound disclosed herein, wherein said compound is covalently bound to an aspartate residue of said Ras protein. Said covalently modified Ras protein may have a modulated activity relative to a control, wherein said activity is selected from GTPase activity, nucleotide exchange, effector protein binding, effector protein activation, guanine exchange factor (GEF) binding, GEF-facilitated nucleotide exchange, phosphate release, nucleotide release, nucleotide binding, Ras subcellular localization, Ras post-translational processing, and Ras post-translational modifications. In some embodiments, said Ras protein is a K-Ras protein which contains a G12D mutation. The covalently bonded compound can be bonded to aspartate residue 12. In other embodiments, the covalently modified Ras protein is a K-Ras protein which contains a G13D mutation. The covalently bonded compound can be bonded to aspartate residue 13.

Further provided herein is a method of identifying a covalent inhibitor of K-Ras protein comprising: contacting a K-Ras protein with a K-Ras inhibitor test compound; allowing said K-Ras inhibitor test compound to covalently inhibit said K-Ras protein; and detecting the level of covalent inhibition of said K-Ras protein thereby identifying a covalent inhibitor of K-Ras protein. In som embodiments, the K-Ras inhibitor test compound is a Switch 2-Binding Pocket covalent inhibitor test compound and said K-Ras protein is a G12C mutant K-Ras protein. The method may also comprise the steps of: contacting a wildtype K-Ras protein with said Switch 2-Binding Pocket covalent inhibitor test compound; allowing said Switch 2-Binding Pocket covalent inhibitor test compound to inhibit said wildtype K-Ras protein; detecting the level of inhibition of said wildtype K-Ras protein; comparing the level of inhibition of said wildtype K-Ras protein to the level of covalent inhibition of said G12C mutant K-Ras protein, wherein a higher level of covalent inhibition of said G12C mutant K-Ras indicates said Switch 2-Binding Pocket covalent inhibitor test compound is specific for said G12C mutant K-Ras protein.

In some embodiments, said K-Ras inhibitor test compound is a Switch 2-Binding Pocket covalent inhibitor test compound and said K-Ras protein is a G12D mutant K-Ras protein. The method of identifying may also comprise the steps of: contacting a wildtype K-Ras protein with said Switch 2-Binding Pocket covalent inhibitor test compound; allowing said Switch 2-Binding Pocket covalent inhibitor test compound to inhibit said wildtype K-Ras protein; detecting the level of inhibition of said wildtype K-Ras protein; comparing the level of inhibition of said wildtype K-Ras protein to the level of covalent inhibition of said G12D mutant K-Ras protein, wherein a higher level of covalent inhibition of said G12D mutant K-Ras indicates said Switch 2-Binding Pocket covalent inhibitor test compound is specific for said G12D mutant K-Ras protein.

In some embodiments, said K-Ras inhibitor test compound is a Switch 2-Binding Pocket covalent inhibitor test compound and said K-Ras protein is a G13C mutant K-Ras protein. The method of identifying may also comprise the steps of: contacting a wildtype K-Ras protein with said Switch 2-Binding Pocket covalent inhibitor test compound; allowing said Switch 2-Binding Pocket covalent inhibitor test compound to inhibit said wildtype K-Ras protein; detecting the level of inhibition of said wildtype K-Ras protein; comparing the level of inhibition of said wildtype K-Ras protein to the level of covalent inhibition of said G13C mutant K-Ras protein, wherein a higher level of covalent inhibition of said G13C mutant K-Ras indicates said Switch 2-Binding Pocket covalent inhibitor test compound is specific for said G13C mutant K-Ras protein.

In some embodiments, said K-Ras inhibitor test compound is a Switch 2-Binding Pocket covalent inhibitor test compound and said K-Ras protein is a G13D mutant K-Ras protein. The method of identifying may also comprise the steps of: contacting a wildtype K-Ras protein with said Switch 2-Binding Pocket covalent inhibitor test compound; allowing said Switch 2-Binding Pocket covalent inhibitor test compound to inhibit said wildtype K-Ras protein; detecting the level of inhibition of said wildtype K-Ras protein; comparing the level of inhibition of said wildtype K-Ras protein to the level of covalent inhibition of said G13D mutant K-Ras protein, wherein a higher level of covalent inhibition of said G13D mutant K-Ras indicates said Switch 2-Binding Pocket covalent inhibitor test compound is specific for said G13D mutant K-Ras protein.

Provided herein is a method of selectively modulating a Ras protein, said method comprising contacting said Ras protein with a compound which contacts at least one amino acid residue forming a Switch 2 binding pocket of said Ras protein, wherein said at least one amino acid residue is selected from valine-7, valine-9, glycine-10, proline-34, threonine-58, glycine-60, glutamine-61, glutamate-62, glutamate-63, arginine-68, tyrosine-71, methionine-72, tyrosine-96, glutamine-99 and isoleucine-100 of said Ras protein, and wherein said compound covalently reacts with an amino acid residue of said Ras protein. In some embodiments, the compound binds to a K-Ras protein with a higher binding affinity as compared to a H-Ras protein. In some embodiments, said compound interacts with at least one of glycine-60, glutamate-62, or glutamate-63. In some embodiments, said interacting between said amino acid residue and said compound involves hydrogen bonding, van der Waals interaction, ionic bonding, covalent bonding, or hydrophobic interaction. In some embodiments, said compound fills space within said Switch 2 binding pocket. In some embodiments, said compound inhibits K-Ras as measured by the fraction of protein covalently labeled by the compound, wherein the compound is present in 50-fold excess and wherein the fraction of protein covalently labeled is determined by mass spectrometry. In some embodiments, said compound covalently reacts with an amino acid residue of said Ras (e.g. K-ras) protein. In some embodiments, said amino acid residue is cysteine-12 of K-Ras G12C mutant protein.

Further provided is a method of designing a compound which covalently binds to a Switch 2 binding pocket of a K-Ras protein, the method comprising the steps of: (a) providing a structural model of a reference compound bound to the Switch 2 binding pocket of the K-Ras protein, wherein the reference compound is non-covalently bound to said Switch 2 binding pocket; (b) identifying a cysteine, aspartate, lysine, tyrosine or glutamate residue located in proximity to said Switch 2 binding pocket when said reference compound is bound to said Switch 2 binding pocket; (c) generating at least one additional structural model of a test compound bound to said Switch 2 binding pocket, wherein said test compound comprises an electrophilic moiety; and (d) selecting said test compound if said electrophilic moiety is located within bonding distance of said cysteine residue when said test compound is bound to said Switch 2 binding pocket.

Compounds are also provided having molecular dimensions compatible with the shape of a K-Ras Switch 2 binding pocket wherein the compound, when present in an aqueous solution comprising 200 µM of the compound and 4 µM K-Ras, covalently binds to at least 50% of K-Ras proteins present in solution after 24 hours.

BRIEF DESCRIPTION OF THE DRAWINGS

FIGS. 2A-2C provide structural insights into nucleotide binding by Ras. FIGS. 2A-2B: The conformation of Ras undergoes significant changes upon binding to different nucleotides. Especially affected are two regions of the protein, termed switch 1 (residue 30-40, black) and Switch 2 (residue 60-76, dark gray), that are involved in binding downstream effectors. Shown here are structures of wildtype Ras bound to GDP (PDB code: 4q21 (Milburn M V, Tong L, deVos A M, Brünger A, Yamaizumi Z, Nishimura S, Kim S H. Science. 1990 Feb. 23; 247 (4945): 939-45), inactive conformation) and GMPPCP (PDB code: 121p (Krengel, U., Thesis, Heidelberg, 1991), active conformation); sequence legend SEQ ID NO:1 left, SEQ ID NO:2 right. FIG. 2C: Detailed view of the nucleotide binding pocket of the G12C mutant of Ras. This structure was solved in the Shokat lab to 2.4 Å resolution. Labeled residues are either known to play important roles in the biological function of Ras (oncogenic mutations often occur in G12, G13 and Q61) (Forbes, S. et al. Cosmic 2005. *Br J Cancer* 94, 318-22 (2006)), can serve as potential sites for cysteine mutant for covalent attachment (C12, G13, S17, A18, Q30)

or show lysine residues that may serve as additional nucleophiles for divalent probes (K16, K117, K147). The nucleophilic sulfur of cysteine-12 is in close proximity to the terminal phosphate group of GDP, supporting the idea of using this cysteine as nucleophilic anchor for covalent (e.g. reversible, irreversible) modification; sequence legend SEQ ID NO:3.

Figure 3:
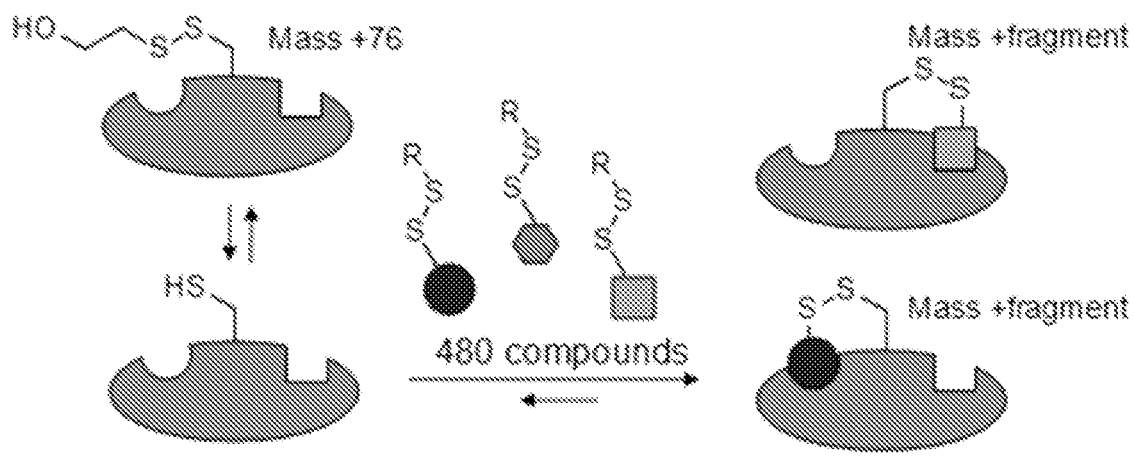

FIG. 3. Tethering to identify drug-like fragments that bind to K-Ras G12C; Tethering depends on a complex equilibrium of disulfide exchange between compounds and reducing agent. K-RasG12C may exchange with compounds binding in the nucleotide-binding pocket (square) or allosteric pocket (circle); mass spectrometry-based; reversible covalent interaction based on complex equilibrium of disulfides; semi-high throughput; identify low-affinity drug-like fragments to use as scaffolds; based on binding, not inhibition of activity.

Figure 4A:
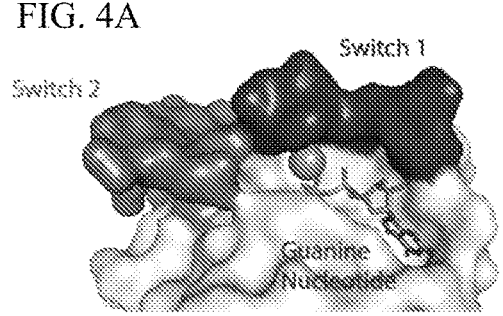
Figure 4B:
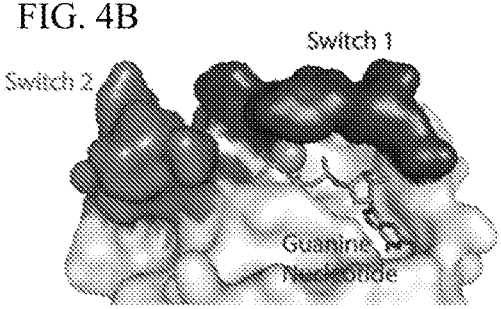
Figure 4C:
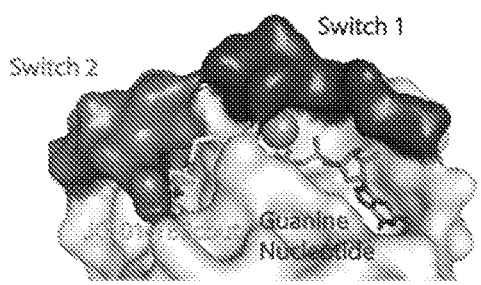
Figure 4D:
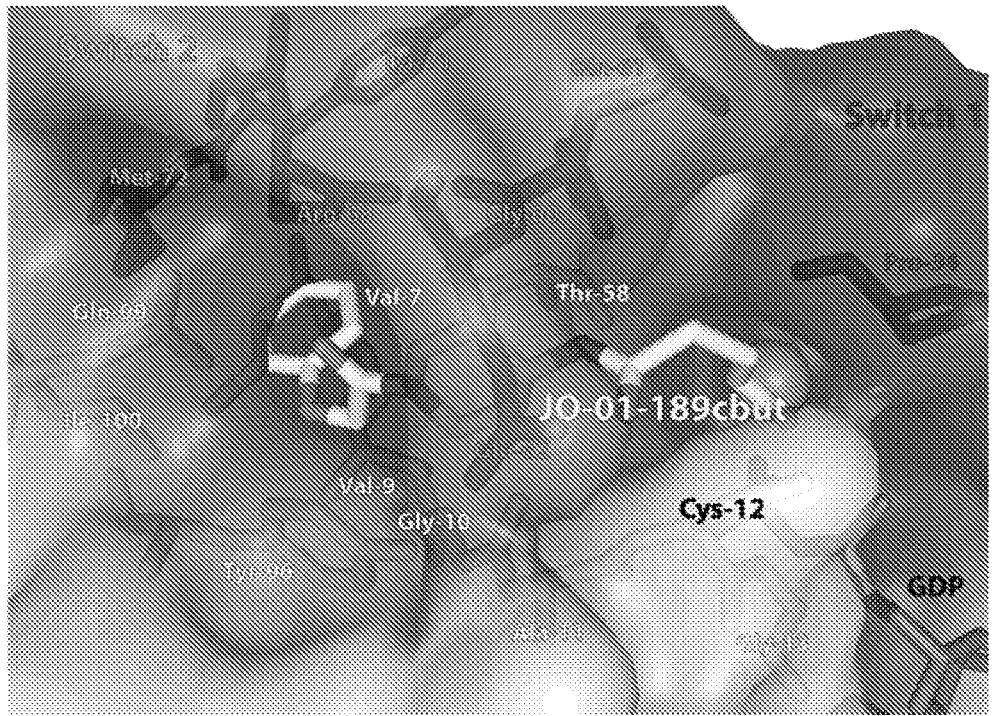

FIGS. 4A-4D show compound (JO-01-189cbut) binding to Switch 2-Binding Pocket of K-Ras. FIGS. 4A-4C: Binding of JO-01-189cbut to the Switch 2-Binding Pocket induces changes in the protein structure, including to the adjacent Switch 2 region. For comparison wild-type Ras bound to GDP (PDB code: 4q212, inactive conformation) and GMPPCP (PDB code: 121p3, active conformation) are shown. Switch 1 (residue 30-40, black) and Switch 2 (residue 60-76, dark gray) are colored for clarity; sequence legend SEQ ID NO: 1 left, SEQ ID NO:2 right, SEQ ID NO:4 bottom. FIG. 4D: JO-01-189cbut binding to the Switch 2-Binding Pocket is shown in three-dimensional detail with interacting amino acids labeled; sequence legend SEQ ID NO:4.

Figure 5:
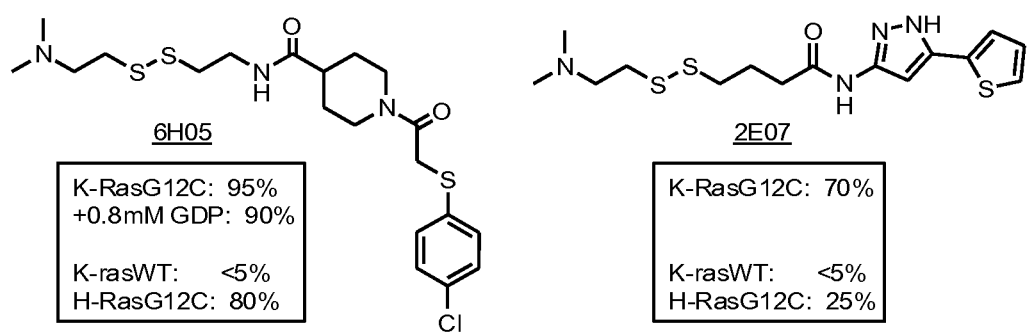

FIG. 5. Two hits from screen of disulfide containing compounds. Percentages represent the amount of modified Ras in the presence of 100 μM each of compound and βME. The screening hits all showed selectivity for the mutant cysteine, causing minimal modification of wild-type K-Ras. Addition of GDP had no significant effect on modification of K-RasG12C by 6H05. Results from 2E07 show that it is possible to achieve some selectivity for K-RasG12C over H-RasG12C. These screens were carried out using K-RasG12C truncated and K-Ras wild-type truncated.

Figure 6:
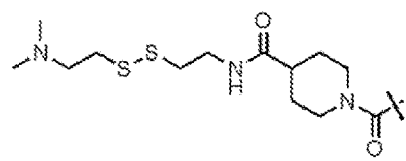

FIG. 6. Structure and DR50 of 6H05 analogues. Compound JO-148A is slightly more potent than the related screening hit.

Figure 7:
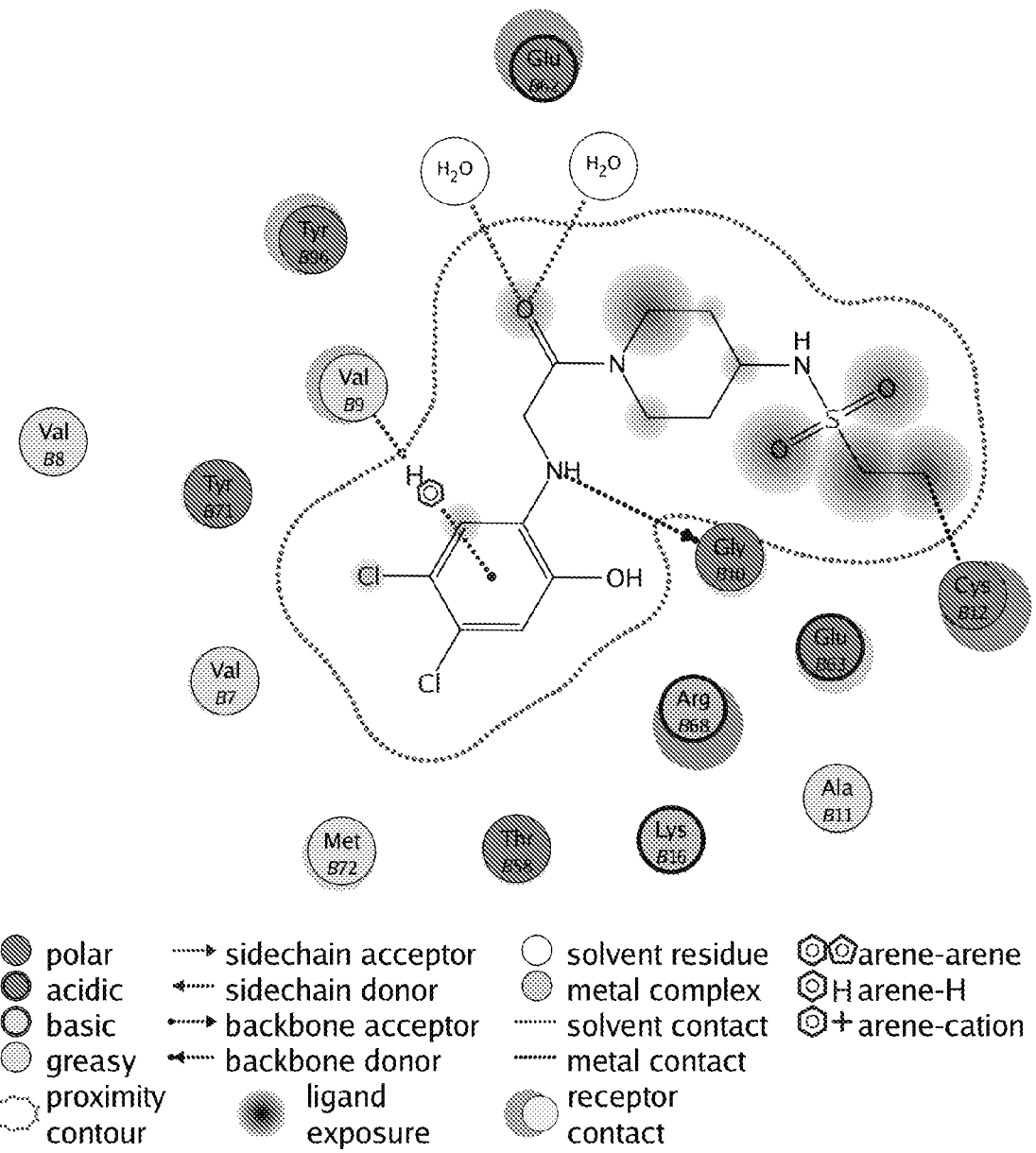

FIG. 7. Compound (ligand): protein contacts/interactions of Rasmed-055: G12C K-Ras, sequence legend (SEQ ID NO:4).

Figure 8:
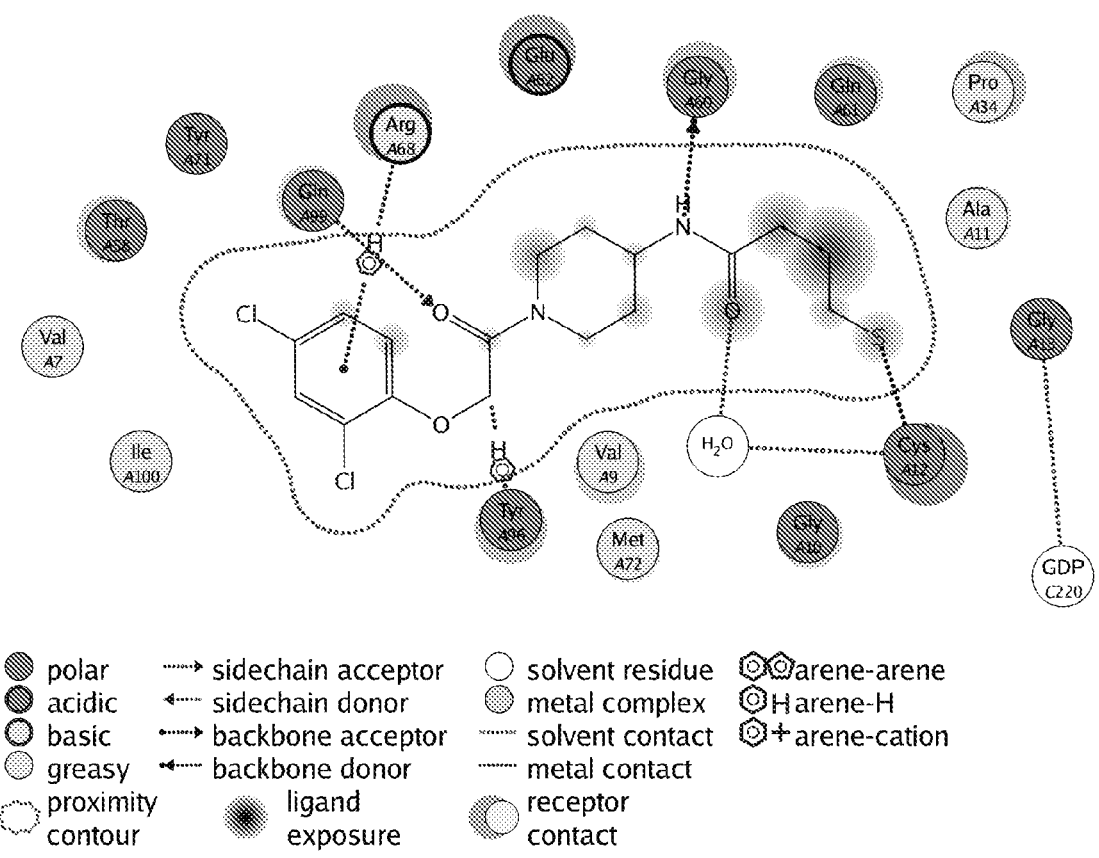

FIG. 8. Compound (ligand): protein contacts/interactions of JO-01-189cbut: G12C K-Ras; sequence legend (SEQ ID NO:4).

FIGS. 9A-9B show protein sequences for human H-Ras and K-Ras (including splice variants and mutants); in some embodiments, a Ras protein may contain one or more amino acids at the amino terminus due to the design of expression constructs (e.g. GAMGS may be in embodiments of H-Ras G12C truncation or G in embodiments of K-Ras constructs), however, amino acid numbering follows the physiological amino acid numbering not including construct introduced amino terminus extra amino acids.

Figure 10A:
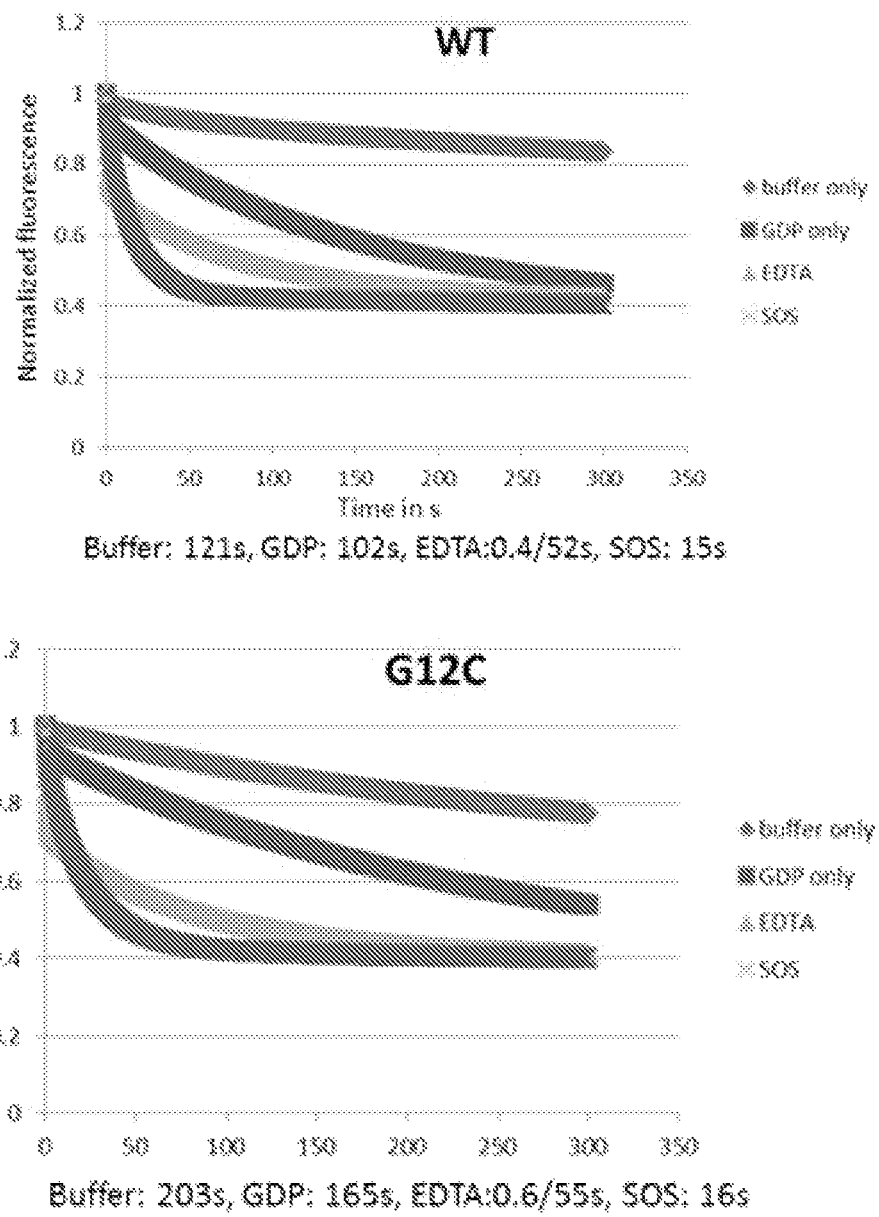

FIGS. 10A-10B. K-Ras*mant-d-GDP exchange with unlabeled GDP, half-life (single exponential) shown (stop-flow experiment with low magnesium).

FIGS. 11A-11B. K-Ras*mant-d-GDP exchange with unlabeled GDP or GTP, half-life (single exponential) shown (stop-flow experiment with low magnesium).

Figure 12:
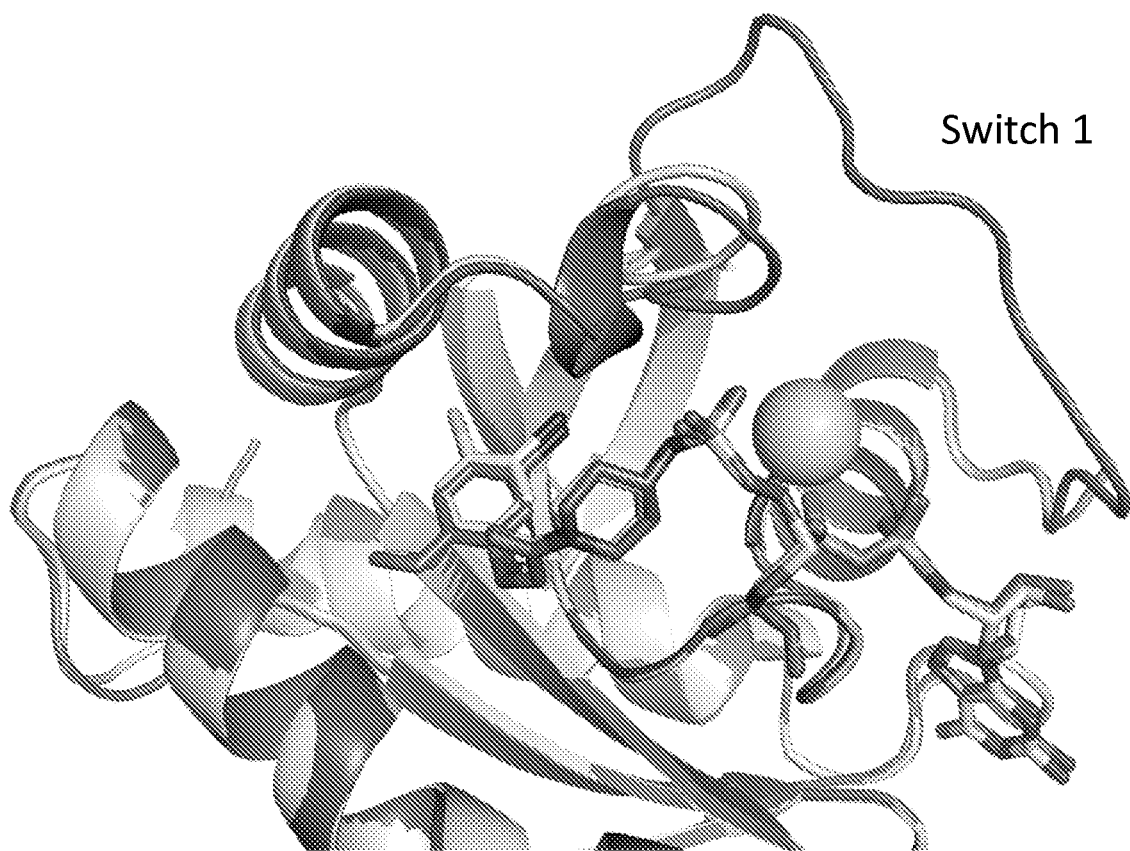

FIG. 12. Ras-079 shows same conformation in two different space groups (C2 vs. P212121); P212121 has switch 1 ordered in unseen conformation, metal present as well in K-Ras sequence legend (SEQ ID NO:4).

Figure 13:
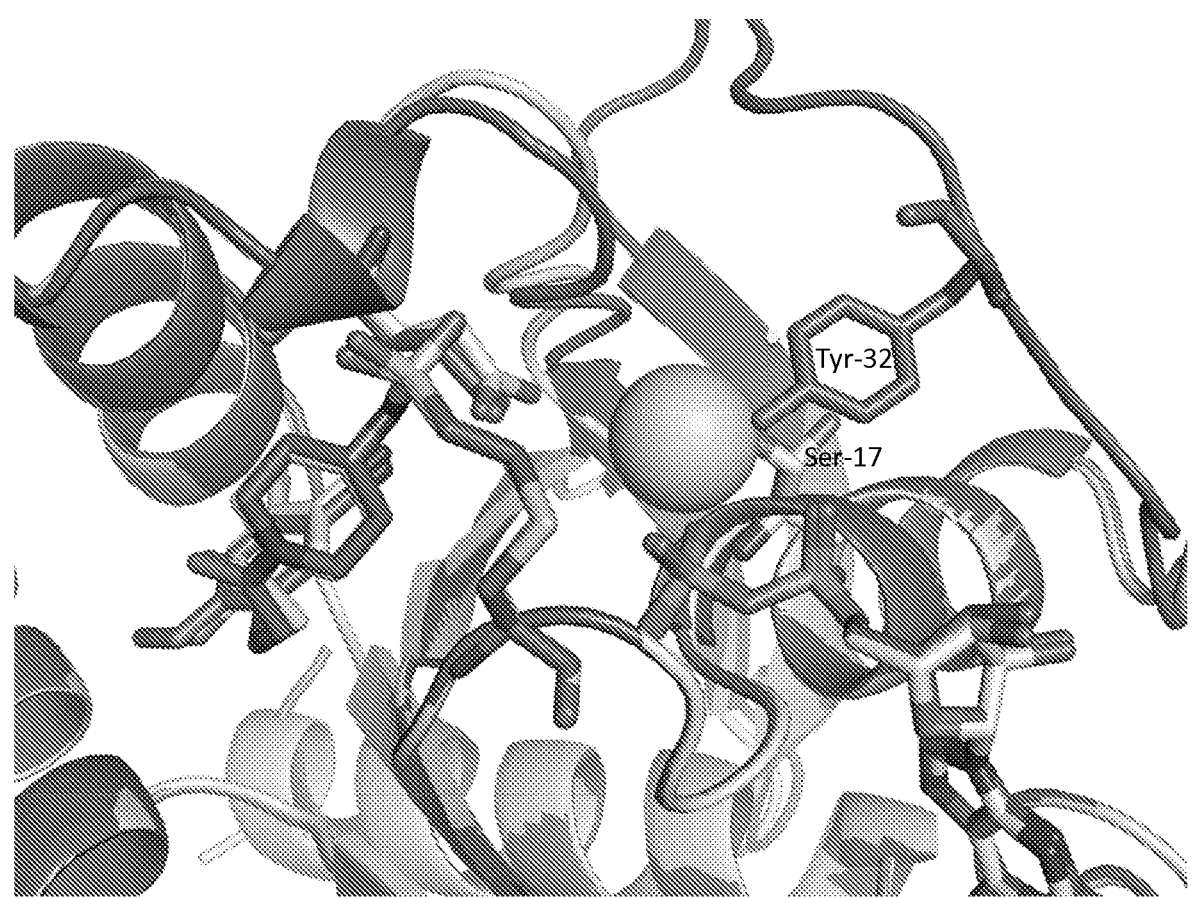

FIG. 13. Unusual metal coordination in new P212121 space group (Tyr-32) of K-Ras, sequence legend (SEQ ID NO:4).

Figure 14B:
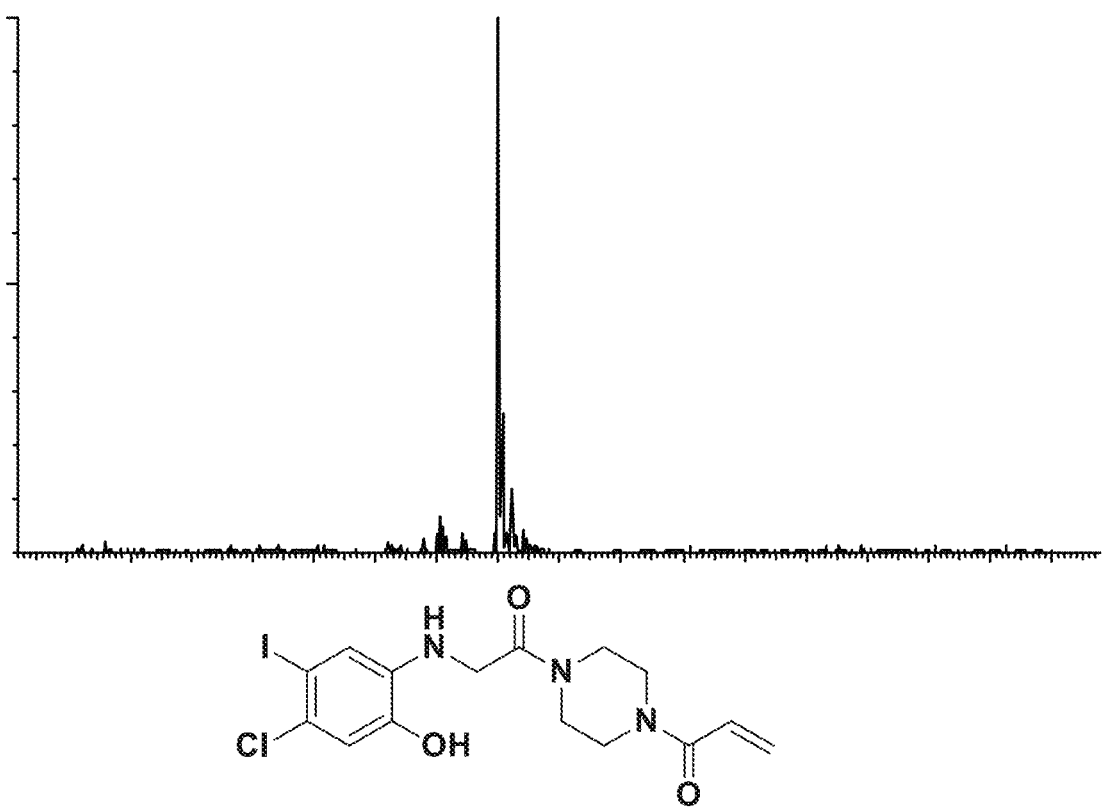

FIGS. 14A-14B. Labeling of H-Ras G12C; labeling successful (>1 day, EDTA, 250 micM); only single labeling visible despite high conc.; Potential degradation products.

Figure 15:
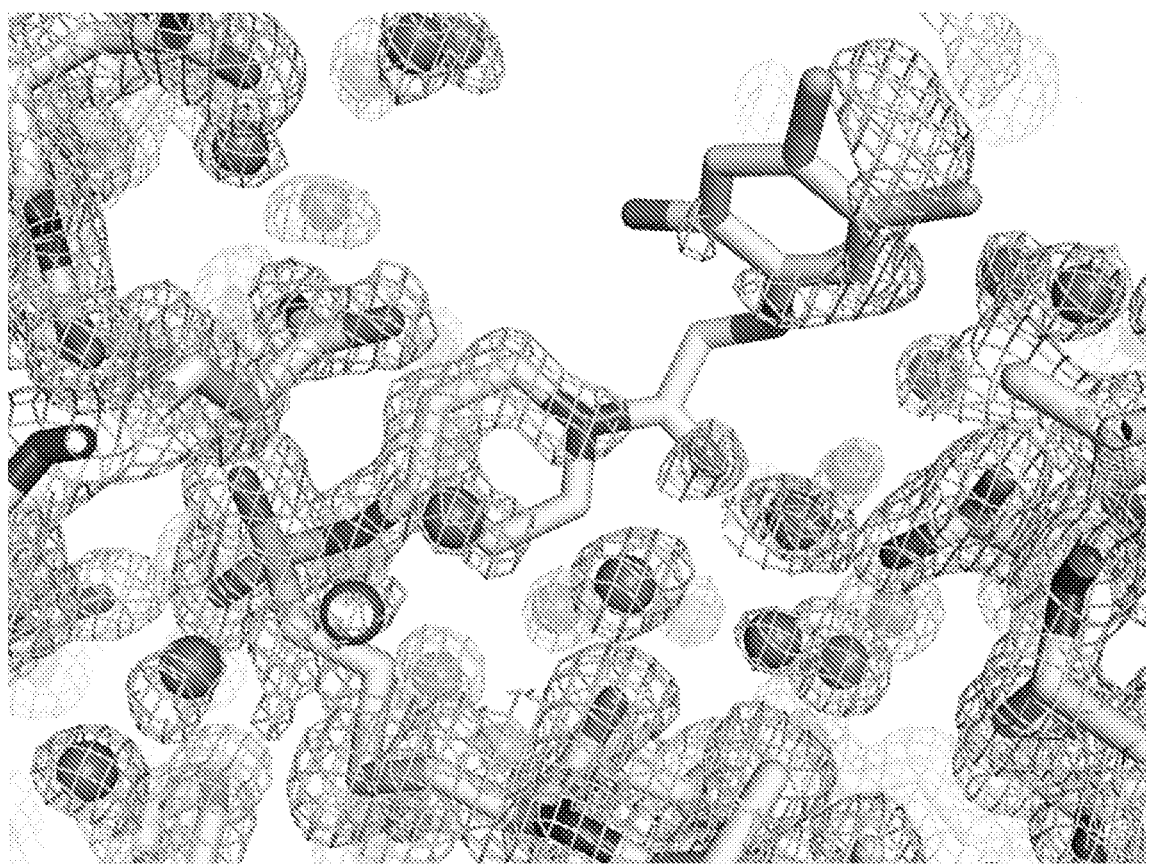

FIG. 15. Evidence of compound in H-Ras; 1 sigma 2fo-fc map shown, H-Ras*GDP*055, 1.18A resolution, 0.1791 Rfree, sequence legend (SEQ ID NO:3).

Figure 16:
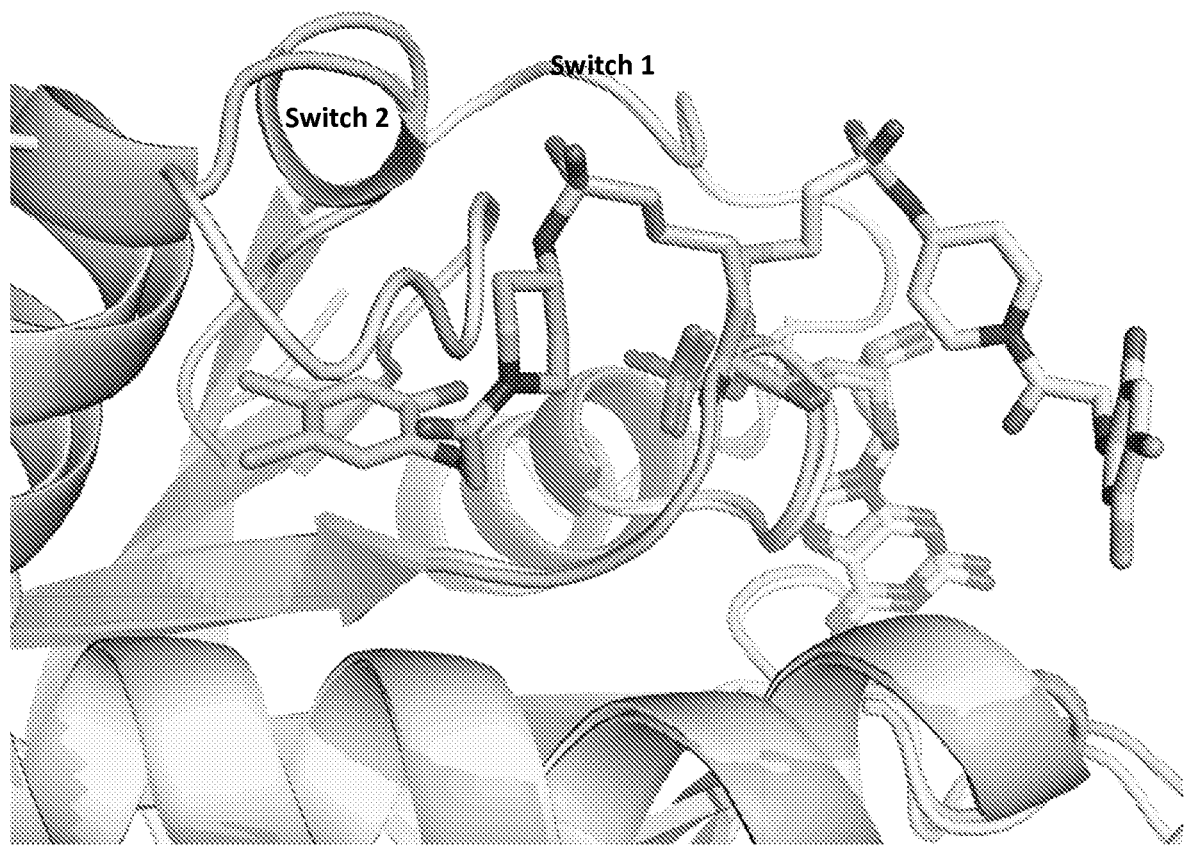

FIG. 16. Compound is out of the pocket in H-Ras compared to K-Ras; H-Ras*GDP*055 (light gray), K-Ras*GDP*055 (dark gray); sequence legend light gray (SEQ ID NO:3), dark gray (SEQ ID NO:4).

Figure 17:
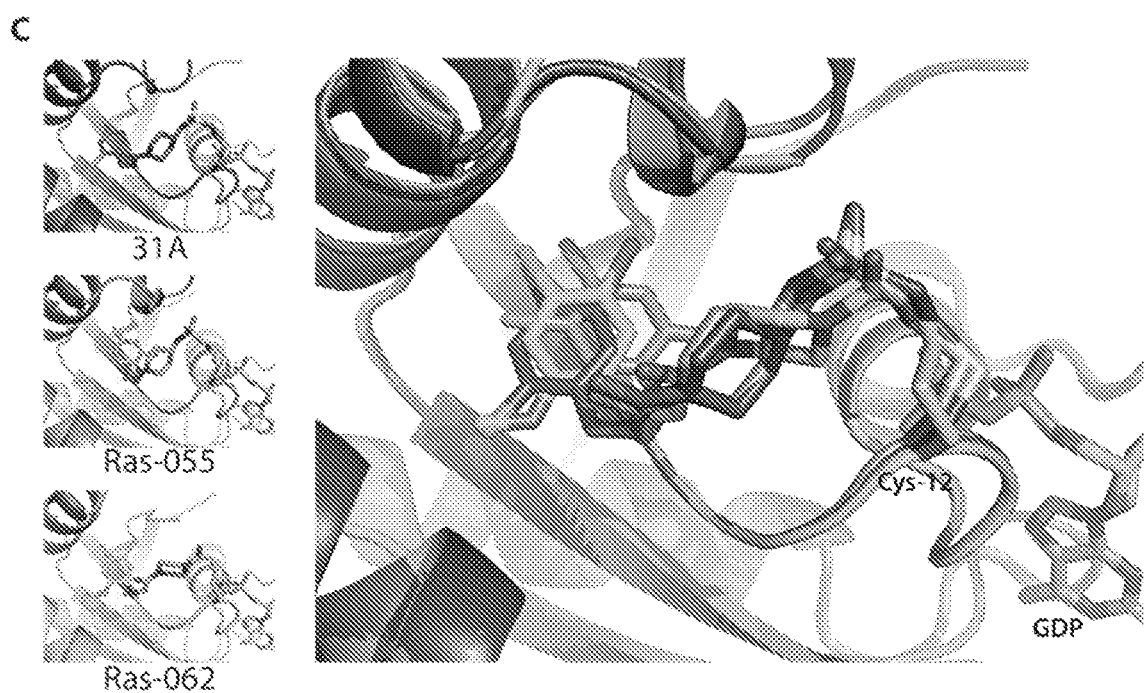

FIG. 17. Co-crystal structures show novel pocket, sequence legend (SEQ ID NO:4).

Figure 18:
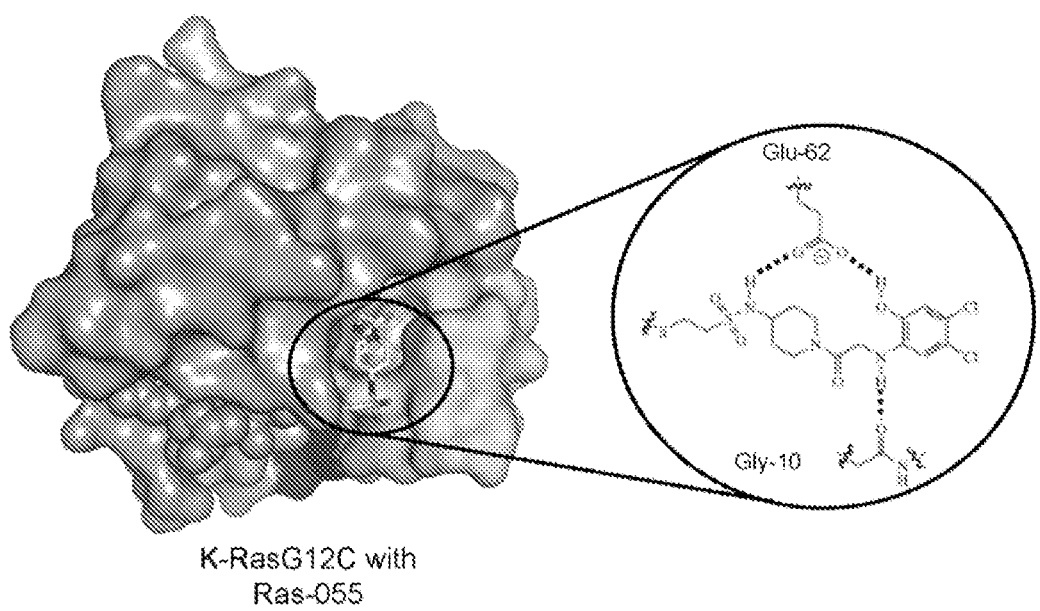

FIG. 18. Co-crystal structures show novel pocket; new polar interactions in optimized compounds; inhibitors bind behind Switch II and disrupt both Switches; bind much more slowly to KrasGTP; switch conformations are critical for activation downstream; may interfere with GTP binding; sequence legend (SEQ ID NO:4).

FIG. 19. G60A in Switch II is dominant negative, glycine-60 to alanine mutation is dominant negative; small changes in Switch II can have huge consequences for function; top Kras-G12C with Ras-055; bottom Kras-WT truncated; sequence legend top (SEQ ID NO:4), bottom (SEQ ID NO:16).

Figure 20:
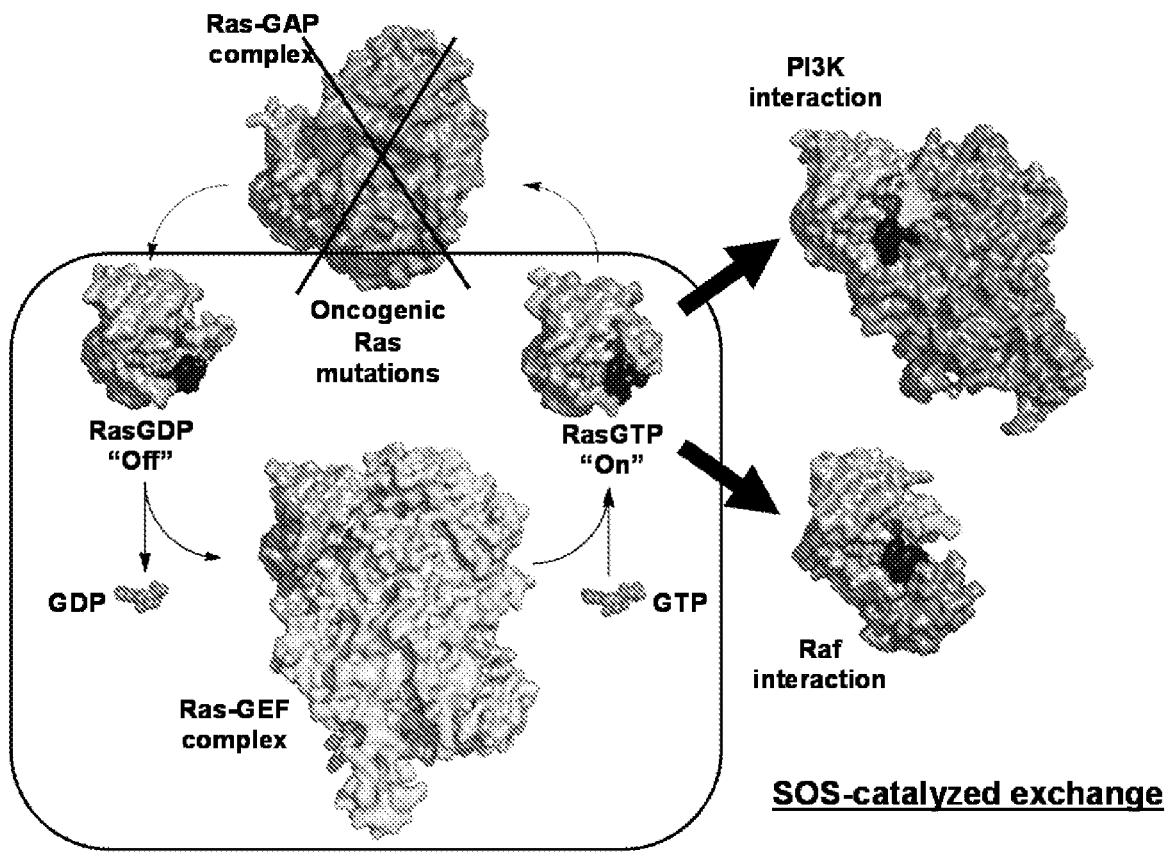

FIG. 20. Ras nucleotide exchange and protein interactions.

FIG. 21. Inhibitors block Ras activation-"OFF exchange"; similar inhibition seen in [a-32P] GTP "ON exchange"; working on plate-based assay to test relative nucleotide affinities.

Figure 22:
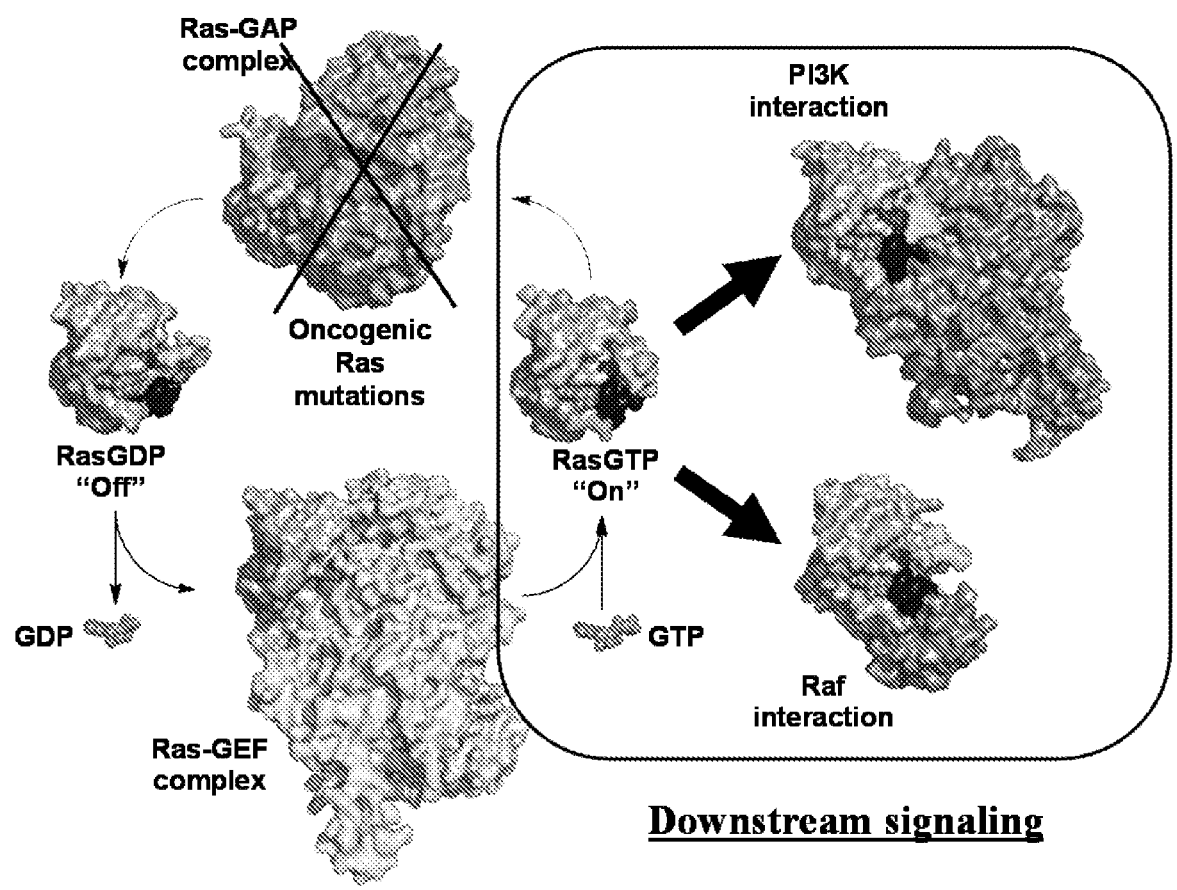

FIG. 22. Ras nucleotide exchange and protein interactions.

FIG. 23. Raf1-RBD pull-downs; inhibitors decrease Raf binding, especially in GTP-GDP mixtures; suggest inhibitors change relative affinity for nucleotides.

Figure 24:
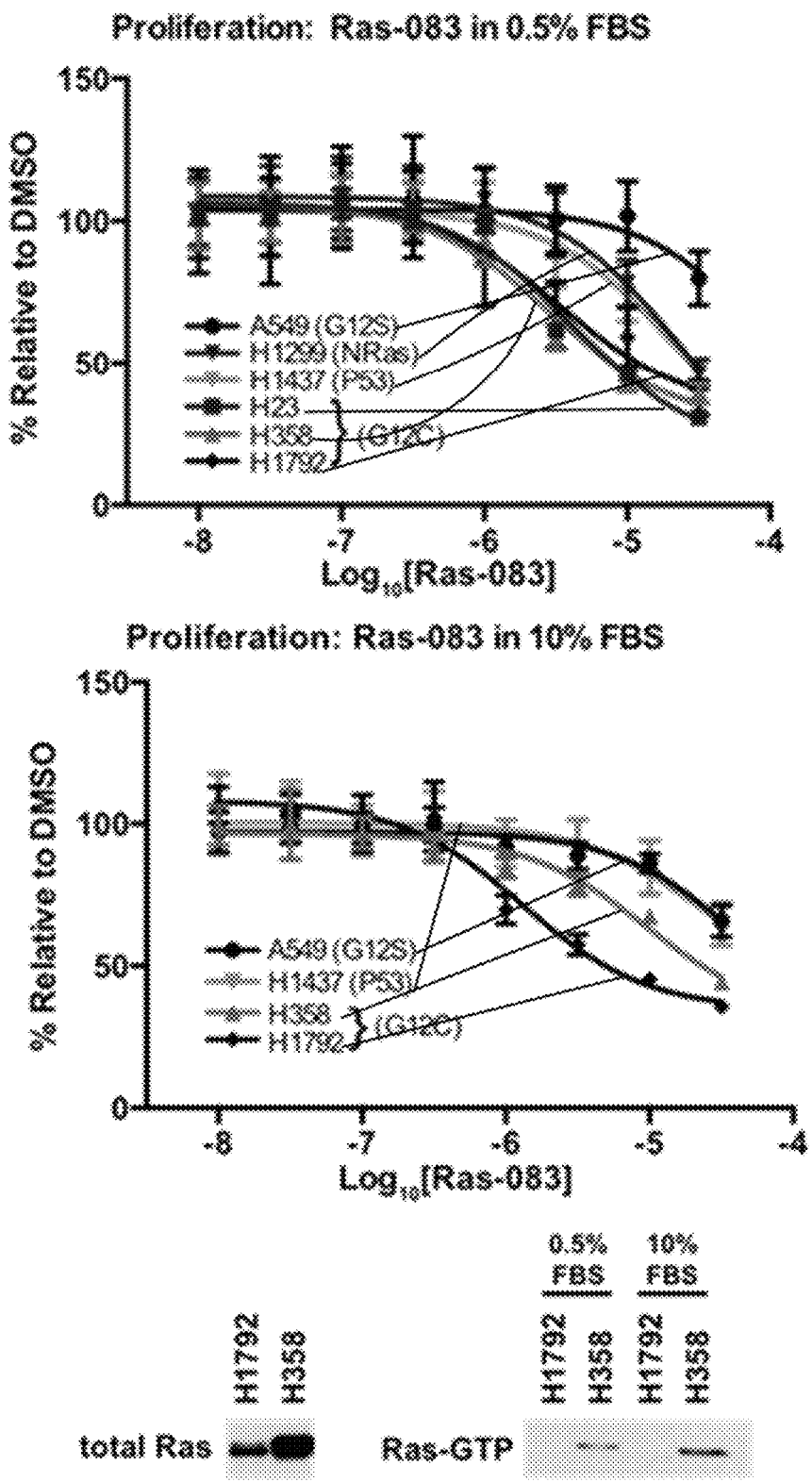

FIG. 24. H358 (G12C) cells less sensitive in high serum; 24 hr treatment in 0.5% FBS followed by proliferation in 10% FBS; larger difference at lower cell density.

FIG. 25. Proliferation of human lung cancer cell lines; 24 hr treatment in 0.5% FBS followed by proliferation in 10% FBS.

Figure 26:
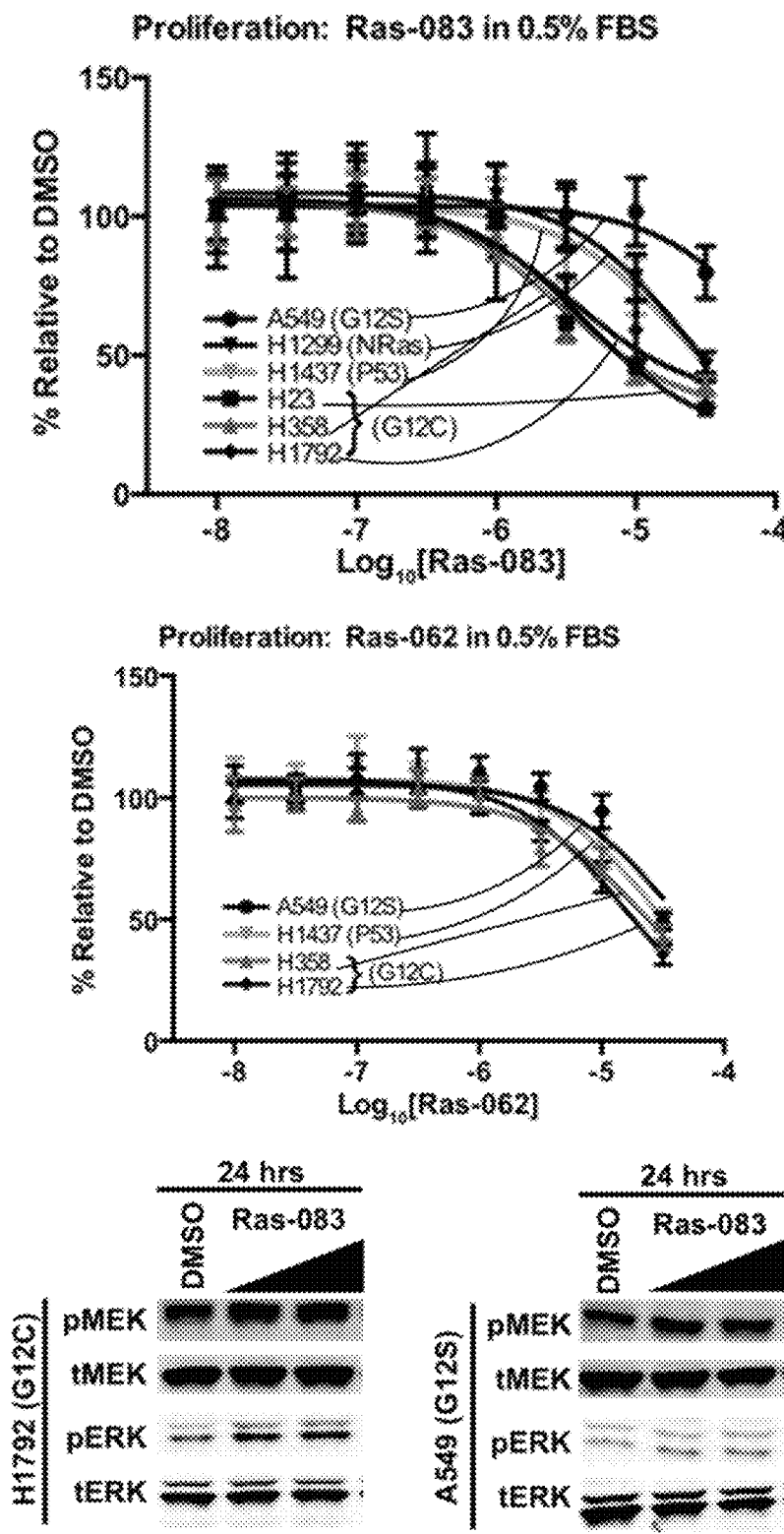

FIG. 26. Induction of pERK after treatment in G12C cells; in Braf melanoma cells, Kras siRNA induces pERK.

Figure 27B:
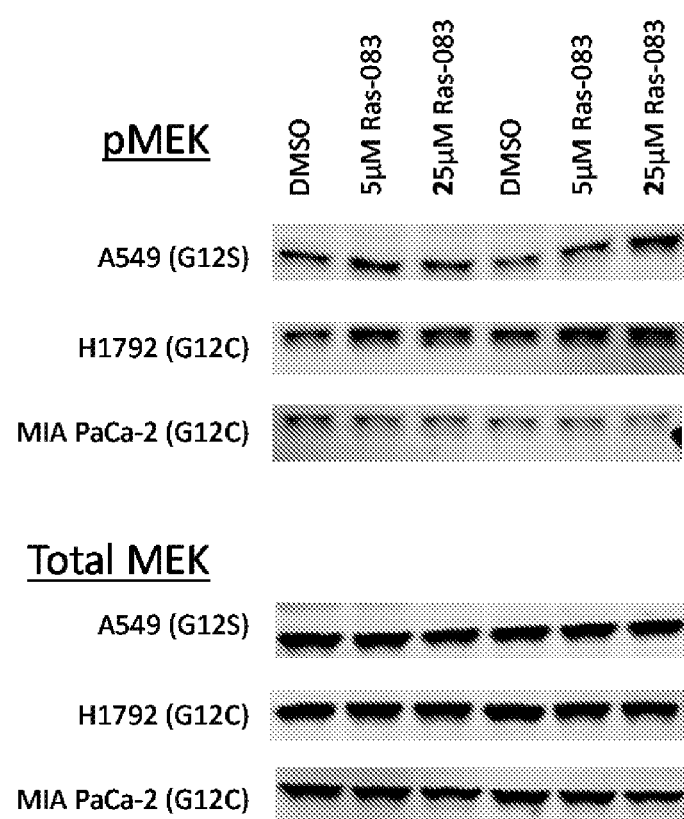

FIGS. 27A-27B show phosphosignaling after treatment with Ras-083.

FIG. 28. Proliferation of human lung cancer cell lines; 2,000 cells/well; 24 hr treatment, 48 hr washout all in 10% FBS.

FIG. 29. Proliferation of human lung cancer cell lines; 24 hr treatment (0.5% FBS), 48 hr washout (10% FBS); now both G12C cell lines look significantly more sensitive to Ras-083.

FIG. 30. Proliferation of human lung cancer cell lines; 4,000 cells/well; 24 hr treatment, 48 hr washout all at 10% FBS; 1 μM lapatinib.

Figure 31:
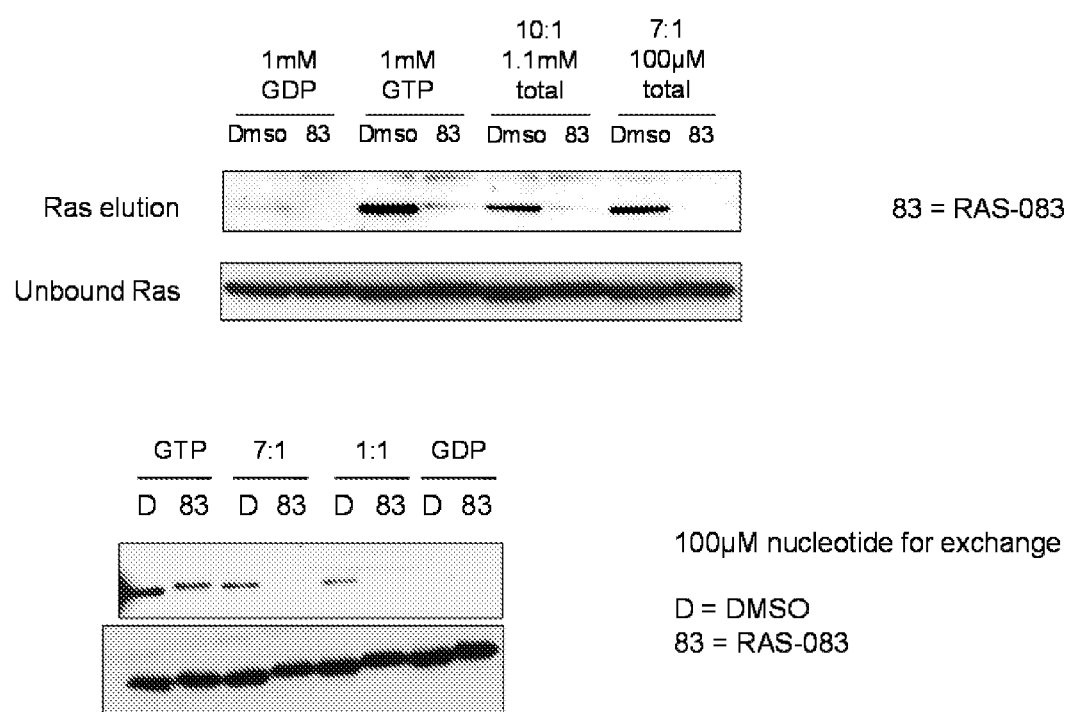

FIG. 31. Raf1-RBD pull-downs; Ras-083 impairs binding of RasGTP to Raf1-RBD after EDTA-catalyzed exchange; Adding a mixture of GTP and GDP allows preferential binding to GDP even when GTP is in excess (10:1 and 7:1); experiment performed as described herein.

Figure 32:
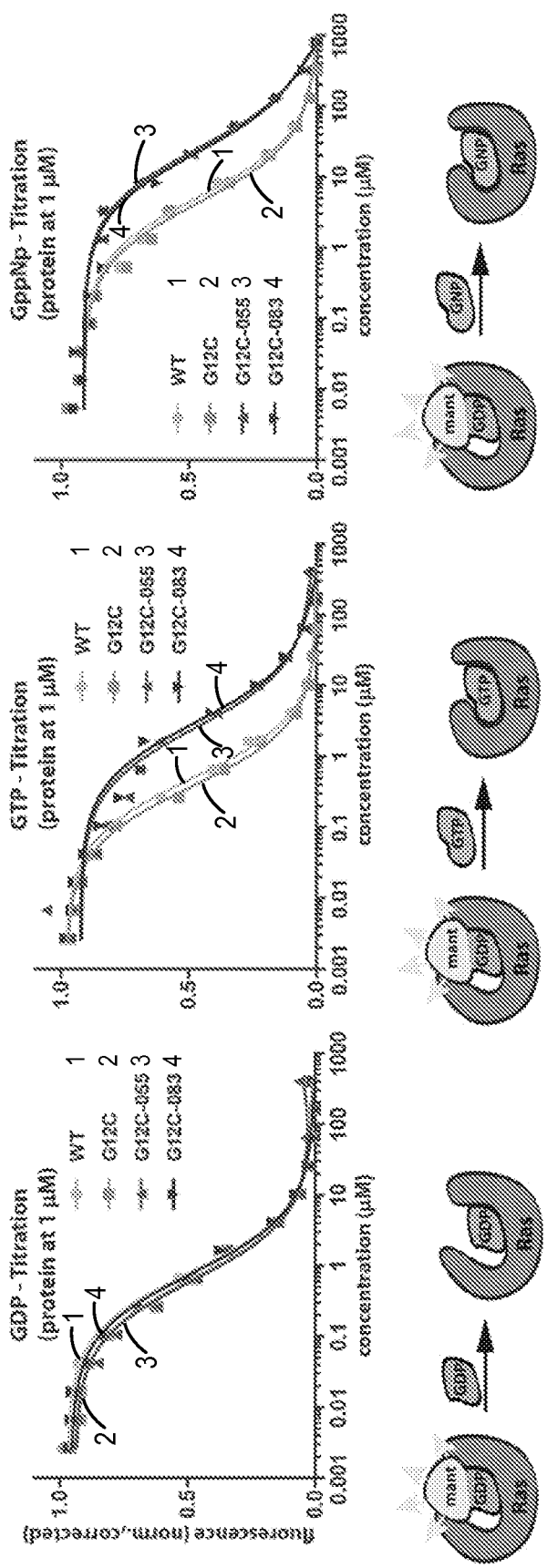

FIG. 32. Compound binding to K-Ras alters affinities for GTP and GppNp (GNP), (competition experiments with mant-dGDP).

Figure 33:
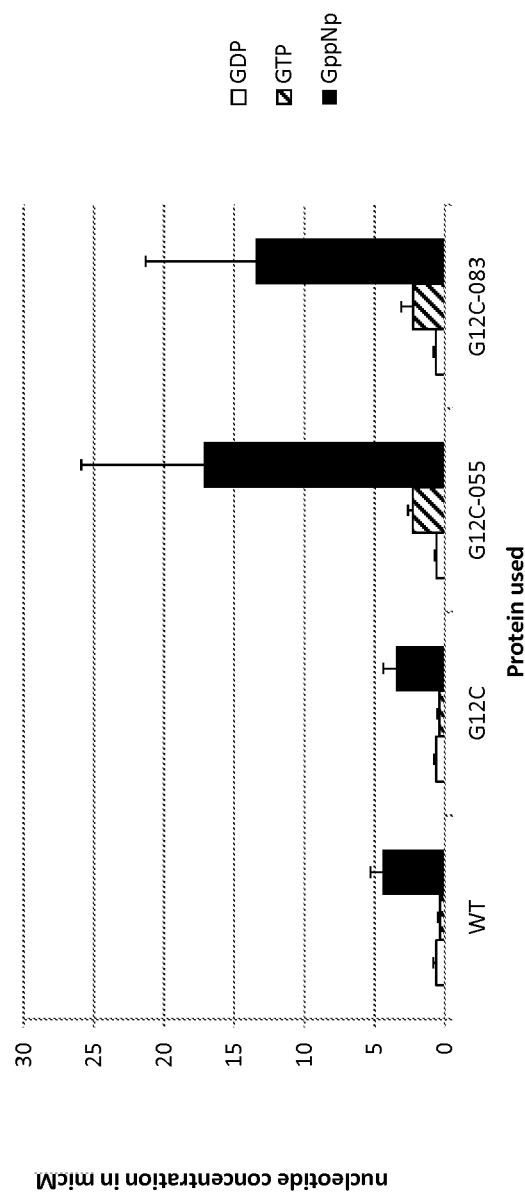

FIG. 33. IC50 of different nucleotides competing with mant-d-GDP (~1 micM); IC50 ratios (representative of relative affinities) shift greatly towards GDP over GTP in case of the compound bound K-Ras.

Figure 34A:
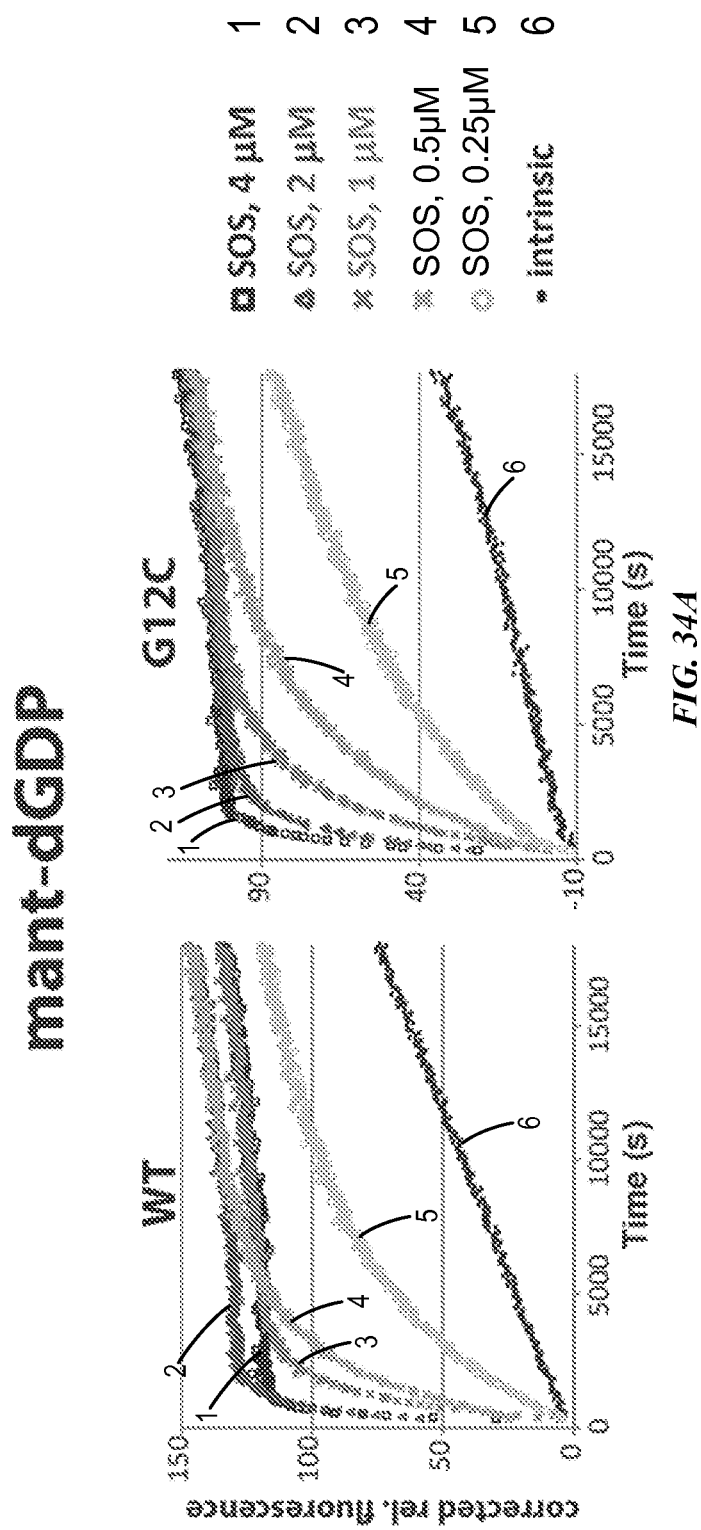
Figure 34B:
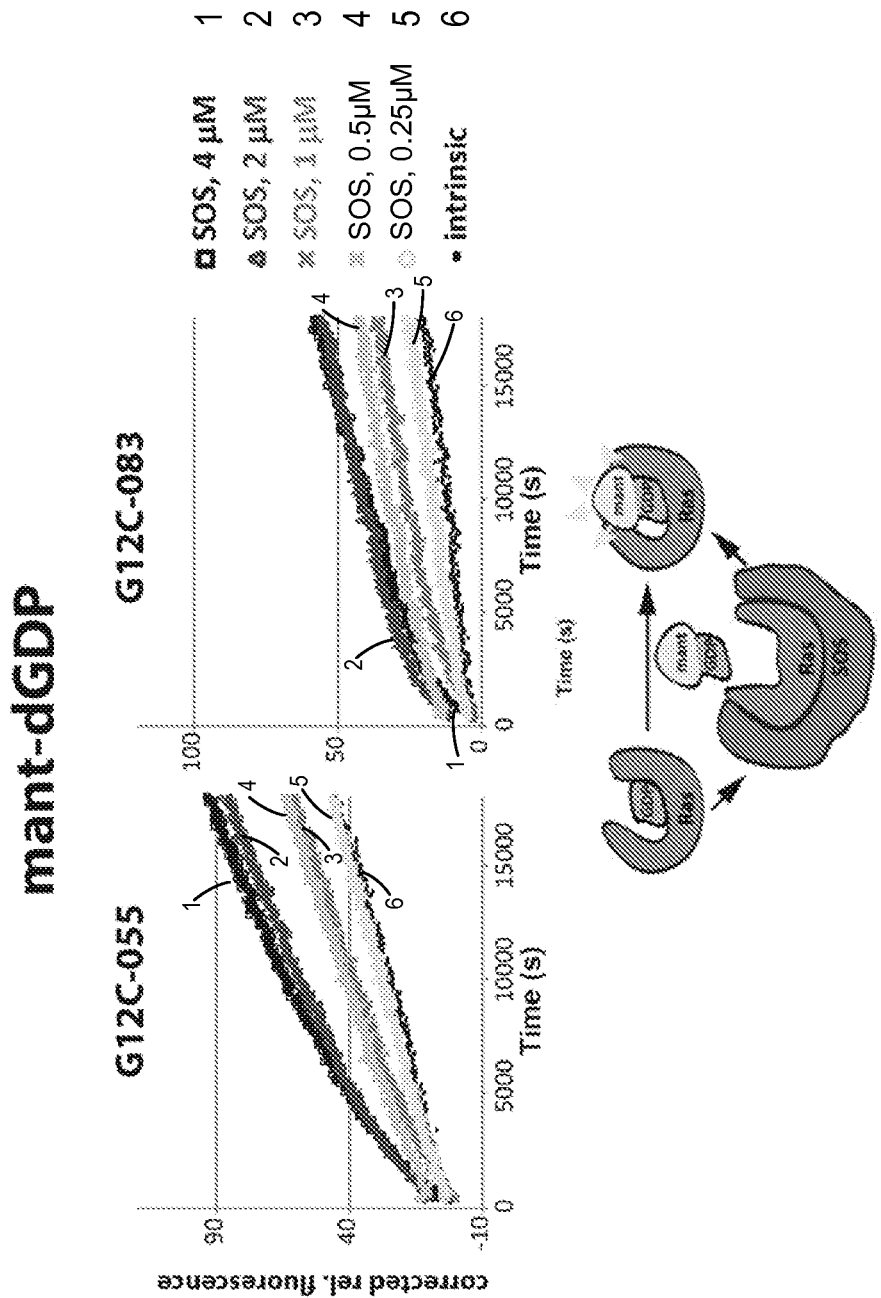

FIG. 34. (A and B) Compound binding to K-Ras reduces SOS-mediated exchange (association of mant-d-GDP monitored).

Figure 35A:
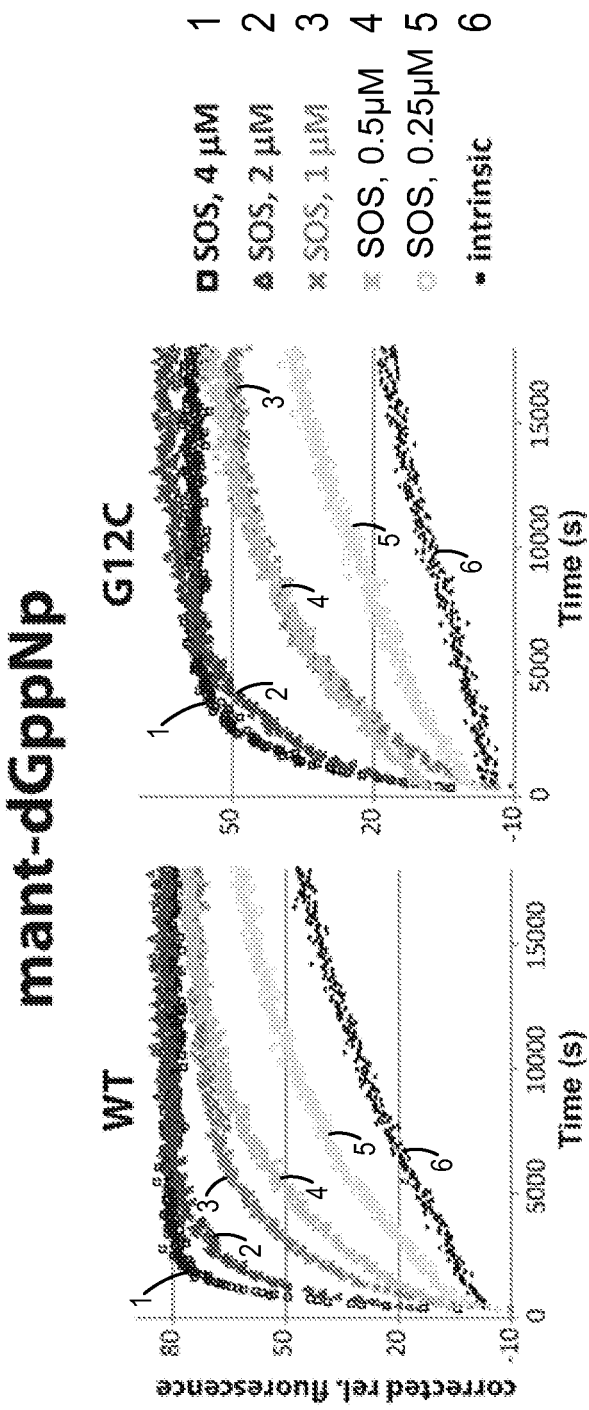
Figure 36A:
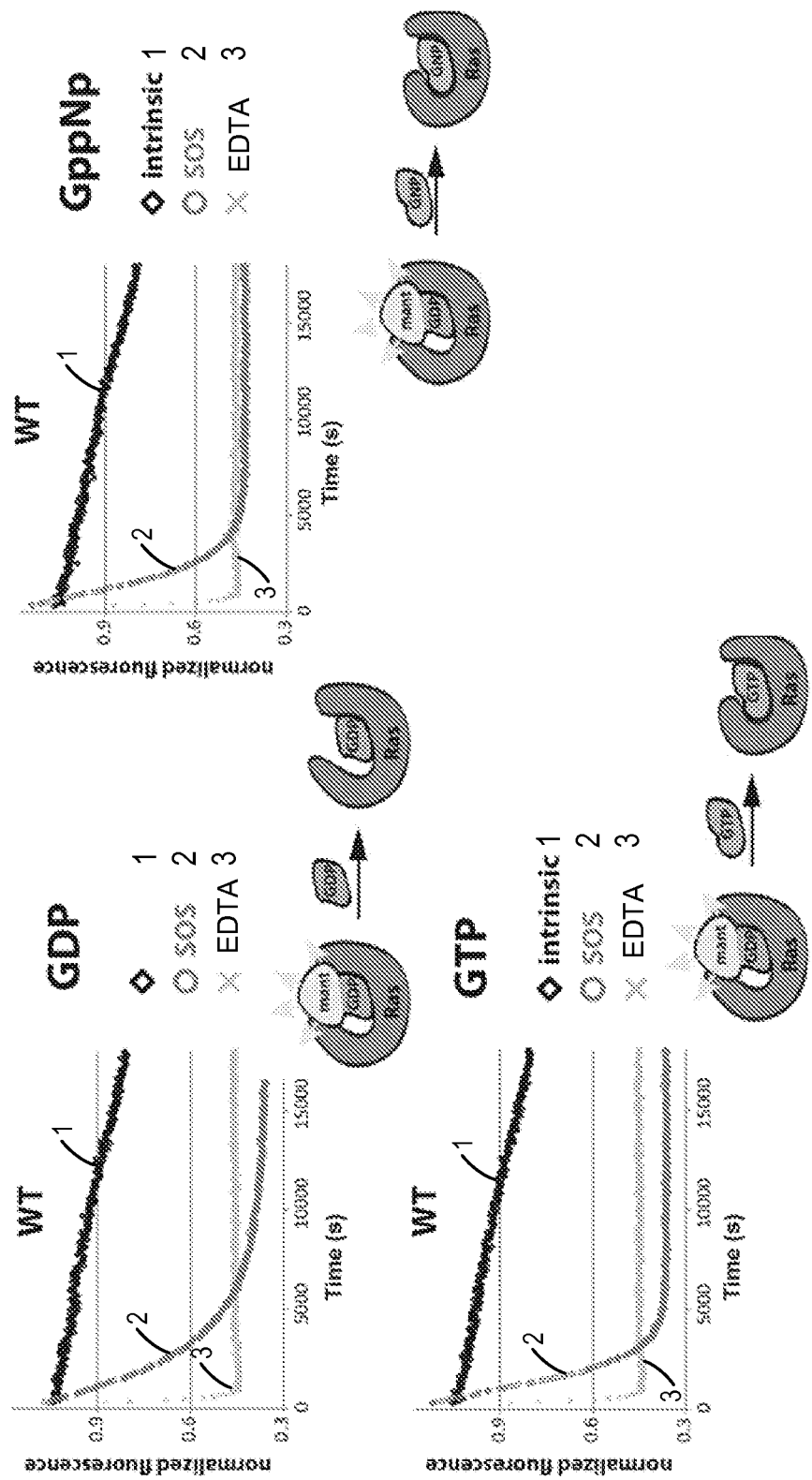
Figure 36B:
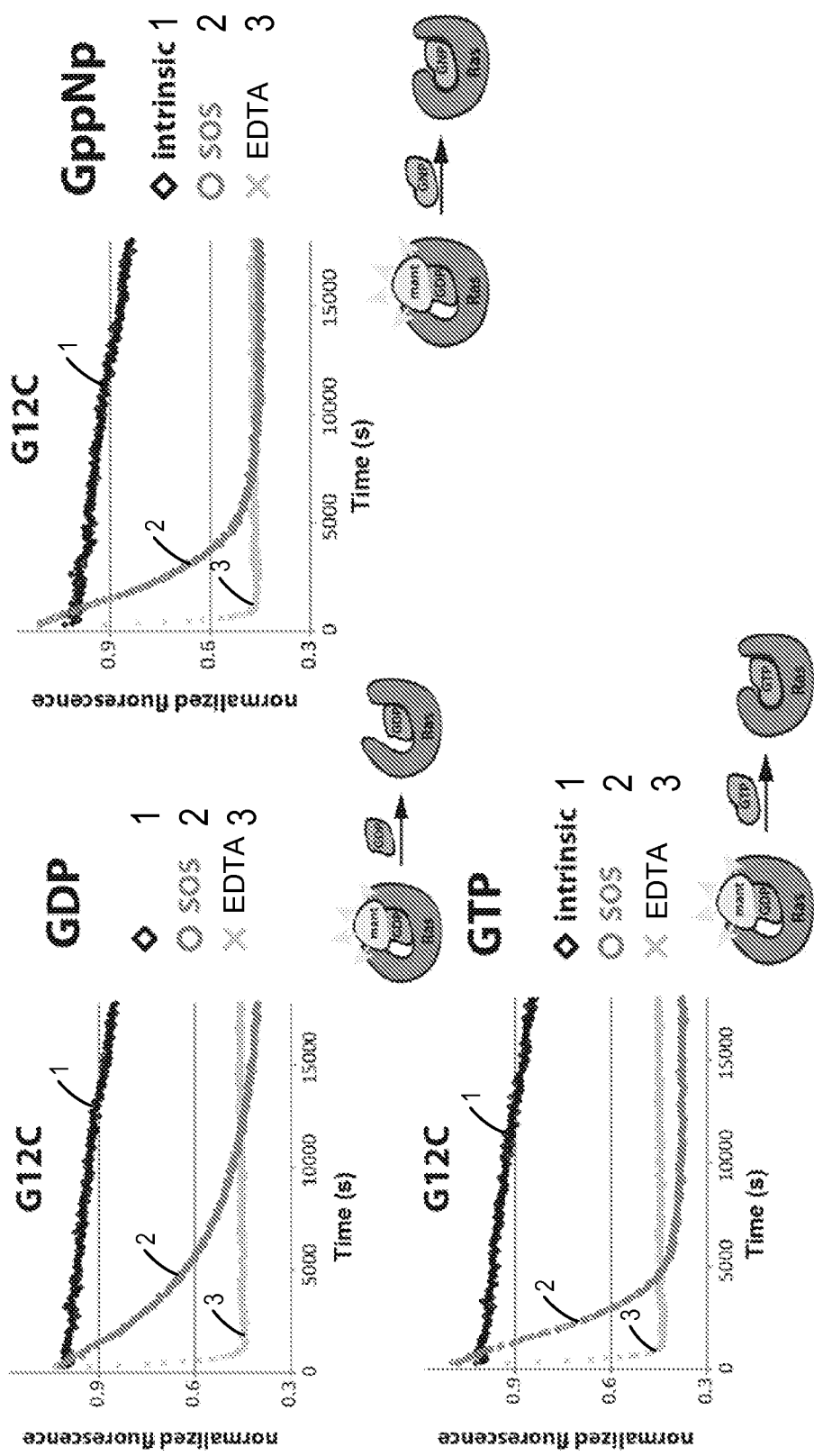
Figure 36C:
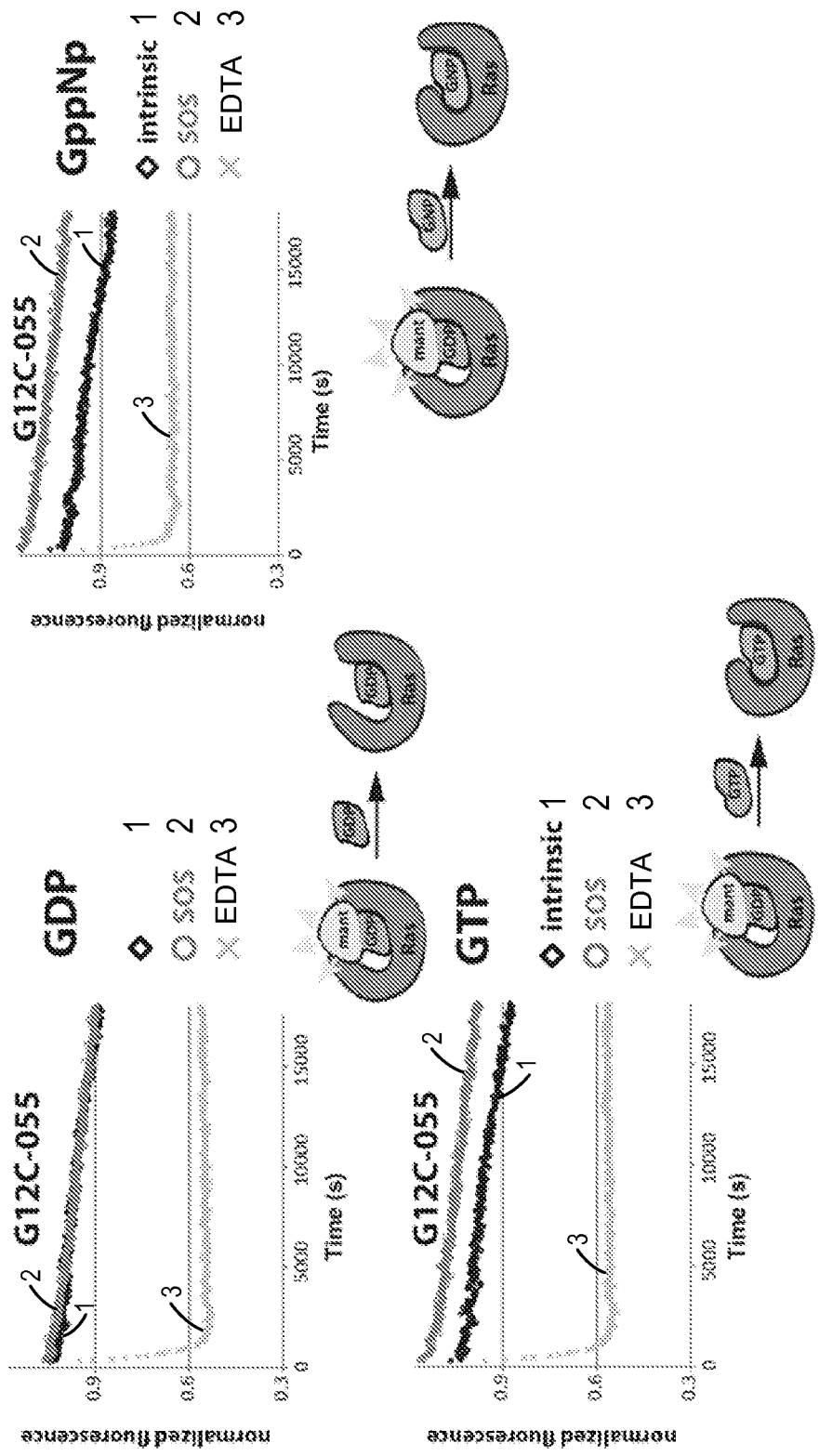
Figure 36D:
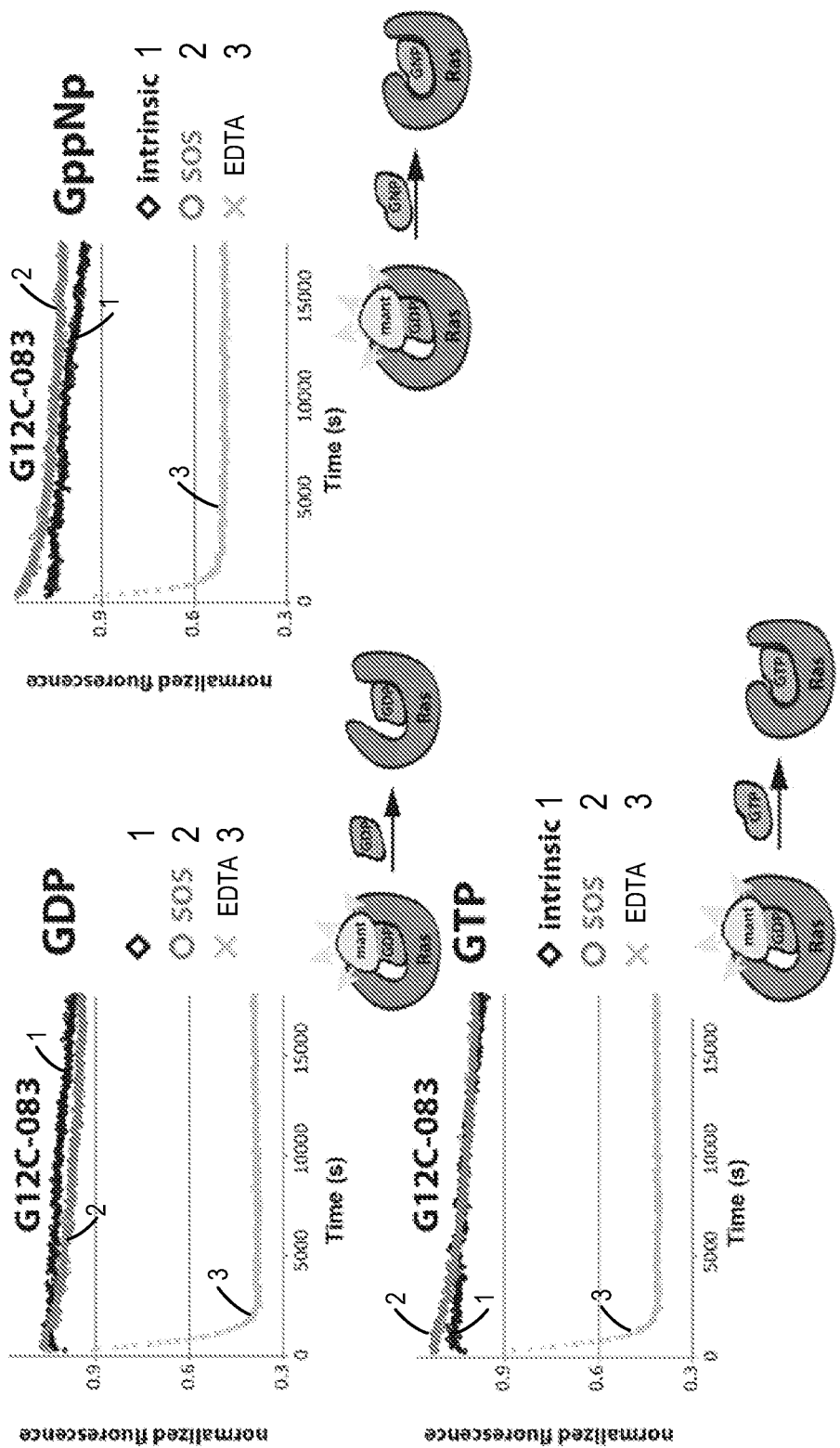

FIGS. 35A-35B. Compound binding to K-Ras reduces SOS-mediated exchange (association of mant-d-GppNp monitored).

FIGS. 36A-36D. Compound binding to K-Ras reduces SOS-mediated exchange (dissociaton of mant-d-GDP monitored).

Figure 37:
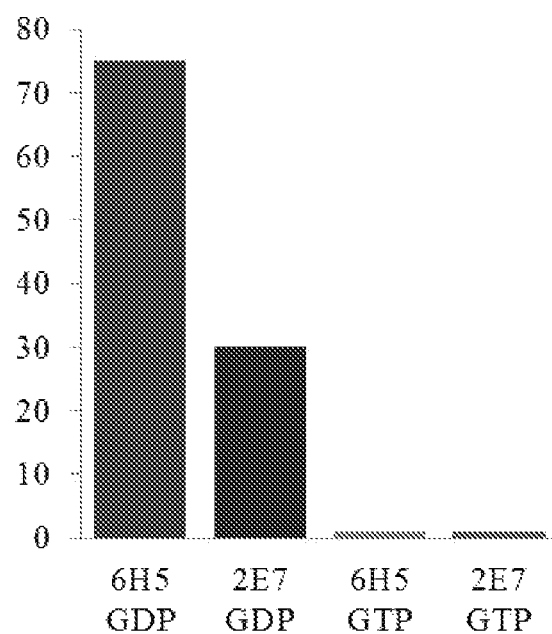

FIG. 37. Labeling of K-Ras G12C loaded with GDP or GTP analog; fragments bind to GDP-loaded K-Ras G12C but not GTP-loaded K-Ras G12C; % modification with 100 μM fragment and 200 μM βME; figure legend SEQ ID NO:15.

Figure 38:
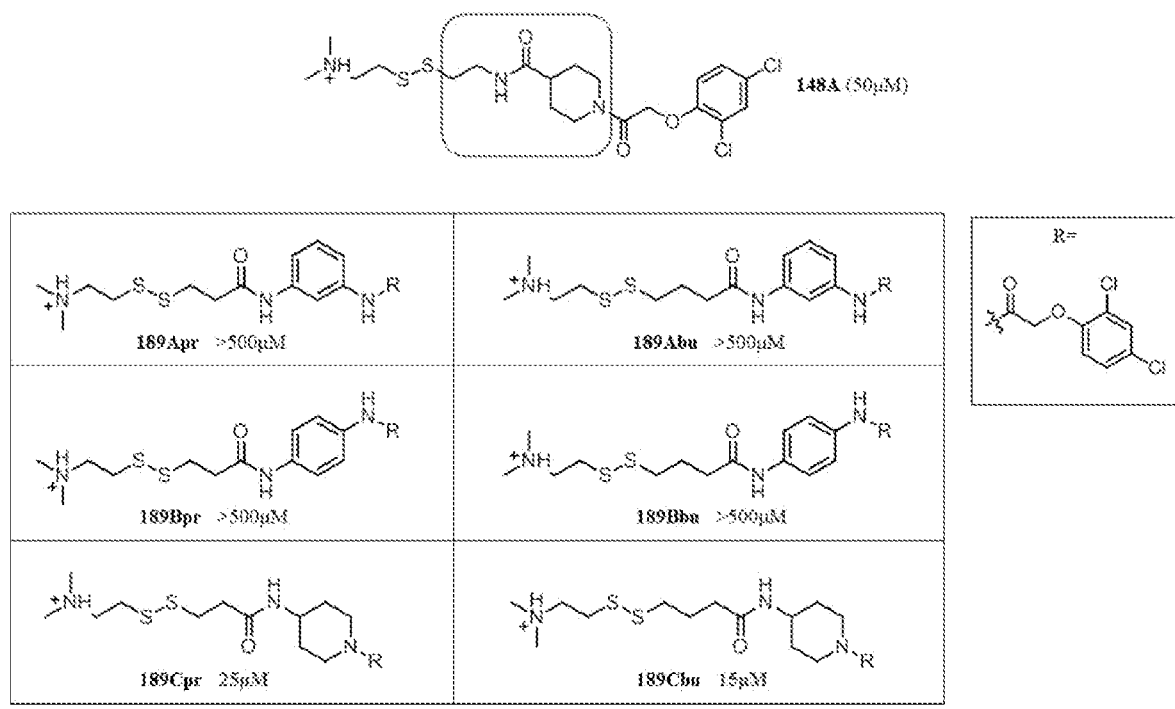

FIG. 38. Concentration of fragment necessary for 50% modification of K-RasG12C in presence of 100 μM βME, figure legend SEQ ID NO:15; several rounds of inhibitor optimization lead to improved labeling at 200 μM βME. This series shows the effect of linker changes on labeling.

Figure 39:
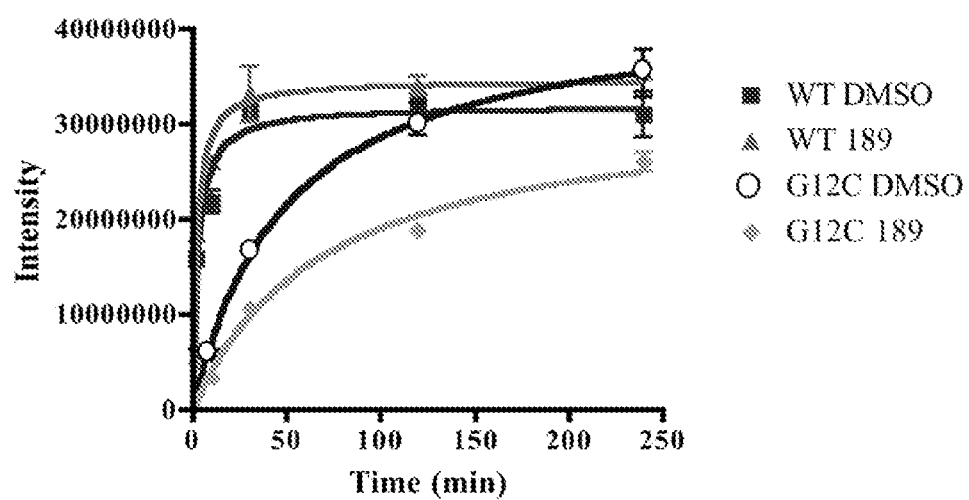

FIG. 39. 189Cbu selectively slows GEF-catalyzed nucleotide exchange by K-Ras G12C without affecting wild type K-Ras, figure legend SEQ ID NO:10 and SEQ ID NO:11.

FIG. 40. Inhibitors induce formation of a pocket behind switch II; switch II is modeled from active (GMPPNP §) and inactive (GDP §) structures into the 189Cbu complex left; the model shows a steric clash between the inhibitor and residues from switch II in the active conformation, suggesting these compounds may disrupt the active state of Ras and impair downstream signaling; left panel K-Ras G12C bound to 189Cbu; § Model, switch II mapped onto 189Cu structure; figure legend SEQ ID NO:4.

Figure 41:
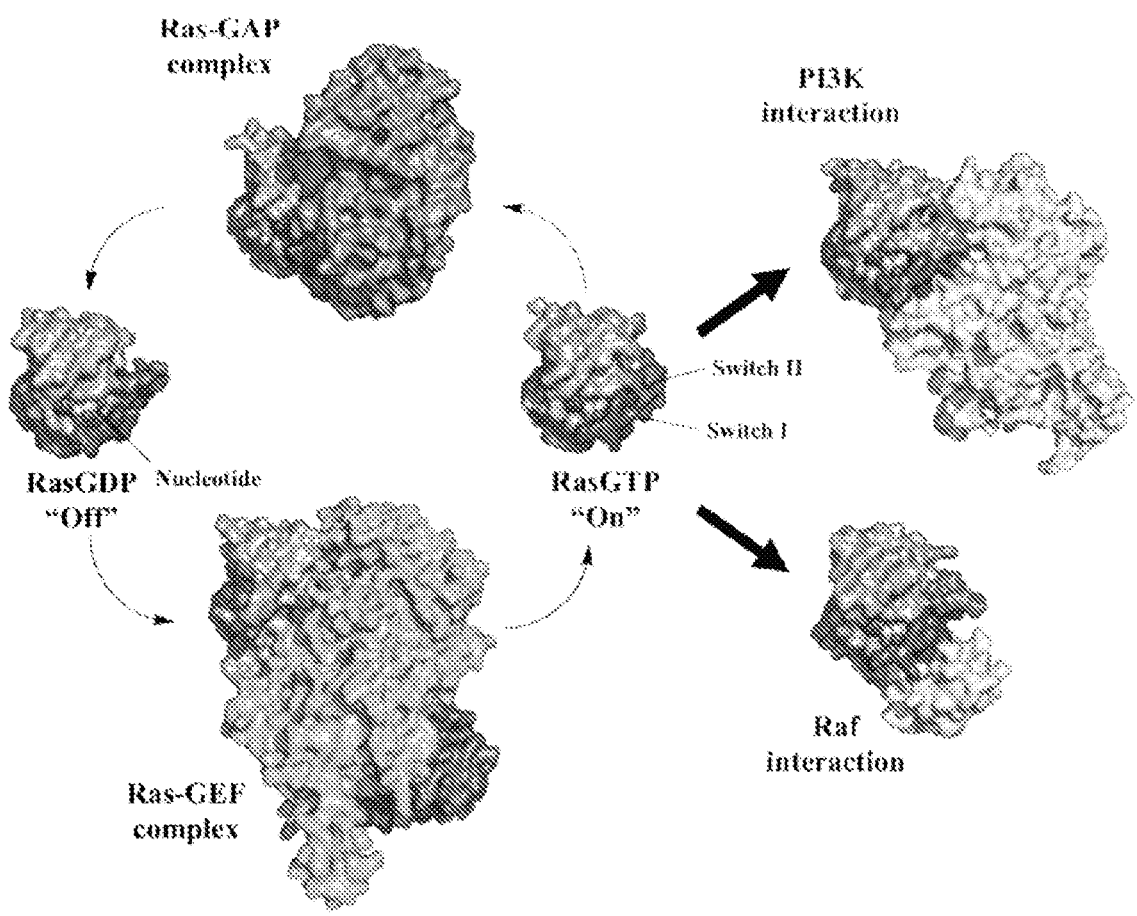

FIG. 41. Ras cycles between an inactive GDP-bound state and an active GTP-bound state; in the active conformation, Ras interacts with downstream effector proteins such as Raf and PI3K; effectors interact with Ras-GTP through switch I and switch II, which differ structurally between nucleotide states; oncogenic mutations in Ras (most frequently at positions 12, 13, or 61) disrupt GAP-facilitated GTP hydrolysis, kinetically locking Ras in the GTP-bound "on" state.

Figure 42:
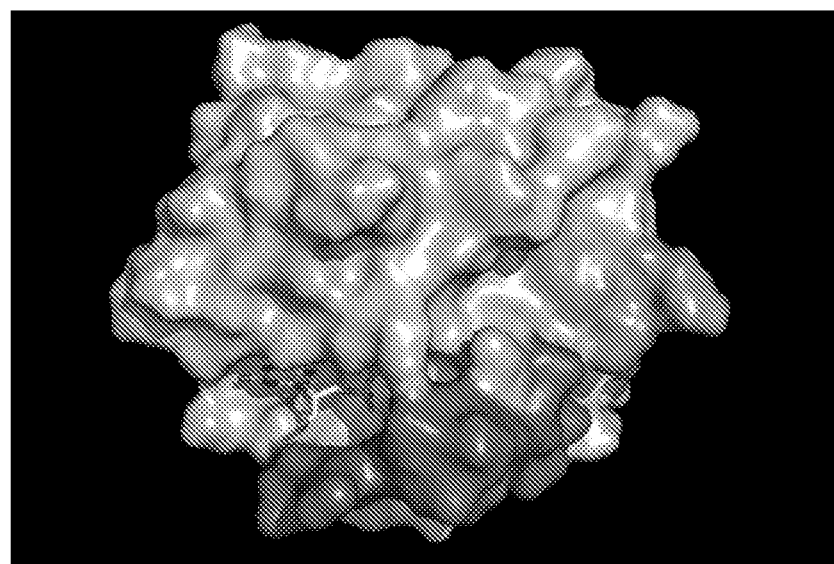

FIG. 42. Targeted glycine-12 to cysteine (G12C) mutant of K-Ras by taking advantage of the high nucleophilicity of the mutant residue; most common K-Ras mutation in lung cancer (~9% NSCLC, COSMIC); adjacent to nucleotide site and switches; covalent handle enhances selectivity and potency.

Figure 43:
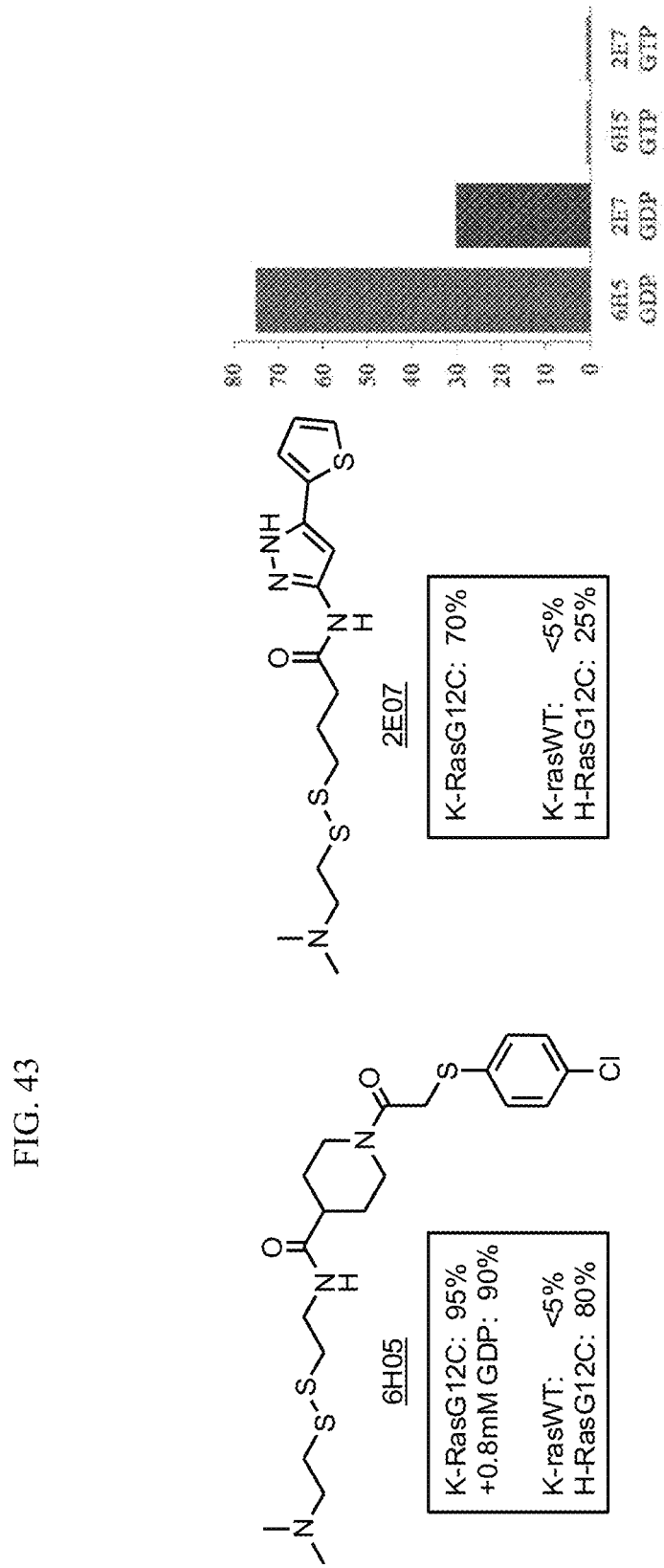

FIG. 43. Screened 480-compound library at 100 μM βME and 100 μM fragment; compounds modifying K-Ras G12C at >50% were considered hits; of 17 hit compounds, none caused >10% modification of wild type K-Ras, which contains a surface exposed cysteine (C118); two hits shown; fragments bind to GDP-loaded K-Ras but not GTP-loaded K-Ras; left panel % modification with 100 μM fragment and 100 μM βME; right panel % modification with 100 μM fragment and 200 μM βME.

DETAILED DESCRIPTION OF THE INVENTION

Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH—CH—O—CH$_3$, —Si(CH$_3$)$_3$, —CH$_2$—CH═N—OCH$_3$, —CH—CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substitutents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "alkylsulfonyl," as used herein, means a moiety having the formula—S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R", —OC(O) R', —C(O)R', —CO$_2$R', —CONR'R", —OC(O)NR'R", —NR"C(O) R', —NR'—C(O)NR"R", —NR"C(O)$_2$R', —NR—C(NR'R"R''')=NR"", —NR—C(NR'R")=NR", —S(O) R', —S(O)$_2$R', —S(O)$_2$NR'R", —NRSO$_2$R', —NR'NR"R'", —ONR'R", —NR'C=(O)NR"NR'''R"", —CN, —NO$_2$, —NR'SO$_2$R", —NR'C=(O) R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example:—OR', —NR'R", —SR', -halogen, —SiR'R"R", —OC(O) R', —C(O)R', —CO$_2$R', —CONR'R", —OC(O)NR'R", —NR"C(O) R', —NR'—C(O)NR"R", —NR"C(O)$_2$R', —NR—C(NR'R"R''')=NR"", —NR—C(NR'R")=NR", —S(O) R', —S(O)$_2$R', —S(O)$_2$NR'R", —NRSO$_2$R', —NR'NR"R'", —ONR'R", —NR'C=(O)NR"NR'''R"", —CN, —NO$_2$, —R', —N$_3$, —CH(Ph)$_2$, fluoro (C$_1$-C$_4$)alkoxy, and fluoro (C$_1$-C$_4$)alkyl, —NR'SO$_2$R", —NR'C=(O) R", —NR'C(O)—OR", —NR'OR", in a number ranging from zero to the total number of open valences on the aromatic ring system; and where R', R", R''', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$-U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties: (A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC—(O)NH$_2$, —NHSO$_2$H, —NHC= (O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC—(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and/or each substituted or unsubstituted heterocycloalkyl is a substituted or unsubstituted 5 to 7 membered heterocycloalkyl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_5$-C$_7$ cycloalkylene, and/or each substituted or unsubstituted heterocycloalkylene is a substituted or unsubstituted 5 to 7 membered heterocycloalkylene.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or(S) or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and(S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C.). All isotopic variations of the compounds of the present invention, whether radioactive or not, are encompassed within the scope of the present invention.

The symbol "---" denotes the point of attachment of a chemical moiety to the remainder of a molecule or chemical formula.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.*

114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3): 309-314 (1996) and PCT/US96/10287), carbohydrate libraries (see, e.g., Liang et al., *Science*, 274: 1520-1522 (1996) and U.S. Pat. No. 5,593,853). The methods above may be used to synthesize single molecular species.

The terms "a" or "an," as used in herein means one or more. In addition, the phrase "substituted with a [n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. In some embodiments of the compositions or methods described herein, treating cancer includes slowing the rate of growth or spread of cancer cells, reducing metastasis, or reducing the growth of metastatic tumors. The term "treating" and conjugations thereof, include prevention of an injury, pathology, condition, or disease.

An "effective amount" is an amount sufficient to accomplish a stated purpose relative to the compound or absence of the compound (e.g. achieve the effect for which it is administered, treat a disease, reduce enzyme activity, increase enzyme activity, reduce signaling pathway, reduce one or more symptoms of a disease or condition (e.g. reduce GTPase activity in a cell, increase GTPase activity, reduce signaling pathway stimulated by GTP bound Ras (e.g. K-Ras), reduce the signaling pathway activity of Ras, reduce the signaling pathway activity of K-Ras, reduce the signaling pathway activity of K-Ras4A, reduce the signaling pathway activity of K-Ras4B, reduce the signaling pathway activity of H-Ras, reduce the signaling pathway activity of N-Ras, reduce the signaling pathway activity of K-Ras G12C, reduce the signaling pathway activity of K-Ras G13C, reduce the signaling pathway activity of K-Ras G13D, reduce the signaling pathway activity of K-Ras G12D, reduce the signaling pathway activity of a mutant K-Ras, increase the activity of Ras, increase the activity of K-Ras, increase the activity of K-Ras4A, increase the activity of K-Ras4B, increase the activity of H-Ras, increase the activity of N-Ras, increase the activity of K-Ras G12C, increase the activity of K-Ras G13C, increase the activity of K-Ras G12D, increase the activity of K-Ras G13D, increase the activity of a mutant K-Ras, inhibit the binding of K-Ras to SOS, inhibit the binding of K-Ras to a GEF, inhibit nucleotide exchange). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist (e.g. disrupt the protein-protein interaction between K-Ras and a signaling pathway binding protein such as PI3K, disrupt the interaction of K-Ras and GEF, disrupt the interaction of K-Ras and SOS, disrupt the interaction of K-Ras with Raf). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity (e.g. GTPase activity, protein-protein interaction, signaling pathway) of a protein (e.g. Ras, K-Ras, mutant K-Ras, K-Ras G12C, K-Ras G12D, K-Ras G13C, K-Ras G13D) in the absence of a compound as described herein (including embodiments, examples, Table 1, 2, 3, 4, or 5).

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme (e.g. Ras, K-Ras, H-Ras, N-Ras, K-Ras4A, K-Ras4B, mutant Ras, mutant K-Ras, K-Ras G12C, K-Ras G13C, K-Ras G12D, K-Ras G13D). In some embodiments, the protein may be K-Ras. In some embodiments, the protein may be a mutant K-Ras (e.g. K-Ras G12C, K-Ras G13C, K-Ras G12D, K-Ras G13D). In some embodiments, the protein may be K-Ras4A. In some embodiments, the protein may be K-Ras4B. In some embodiments contacting includes allowing a compound described herein to interact with a protein or enzyme that is involved in a signaling pathway. In some embodiments contacting includes allowing a compound described herein to interact with a Switch 2—Binding Pocket.

As defined herein, the term "inhibition", "inhibit", "inhibiting" and the like in reference to a protein-inhibitor interaction means negatively affecting (e.g. decreasing) the activity or function of the protein (e.g. decreasing the signaling pathway stimulated by GTP bound Ras (e.g. K-Ras, K-Ras G12C, K-Ras G13C, K-Ras G12D, K-Ras G13D), nucleotide exchange, effector protein binding, effector protein activation, guanine exchange factor (GEF) binding, SOS binding, GEF-facilitated nucleotide exchange, phosphate release, nucleotide release, nucleotide binding) relative to the activity or function of the protein in the absence of the inhibitor (e.g. mutant K-Ras inhibitor, activitated K-Ras inhibitor). In some embodiments inhibition refers to reduction of a disease or symptoms of disease. In some embodiments, inhibition refers to a reduction in the activity of a signal transduction pathway or signaling pathway (e.g. reduction of a pathway involving GTP bound Ras (e.g. K-Ras, K-Ras G12C, K-Ras G13C, K-Ras G12D, K-Ras G13D), reduction of a pathway involving mutant K-Ras (e.g. K-Ras G12C, K-Ras G13C, K-Ras G12D, K-Ras G13D)). Thus, inhibition includes, at least in part, partially or totally blocking stimulation, decreasing, preventing, or delaying activation, or inactivating, desensitizing, or downregulating the signaling pathway or enzymatic activity or the amount of a protein (e.g. K-Ras, K-Ras G12C, K-Ras G13C, K-Ras G12D, K-Ras G13D). In some embodiments, inhibition refers to inhibition of interactions of Ras (K-Ras, K-Ras G12C, K-Ras G13C, K-Ras G12D, K-Ras G13D) with signaling pathway binding partners (e.g. PI3K, SOS, Raf). In some embodiments, inhibition refers to inhibition of interactions of Ras with a GEF (e.g. SOS).

The term "modulator" refers to a composition that increases or decreases the level of a target molecule or the function (e.g. GTPase activity, nucleotide exchange, effector protein binding, effector protein activation, guanine exchange factor (GEF) binding, SOS binding, GEF-facilitated nucleotide exchange, phosphate release, nucleotide release, nucleotide binding) of a target molecule or the physical state (e.g. Ras subcellular localization, Ras post-translational processing, Ras post-translational modifications) of the target of the molecule (e.g. a target may be K-Ras and the function may be to hydrolyze GTP or activate a signaling pathway that is activated by GTP bound K-Ras, interaction of K-Ras with protein binding partners (e.g. PI3K, SOS, Raf)). In some embodiments, a GTPase modulator is a compound that reduces the activity of a GTPase in a cell. In some embodiments, a GTPase modulator is a compound that increases the activity of a GTPase in a cell. In some embodiments, a GTPase modulator is a compound that reduces the signaling pathway in a cell that is activated by the GTP bound form of Ras. In some embodiments, a GTPase modulator is a compound that increases the signaling pathway in a cell that is activated by the GTP bound form of Ras. In some embodiments, a K-Ras disease modulator is a compound that reduces the severity of one or more symptoms of a disease associated with K-Ras (e.g. cancer, metastatic cancer). A K-Ras modulator is a compound that increases or decreases the activity or function or level of activity or level of function of K-Ras or level of K-Ras or level of K-Ras in a particular physical state. A mutant K-Ras modulator is a compound that that increases or decreases the activity or function or level of activity or level of function of mutant K-Ras or level of mutant K-Ras or level of mutant K-Ras in a particular physical state. A K-Ras G12C modulator, K-Ras G12D modulator, K-Ras G13C modulator, or K-Ras G13D modulator is a compound that increases or decreases the activity or function or level of activity or level of function of that particular mutant K-Ras or level of that particular mutant K-Ras or level of that particular mutant K-Ras in a particular physical state. A K-Ras inhibitor is a compound that decreases the activity or function or level of activity or level of function of K-Ras or level of K-Ras or level of K-Ras in a particular physical state. A mutant K-Ras inhibitor is a compound that that decreases the activity or function or level of activity or level of function of mutant K-Ras or level of mutant K-Ras or level of mutant K-Ras in a particular physical state. A K-Ras G12C inhibitor, K-Ras G12D inhibitor, K-Ras G13C inhibitor, or K-Ras G13D inhibitor is a compound that decreases the activity or function or level of activity or level of function of that particular mutant K-Ras or level of that particular mutant K-Ras or level of that particular mutant K-Ras in a particular physical state.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. In some embodiments, the disease is a disease related to (e.g. caused by) a mutant Ras. In some embodiments, the disease is a disease related to (e.g. caused by) a mutant K-Ras (e.g. K-Ras G12C, G13C, G12D, or G13D) or aberrant K-Ras signaling pathway activity (e.g. lung cancer, breast cancer, colon cancer, colorectal cancer, pancreatic cancer, leukemia). Examples of diseases, disorders, or conditions include, but are not limited to cancer. Examples of diseases, disorders, or conditions include, but are not limited to MYH-associated polyposis. In some instances, "disease" or "condition" refers to cancer. In some instances, "disease" or "condition" refers to MYH-associated polyposis. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

"Ras associated cancer" (also referred to herein as "Ras related cancer") refers to a cancer caused by aberrant Ras activity or signaling. A "cancer associated with aberrant K-Ras activity" (also referred to herein as "K-Ras related cancer") is a cancer caused by aberrant K-Ras activity or signaling (e.g. a mutant K-Ras). K-Ras related cancers may include lung cancer, non-small cell lung cancer, breast cancer, leukemia, pancreatic cancer, colon cancer, colorectal cancer. Other cancers that are associated with aberrant activity of one or more of Ras, K-Ras, H-Ras, N-Ras, mutant K-Ras (including K-Ras G12C, K-Ras G13C, K-Ras G12D, K-Ras G13D mutants), mutant N-Ras, and mutant H-Ras are well known in the art and determining such cancers are within the skill of a person of skill in the art.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "administer (or administering) a Ras inhibitor" means administering a compound that inhibits the activity or level (e.g. amount) or level of a signaling pathway of one or more Ras proteins (e.g. a Ras inhibitor, K-Ras inhibitor, N-Ras inhibitor, H-Ras inhibitor, mutant K-Ras inhibitor, K-Ras G12C inhibitor, K-Ras G13C inhibitor, K-Ras G12D inhibitor, K-Ras G13D inhibitor) to a subject. Administration may include, without being limited by mechanism, allowing sufficient time for the Ras inhibitor to reduce the activity of one or more Ras proteins or for the Ras inhibitor to reduce one or more symptoms of a disease (e.g. cancer, wherein the Ras inhibitor may arrest the cell cycle, slow the cell cycle, reduce DNA replication, reduce cell replication, reduce cell growth, reduce metastasis, or cause cell death). The term "administer (or administering) a K-Ras inhibitor" means administering a compound that inhibits the activity or level (e.g. amount) or level of a signaling pathway of one or more K-Ras proteins (K-Ras, mutant K-Ras, K-Ras G12C, K-Ras G12D, K-Ras G13C, K-Ras G13D).

The term "associated" or "associated with" in the context of a substance or substance activity or function associated with a disease (e.g. a protein associated disease, a cancer associated with aberrant Ras activity, K-Ras associated cancer, mutant K-Ras associated cancer, activated K-Ras associated cancer, K-Ras G12C associated cancer, K-Ras G13C associated cancer, K-Ras G12D associated cancer, K-Ras G13D associated cancer) means that the disease (e.g. cancer) is caused by (in whole or in part), or a symptom of the disease is caused by (in whole or inpart) the substance or substance activity or function. For example, a cancer associated with aberrant Ras activity or function may be a cancer that results (entirely or partially) from aberrant Ras activity or function (e.g. enzyme activity, protein-protein interaction, signaling pathway) or a cancer wherein a particular symptom of the disease is caused (entirely or partially) by aberrant Ras activity or function. As used herein, what is described as being associated with a disease, if a causative agent, could be a target for treatment of the disease. For example, a cancer associated with aberrant Ras activity or function or a Ras associated cancer, may be treated with a Ras modulator or Ras inhibitor, in the instance where increased Ras activity or function (e.g. signaling pathway activity) causes the cancer. For example, a cancer associated with K-Ras G12C may be a cancer that a subject with K-Ras G12C is at higher risk of developing as compared to a subject without K-Ras G12C.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "electrophilic chemical moiety" is used in accordance with its plain ordinary chemical meaning and refers to a monovalent chemical group that is electrophilic.

The term "Ras" refers to one or more of the family of human Ras GTPase proteins (e.g. K-Ras, H-Ras, N-Ras). The term "K-Ras" refers to the nucleotide sequences or proteins of human K-Ras (e.g. human K-Ras4A (NP_203524.1), human K-Ras4B (NP_004976.2), or both K-Ras4A and K-Ras4B). The term "K-Ras" includes both the wild-type form of the nucleotide sequences or proteins as well as any mutants thereof. In some embodiments, "K-Ras" is wild-type K-Ras. In some embodiments, "K-Ras" is one or more mutant forms. The term "K-Ras" XYZ refers to a nucleotide sequence or protein of a mutant K-Ras wherein the Y numbered amino acid of K-Ras that has an X amino acid in the wildtype instead has a Z amino acid in the mutant (e.g. K-Ras G12C has a G in wildtype protein but a C in the K-Ras G12C mutant protein). In some embodiments K-Ras refers to K-Ras4A and K-Ras4B. In some embodiments, K-Ras refers to K-Ras4A. In some embodiments, K-Ras refers to K-Ras4B.

The term "Ras inhibitor test compound" as used herein refers to a compound that is being characterized in an assay for the ability to inhibit an activity, function, or level (e.g. amount) of a Ras protein. The term "K-Ras inhibitor test compound" as used herein refers to a compound that is being characterized in an assay for the ability to inhibit an activity, function, or level (e.g. amount) of K-Ras protein. A "Switch 2—Binding Pocket covalent inhibitor test compound" is a Ras inhibitor test compound that binds to a Ras Switch 2—Binding Pocket and is being tested for the ability to covalently inhibit an activity, function, or level (e.g. amount) of a Ras protein.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components. For example, binding of a K-Ras with a compound as described herein may result in a change in one or more protein-protein interactions of the K-Ras, resulting in changes in cell growth, proliferation, or survival.

An amino acid residue in a protein "corresponds" to a given residue when it occupies the same essential structural position within the protein as the given residue. For example, a selected residue in a selected protein corresponds to Gly 12 of Human K-Ras4A or Human K-Ras 4B or both when the selected residue occupies the same essential spatial or other structural relationship as Gly 12 in Human K-Ras4A or Human K-Ras 4B or both. In some embodiments, where a selected protein is aligned for maximum homology with the Human K-Ras4A or Human K-Ras 4B protein, the position in the aligned selected protein aligning with Gly 12 is said to correspond to Gly 12. Instead of a primary sequence alignment, a three dimensional structural alignment can also be used, e.g., where the structure of the selected protein is aligned for maximum correspondence with the Human K-Ras4A or Human K-Ras 4B protein and the overall structures compared. In this case, an amino acid that occupies the same essential position as Gly 12 in the structural model is said to correspond to the Gly 12 residue.

The terms "unsubstituted vinyl sulfone moiety", "unsubstituted vinyl sulfonamide moiety", "unsubstituted fluoro $(C_1-C_4)$ alkylketone moiety", "unsubstituted chloro$(C_1-C_4)$ alkylketone moiety", "unsubstituted acrylamide moiety", "unsubstituted disulfide moiety", "unsubstituted thiol moiety", "unsubstituted phosphonate moiety", "unsubstituted aldehyde moiety", "unsubstituted enone moiety", "unsubstituted diazomethylketone moiety", "unsubstituted diazomethylamide moiety", "unsubstituted cyanocyclopropyl carboxamide moiety", "unsubstituted epoxide moiety", "unsubstituted epoxyketone moiety", "unsubstituted epoxyamide moiety", "unsubstituted aryl aldehyde moiety", "unsubstituted aryl dialdehyde moiety", "unsubstituted dialdehyde moiety", "unsubstituted nitrogen mustard moiety", "unsubstituted propargyl moiety", or "unsubstituted propargylamide moiety" are used according to their plain ordinary chemical meaning and refer to those monovalent chemical groups named having the lowest molecular weight for each such group while obeying the rules of chemical valency. A substituted form of one of the named groups may be substituted with one or more of any of the substituent groups described herein while obeying the rules of chemical valency.

"Switch 2," as used herein, refers to a protein domain of a Ras protein (e.g. K-Ras) formed by residues corresponding to residues 60-76 of K-Ras (e.g. K-Ras Switch 2 refers to residues 60-76 of K-Ras). A "Switch 2 Binding Region" is a region of a Ras protein (e.g. K-Ras) that is formed by amino acid residues that contact at least a portion of Switch 2 when Ras is bound to GTP. A "Switch 2—Binding Pocket" or "S2BP" is a cavity bound (the limits or boundaries of which are made), at least in part, by the amino acid residues that form Switch 2 and the Switch 2 Binding Region. In some embodiments, a "Switch 2—Binding Pocket" or "S2BP" is a cavity, in the GDP bound form of Ras (e.g. K-Ras), bound (the limits or boundaries of which are made), at least in part, by the amino acid residues that form Switch 2 and the Switch 2 Binding Region.

In some embodiments, the Switch 2—Binding Pocket is bound at least in part by one or more of V7, V9, G10, P34, T58, G60, Q61, E62, E63, $R^{68}$, Y71, M72, Y96, Q99, and/or 1100 of K-Ras or equivalent residues in homologous, related (e.g. H-Ras, N-Ras), or mutant Ras proteins. In some embodiments, the S2BP is bound at least in part by an amino acid residue shown to be interacting with the JO-01-189cbut compound in FIG. 4B or contributing to the surface contacting the JO-01-189cbut compound in FIG. 4A. In some embodiments, the S2BP is bound at least in part by the left portion of the proximity contour in FIG. 7 or 8. A compound as described herein (including embodiments, examples, and compounds of Table 1, 2, 3, 4, or 5), which binds to amino acids that form or contacts amino acids that form the Switch 2—Binding Pocket is a "Switch 2-Binding Pocket binding compound" and a moiety of a compound that binds to amino acids that form or contacts amino acids that form the Switch 2—Binding Pocket is a "Switch 2—Binding Pocket binding moiety".

In some embodiments, a Switch 2—Binding Pocket binding compound or Switch 2—Binding Pocket binding moiety binds or contacts one amino acid that forms the Switch 2—Binding Pocket. In some embodiments, a Switch 2—Binding Pocket binding compound or Switch 2—Binding Pocket binding moiety binds or contacts multiple amino acids that form the Switch 2—Binding Pocket. In some embodiments, a Switch 2—Binding Pocket binding compound or Switch 2 Binding Pocket binding moiety binds or contacts one K-Ras amino acid selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts multiple K-Ras amino acids selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts two K-Ras amino acids selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts three K-Ras amino acids selected from V7, V9, G10, P34, T58, G60, Q61, E62, E63, $R^{68}$, Y71, M72, Y96, Q99, and I100. In some embodiments, a Switch 2 Binding Pocket binding compound or Switch 2—Binding Pocket binding moiety binds or contacts four K-Ras amino acids selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts five K-Ras amino acids selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts six K-Ras amino acids selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts seven K-Ras amino acids selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts eight K-Ras amino acids selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts nine K-Ras amino acids selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts ten K-Ras amino acids selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts eleven K-Ras amino acids selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts twelve K-Ras amino acids selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts thirteen K-Ras amino acids selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts fourteen K-Ras amino acids selected from V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts fifteen K-Ras amino acids selected from V7, V9, G10, P34, T58, G60, Q61, E62, E63, $R^{68}$, Y71, M72, Y96, Q99, and I100.

In some embodiments, a Switch 2—Binding Pocket binding compound or Switch 2—Binding Pocket binding moiety binds or contacts one amino acid selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts multiple K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts two K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts three K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts four K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts five K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts six K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts seven K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts eight K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts nine K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts ten K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts eleven K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts twelve K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts thirteen K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts fourteen K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100. In some embodiments, a Switch 2—Binding Pocket binding compound or Switch 2—Binding Pocket binding moiety binds or contacts fifteen K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, $R^{68}$, Y71, M72, Y96, Q99, and I100.

Compounds

In a first aspect is provided a compound which is capable of reacting with an amino acid residue of a Ras protein (including K-Ras, N-Ras and H-Ras proteins). For example, the compound may contact a residue of a Ras protein Switch 2 binding pocket. For example, where the residue of the Switch 2 binding pocket that contacts the compound may be V7, V9, G10, P34, T58, G60, Q61, E62, E63, $R^{68}$, Y71, M72, Y96, Q99, or I100. In some embodiments, the compound interacts with at least one of G60, E62, or E63.

In some embodiments, the compound covalently reacts with an amino acid residue of the Ras protein to form a covalent bond (e.g. reversible or irreversible). For example the amino acid residue is a cysteine, aspartate, lysine, tyrosine or glutamate residue of the Ras protein. In some embodiments, the amino acid residue is a cysteine residue, for example a G12C or G13C residue of a K-Ras protein. In some embodiments, the amino acid residue is an aspartate residue, for example a G12D or G13D residue of a K-Ras protein.

In some embodiments, a compound having the formula $R^1$-$L^1$-$L^2$-$L^3$-E is provided. $R^1$ is a Switch 2—Binding Pocket binding moiety. $L^1$ is a bond or a divalent radical chemical linker. $L^2$ is a bond or a divalent radical chemical linker. $L^3$ is a bond or a divalent radical chemical linker. E is an electrophilic chemical moiety capable of forming a covalent bond with a Ras cysteine residue or a Ras aspartate residue. In some embodiments, Ras is a K-Ras. In some embodiments, the compound contacts a residue of K-Ras Switch 2. In some embodiments, wherein the compound contacts K-Ras, $R^1$ contacts V7, V9, G10, P34, T58, G60, Q61, E62, E63, $R^{68}$, Y71, M72, Y96, Q99, or I100. For example, $R^1$ contacts at least one of G60, E62, or E63. In some embodiments, the compound does not contact the residues of K-Ras that contact GTP. In some embodiments, the compound does not contact the residues of K-Ras that contact the guanine of GTP or GDP. In some embodiments, the compound does not contact the residues of K-Ras that contact GDP. In some embodiments, the compound forms an irreversible covalent bond with a K-Ras cysteine residue. In some embodiments, the compound forms a reversible covalent bond with a K-Ras cysteine residue. In some embodiments, the compound forms an irreversible covalent bond with a K-Ras aspartate residue. In some embodiments, the compound forms a reversible covalent bond with a K-Ras aspartate residue. In some embodiments, $R^1$ contacts residues that contact Switch 2 in the GTP bound form of K-Ras. In some embodiments, $R^1$ contacts residues that contact Switch 2 in the GDP bound form of K-Ras. In some embodiments, $R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^1$ is substituted or unsubstituted cycloalkyl, substituted or unsubstituted heterocycloalkyl, substituted or unsubstituted aryl, or substituted or unsubstituted heteroaryl. In some embodiments, $R^1$ is substituted or unsubstituted aryl or substituted or unsubstituted heteroaryl. In some embodiments, $R^1$ is $R^3$-substituted or unsubstituted aryl or $R^3$-substituted or unsubstituted heteroaryl. In some embodiments, $R^1$ is $R^3$-substituted or unsubstituted fused ring aryl. In some embodiments, $R^1$ is $R^3$-substituted or unsubstituted fused ring heteroaryl.

In some embodiments, $R^1$ is

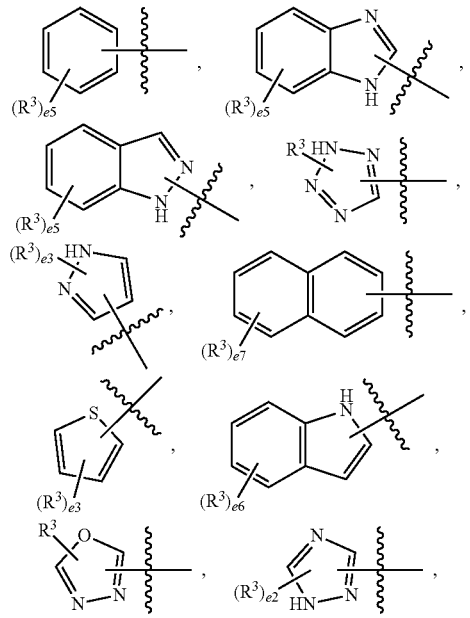

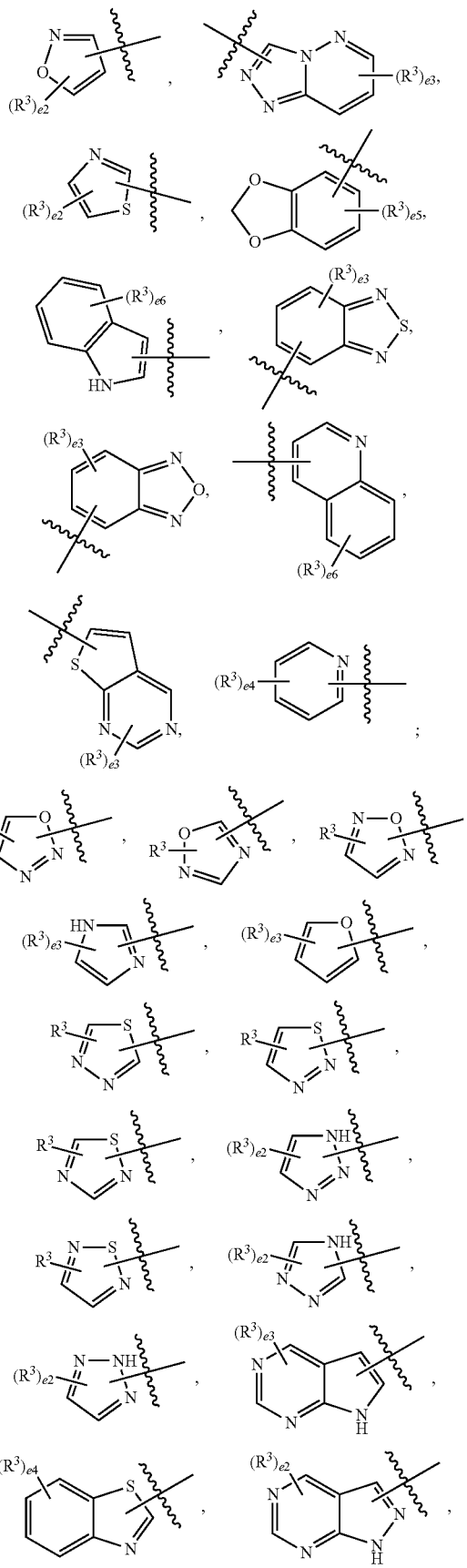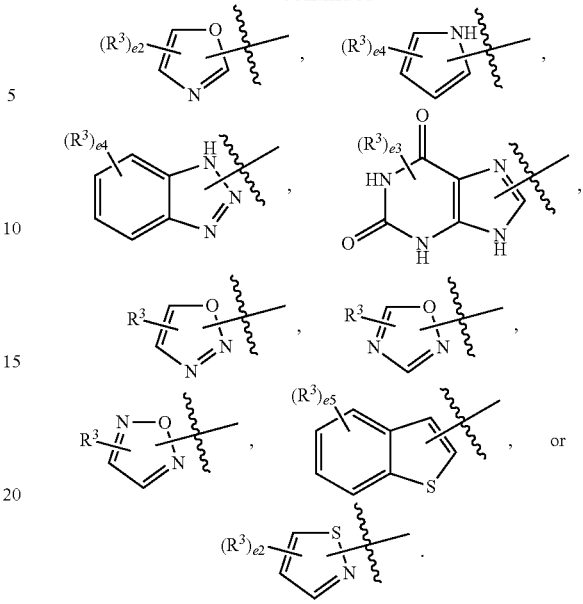

In some embodiments $R^1$ is $R^3$-substituted pyridinyl, $R^3$-substituted pyrimidinyl, $R^3$-substituted thiophenyl, $R^3$-substituted furanyl, $R^3$-substituted indolyl, $R^3$-substituted benzoxadiazolyl, $R^3$-substituted benzodioxolyl, $R^3$-substituted benzodioxanyl, $R^3$-substituted thianaphthanyl, $R^3$-substituted pyrrolopyridinyl, $R^3$-substituted indazolyl, $R^3$-substituted quinolinyl, $R^3$-substituted quinoxalinyl, $R^3$-substituted pyridopyrazinyl, $R^3$-substituted quinazolinonyl, $R^3$-substituted benzoisoxazolyl, $R^3$-substituted imidazopyridinyl, $R^3$-substituted benzofuranyl, $R^3$-substituted benzothiophenyl, $R^3$-substituted phenyl, $R^3$-substituted naphthyl, $R^3$-substituted biphenyl, $R^3$-substituted pyrrolyl, $R^3$-substituted pyrazolyl, $R^3$-substituted imidazolyl, $R^3$-substituted pyrazinyl, $R^3$-substituted oxazolyl, $R^3$-substituted isoxazolyl, $R^3$-substituted thiazolyl, $R^3$-substituted furylthienyl, $R^3$-substituted pyridyl, $R^3$-substituted pyrimidyl, $R^3$-substituted benzothiazolyl, $R^3$-substituted purinyl, $R^3$-substituted benzimidazolyl, $R^3$-substituted isoquinolyl, $R^3$-substituted thiadiazolyl, $R^3$-substituted oxadiazolyl, $R^3$-substituted pyrrolyl, $R^3$-substituted diazolyl, $R^3$-substituted triazolyl, $R^3$-substituted tetrazolyl, $R^3$-substituted benzothiadiazolyl, $R^3$-substituted isothiazolyl, $R^3$-substituted pyrazolopyrimidinyl, $R^3$-substituted pyrrolopyrimidinyl, $R^3$-substituted benzotriazolyl, or $R^3$-substituted quinolyl. In some embodiments $R^1$ is substituted pyridinyl, substituted pyrimidinyl, substituted thiophenyl, substituted furanyl, substituted indolyl, substituted benzoxadiazolyl, substituted benzodioxolyl, substituted benzodioxanyl, substituted thianaphthanyl, substituted pyrrolopyridinyl, substituted indazolyl, substituted quinolinyl, substituted quinoxalinyl, substituted pyridopyrazinyl, substituted quinazolinonyl, substituted benzoisoxazolyl, substituted imidazopyridinyl, substituted benzofuranyl, substituted benzothiophenyl, substituted phenyl, substituted naphthyl, substituted biphenyl, substituted pyrrolyl, substituted pyrazolyl, substituted imidazolyl, substituted pyrazinyl, substituted oxazolyl, substituted isoxazolyl, substituted thiazolyl, substituted furylthienyl, substituted pyridyl, substituted pyrimidyl, substituted benzothiazolyl, substituted purinyl, substituted benzimidazolyl, substituted isoquinolyl, substituted thiadiazolyl, substituted oxadiazolyl, substituted pyrrolyl, substituted diazolyl, substituted triazolyl, substituted tetrazolyl, substituted benzothiadiazolyl, substituted isothiazolyl, substituted pyrazolopyrimidinyl, substituted pyrrolopyrimidinyl, substituted benzotriazolyl, or substituted quinolyl.

In some embodiments $R^1$ is unsubstituted pyridinyl, unsubstituted pyrimidinyl, unsubstituted thiophenyl, unsubstituted furanyl, unsubstituted indolyl, unsubstituted benzoxadiazolyl, unsubstituted benzodioxolyl, unsubstituted benzodioxanyl, unsubstituted thianaphthanyl, unsubstituted pyrrolopyridinyl, unsubstituted indazolyl, unsubstituted quinolinyl, unsubstituted quinoxalinyl, unsubstituted pyridopyrazinyl, unsubstituted quinazolinonyl, unsubstituted benzoisoxazolyl, unsubstituted imidazopyridinyl, unsubstituted benzofuranyl, unsubstituted benzothiophenyl, unsubstituted phenyl, unsubstituted naphthyl, unsubstituted biphenyl, unsubstituted pyrrolyl, unsubstituted pyrazolyl, unsubstituted imidazolyl, unsubstituted pyrazinyl, unsubstituted oxazolyl, unsubstituted isoxazolyl, unsubstituted thiazolyl, unsubstituted furylthienyl, unsubstituted pyridyl, unsubstituted pyrimidyl, unsubstituted benzothiazolyl, unsubstituted purinyl, unsubstituted benzimidazolyl, unsubstituted isoquinolyl, unsubstituted thiadiazolyl, unsubstituted oxadiazolyl, unsubstituted pyrrolyl, unsubstituted diazolyl, unsubstituted triazolyl, unsubstituted tetrazolyl, unsubstituted benzothiadiazolyl, unsubstituted isothiazolyl, unsubstituted pyrazolopyrimidinyl, unsubstituted pyrrolopyrimidinyl, unsubstituted benzotriazolyl, or unsubstituted quinolyl.

$R^3$ is independently hydrogen, oxo, halogen, —$CX_3$, —CN, —$SO_2Cl$, —$SO_nR^{10}$, —$SO_vNR^7R^8$, —$NHNH_2$, —$ONR^7R^8$, —NHC=(O)$NHNH_2$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, —$NR^7SO_2R^{10}$, —$NR^{7c}$=(O) $R^9$, —$NR^{7c}$(O)—$OR^9$, —$NR^7OR^9$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^3$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl. Two $R^3$ substituents bonded to the same atom may optionally be joined to form a substituted or unsubstituted cycloalkyl or substituted or unsubstituted heterocycloalkyl. In some embodiments, $R^3$ is methyl, —Cl, —$NH_2$, —I, —CCH, —$CH_2CH_2OH$, —$OCH_2CCH$, —$CF_3$, —$OCH_3$, —OH, —$CH_2CH_3$, —NHS(O)$_2CH_3$, —$CH_2NH_2$, —Br, isoxazolyl, —NHC(O)OC(CH$_3$)$_3$, p-chlorophenyl, thiophenyl, —F, pyrazolyl, —$CH_2OH$, —C(O)$NHCH_2CH_2OH$, —$OCH_2CH_2OH$, —S(O)$_2NH_2$, tetrazolyl, —$CHCH_3OH$, —C(O)$CH_3$, —C(O)H, —$OCH_3$, —C(O) OH, —C(O)$OCH_3$, —C(O)$NH_2$, —N(CH$_3$)$_2$, —$CH_2NH_2$, —$CH_2NHC(O)$ $CH_3$, pyrrolidinyl, —$OCH_2CH_2NH_2$, —C(O) N(CH$_3$)$_2$, NHCH$_3$, —NHC(O)$CH_3$, —CN, —C(O)$OCH_3$, or

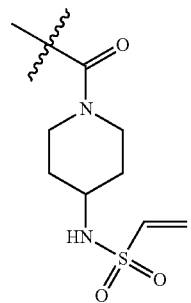

$R^7$, $R^8$, $R^9$, and $R^{10}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^7$, $R^8$, $R^9$, and $R^{10}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ and $R^8$ substituents bonded to the same nitrogen atom may optionally be joined to form a substituted or unsubstituted heterocycloalkyl or substituted or unsubstituted heteroaryl.

The symbol m is independently 1 or 2. The symbol v is independently 1 or 2. The symbol n is independently an integer from 0 to 4. The symbol X is independently —Cl, —Br, —I, or —F. In some embodiments v is 1. In other embodiments, v is 2. In some embodiments m is 1. In some embodiments m is 2. In some embodiments n is 0. In some embodiments n is 1. In some embodiments n is 2. In some embodiments n is 3. In some embodiments n is 4. In some embodiments, X is —Cl. In some embodiments, X is —Br. In some embodiments, X is —I. In some embodiments, X is —F.

The symbol e2 is independently an integer from 0 to 2. The symbol e3 is independently an integer from 0 to 3. The symbol e4 is independently an integer from 0 to 4. The symbol e5 is independently an integer from 0 to 5. The symbol e6 is independently an integer from 0 to 6. The symbol e7 is independently an integer from 0 to 7. The symbol f2 is independently an integer from 0 to 2. The symbol f6 is independently an integer from 0 to 6. The symbol f7 is independently an integer from 0 to 7. The symbol f8 is independently an integer from 0 to 8. The symbol f9 is independently an integer from 0 to 9. The symbol f10 is independently an integer from 0 to 10. The symbol f12 is independently an integer from 0 to 12. The symbol f14 is independently an integer from 0 to 14.

$L^1$, $L^2$ and $L^3$ are independently a bond, —$NR^{2C}$—, —O—, —S—, —C(O)—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker. In some embodiments, $L^1$ is a bond. In some embodiments, $L^2$ is a bond. In some embodiments, $L^3$ is a bond. In some embodiments, $L^1$ is substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker. In some embodiments, $L^2$ is substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker. In some embodiments, $L^3$ is substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker. In some embodiments, $L^1$ is —$NR^{2C}$—. In some embodiments, $L^1$ is —O—. In some embodiments, $L^1$ is —S—. In some embodiments, $L^1$ is —C(O)—. In some embodiments, $L^1$ is —S(O)—. In some embodiments, $L^1$ is —$S(O)_2$—. In some embodiments, $L^2$ is —$NR^{2C}$—. In some embodiments, $L^2$ is —O—. In some embodiments, $L^2$ is —S—. In some embodiments, $L^2$ is —C(O)—. In some embodiments, $L^2$ is—S(O)—. In some embodiments, $L^2$ is—$S(O)_2$—. In some embodiments, $L^3$ is —$NR^{2C}$—. In some embodiments, $L^3$ is —O—. In some embodiments, $L^3$ is —S—. In some embodiments, $L^3$ is —C(O)—. In some embodiments, $L^3$ is—S(O)—. In some embodiments, $L^3$ is—$S(O)_2$—. In some embodiments, $L^1$ is independently-$CR^{2A}R^{2B}$—. In some embodiments, $L^2$ is independently —$CR^{2A}R^{2B}$—. In some embodiments, $L^3$ is independently —$CR^{2A}R^{2B}$—. In some embodiments, $L^1$ is independently

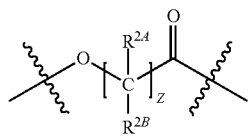

In some embodiments, $L^2$ is independently

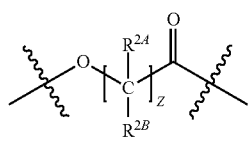

In some embodiments, $L^3$ is independently

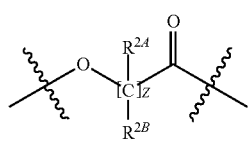

In some embodiments, $L^1$ is independently

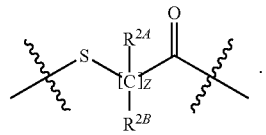

In some embodiments, $L^2$ is independently

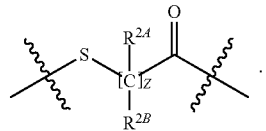

In some embodiments, $L^3$ is independently

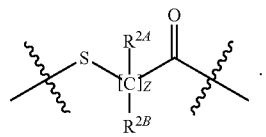

In some embodiments, $L^1$ is independently

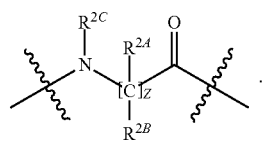

In some embodiments, $L^2$ is independently

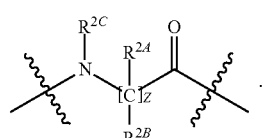

In some embodiments, $L^3$ is independently

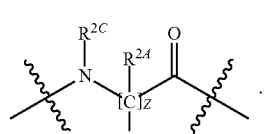

In some embodiments, $L^1$ is independently substituted or unsubstituted cycloalkylene, substituted or unsubstituted heterocycloalkylene, substituted or unsubstituted arylene, substituted or unsubstituted heteroarylene, or substituted or unsubstituted spirocyclic linker. In some embodiments, $L^1$ is independently $R^{2C}$-substituted or unsubstituted cycloalkylene, $R^{2C}$-substituted or unsubstituted heterocycloalkylene, $R^{2C}$-substituted or unsubstituted arylene, $R^{2C}$-substituted or unsubstituted heteroarylene, or $R^{2C}$-substituted or unsubstituted spirocyclic linker. In some embodiments, $L^1$ is independently

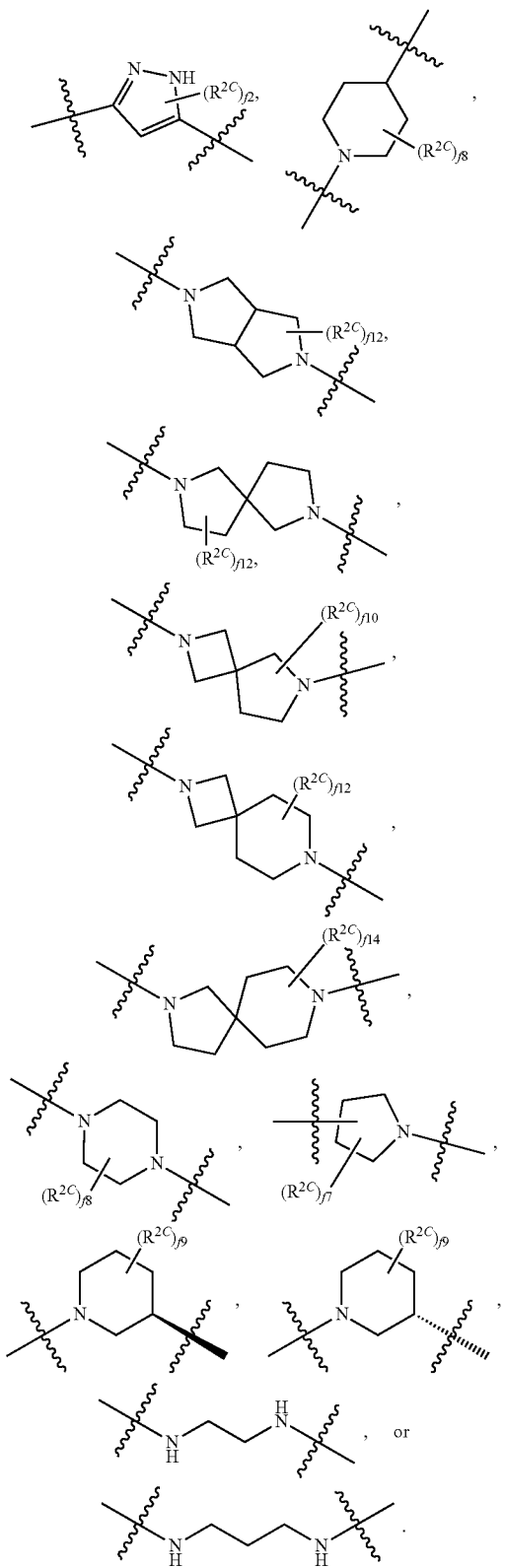

In some embodiments, $L^2$ is independently substituted or unsubstituted cycloalkylene, substituted or unsubstituted heterocycloalkylene, substituted or unsubstituted arylene, substituted or unsubstituted heteroarylene, or substituted or unsubstituted spirocyclic linker. In some embodiments, $L^2$ is independently $R^{2C}$-substituted or unsubstituted cycloalkylene, $R^{2C}$-substituted or unsubstituted heterocycloalkylene, $R^{2C}$-substituted or unsubstituted arylene, $R^{2C}$-substituted or unsubstituted heteroarylene, or $R^{2C}$-substituted or unsubstituted spirocyclic linker. In some embodiments, $L^2$ is independently -continued

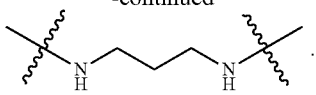

In some embodiments, L³ is independently substituted or unsubstituted cycloalkylene, substituted or unsubstituted heterocycloalkylene, substituted or unsubstituted arylene, substituted or unsubstituted heteroarylene, or substituted or unsubstituted spirocyclic linker. In some embodiments, L³ is independently $R^{2C}$-substituted or unsubstituted cycloalkylene, $R^{2C}$-substituted or unsubstituted heterocycloalkylene, $R^{2C}$-substituted or unsubstituted arylene, $R^{2C}$-substituted or unsubstituted heteroarylene, or $R^{2C}$-substituted or unsubstituted spirocyclic linker. In some embodiments, L³ is independently

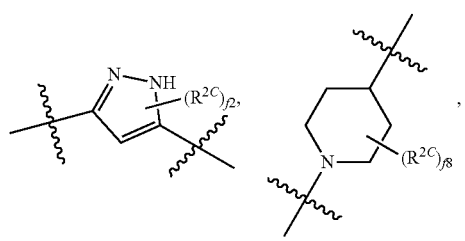

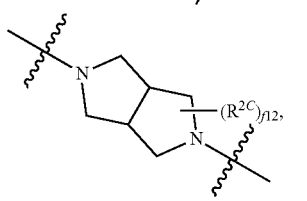

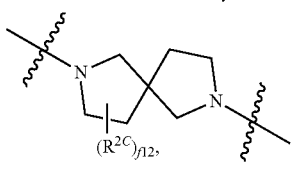

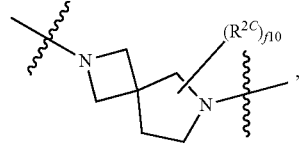

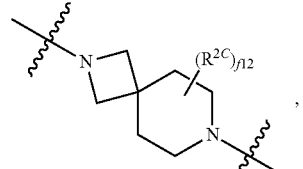

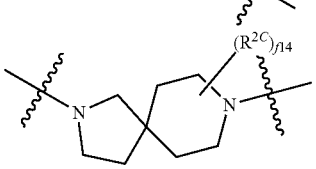

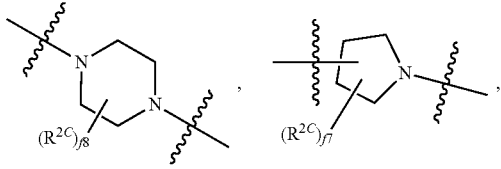

-continued

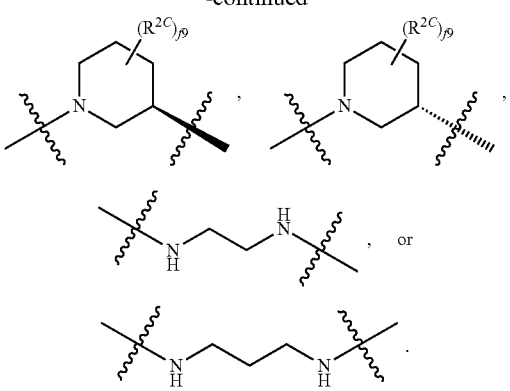

In some embodiments, L² is independently a bond, L³ is independently a bond, and L¹ is independently

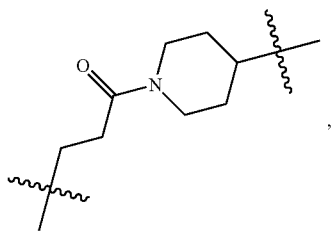

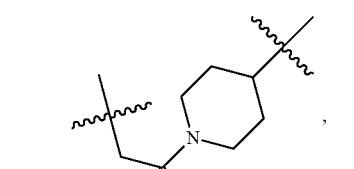

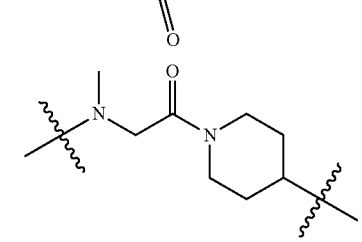

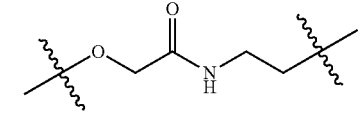

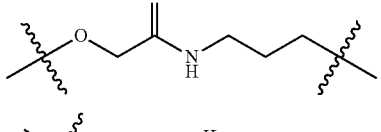

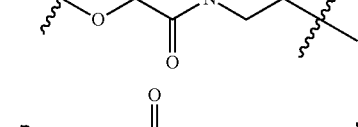

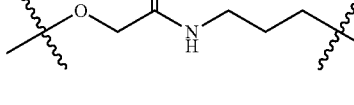

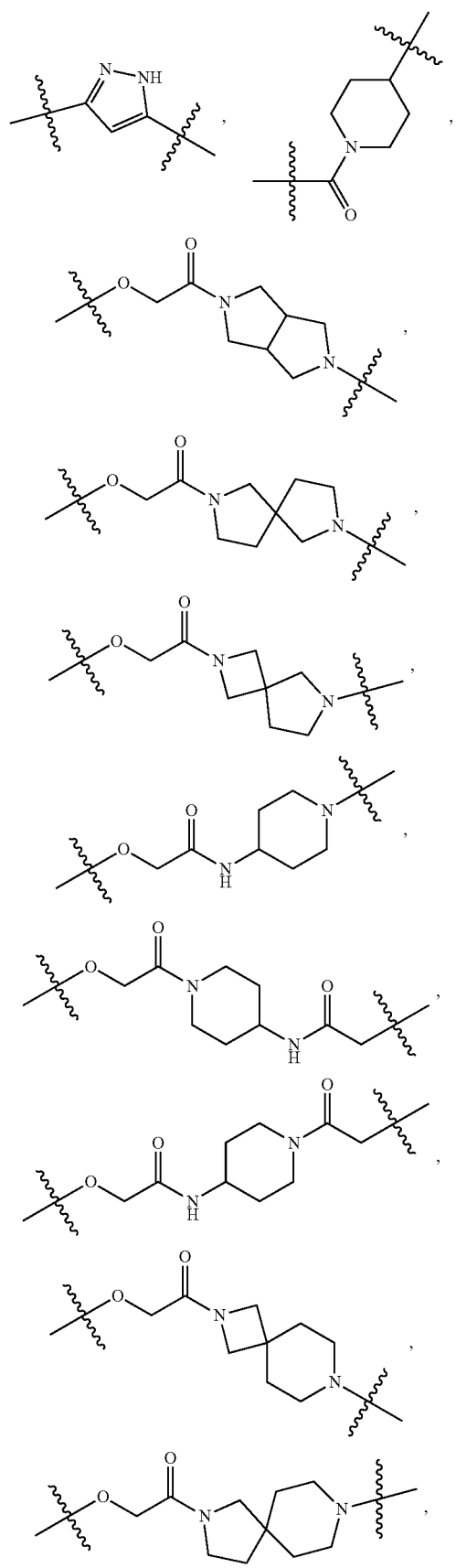
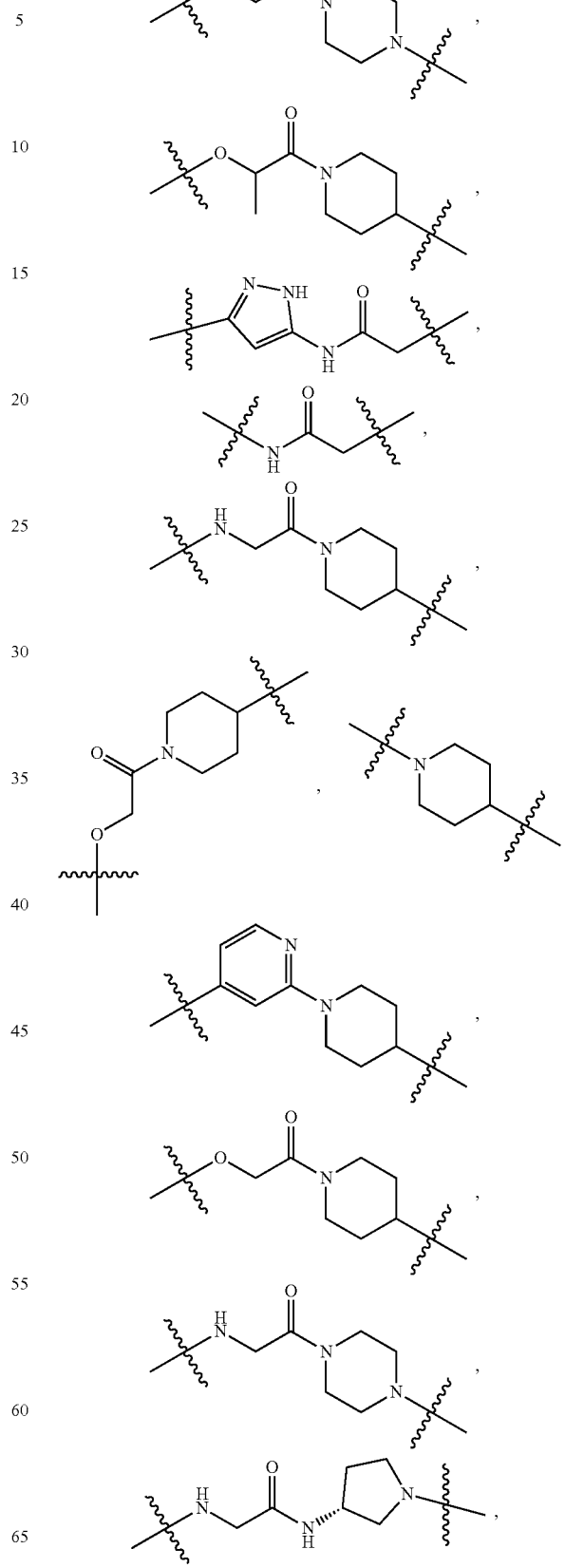

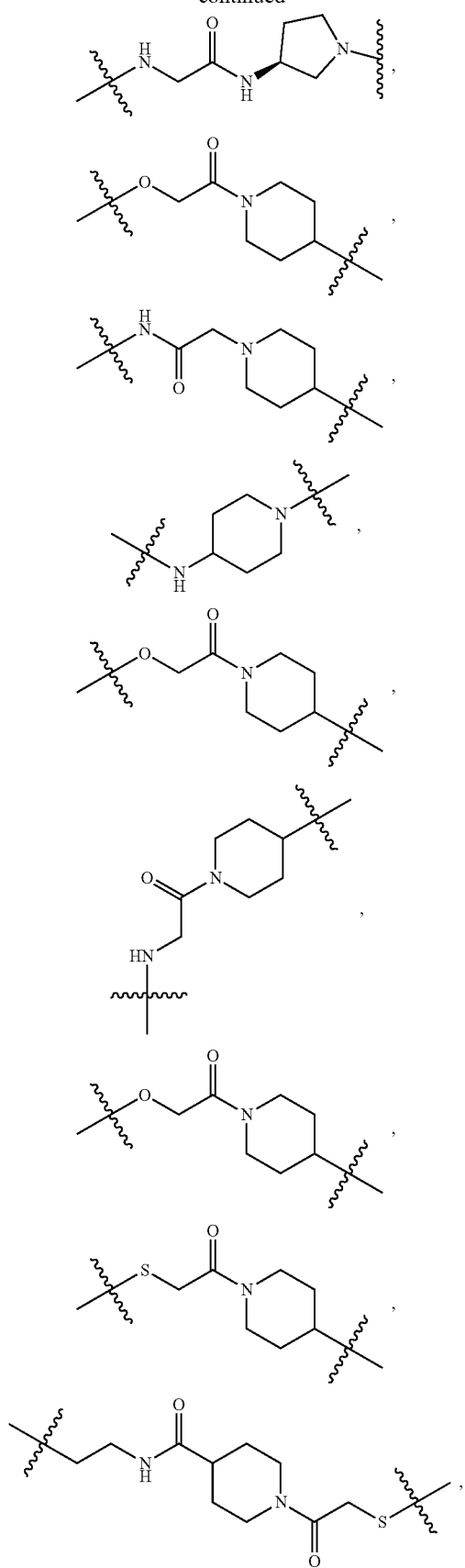
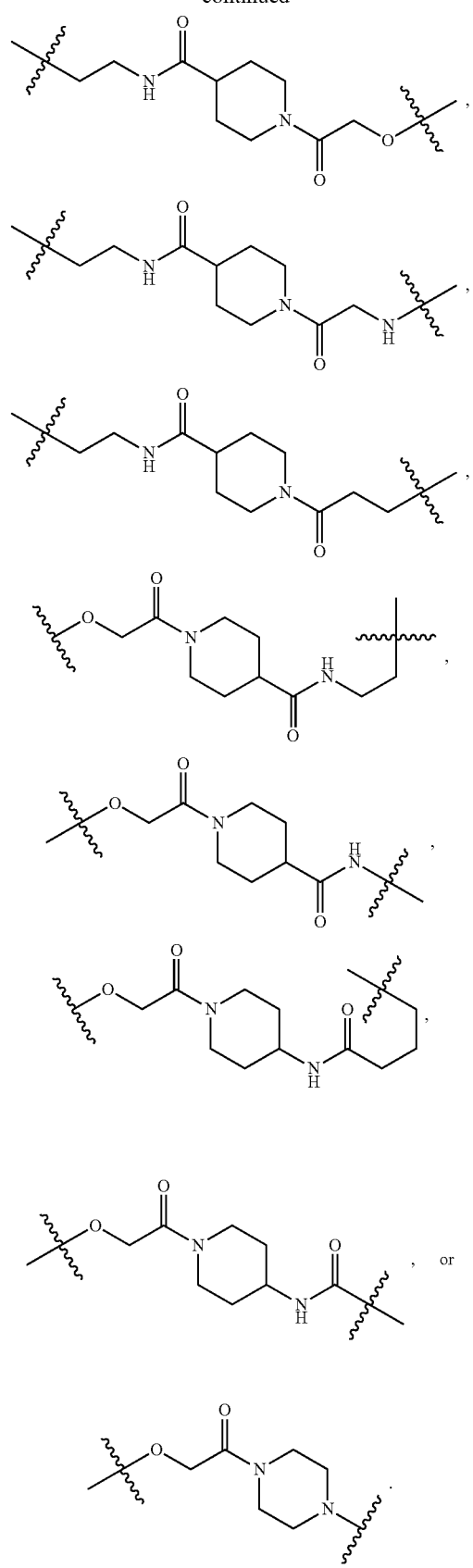

In some embodiments, $L^1$ is independently
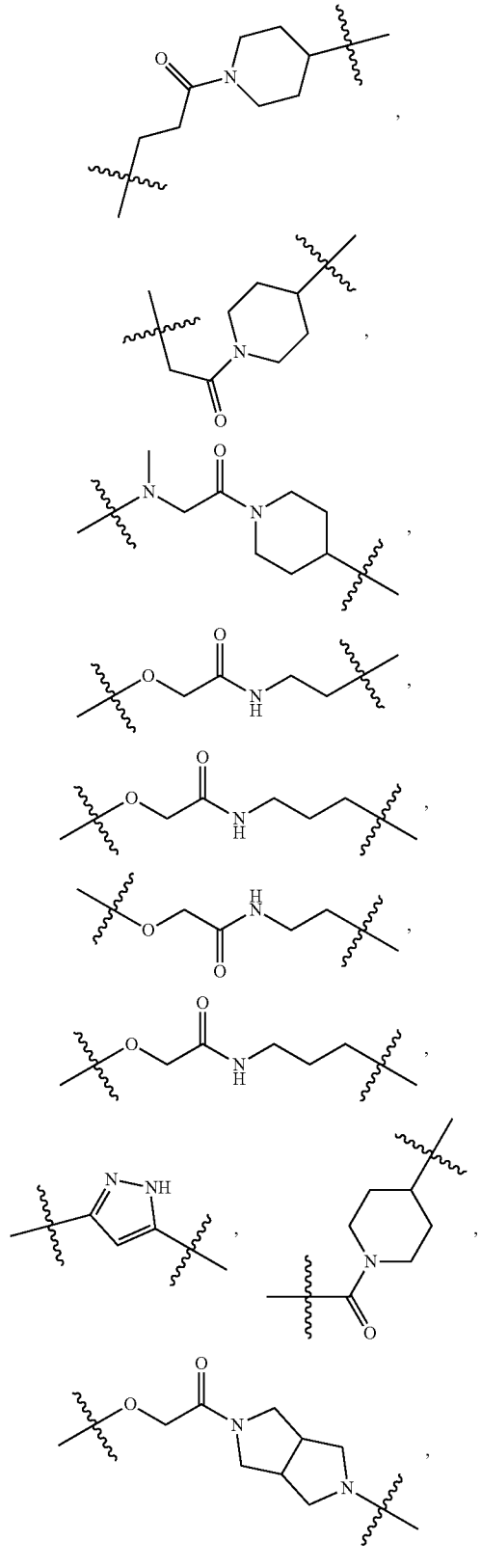
-continued
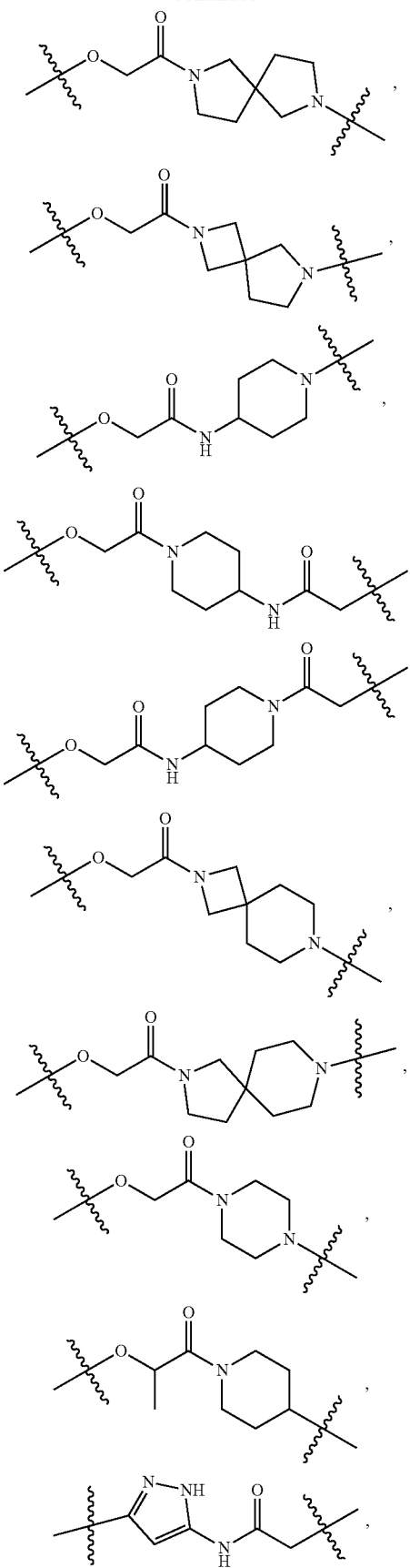

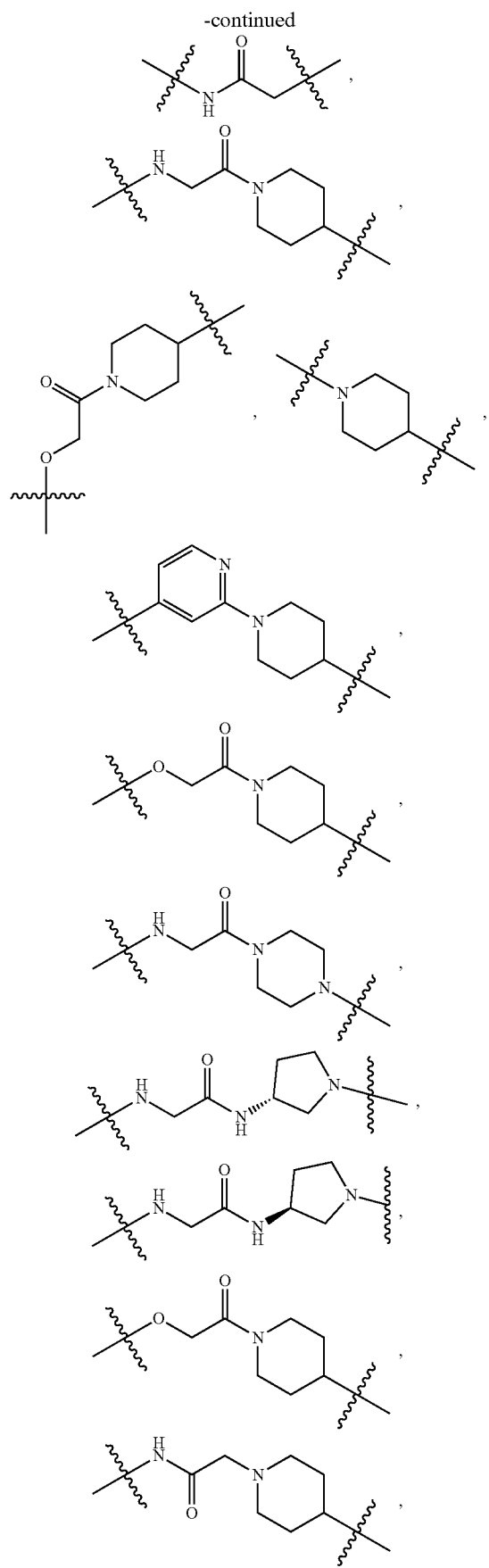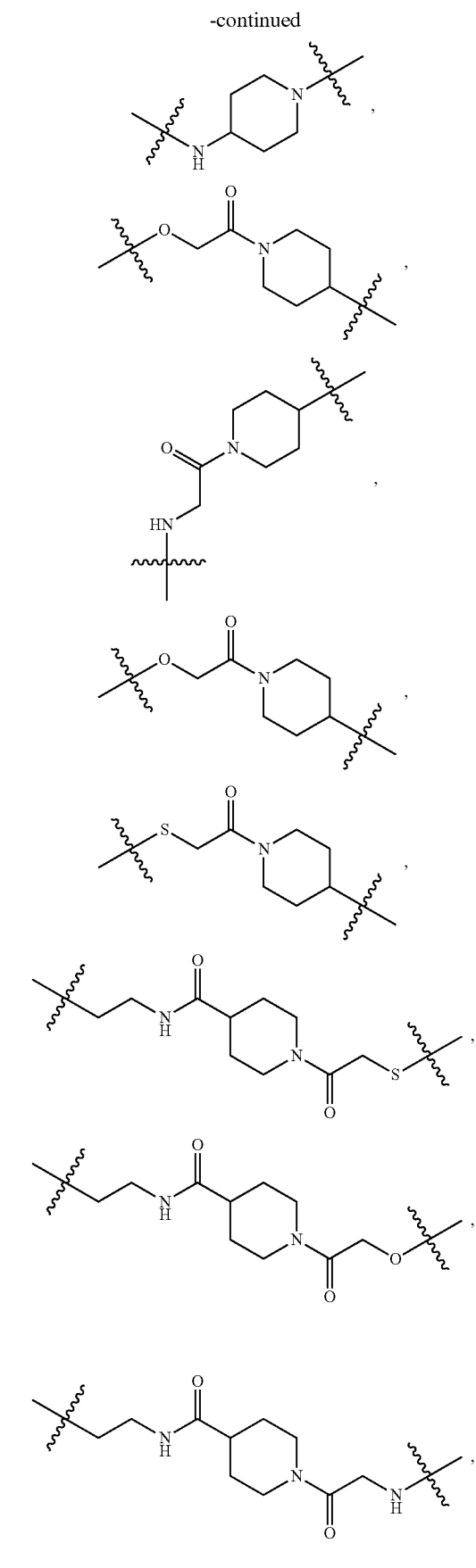

87
-continued
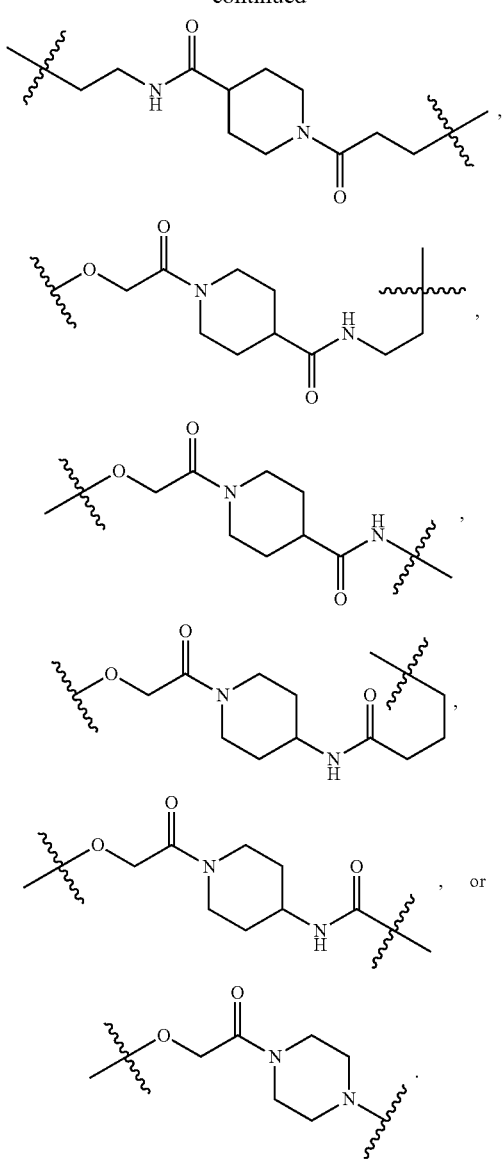
In some embodiments, L² is independently
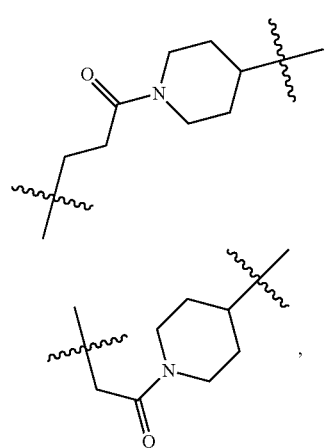
88
-continued
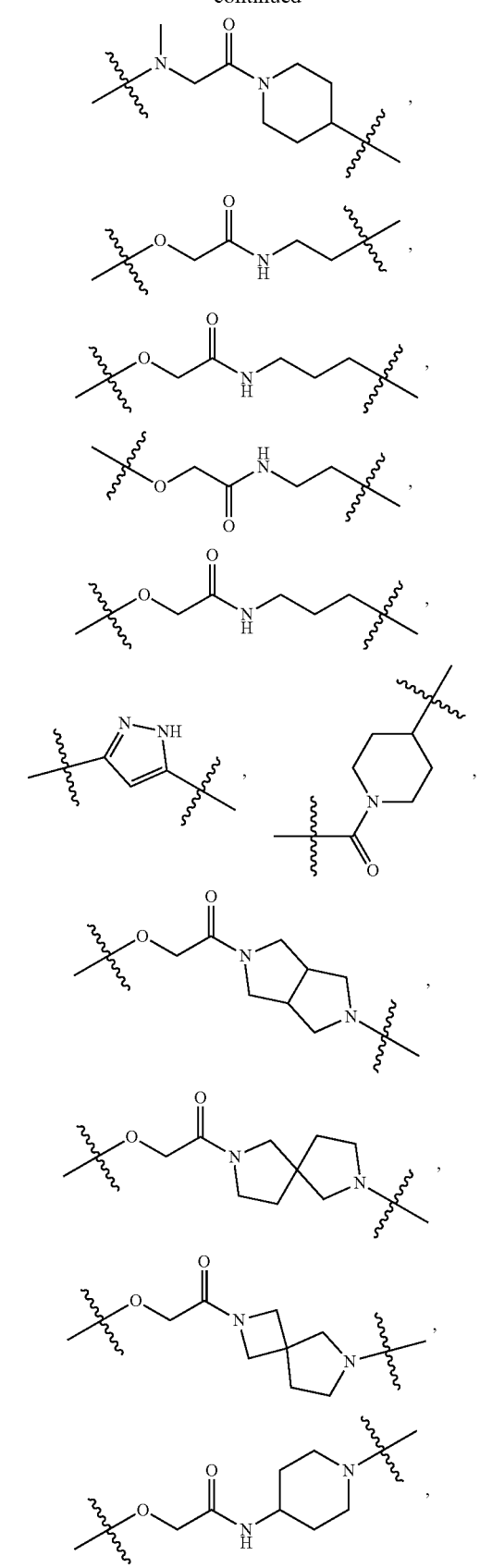

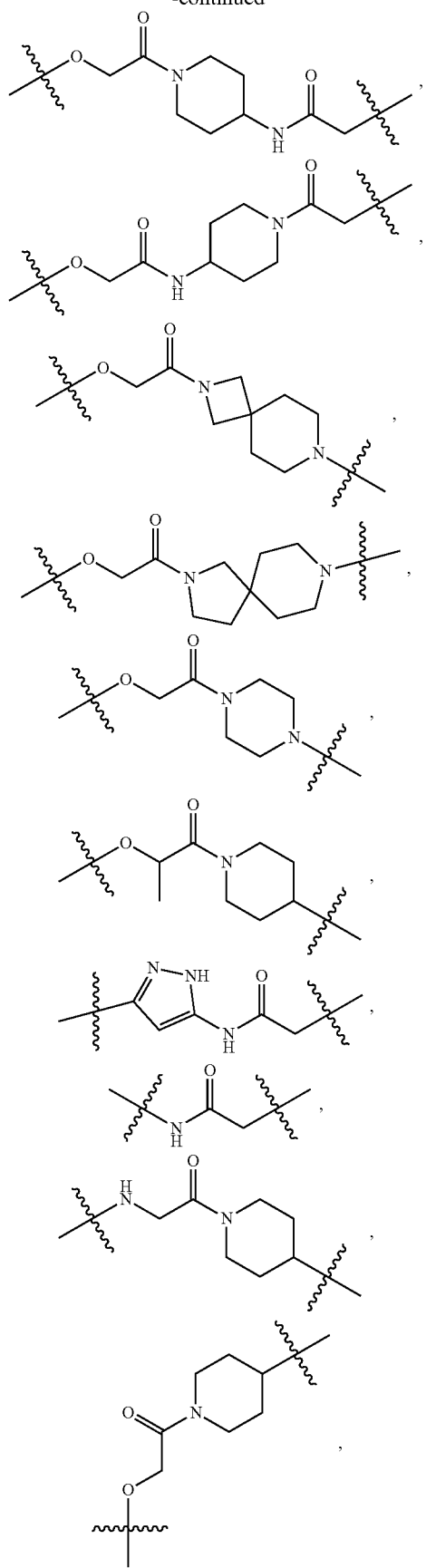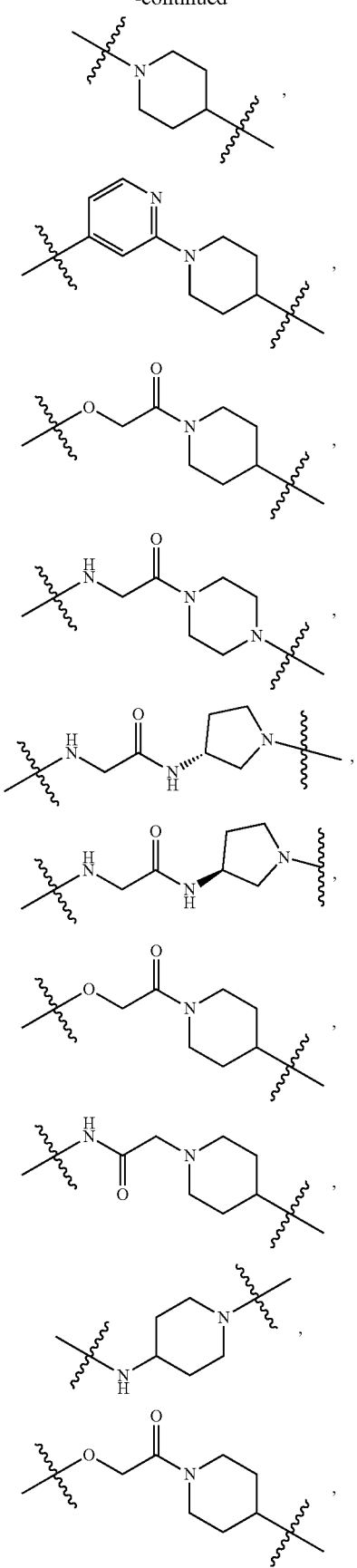

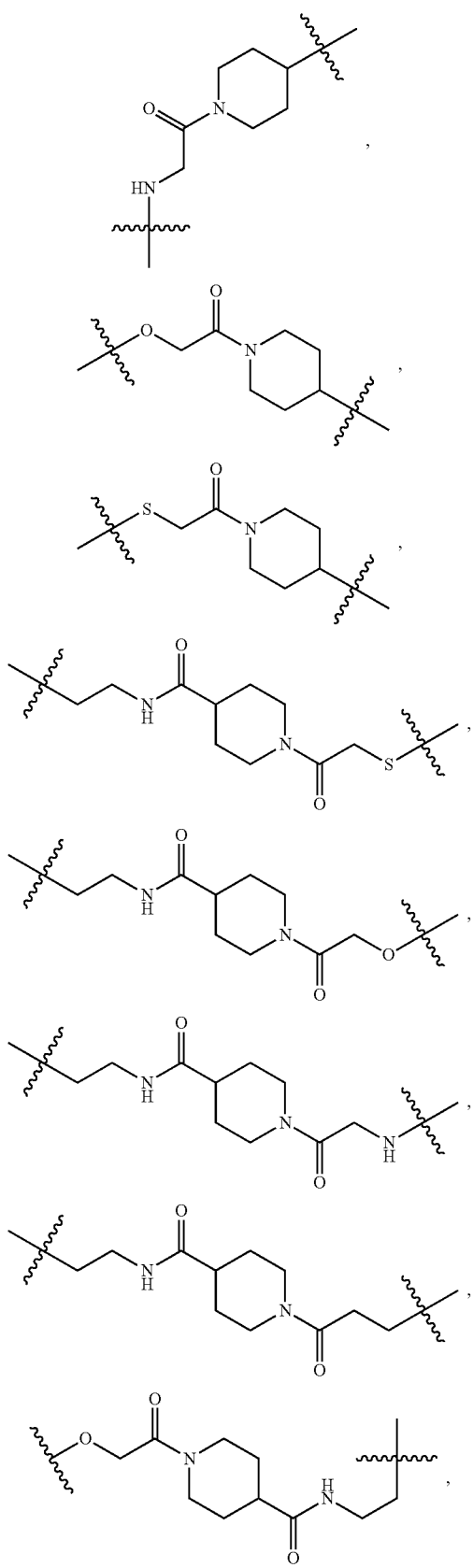
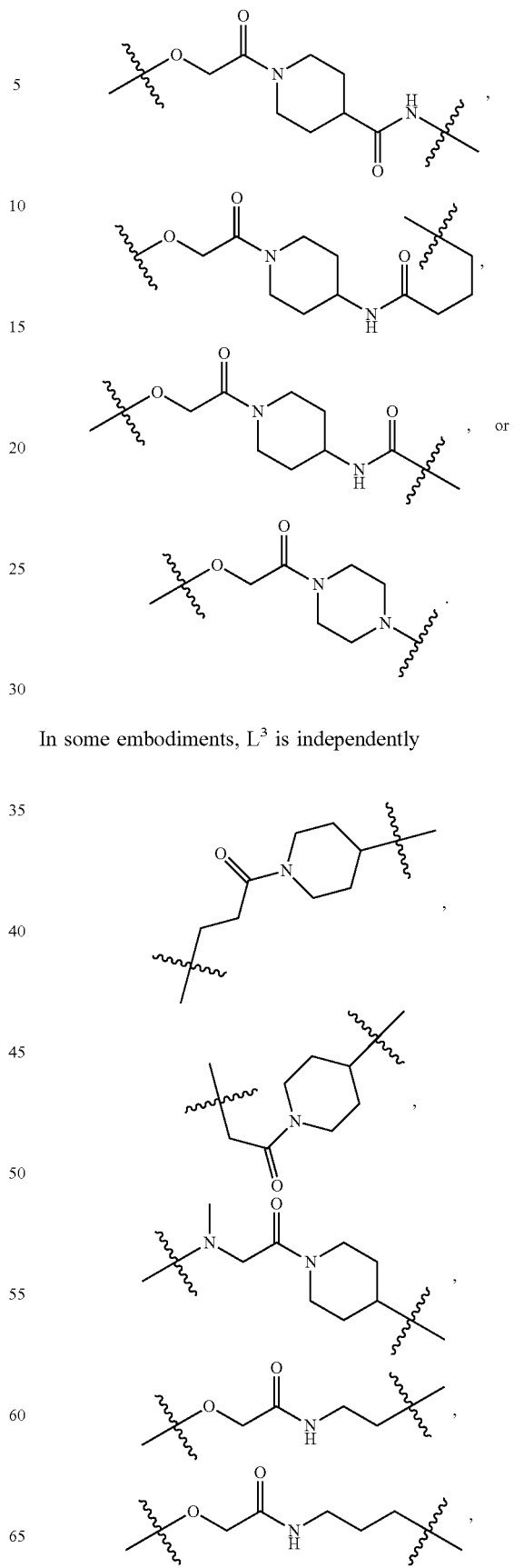
In some embodiments, $L^3$ is independently

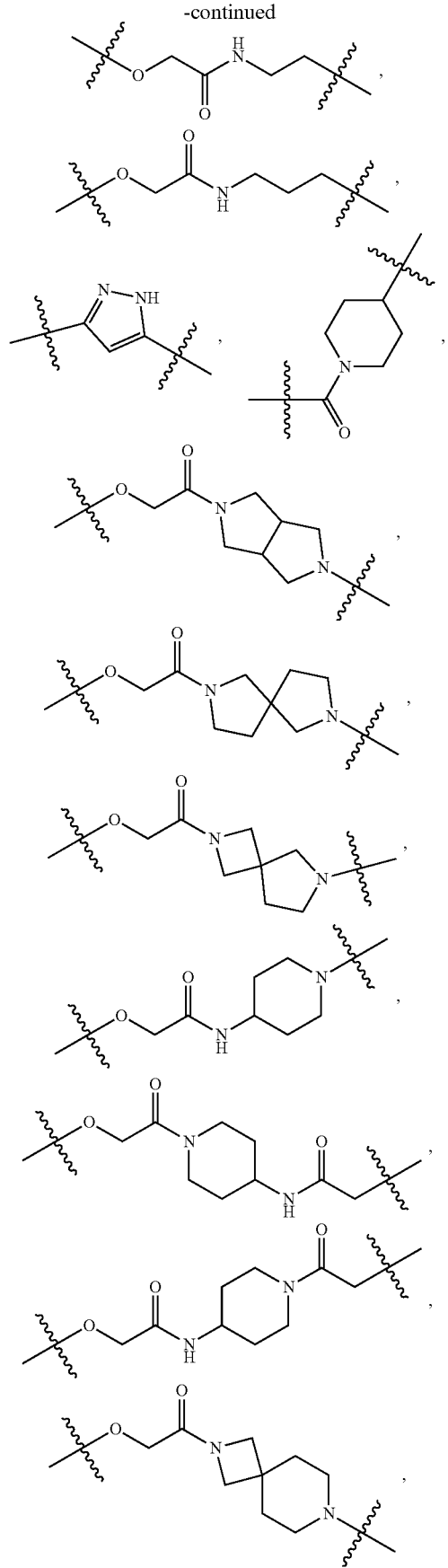
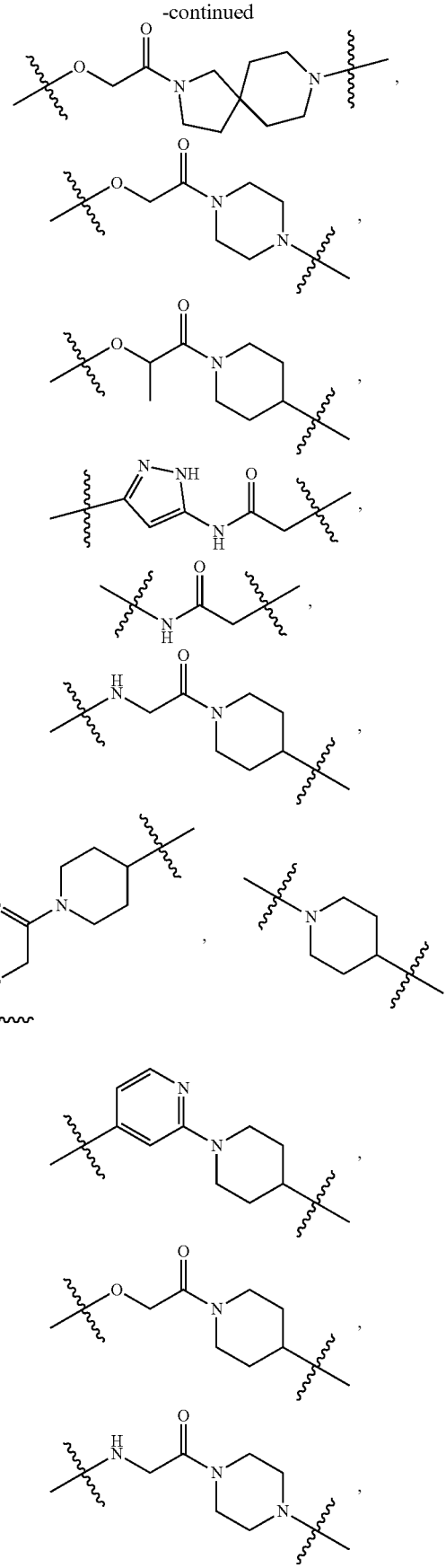

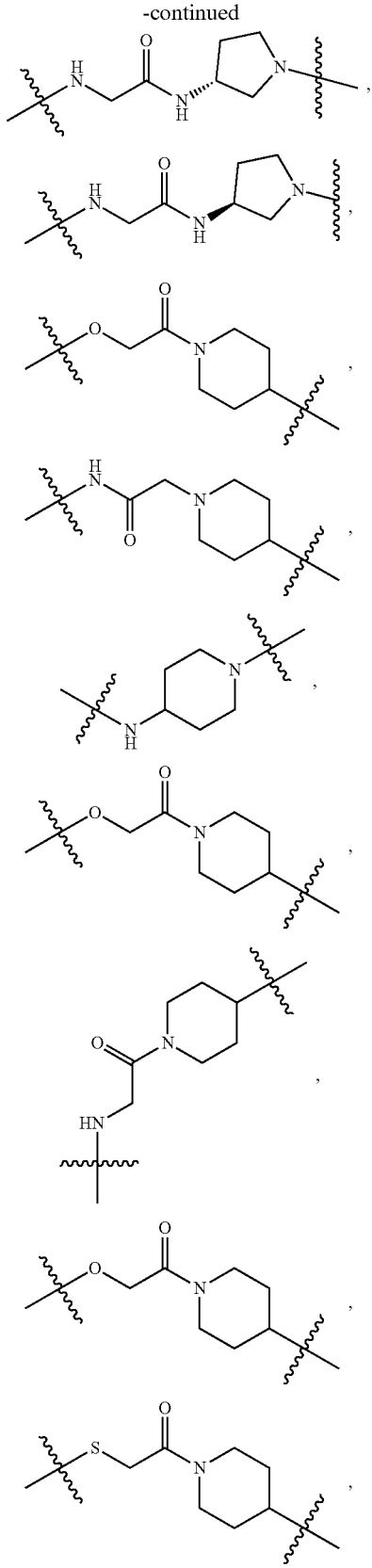
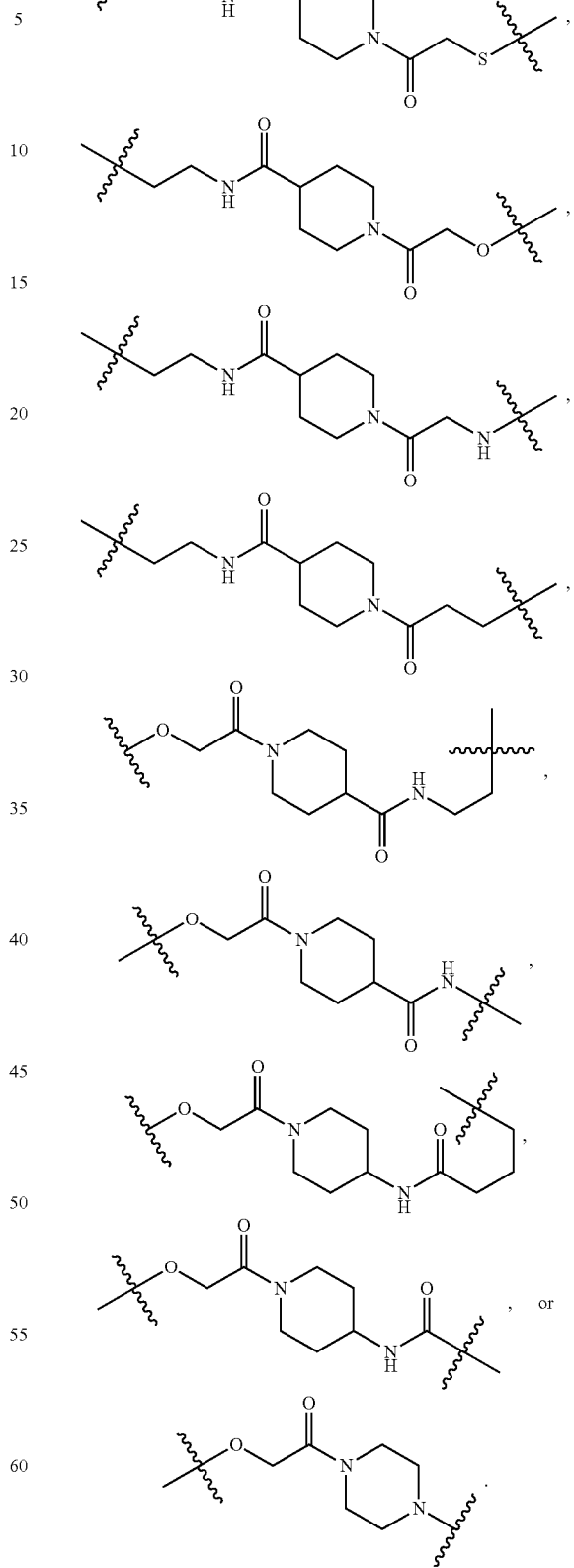
$R^{2A}$ and $R^{2B}$ are independently hydrogen, oxo, halogen, —$CX^a_3$, —CN, —$SO_2Cl$, —$SO_{n1}{}^{10a}$, —$SO_{v1}NR^{7a}R^{8a}$, —NHNH$_2$, —ONR$^{7a}$R$^{8a}$, —NHC=(O)NHNH$_2$, —NHC=(O)NR$^{7a}$R$^{8a}$, —N(O)$_{m1}$, —NR$^{7a}$R$^{8a}$, —C(O)R$^{9a}$, —C(O)—OR$^{9a}$, —C(O)NR$^{7a}$R$^{8a}$, —OR$^{10a}$, —NR$^{7a}$SO$_2$R$^{10a}$, —NR$^{7a}$C=(O) R$^{9a}$, —NR$^{7a}$C(O)—OR$^{9a}$, —NR$^{7a}$OR$^{9a}$, —OCX$^a{}_3$, —OCHX$^a{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{2A}$ and R$^{2B}$ substituents bonded to the same atom may optionally be joined to form a substituted or unsubstituted cycloalkyl or substituted or unsubstituted heterocycloalkyl. In some embodiments, R$^{2A}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, R$^{2B}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{7a}$, R$^{8a}$, R$^{9a}$ and R$^{10a}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{7a}$ and R$^{8a}$ substituents bonded to the same nitrogen atom may optionally be joined to form a substituted or unsubstituted heterocycloalkyl or substituted or unsubstituted heteroaryl. In some embodiments, R$^{7a}$, R$^{8a}$, R$^{9a}$ and R$^{10a}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{2C}$ is independently hydrogen, oxo, halogen, —CX$_{c3}$, —CN, —SO$_2$Cl, —SO$_{n3}$R$^{10c}$, —SO$_{v3}$NR$^{7c}$CR$^{8c}$, —NHNH$_2$, —ONR$^7$R$^{8c}$, —NHC=(O)NHNH$_2$, —NHC=(O)NR$^{7c}$R$^{8c}$, —N(O)$_{m3}$, —NR$^{7c}$R$^{8c}$, —C(O)R$^{9c}$, —C(O)—OR$^{9c}$, —C(O)NR$^{7c}$R$^{8c}$, —OR$^{10c}$, —NR$^{7c}$SO$_2$R$^{10c}$, —NR$^{7c}$=(O) R$^{9c}$, —NR$^{7c}$ (O)—OR$^{9c}$, —NR$^{7c}$OR$^{9c}$, —OCX$^c{}_3$, —OCHX$^c{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent R$^{2C}$ substituents may optionally be joined to form a substituted or unsubstituted cycloalkyl, substituted or unsubstituted heterocycloalkyl, substituted or unsubstituted aryl, or substituted or unsubstituted heteroaryl. Two R$^{2C}$ substituents bonded to the same atom may optionally be joined to form a substituted or unsubstituted cycloalkyl or substituted or unsubstituted heterocycloalkyl. In some embodiments, R$^{2C}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{7c}$, R$^{8c}$, R$^{9c}$ and R$^{10c}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{7c}$ and R$^{8c}$ substituents bonded to the same nitrogen atom may optionally be joined to form a substituted or unsubstituted heterocycloalkyl or substituted or unsubstituted heteroaryl. In some embodiments, R$^{7c}$, R$^{8c}$, R$^{9c}$, and R$^{10c}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The symbols m1, m3, v1, and v3 are independently an integer from 1 to 2. The symbols n1 and n3 are independently an integer from 0 to 4. The symbols X$^a$ and Xe are independently —Cl, —Br, —I, or —F. The symbol v1 is independently 1 or 2. In some embodiments, v1 is 1. In some embodiments, v1 is 2. The symbol m1 is independently an integer from 1 to 2. In some embodiments, m1 is 1. In some embodiments, m1 is 2. The symbol n1 is independently an integer from 0 to 4. In some embodiments, n1 is 0. In some embodiments, n1 is 1. In some embodiments, n1 is 2. In some embodiments, n1 is 3. In some embodiments, n1 is 4. X$^a$ is independently —Cl, —Br, —I, or —F. In some embodiments, X$^a$ is —Cl. In some embodiments, X$^a$ is —Br. In some embodiments, X$^a$ is —I. In some embodiments, X$^a$ is —F. The symbol v3 is independently 1 or 2. In some embodiments, v3 is 1. In some embodiments, v3 is 2. The symbol m3 is independently an integer from 1 to 2. In some embodiments, m3 is 1. In some embodiments, m3 is 2. The symbol n3 is independently an integer from 0 to 4. In some embodiments, n3 is 0. In some embodiments, n3 is 1. In some embodiments, n3 is 2. In some embodiments, n3 is 3. In some embodiments, n3 is 4. X$^c$ is independently —Cl, —Br, —I, or —F. In some embodiments, X$^c$ is —Cl. In some embodiments, X$^c$ is —Br. In some embodiments, X$^c$ is —I. In some embodiments, X$^c$ is —F. The symbol z is independently an integer from 0 to 10. In some embodiments, z is 0. In some embodiments, z is 1. In some embodiments, z is 2. In some embodiments, z is 3. In some embodiments, z is 4. In some embodiments, z is 5. In some embodiments, z is 6. In some embodiments, z is 7. In some embodiments, z is 8. In some embodiments, z is 9. In some embodiments, z is 10.

In some embodiments, E is an electrophilic chemical moiety capable of forming a covalent bond with a K-Ras cysteine residue. In some embodiments, E is an electrophilic chemical moiety capable of forming a covalent bond with a K-Ras aspartate residue. In some embodiments, E is an electrophilic chemical moiety capable of forming a covalent bond with a K-Ras cysteine sidechain. In some embodiments, E is an electrophilic chemical moiety capable of forming a covalent bond with a K-Ras aspartate sidechain. In some embodiments, E is an electrophilic chemical moiety capable of forming a covalent bond with a K-Ras cysteine sulfur. In some embodiments, E is an electrophilic chemical moiety capable of forming a covalent bond with a K-Ras aspartate sidechain oxygen. In some embodiments, E is an electrophilic chemical moiety capable of forming a covalent bond with a K-Ras residue 12 cysteine. In some embodiments, E is an electrophilic chemical moiety capable of forming a covalent bond with a K-Ras residue 12 asparate. In some embodiments, E is an electrophilic chemical moiety capable of forming a covalent bond with a K-Ras residue 13 cysteine. In some embodiments, E is an electrophilic chemical moiety capable of forming a covalent bond with a K-Ras residue 13 asparate. In some embodiments, E is an electrophilic chemical moiety capable of forming a covalent bond with a K-Ras residue near the Switch 2—Binding Pocket in the folded protein. In some embodiments, E is an electrophilic chemical moiety capable of forming a covalent bond with a K-Ras residue in the Switch 2—Binding Pocket in the folded protein. In some embodiments, E is an electrophilic chemical moiety capable of forming an irreversible covalent bond with a K-Ras residue. In some embodiments, E is an electrophilic chemical moiety capable of forming a reversible covalent bond with a K-Ras residue.

In some embodiments, E comprises a substituted or unsubstituted vinyl sulfone moiety, substituted or unsubstituted vinyl sulfonamide moiety, substituted or unsubstituted fluoro ($C_1$-$C_4$) alkylketone moiety, substituted or unsubstituted chloro($C_1$-$C_4$) alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety,

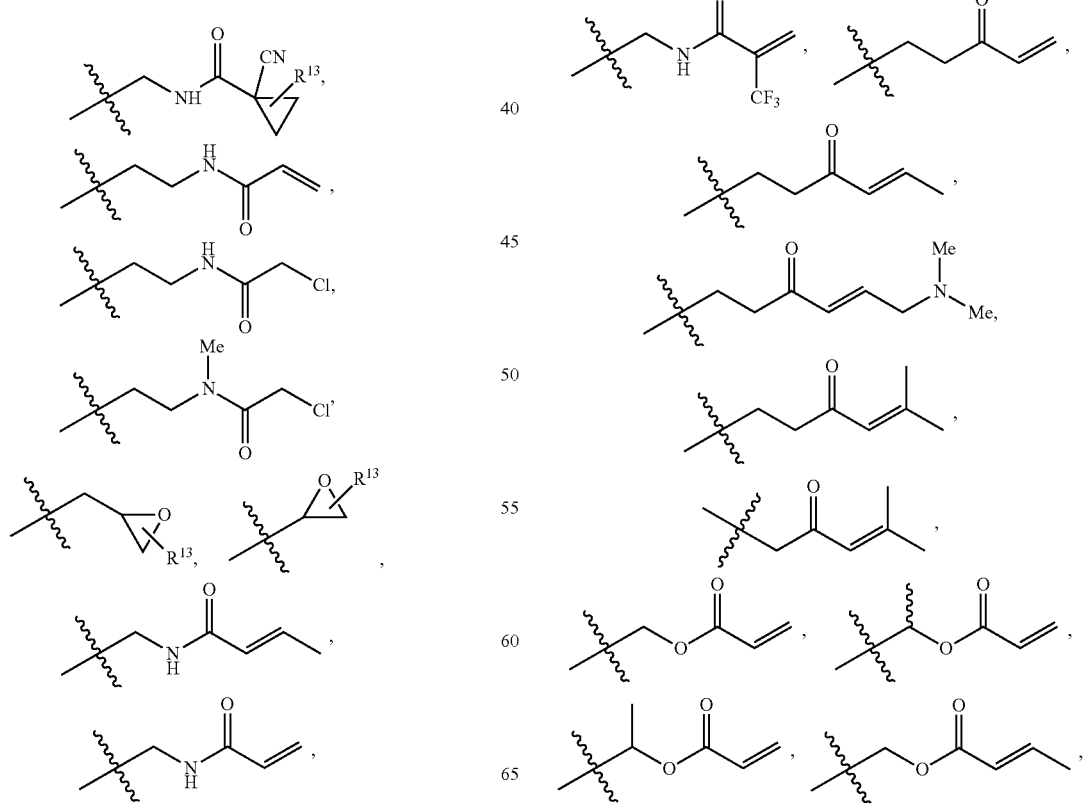

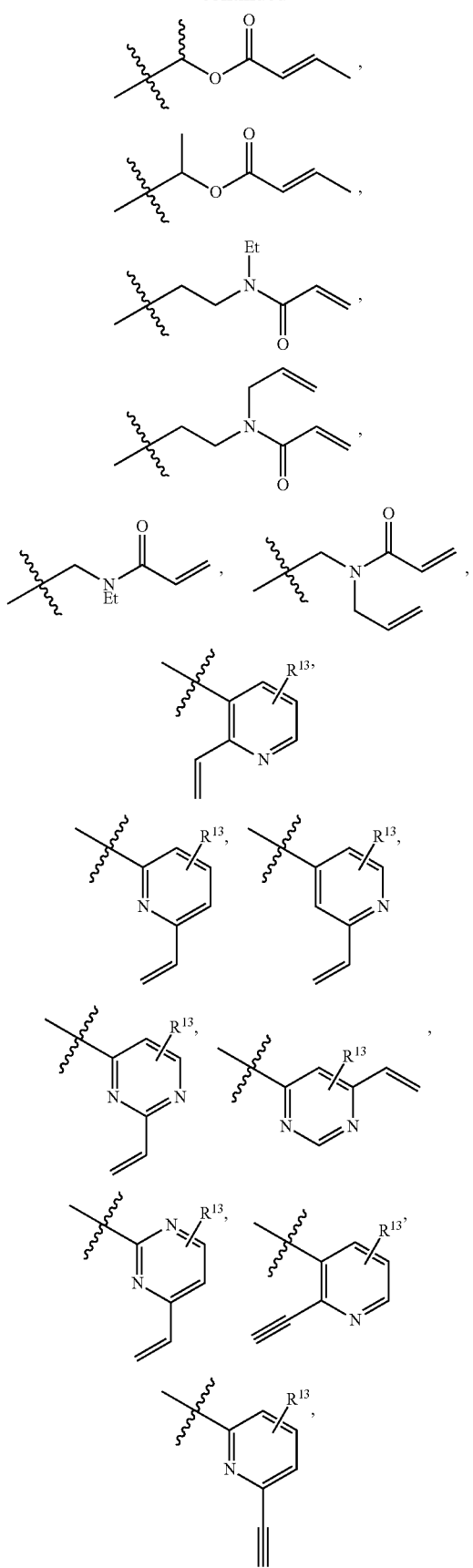
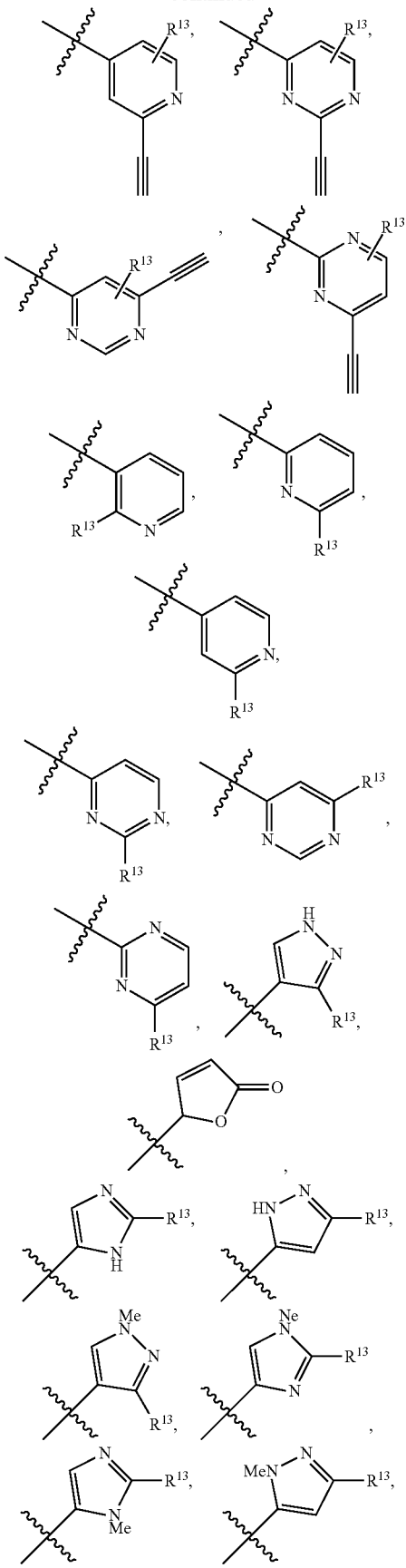

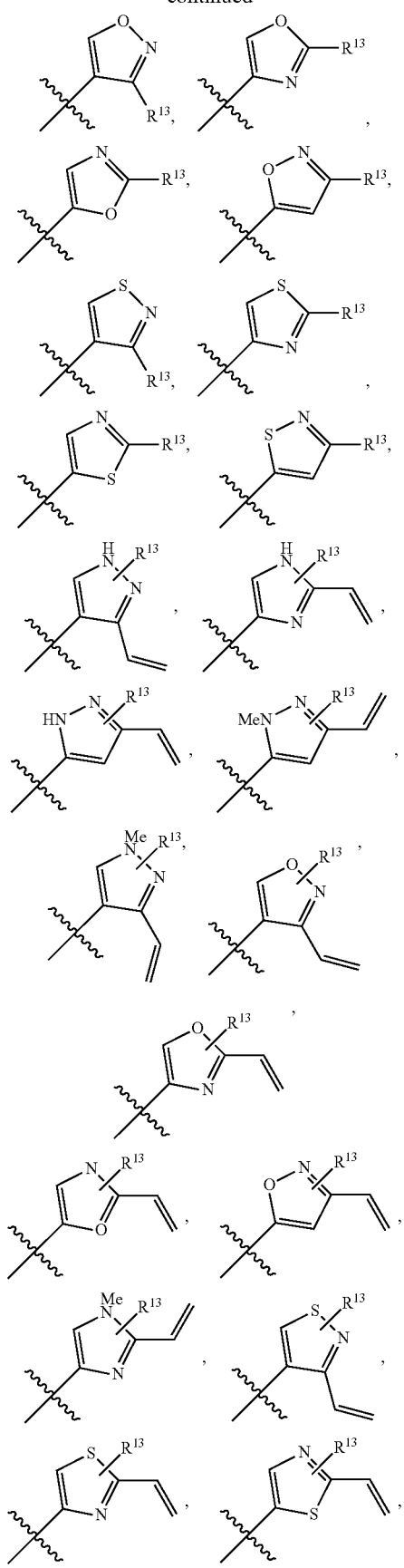
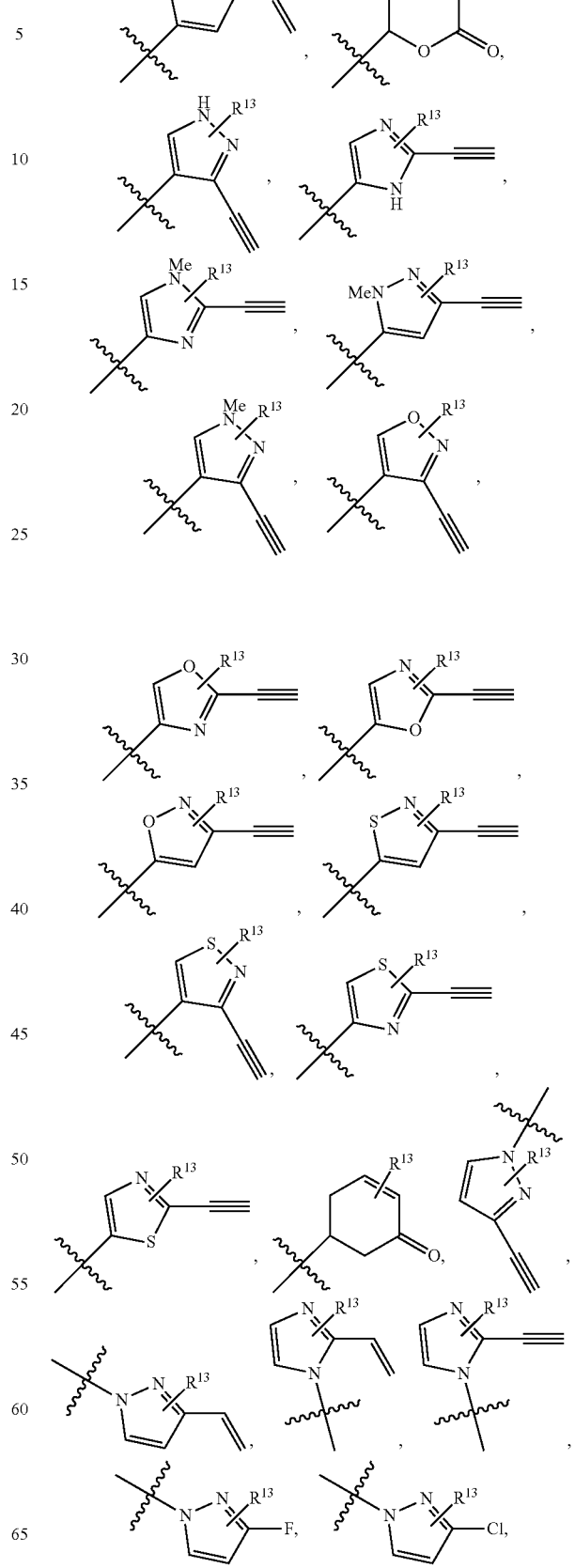

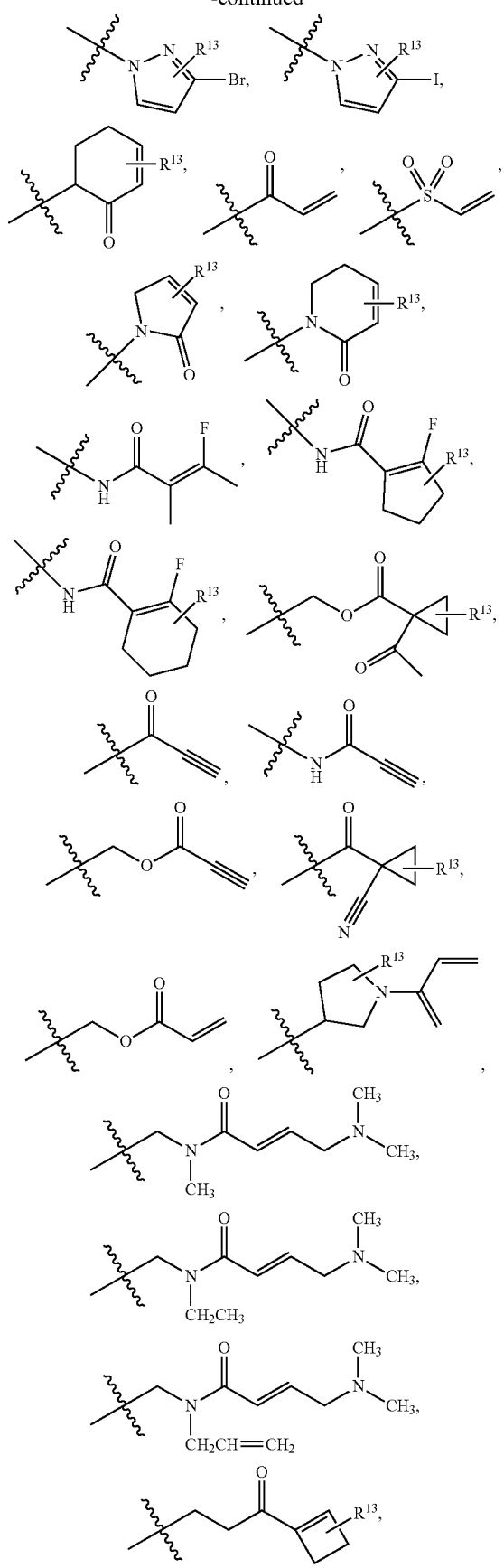
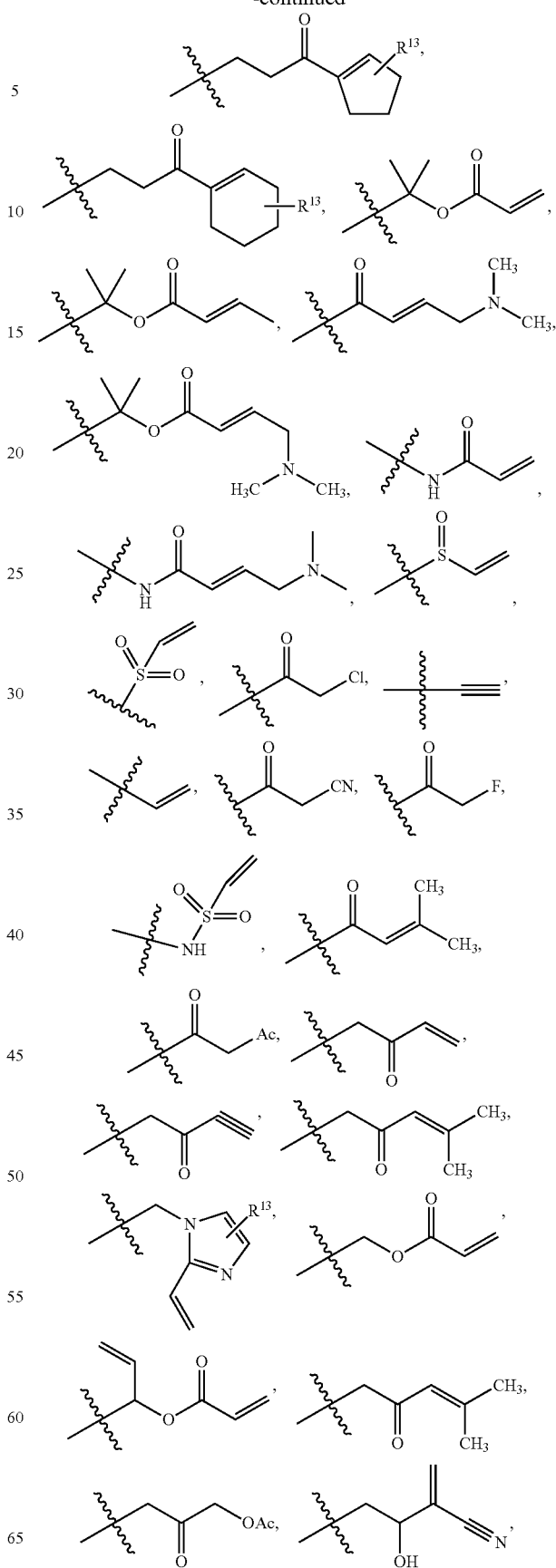

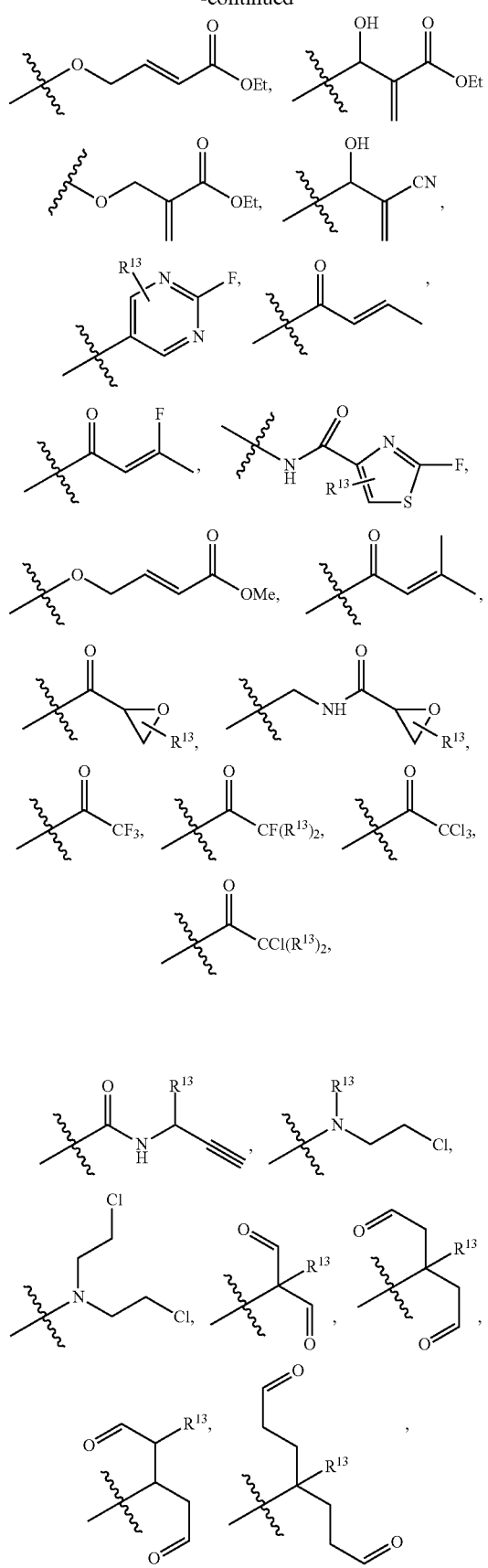
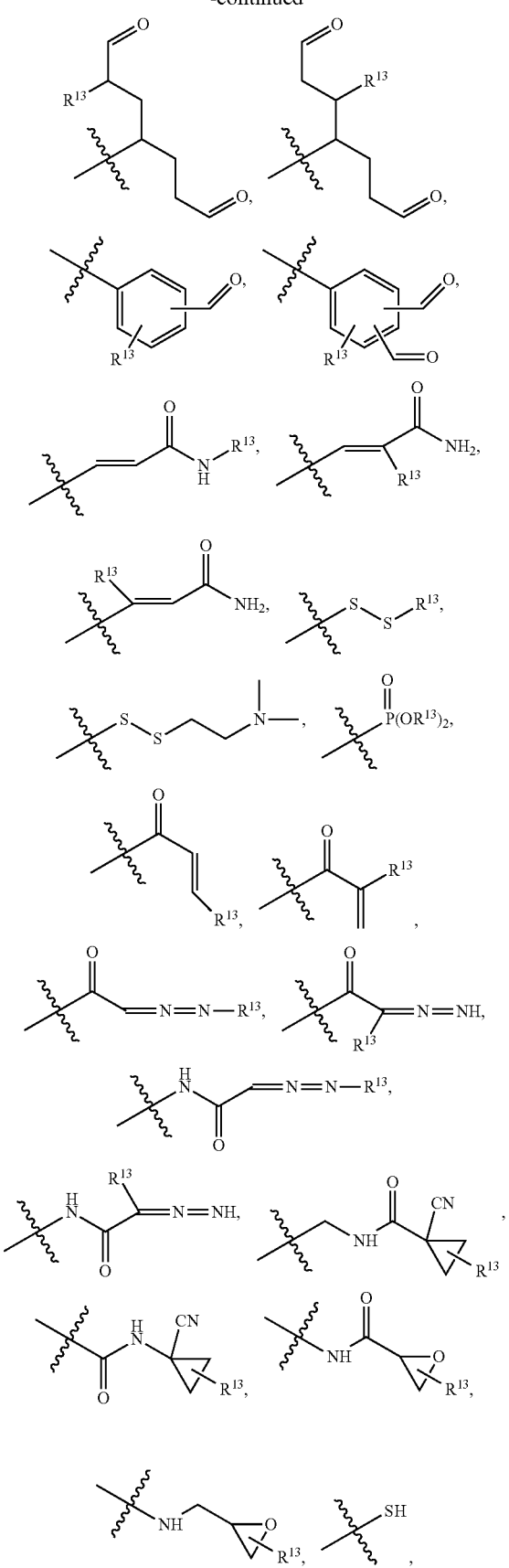

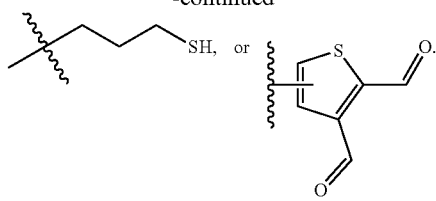

In some embodiments, E is a substituted or unsubstituted vinyl sulfone moiety, substituted or unsubstituted vinyl sulfonamide moiety, substituted or unsubstituted fluoro ($C_1$-$C_4$) alkylketone moiety, substituted or unsubstituted chloro ($C_1$-$C_4$) alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety,

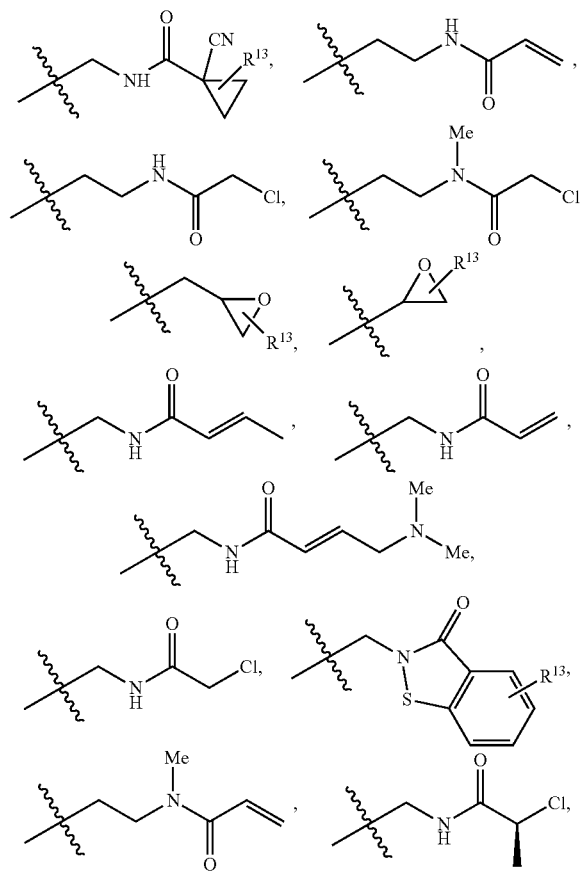

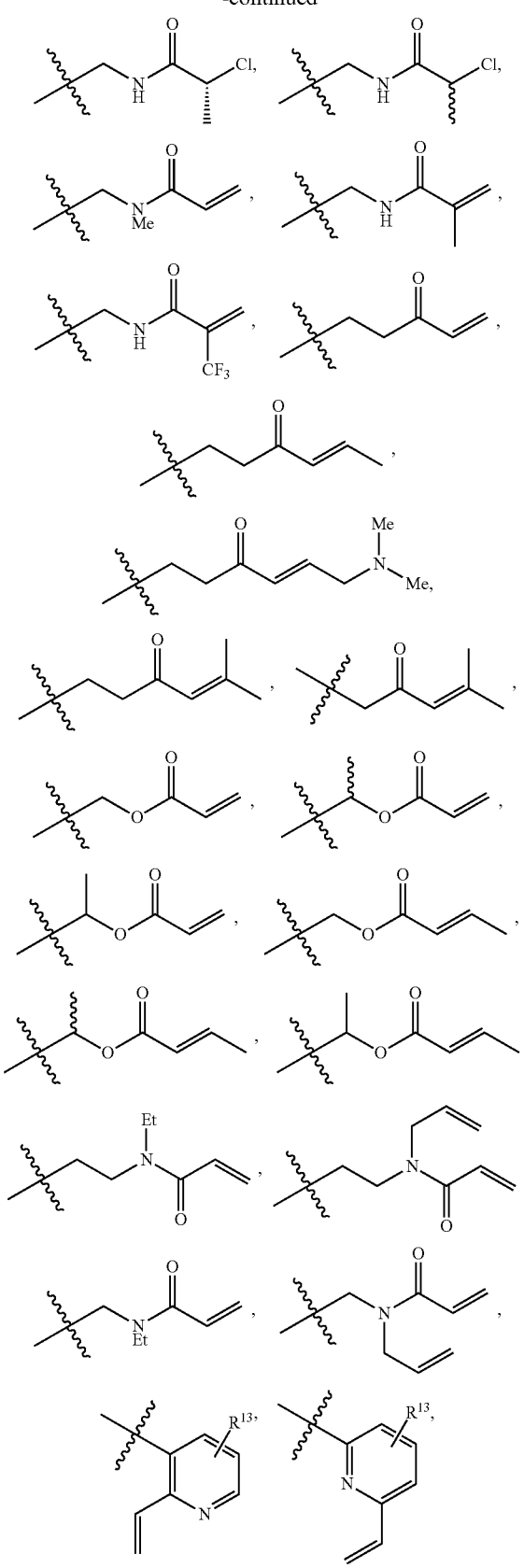

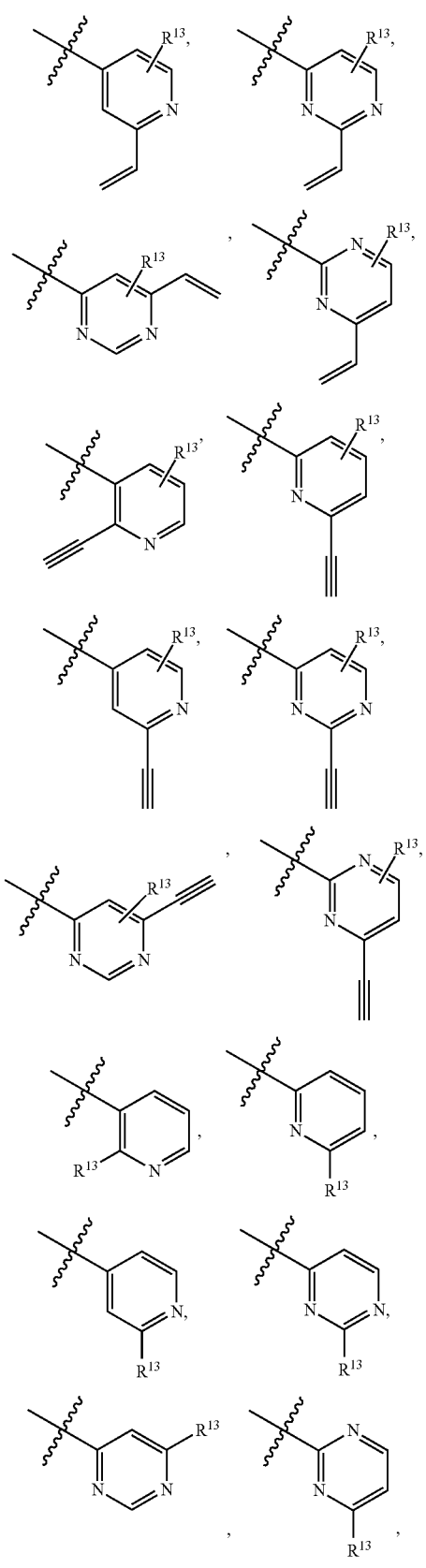
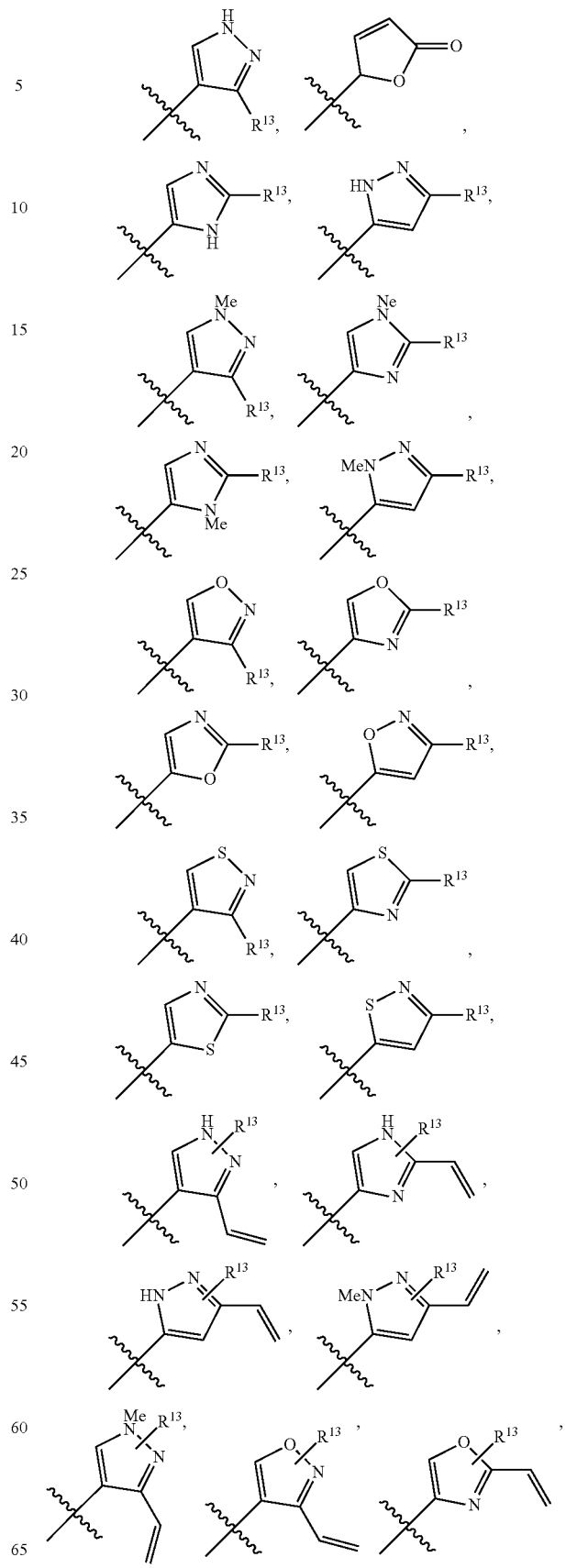

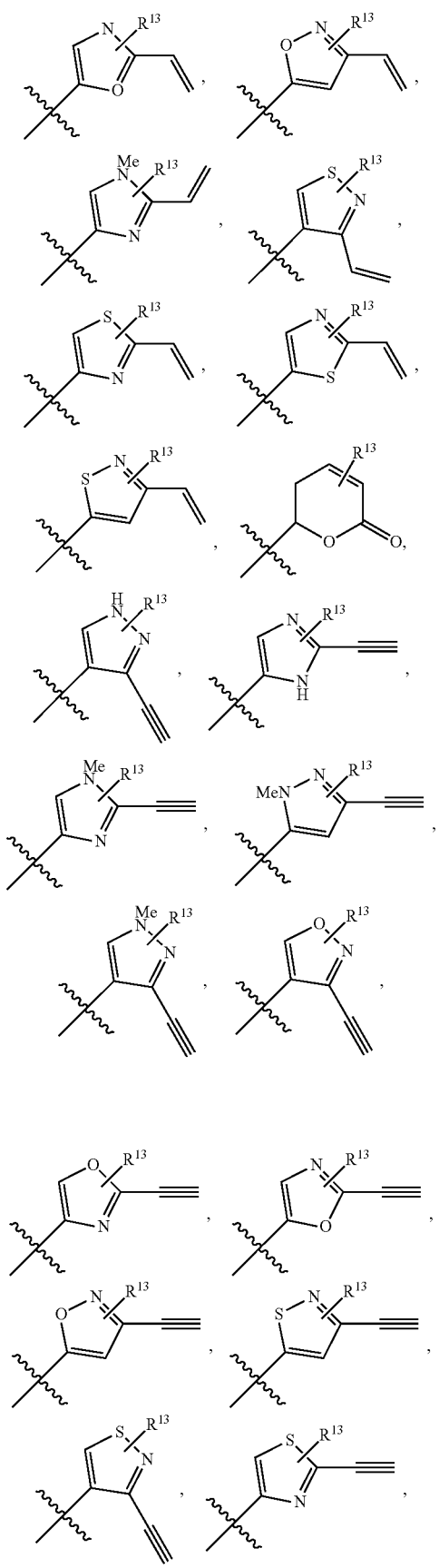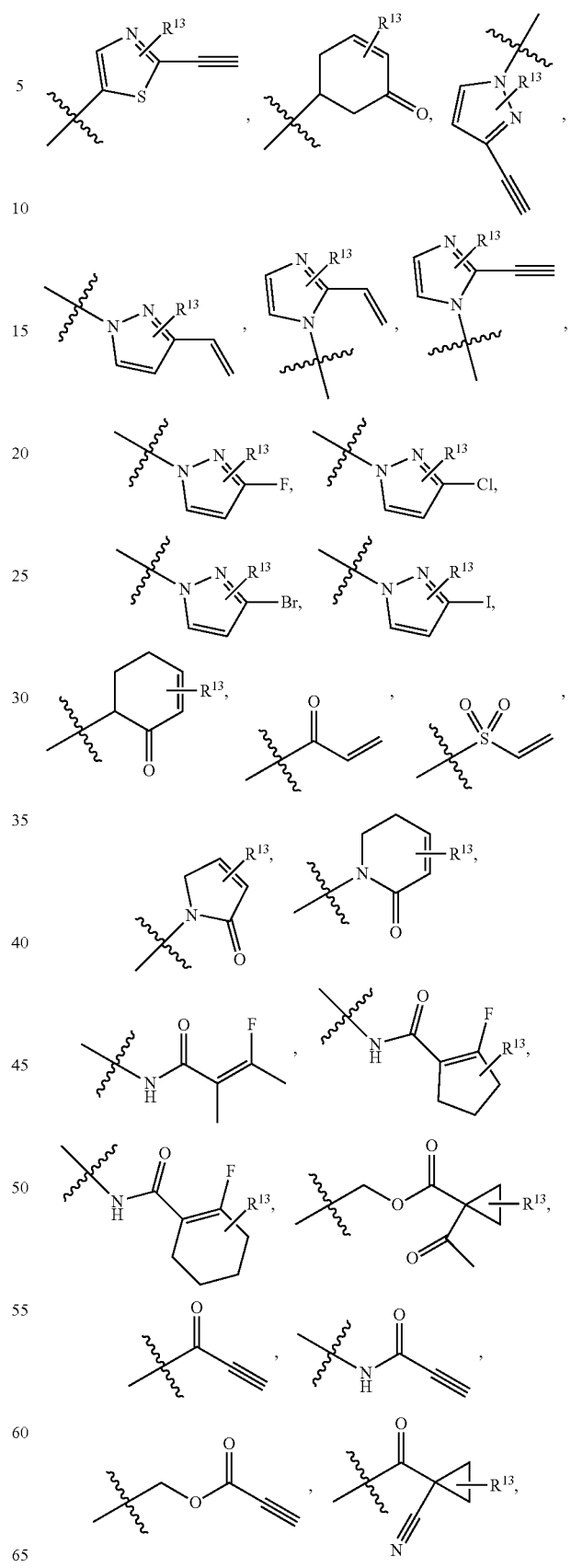

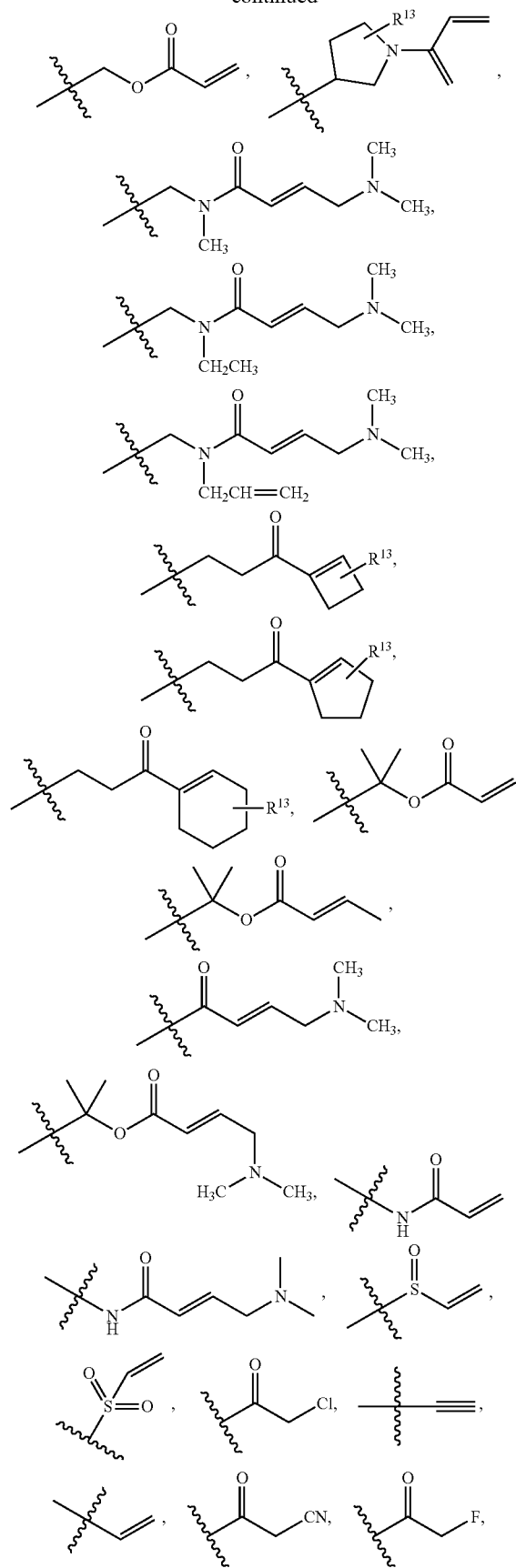
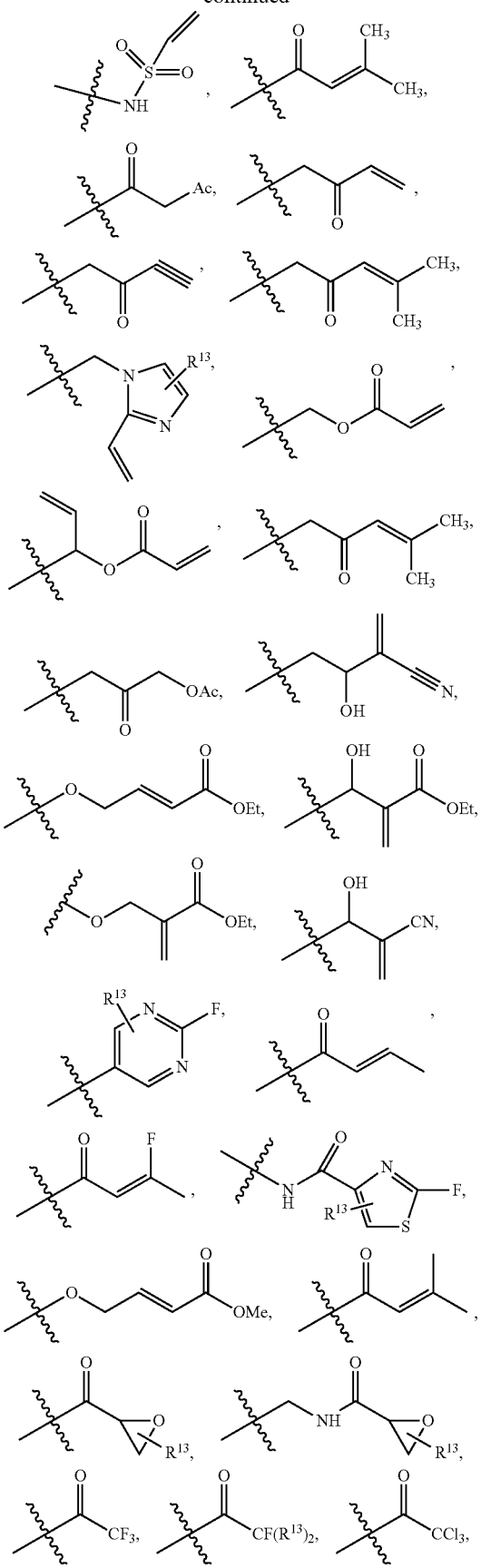

-continued

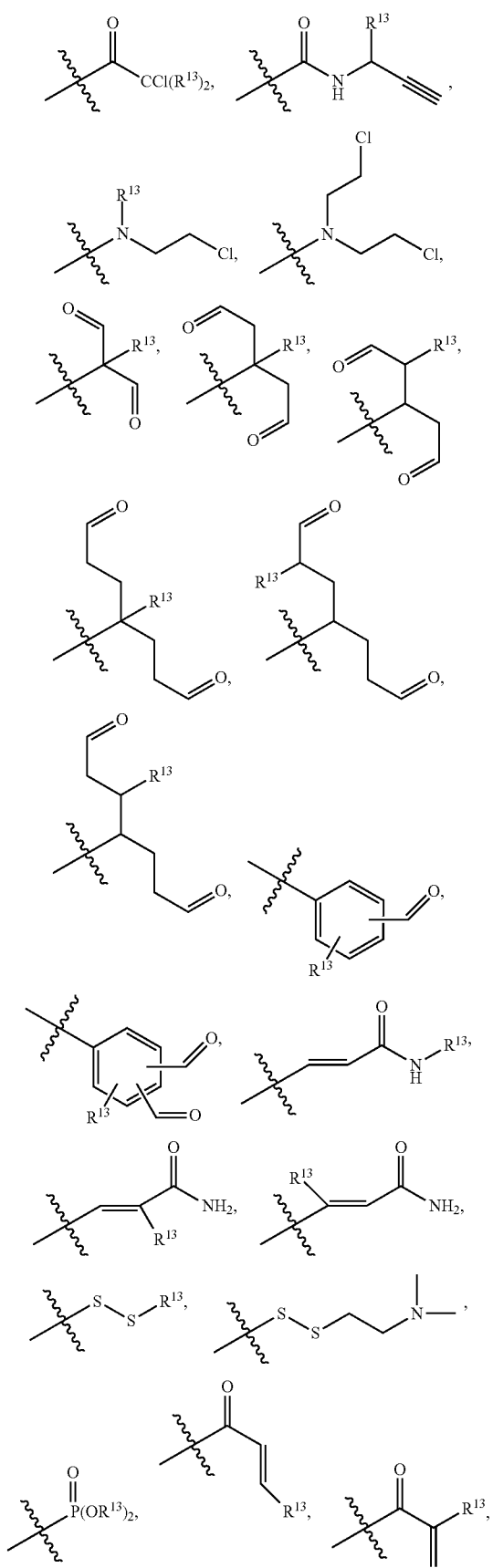

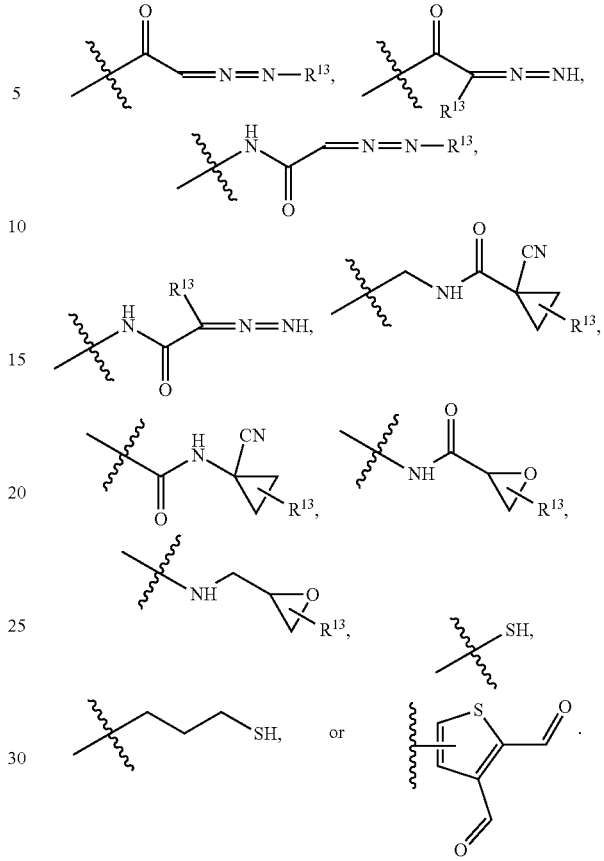

In some embodiments, E comprises an unsubstituted vinyl sulfone moiety, unsubstituted vinyl sulfonamide moiety, unsubstituted fluoro ($C_1$-$C_4$) alkylketone moiety, unsubstituted chloro($C_1$-$C_4$) alkylketone moiety, unsubstituted acrylamide moiety, unsubstituted disulfide moiety, unsubstituted thiol moiety, unsubstituted phosphonate moiety, unsubstituted aldehyde moiety, unsubstituted enone moiety, unsubstituted diazomethylketone moiety, unsubstituted diazomethylamide moiety, unsubstituted cyanocyclopropyl carboxamide moiety, unsubstituted epoxide moiety, unsubstituted epoxyketone moiety, unsubstituted epoxyamide moiety, unsubstituted aryl aldehyde moiety, unsubstituted aryl dialdehyde moiety, unsubstituted dialdehyde moiety, unsubstituted nitrogen mustard moiety, unsubstituted propargyl moiety, or unsubstituted propargylamide moiety. In some embodiments, E is an unsubstituted vinyl sulfone moiety, unsubstituted vinyl sulfonamide moiety, unsubstituted fluoro ($C_1$-$C_4$) alkylketone moiety, unsubstituted chloro($C_1$-$C_4$) alkylketone moiety, unsubstituted acrylamide moiety, unsubstituted disulfide moiety, unsubstituted thiol moiety, unsubstituted phosphonate moiety, unsubstituted aldehyde moiety, unsubstituted enone moiety, unsubstituted diazomethylketone moiety, unsubstituted diazomethylamide moiety, unsubstituted cyanocyclopropyl carboxamide moiety, unsubstituted epoxide moiety, unsubstituted epoxyketone moiety, unsubstituted epoxyamide moiety, unsubstituted aryl aldehyde moiety, unsubstituted aryl dialdehyde moiety, unsubstituted dialdehyde moiety, unsubstituted nitrogen mustard moiety, unsubstituted propargyl moiety, or unsubstituted propargylamide moiety.

$R^{13}$ is independently hydrogen, oxo, halogen, —$CX^b_3$, —CN, —$SO_2Cl$, —$SO_rR^{17}$, —$SO_pNR^{14}R_{15}$, —$NHNH_2$, —ONR$^{14}$R$^{15}$, —NHC=(O)NHNH$_2$, —NHC=(O)NR$^{14}$R$^{15}$, —N(O) q, —NR$^{14}$R$^{15}$, —C(O)R$^{16}$, —C(O)—OR$^{16}$, —C(O)NR$^{14}$R$^{15}$, —OR$^{17}$, —NR$^{14}$SO$_2$R$^{17}$, —NR$^{14}$C=(O) R$^{16}$, —NR$^{14}$C(O)—OR$^{16}$, —NR$^{14}$OR$^{16}$, —OCX$^b{}_3$, —OCHX$^b$2, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent R$^{13}$ substituents may optionally be joined to form a substituted or unsubstituted cycloalkyl, substituted or unsubstituted heterocycloalkyl, substituted or unsubstituted aryl, or substituted or unsubstituted heteroaryl. Two R$^{13}$ substituents bonded to the same atom may optionally be joined to form a substituted or unsubstituted cycloalkyl or substituted or unsubstituted heterocycloalkyl. In some embodiments, R$^{13}$ is hydrogen. In some embodiments, R$^{13}$ is methyl. In some embodiments, R$^{13}$ is ethyl. In some embodiments, R$^{13}$ is —CN. In some embodiments, R$^{13}$ is —NO$_2$.

R$^{14}$, R$^{15}$, R$^{16}$, and R$^{17}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{14}$ and R$^{15}$ substituents bonded to the same nitrogen atom may optionally be joined to form a substituted or unsubstituted heterocycloalkyl or substituted or unsubstituted heteroaryl. In some embodiments, R$^{14}$, R$^{15}$, R$^{16}$, and R$^{17}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol p is independently 1 or 2. In some embodiments, p is 1. In some embodiments, p is 2. The symbol q is independently an integer from 1 to 2. In some embodiments, q is 1. In some embodiments, q is 2. The symbol r is independently an integer from 0 to 4. In some embodiments, r is 0. In some embodiments, r is 1. In some embodiments, r is 2. In some embodiments, r is 3. In some embodiments, r is 4. X$^b$ is independently —Cl, —Br, —I, or —F. In some embodiments, X$^b$ is —Cl. In some embodiments, X$^b$ is —Br. In some embodiments, X$^b$ is —I. In some embodiments, X$^b$ is —F.

In some embodiments of the compounds provided herein, R$^1$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC—(O)NHNH$_2$, —NHC—(O)NH$_2$, —NHSO$_2$H, —NHC=(O)H, —NHC(O)—OH, —NHOH, —OCF$_3$, —OCHF$_2$, R$^{20}$-substituted or unsubstituted alkyl, R$^{20}$-substituted or unsubstituted heteroalkyl, R$^{20}$-substituted or unsubstituted cycloalkyl, R$^{20}$-substituted or unsubstituted heterocycloalkyl, R$^{20}$-substituted or unsubstituted aryl, or R$^{20}$-substituted or unsubstituted heteroaryl.

R$^{20}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{21}$-substituted or unsubstituted alkyl, R$^{21}$-substituted or unsubstituted heteroalkyl, R$^{21}$-substituted or unsubstituted cycloalkyl, R$^{21}$-substituted or unsubstituted heterocycloalkyl, R$^{21}$-substituted or unsubstituted aryl, or R$^{21}$, substituted or unsubstituted heteroaryl.

R$^{21}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC—(O)NH$_2$, —NHSO$_2$H, —NHC=(O)H, —NHC(O)—OH, —NHOH, —OCF$_3$, —OCHF$_2$, R$^{22}$-substituted or unsubstituted alkyl, R$^{22}$-substituted or unsubstituted heteroalkyl, R$^{22}$-substituted or unsubstituted cycloalkyl, R$^{22}$-substituted or unsubstituted heterocycloalkyl, R$^{22}$-substituted or unsubstituted aryl, or R$^{22}$-substituted or unsubstituted heteroaryl.

In some embodiments of the compounds provided herein, R$^2$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{23}$-substituted or unsubstituted alkyl, R$^{23}$-substituted or unsubstituted heteroalkyl, R$^{23}$-substituted or unsubstituted cycloalkyl, R$^{23}$-substituted or unsubstituted heterocycloalkyl, R$^{23}$-substituted or unsubstituted aryl, or R$^{23}$-substituted or unsubstituted heteroaryl.

R$^{23}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{24}$-substituted or unsubstituted alkyl, R$^{24}$-substituted or unsubstituted heteroalkyl, R$^{24}$-substituted or unsubstituted cycloalkyl, R$^{24}$-substituted or unsubstituted heterocycloalkyl, R$^{24}$-substituted or unsubstituted aryl, or R$^{24}$-substituted or unsubstituted heteroaryl.

R$^{24}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC—(O)NH$_2$, —NHSO$_2$H, —NHC=(O)H, —NHC(O)—OH, —NHOH, —OCF$_3$, —OCHF$_2$, R$^{25}$-substituted or unsubstituted alkyl, R$^{25}$-substituted or unsubstituted heteroalkyl, R$^{25}$-substituted or unsubstituted cycloalkyl, R$^{25}$-substituted or unsubstituted heterocycloalkyl, R$^{25}$-substituted or unsubstituted aryl, or R$^{25}$-substituted or unsubstituted heteroaryl.

In some embodiments of the compounds provided herein, R$^{2A}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{23A}$-substituted or unsubstituted alkyl, R$^{23A}$-substituted or unsubstituted heteroalkyl, R$^{23A}$-substituted or unsubstituted cycloalkyl, R$^{23A}$-substituted or unsubstituted heterocycloalkyl, R$^{23A}$-substituted or unsubstituted aryl, or R$^{23A}$-substituted or unsubstituted heteroaryl.

R$^{23A}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC—(O)NHNH$_2$, —NHC=(O)NH$_2$, —NHSO$_2$H, —NHC=(O)H, —NHC(O)—OH, —NHOH, —OCF$_3$, —OCHF$_2$, R$^{24A}$-substituted or unsubstituted alkyl, R$^{24A}$-substituted or unsubstituted heteroalkyl, R$^{24A}$-substituted or unsubstituted cycloalkyl, R$^{24A}$-substituted or unsubstituted heterocycloalkyl, R$^{24A}$-substituted or unsubstituted aryl, or R$^{24A}$ substituted or unsubstituted heteroaryl.

R$^{24A}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{25A}$-substituted or unsubstituted alkyl, R$^{25A}$-substituted or unsubstituted heteroalkyl, R$^{25A}$-substituted or unsubstituted cycloalkyl, R$^{25A}$-substituted or unsubstituted heterocycloalkyl, R$^{25A}$-substituted or unsubstituted aryl, or R$^{25A}$ substituted or unsubstituted heteroaryl.

In some embodiments of the compounds provided herein, R$^{2B}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{23B}$-substituted or unsubstituted alkyl, R$^{23B}$-substituted or unsubstituted heteroalkyl, R$^{23B}$-substituted or unsubstituted cycloalkyl, R$^{23B}$-substituted or unsubstituted heterocycloalkyl, R$^{23B}$-substituted or unsubstituted aryl, or R$^{23B}$-substituted or unsubstituted heteroaryl.

R$^{23B}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{24B}$-substituted or unsubstituted alkyl, R$^{24B}$-substituted or unsubstituted heteroalkyl, R$^{24B}$-substituted or unsubstituted cycloalkyl, R$^{24B}$-substituted or unsubstituted heterocycloalkyl, R$^{24B}$-substituted or unsubstituted aryl, or R$^{24B}$-substituted or unsubstituted heteroaryl.

R$^{24B}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{25B}$-substituted or unsubstituted alkyl, R$^{25B}$-substituted or unsubstituted heteroalkyl, R$^{25B}$-substituted or unsubstituted cycloalkyl, R$^{25B}$-substituted or unsubstituted heterocycloalkyl, R$^{25B}$-substituted or unsubstituted aryl, or R$^{25B}$-substituted or unsubstituted heteroaryl.

In some embodiments of the compounds provided herein, R$^{2C}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC—(O)NH$_2$, —NHSO$_2$H, —NHC=(O)H, —NHC(O)—OH, —NHOH, —OCF$_3$, —OCHF$_2$, R$^{23C}$-substituted or unsubstituted alkyl, R$^{23C}$-substituted or unsubstituted heteroalkyl, R$^{23C}$-substituted or unsubstituted cycloalkyl, R$^{23C}$-substituted or unsubstituted heterocycloalkyl, R$^{23C}$-substituted or unsubstituted aryl, or R$^{23C}$-substituted or unsubstituted heteroaryl.

R$^{23C}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{24C}$-substituted or unsubstituted alkyl, R$^{24C}$-substituted or unsubstituted heteroalkyl, R$^{24C}$-substituted or unsubstituted cycloalkyl, R$^{24C}$-substituted or unsubstituted heterocycloalkyl, R$^{24C}$-substituted or unsubstituted aryl, or R$^{24C}$-substituted or unsubstituted heteroaryl.

R$^{24C}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{25C}$-substituted or unsubstituted alkyl, R$^{25C}$-substituted or unsubstituted heteroalkyl, R$^{25C}$-substituted or unsubstituted cycloalkyl, R$^{25C}$-substituted or unsubstituted heterocycloalkyl, R$^{25C}$-substituted or unsubstituted aryl, or R$^{25C}$-substituted or unsubstituted heteroaryl.

In some embodiments of the compounds provided herein, R$^3$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC—(O)NH$_2$, —NHSO$_2$H, —NHC=(O)H, —NHC(O)—OH, —NHOH, —OCF$_3$, —OCHF$_2$, R$^{26}$-substituted or unsubstituted alkyl, R$^{26}$-substituted or unsubstituted heteroalkyl, R$^{26}$-substituted or unsubstituted cycloalkyl, R$^{26}$-substituted or unsubstituted heterocycloalkyl, R$^{26}$-substituted or unsubstituted aryl, or R$^{26}$-substituted or unsubstituted heteroaryl.

R$^{26}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{27}$-substituted or unsubstituted alkyl, R$^{27}$-substituted or unsubstituted heteroalkyl, R$^{27}$-substituted or unsubstituted cycloalkyl, R$^{27}$ substituted or unsubstituted heterocycloalkyl, R$^{27}$-substituted or unsubstituted aryl, or R$^{27}$-substituted or unsubstituted heteroaryl.

R$^{27}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{28}$-substituted or unsubstituted alkyl, R$^{28}$-substituted or unsubstituted heteroalkyl, R$^{28}$-substituted or unsubstituted cycloalkyl, R$^{28}$-substituted or unsubstituted heterocycloalkyl, R$^{28}$-substituted or unsubstituted aryl, or R$^{28}$-substituted or unsubstituted heteroaryl.

In some embodiments of the compounds provided herein, L$^1$ is independently a bond, —NH—, —O—, —S—, —C(O)—, —S(O)—, —S(O)$_2$—, R$^{29}$-substituted or unsubstituted alkylene, R$^{29}$-substituted or unsubstituted heteroalkylene, R$^{29}$-substituted or unsubstituted cycloalkylene, R$^{29}$-substituted or unsubstituted heterocycloalkylene, R$^{29}$-substituted or unsubstituted arylene, or R$^{29}$-substituted or unsubstituted heteroarylene.

R$^{29}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{30}$-substituted or unsubstituted alkyl, R$^{30}$-substituted or unsubstituted heteroalkyl, R$^{30}$-substituted or unsubstituted cycloalkyl, R$^{30}$ substituted or unsubstituted heterocycloalkyl, R$^{30}$-substituted or unsubstituted aryl, or R$^{30}$-substituted or unsubstituted heteroaryl.

R$^{30}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC—(O)NHNH$_2$, —NHC=(O)NH$_2$, —NHSO$_2$H, —NHC=(O)H, —NHC(O)—OH, —NHOH, —OCF$_3$, —OCHF$_2$, R$^{31}$-substituted or unsubstituted alkyl, R$^{31}$-substituted or unsubstituted heteroalkyl, R$^{31}$-substituted or unsubstituted cycloalkyl, R$^{31}$-substituted or unsubstituted heterocycloalkyl, R$^{31}$-substituted or unsubstituted aryl, or R$^{31}$-substituted or unsubstituted heteroaryl.

In some embodiments of the compounds provided herein, L$^2$ is independently a bond, —NH—, —O—, —S—, —C(O)—, —S(O)—, —S(O)$_2$—, R$^{32}$-substituted or unsubstituted alkylene, R$^{32}$-substituted or unsubstituted heteroalkylene, R$^{32}$-substituted or unsubstituted cycloalkylene, R$^{32}$- substituted or unsubstituted heterocycloalkylene, $R^{32}$-substituted or unsubstituted arylene, or $R^{32}$-substituted or unsubstituted heteroarylene.

$R^{32}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{33}$-substituted or unsubstituted alkyl, $R^{33}$-substituted or unsubstituted heteroalkyl, $R^{33}$-substituted or unsubstituted cycloalkyl, $R^{33}$ substituted or unsubstituted heterocycloalkyl, $R^{33}$-substituted or unsubstituted aryl, or $R^{33}$-substituted or unsubstituted heteroaryl.

$R^{33}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

In some embodiments of the compounds provided herein, $L^3$ is independently a bond, —NH—, —O—, —S—, —C(O)—, —S(O)—, —S(O)$_2$—, $R^{35}$-substituted or unsubstituted alkylene, $R^{35}$-substituted or unsubstituted heteroalkylene, $R^{35}$-substituted or unsubstituted cycloalkylene, $R^{35}$-substituted or unsubstituted heterocycloalkylene, $R^{35}$-substituted or unsubstituted arylene, or $R^{35}$-substituted or unsubstituted heteroarylene.

$R^{35}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{36}$-substituted or unsubstituted alkyl, $R^{36}$-substituted or unsubstituted heteroalkyl, $R^{36}$-substituted or unsubstituted cycloalkyl, $R^{36}$ substituted or unsubstituted heterocycloalkyl, $R^{36}$-substituted or unsubstituted aryl, or $R^{36}$-substituted or unsubstituted heteroaryl.

$R^{36}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

In some embodiments of the compounds provided herein, $R^7$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC—(O)$NH_2$, —$NHSO_2H$, —NHC=(O)H, —NHC(O)—OH, —NHOH, —$OCF_3$, —$OCHF_2$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl.

$R^{38}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$S(O)_2CHCH_2$, —$NHS(O)_2CHCH_2$, $R^{39}$-substituted or unsubstituted alkyl, $R^{39}$-substituted or unsubstituted heteroalkyl, $R^{39}$-substituted or unsubstituted cycloalkyl, $R^{39}$ substituted or unsubstituted heterocycloalkyl, $R^{39}$-substituted or unsubstituted aryl, or $R^{39}$-substituted or unsubstituted heteroaryl.

$R^{39}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$S(O)_2CHCH_2$, —$NHS(O)_2CHCH_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

In some embodiments of the compounds provided herein, $R^8$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

$R^{41}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$S(O)_2CHCH_2$, —$NHS(O)_2CHCH_2$, $R^{42}$-substituted or unsubstituted alkyl, $R^{42}$-substituted or unsubstituted heteroalkyl, $R^{42}$-substituted or unsubstituted cycloalkyl, $R^{42}$ substituted or unsubstituted heterocycloalkyl, $R^{42}$-substituted or unsubstituted aryl, or $R^{42}$-substituted or unsubstituted heteroaryl.

$R^{42}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$S(O)_2CHCH_2$, —$NHS(O)_2CHCH_2$, $R^{43}$-substituted or unsubstituted alkyl, $R^{43}$-substituted or unsubstituted heteroalkyl, $R^{43}$-substituted or unsubstituted cycloalkyl, $R^{43}$-substituted or unsubstituted heterocycloalkyl, $R^{43}$-substituted or unsubstituted aryl, or $R^{43}$-substituted or unsubstituted heteroaryl.

In some embodiments of the compounds provided herein, $R^9$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{44}$-substituted or unsubstituted alkyl, $R^{44}$-substituted or unsubstituted heteroalkyl, $R^{44}$-substituted or unsubstituted cycloalkyl, $R^{44}$-substituted or unsubstituted heterocycloalkyl, $R^{44}$-substituted or unsubstituted aryl, or $R^{44}$-substituted or unsubstituted heteroaryl.

$R^{44}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{45}$-substituted or unsubstituted alkyl, $R^{45}$-substituted or unsubstituted heteroalkyl, $R^{45}$-substituted or unsubstituted cycloalkyl, $R^{45}$ substituted or unsubstituted heterocycloalkyl, $R^{45}$-substituted or unsubstituted aryl, or $R^{45}$-substituted or unsubstituted heteroaryl.

$R^{45}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{46}$-substituted or unsubstituted alkyl, $R^{46}$-substituted or unsubstituted heteroalkyl, $R^{46}$-substituted or unsubstituted cycloalkyl, $R^{46}$ substituted or unsubstituted heterocycloalkyl, $R^{46}$-substituted or unsubstituted aryl, or $R^{46}$-substituted or unsubstituted heteroaryl.

In some embodiments of the compounds provided herein, $R^{10}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{47}$-substituted or unsubstituted alkyl, $R^{47}$-substituted or unsubstituted heteroalkyl, $R^{47}$-substituted or unsubstituted cycloalkyl, $R^{47}$-substituted or unsubstituted heterocycloalkyl, $R^{47}$-substituted or unsubstituted aryl, or $R^{47}$-substituted or unsubstituted heteroaryl.

$R^{47}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC—(O)$NH_2$, —$NHSO_2H$, —NHC=(O)H, —NHC(O)—OH, —NHOH, —$OCF_3$, —$OCHF_2$, $R^{48}$-substituted or unsubstituted alkyl, $R^{48}$-substituted or unsubstituted heteroalkyl, $R^{48}$-substituted or unsubstituted cycloalkyl, $R^{48}$ substituted or unsubstituted heterocycloalkyl, $R^{48}$-substituted or unsubstituted aryl, or $R^{48}$-substituted or unsubstituted heteroaryl.

$R^{48}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{49}$-substituted or unsubstituted alkyl, $R^{49}$-substituted or unsubstituted heteroalkyl, $R^{49}$-substituted or unsubstituted cycloalkyl, $R^{49}$-substituted or unsubstituted heterocycloalkyl, $R^{49}$-substituted or unsubstituted aryl, or $R^{49}$-substituted or unsubstituted heteroaryl.

In some embodiments of the compounds provided herein, $R^{13}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{56}$-substituted or unsubstituted alkyl, $R^{56}$-substituted or unsubstituted heteroalkyl, $R^{56}$-substituted or unsubstituted cycloalkyl, $R^{56}$-substituted or unsubstituted heterocycloalkyl, $R^{56}$-substituted or unsubstituted aryl, or $R^{56}$-substituted or unsubstituted heteroaryl.

$R^{56}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{57}$-substituted or unsubstituted alkyl, $R^{57}$-substituted or unsubstituted heteroalkyl, $R^{57}$-substituted or unsubstituted cycloalkyl, $R^{57}$ substituted or unsubstituted heterocycloalkyl, $R^{57}$-substituted or unsubstituted aryl, or $R^{57}$, substituted or unsubstituted heteroaryl.

$R^{57}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{58}$-substituted or unsubstituted alkyl, $R^{58}$-substituted or unsubstituted heteroalkyl, $R^{58}$-substituted or unsubstituted cycloalkyl, $R^{58}$-substituted or unsubstituted heterocycloalkyl, $R^{58}$-substituted or unsubstituted aryl, or $R^{58}$ substituted or unsubstituted heteroaryl.

In another embodiment of the compounds provided herein, $R^{14}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{59}$-substituted or unsubstituted alkyl, $R^{59}$-substituted or unsubstituted heteroalkyl, $R^{59}$-substituted or unsubstituted cycloalkyl, $R^{59}$-substituted or unsubstituted heterocycloalkyl, $R^{59}$-substituted or unsubstituted aryl, or $R^{59}$-substituted or unsubstituted heteroaryl.

$R^{59}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl.

$R^{60}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl.

In a further embodiment of the compounds provided herein, $R^{15}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl.

$R^{62}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{63}$-substituted or unsubstituted alkyl, $R^{63}$-substituted or unsubstituted heteroalkyl, $R^{63}$-substituted or unsubstituted cycloalkyl, $R^{63}$-substituted or unsubstituted heterocycloalkyl, $R^{63}$-substituted or unsubstituted aryl, or $R^{63}$-substituted or unsubstituted heteroaryl.

$R^{63}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —OCHF$_2$, R$^{64}$-substituted or unsubstituted alkyl, R$^{64}$-substituted or unsubstituted heteroalkyl, R$^{64}$-substituted or unsubstituted cycloalkyl, R$^{64}$-substituted or unsubstituted heterocycloalkyl, R$^{64}$-substituted or unsubstituted aryl, or R$^{64}$-substituted or unsubstituted heteroaryl.

In some embodiments of the compounds provided herein, R$^{16}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{65}$-substituted or unsubstituted alkyl, R$^{65}$-substituted or unsubstituted heteroalkyl, R$^{65}$-substituted or unsubstituted cycloalkyl, R$^{65}$-substituted or unsubstituted heterocycloalkyl, R$^{65}$-substituted or unsubstituted aryl, or R$^{65}$-substituted or unsubstituted heteroaryl.

R$^{65}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{66}$-substituted or unsubstituted alkyl, R$^{66}$-substituted or unsubstituted heteroalkyl, R$^{66}$-substituted or unsubstituted cycloalkyl, R$^{66}$-substituted or unsubstituted heterocycloalkyl, R$^{66}$-substituted or unsubstituted aryl, or R$^{66}$-substituted or unsubstituted heteroaryl.

R$^{66}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{67}$-substituted or unsubstituted alkyl, R$^{67}$-substituted or unsubstituted heteroalkyl, R$^{67}$-substituted or unsubstituted cycloalkyl, R$^{67}$-substituted or unsubstituted heterocycloalkyl, R$^{67}$-substituted or unsubstituted aryl, or R$^{67}$-substituted or unsubstituted heteroaryl.

In some embodiments of the compounds provided herein, R$^{17}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{68}$-substituted or unsubstituted alkyl, R$^{68}$-substituted or unsubstituted heteroalkyl, R$^{68}$-substituted or unsubstituted cycloalkyl, R$^{68}$-substituted or unsubstituted heterocycloalkyl, R$^{68}$-substituted or unsubstituted aryl, or R$^{68}$-substituted or unsubstituted heteroaryl.

R$^{68}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{69}$-substituted or unsubstituted alkyl, R$^{69}$-substituted or unsubstituted heteroalkyl, R$^{69}$-substituted or unsubstituted cycloalkyl, R$^{69}$-substituted or unsubstituted heterocycloalkyl, R$^{69}$-substituted or unsubstituted aryl, or R$^{69}$-substituted or unsubstituted heteroaryl.

R$^{69}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{70}$-substituted or unsubstituted alkyl, R$^{70}$-substituted or unsubstituted heteroalkyl, R$^{70}$-substituted or unsubstituted cycloalkyl, R$^{70}$ substituted or unsubstituted heterocycloalkyl, R$^{70}$-substituted or unsubstituted aryl, or R$^{70}$-substituted or unsubstituted heteroaryl.

In some embodiments of the compounds provided herein, R$^{7a}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{38a}$-substituted or unsubstituted alkyl, R$^{38a}$-substituted or unsubstituted heteroalkyl, R$^{38a}$-substituted or unsubstituted cycloalkyl, R$^{38a}$-substituted or unsubstituted heterocycloalkyl, R$^{38a}$-substituted or unsubstituted aryl, or R$^{38a}$-substituted or unsubstituted heteroaryl.

R$^{38a}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{39a}$-substituted or unsubstituted alkyl, R$^{39a}$-substituted or unsubstituted heteroalkyl, R$^{39a}$-substituted or unsubstituted cycloalkyl, R$^{39a}$ substituted or unsubstituted heterocycloalkyl, R$^{39a}$-substituted or unsubstituted aryl, or R$^{39a}$-substituted or unsubstituted heteroaryl.

R$^{39a}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{40a}$-substituted or unsubstituted alkyl, R$^{40a}$-substituted or unsubstituted heteroalkyl, R$^{40a}$-substituted or unsubstituted cycloalkyl, R$^{40a}$-substituted or unsubstituted heterocycloalkyl, R$^{40a}$-substituted or unsubstituted aryl, or R$^{40a}$-substituted or unsubstituted heteroaryl.

In some embodiments of the compounds provided herein, R$^{8a}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{41a}$-substituted or unsubstituted alkyl, R$^{41a}$-substituted or unsubstituted heteroalkyl, R$^{41a}$-substituted or unsubstituted cycloalkyl, R$^{41a}$-substituted or unsubstituted heterocycloalkyl, R$^{41a}$-substituted or unsubstituted aryl, or R$^{41a}$-substituted or unsubstituted heteroaryl.

R$^{41a}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{42a}$-substituted or unsubstituted alkyl, R$^{42a}$-substituted or unsubstituted heteroalkyl, R$^{42a}$-substituted or unsubstituted cycloalkyl, R$^{42a}$ substituted or unsubstituted heterocycloalkyl, R$^{42a}$-substituted or unsubstituted aryl, or R$^{42a}$ substituted or unsubstituted heteroaryl.

R$^{42a}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{43a}$-substituted or unsubstituted alkyl, R$^{43a}$-substituted or unsubstituted heteroalkyl, R$^{43a}$-substituted or unsubstituted cycloalkyl, R$^{43a}$-substituted or unsubstituted heterocycloalkyl, R$^{43a}$-substituted or unsubstituted aryl, or R$^{43a}$-substituted or unsubstituted heteroaryl.

In some embodiments of the compounds provided herein, R$^{9a}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{44a}$-substituted or unsubstituted alkyl, R$^{44a}$-substituted or unsubstituted heteroalkyl, R$^{44a}$-substituted or unsubstituted cycloalkyl, R$^{44a}$-substituted or unsubstituted heterocycloalkyl, R$^{44a}$-substituted or unsubstituted aryl, or R$^{44a}$-substituted or unsubstituted heteroaryl.

R$^{44a}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{45a}$-substituted or unsubstituted alkyl, R$^{45a}$-substituted or unsubstituted heteroalkyl, R$^{45a}$-substituted or unsubstituted cycloalkyl, R$^{45a}$ substituted or unsubstituted heterocycloalkyl, R$^{45a}$-substituted or unsubstituted aryl, or R$^{45a}$ substituted or unsubstituted heteroaryl.

R$^{45a}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{46a}$-substituted or unsubstituted alkyl, R$^{46a}$-substituted or unsubstituted heteroalkyl, R$^{46a}$-substituted or unsubstituted cycloalkyl, R$^{46a}$-substituted or unsubstituted heterocycloalkyl, R$^{46a}$-substituted or unsubstituted aryl, or R$^{46a}$-substituted or unsubstituted heteroaryl.

In some embodiments of the compounds provided herein, R$^{10a}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{47a}$-substituted or unsubstituted alkyl, R$^{47a}$-substituted or unsubstituted heteroalkyl, R$^{47a}$-substituted or unsubstituted cycloalkyl, R$^{47a}$-substituted or unsubstituted heterocycloalkyl, R$^{47a}$-substituted or unsubstituted aryl, or R$^{47a}$-substituted or unsubstituted heteroaryl.

R$^{47a}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{48a}$-substituted or unsubstituted alkyl, R$^{48a}$-substituted or unsubstituted heteroalkyl, R$^{48a}$-substituted or unsubstituted cycloalkyl, R$^{48a}$ substituted or unsubstituted heterocycloalkyl, R$^{48a}$-substituted or unsubstituted aryl, or R$^{48a}$ substituted or unsubstituted heteroaryl.

R$^{48a}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC—(O)NHNH$_2$, —NHC—(O)NH$_2$, —NHSO$_2$H, —NHC=(O)H, —NHC(O)—OH, —NHOH, —OCF$_3$, —OCHF$_2$, R$^{49a}$-substituted or unsubstituted alkyl, R$^{49a}$-substituted or unsubstituted heteroalkyl, R$^{49a}$-substituted or unsubstituted cycloalkyl, R$^{49a}$-substituted or unsubstituted heterocycloalkyl, R$^{49a}$-substituted or unsubstituted aryl, or R$^{49a}$-substituted or unsubstituted heteroaryl.

In some embodiments of the compounds provided herein, R$^{7c}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC—(O)NHNH$_2$, —NHC—(O)NH$_2$, —NHSO$_2$H, —NHC=(O)H, —NHC(O)—OH, —NHOH, —OCF$_3$, —OCHF$_2$, R$^{38c}$-substituted or unsubstituted alkyl, R$^{38c}$-substituted or unsubstituted heteroalkyl, R$^{38c}$-substituted or unsubstituted cycloalkyl, R$^{38c}$-substituted or unsubstituted heterocycloalkyl, R$^{38c}$-substituted or unsubstituted aryl, or R$^{38c}$-substituted or unsubstituted heteroaryl.

R$^{38c}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{39c}$-substituted or unsubstituted alkyl, R$^{39c}$-substituted or unsubstituted heteroalkyl, R$^{39c}$-substituted or unsubstituted cycloalkyl, R$^{39c}$-substituted or unsubstituted heterocycloalkyl, R$^{39c}$-substituted or unsubstituted aryl, or R$^{39c}$-substituted or unsubstituted heteroaryl.

R$^{39c}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{40c}$-substituted or unsubstituted alkyl, R$^{40c}$-substituted or unsubstituted heteroalkyl, R$^{40c}$-substituted or unsubstituted cycloalkyl, R$^{40c}$-substituted or unsubstituted heterocycloalkyl, R$^{40c}$-substituted or unsubstituted aryl, or R$^{40c}$-substituted or unsubstituted heteroaryl.

In some embodiments of the compounds provided herein, R$^{8c}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC—(O)NH$_2$, —NHSO$_2$H, —NHC=(O)H, —NHC(O)—OH, —NHOH, —OCF$_3$, —OCHF$_2$, R$^{41c}$-substituted or unsubstituted alkyl, R$^{41c}$-substituted or unsubstituted heteroalkyl, R$^{41c}$-substituted or unsubstituted cycloalkyl, R$^{41c}$-substituted or unsubstituted heterocycloalkyl, R$^{41c}$-substituted or unsubstituted aryl, or R$^{41c}$-substituted or unsubstituted heteroaryl.

R$^{41c}$ is independently oxo, halogen, —CF$_3$, —CN, —OH, —NH$_2$, —COOH, —CONH$_2$, —NO$_2$, —SH, —SO$_2$C$_1$, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{42c}$-substituted or unsubstituted alkyl, R$^{42c}$-substituted or unsubstituted heteroalkyl, R$^{42c}$-substituted or unsubstituted cycloalkyl, R$^{42c}$-substituted or unsubstituted heterocycloalkyl, R$^{42c}$-substituted or unsubstituted aryl, or R$^{42c}$-substituted or unsubstituted heteroaryl.

R$^{42c}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{43c}$-substituted or unsubstituted alkyl, R$^{43c}$-substituted or unsubstituted heteroalkyl, R$^{43c}$-substituted or unsubstituted cycloalkyl, R$^{43c}$-substituted or unsubstituted heterocycloalkyl, R$^{43c}$-substituted or unsubstituted aryl, or R$^{43c}$-substituted or unsubstituted heteroaryl.

In some embodiments of the compounds provided herein, R$^{9c}$, is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{44c}$-substituted or unsubstituted alkyl, R$^{44c}$-substituted or unsubstituted heteroalkyl, R$^{44c}$-substituted or unsubstituted cycloalkyl, R$^{44c}$-substituted or unsubstituted heterocycloalkyl, R$^{44c}$-substituted or unsubstituted aryl, or R$^{44c}$-substituted or unsubstituted heteroaryl.

R$^{44c}$ is independently oxo, halogen, —CF$_3$, —CN, —OH, —NH$_2$, —COOH, —CONH$_2$, —NO$_2$, —SH, —SO$_2$Cl, —SO$_3$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, R$^{45c}$-substituted or unsubstituted alkyl, R$^{45c}$-substituted or unsubstituted heteroalkyl, R$^{45c}$-substituted or unsubstituted cycloalkyl, R$^{45c}$-substituted or unsubstituted heterocycloalkyl, R$^{45c}$-substituted or unsubstituted aryl, or R$^{45c}$ substituted or unsubstituted heteroaryl.

R$^{45c}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC—(O)NH$_2$, —NHSO$_2$H, —NHC═(O)H, —NHC(O)—OH, —NHOH, —OCF$_3$, —OCHF$_2$, R$^{46c}$-substituted or unsubstituted alkyl, R$^{46c}$-substituted or unsubstituted heteroalkyl, R$^{46c}$-substituted or unsubstituted cycloalkyl, R$^{46c}$-substituted or unsubstituted heterocycloalkyl, R$^{46c}$-substituted or unsubstituted aryl, or R$^{46c}$-substituted or unsubstituted heteroaryl.

In some embodiments of the compounds provided herein, R$^{10c}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, R$^{47c}$-substituted or unsubstituted alkyl, R$^{47c}$-substituted or unsubstituted heteroalkyl, R$^{47c}$-substituted or unsubstituted cycloalkyl, R$^{47c}$-substituted or unsubstituted heterocycloalkyl, R$^{47c}$-substituted or unsubstituted aryl, or R$^{47c}$-substituted or unsubstituted heteroaryl.

R$^{47c}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC—(O)NHNH$_2$, —NHC═(O)NH$_2$, —NHSO$_2$H, —NHC═(O)H, —NHC(O)—OH, —NHOH, —OCF$_3$, —OCHF$_2$, R$^{48c}$-substituted or unsubstituted alkyl, R$^{48c}$-substituted or unsubstituted heteroalkyl, R$^{48c}$-substituted or unsubstituted cycloalkyl, R$^{48c}$-substituted or unsubstituted heterocycloalkyl, R$^{48c}$-substituted or unsubstituted aryl, or R$^{48c}$-substituted or unsubstituted heteroaryl.

R$^{48c}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, R$^{49c}$-substituted or unsubstituted alkyl, R$^{49c}$-substituted or unsubstituted heteroalkyl, R$^{49c}$-substituted or unsubstituted cycloalkyl, R$^{49c}$-substituted or unsubstituted heterocycloalkyl, R$^{49c}$-substituted or unsubstituted aryl, or R$^{49c}$-substituted or unsubstituted heteroaryl.

In some embodiments of the compounds provided herein, R$^{22}$, R$^{25}$, R$^{25A}$, R$^{25B}$, R$^{25C}$, R$^{28}$R$^{31}$, R$^{34}$, R$^{37}$, R$^{40}$, R$^{43}$, R$^{46}$, R$^{49}$, R$^{58}$, R$^{61}$, R$^{64}$, R$^{67}$, R$^{70}$, R$^{40a}$, R$^{43a}$, R$^{46a}$, R$^{49a}$, R$^{40c}$, R$^{43c}$, R$^{46c}$, R$^{49c}$, are independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, the compound has the Formula:

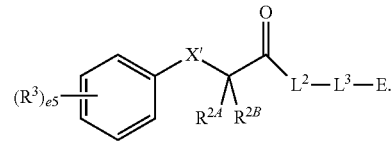

R$^3$, e5, R$^{2A}$, R$^{2B}$, L$^2$, L$^3$, and E are as described herein and above (including embodiments). X' is —O—, —NH—, or —S—. E is an electrophilic chemical moiety capable of forming a covalent bond with a cysteine or aspartate residue; R$^{2C}$ is independently hydrogen, oxo, halogen, —CX$^c_3$, —CN, —SO$_2$Cl, —SO$_{n3}$R$^{10c}$, —SO$_{v3}$NR$^{7c}$R$^{8c}$, —NHNH$_2$, —ONR$^7$R$^{8c}$, —NHC═(O)NHNH$_2$, —NHC═(O)NR$^1$CR$^{8c}$, —N(O)$_{m3}$, —NR$^{7c}$R &C, —C(O)R$^{9c}$, —C(O)—OR$^{9c}$, —C(O)NR$^{7c}$R$^{8c}$, —OR$^{10c}$, —NR$^{7c}$SO$_2$R$^{10c}$, —NR$^{7c}$═(O) R$^9$, —NR$^{7c}$ (O)—OR$^9$, —NR$^{7c}$OR$^{9c}$, —OCX$^c_3$, —OCHX$^c_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^{2C}$ substituents may optionally be joined to form a substituted or unsubstituted cycloalkyl, substituted or unsubstituted heterocycloalkyl, substituted or unsubstituted aryl, or substituted or unsubstituted heteroaryl; two R$^{2C}$ substituents bonded to the same atom may optionally be joined to form a substituted or unsubstituted cycloalkyl or substituted or unsubstituted heterocycloalkyl; R$^7$, R$^8$, R$^9$, and R$^{10}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{7a}$, R$^{8a}$, R$^{9a}$ and R$^{10a}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC (O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{7a}$ and R$^{8a}$ substituents bonded to the same nitrogen atom may optionally be joined to form a substituted or unsubstituted heterocycloalkyl or substituted or unsubstituted heteroaryl; R$^{7c}$, R$^{8C}$, R$^{9c}$, and R$^{10c}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; m, m1, m3, v, v1, and v3 are independently 1 or 2; n, n1, and n3 are independently an integer from 0 to 4; X, X$^a$ and X$^c$ are independently —Cl, —Br, —I, or —F.

In some embodiments, E comprises a substituted or unsubstituted vinyl sulfone moiety, substituted or unsubstituted vinyl sulfonamide moiety, substituted or unsubstituted peroxide moiety, substituted or unsubstituted fluoro ($C_1$-$C_4$) alkylketone moiety, substituted or unsubstituted chloro($C_1$-$C_4$) alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety. In some embodiments, E is a substituted or unsubstituted vinyl sulfone moiety, substituted or unsubstituted vinyl sulfonamide moiety, substituted or unsubstituted peroxide moiety, substituted or unsubstituted fluoro ($C_1$-$C_4$) alkylketone moiety, substituted or unsubstituted chloro($C_1$-$C_4$) alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety.

In some embodiments, $L^2$ is independently $R^{2C}$-substituted or unsubstituted heterocycloalkylene or $R^{2C}$-substituted or unsubstituted spirocyclic linker and $L^3$ is a bond. For exmaple, $L^2$ is monocyclic 4, 5, or 6-membered heterocycloalkylene. In some embodiments, $L^2$ is unsubstituted piperazino or unsubstituted piperidino. In other embodiments, $L^2$ is bicyclic fused heterocycloalkylene. In yet other embodiments, $L^2$ is an unsubstituted spirocyclic linker.

In some embodiments of the above compounds, E comprises a substituted or unsubstituted vinyl sulfone moiety, substituted or unsubstituted vinyl sulfonamide moiety, or a substituted or unsubstituted acrylamide moiety. In some embodiments of the above compounds, E is a substituted or unsubstituted vinyl sulfone moiety, substituted or unsubstituted vinyl sulfonamide moiety, or a substituted or unsubstituted acrylamide moiety.

In some embodiments, the compound has the Formula:

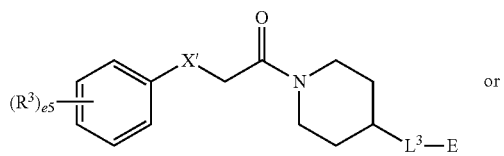

or

-continued

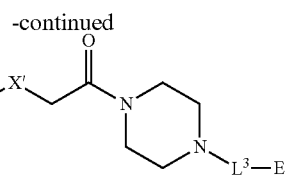

In some embodiments, the compound binds Ras (e.g. K-Ras, H-Ras, N-Ras, mutant Ras, K-Ras G12C, K-Ras G13C, K-Ras G12D, K-Ras G13D) behind Switch II. In embodiments, the compound modulates the conformation of Switch II. In embodiments, the compound modulates the conformation of Switch I. In embodiments, the compound modulates the conformation of Switch I and Switch II. In embodiments, the compound inhibits (e.g. by about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000, 10000 fold or more) Ras (e.g. K-Ras, H-Ras, N-Ras, mutant Ras, K-Ras G12C, K-Ras G13C, K-Ras G12D, K-Ras G13D) nucleotide exchange (e.g. GDP for GTP or GTP for GDP) relative to the absence of the compound. In embodiments, the compound inhibits release of GDP from Ras (e.g. K-Ras, H-Ras, N-Ras, mutant Ras, K-Ras G12C, K-Ras G13C, K-Ras G12D, K-Ras G13D) relative to the absence of the compound. In embodiments, the compound inhibits binding of GDP to Ras (e.g. K-Ras, H-Ras, N-Ras, mutant Ras, K-Ras G12C, K-Ras G13C, K-Ras G12D, K-Ras G13D) relative to the absence of the compound. In embodiments, the compound inhibits binding of GTP to Ras (e.g. K-Ras, H-Ras, N-Ras, mutant Ras, K-Ras G12C, K-Ras G13C, K-Ras G12D, K-Ras G13D) relative to the absence of the compound. In embodiments, the compound increases (e.g. by about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000, 10000 fold or more) Ras (e.g. K-Ras, H-Ras, N-Ras, mutant Ras, K-Ras G12C, K-Ras G13C, K-Ras G12D, K-Ras G13D) nucleotide exchange (e.g. GDP for GTP or GTP for GDP) relative to the absence of the compound. In embodiments, the compound increases release of GDP from Ras (e.g. K-Ras, H-Ras, N-Ras, mutant Ras, K-Ras G12C, K-Ras G13C, K-Ras G12D, K-Ras G13D) relative to the absence of the compound. In embodiments, the compound increases release of GTP from Ras (e.g. K-Ras, H-Ras, N-Ras, mutant Ras, K-Ras G12C, K-Ras G13C, K-Ras G12D, K-Ras G13D) relative to the absence of the compound. In embodiments, the compound increases binding of GDP to Ras (e.g. K-Ras, H-Ras, N-Ras, mutant Ras, K-Ras G12C, K-Ras G13C, K-Ras G12D, K-Ras G13D) relative to the absence of the compound. In embodiments, the compound inhibits binding of GTP to Ras (e.g. K-Ras, H-Ras, N-Ras, mutant Ras, K-Ras G12C, K-Ras G13C, K-Ras G12D, K-Ras G13D) relative to the absence of the compound. In embodiments, the compound inhibits binding of a GTP analog (e.g. mant-dGTP) to Ras (e.g. K-Ras, H-Ras, N-Ras, mutant Ras, K-Ras G12C, K-Ras G13C, K-Ras G12D, K-Ras G13D) relative to the absence of the compound. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid that contacts GTP in the absence of the compound. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid that contacts GDP in the absence of the compound. In embodiments, the compound modulates the conformation of a plurality of Ras (e.g. K-Ras, H-Ras, N-Ras, mutant Ras, K-Ras G12C, K-Ras G13C, K-Ras G12D, K-Ras G13D) amino acids that contact GTP in the absence of the compound. In embodiments, the compound modulates the conformation of a plurality of Ras (e.g. K-Ras, H-Ras, N-Ras, mutant Ras, K-Ras G12C, K-Ras G13C, K-Ras G12D, K-Ras G13D) amino acids that contact GDP in the absence of the compound. In embodiments, the compound modulates the binding of GTP and/or GDP to Ras (e.g. K-Ras, H-Ras, N-Ras, mutant Ras, K-Ras G12C, K-Ras G13C, K-Ras G12D, K-Ras G13D) compared to binding in the absence of the compound. In embodiments, the compound modulates the release of GTP and/or GDP from Ras (e.g. K-Ras, H-Ras, N-Ras, mutant Ras, K-Ras G12C, K-Ras G13C, K-Ras G12D, K-Ras G13D) compared to release in the absence of the compound. In embodiments, the compound modulates the ratio of the binding of GTP and GDP to Ras (e.g. K-Ras, H-Ras, N-Ras, mutant Ras, K-Ras G12C, K-Ras G13C, K-Ras G12D, K-Ras G13D) compared to the ratio in the absence of the compound. In embodiments, the compound modulates the ratio of the rate of release of GTP and GDP from Ras (e.g. K-Ras, H-Ras, N-Ras, mutant Ras, K-Ras G12C, K-Ras G13C, K-Ras G12D, K-Ras G13D) compared to the ratio in the absence of the compound. In embodiments, the compound modulates the conformation of a Ras amino acid that contacts the gamma phosphate of GTP when GTP is bound to Ras. In embodiments, the compound inhibits the binding of the gamma phosphate of GTP relative to the binding in the absence of the compound. In embodiments, the compound binds Ras (e.g. K-Ras, H-Ras, N-Ras, mutant Ras, K-Ras G12C, K-Ras G13C, K-Ras G12D, K-Ras G13D) protein bound to GDP and, after release of the GDP, modulates the subsequent binding of GDP or GTP to the Ras bound to the compound. In embodiments, the compound binds Ras (e.g. K-Ras, H-Ras, N-Ras, mutant Ras, K-Ras G12C, K-Ras G13C, K-Ras G12D, K-Ras G13D) protein bound to GDP and, after release of the GDP, modulates the subsequent binding of GDP to the Ras bound to the compound. In embodiments, the compound binds Ras (e.g. K-Ras, H-Ras, N-Ras, mutant Ras, K-Ras G12C, K-Ras G13C, K-Ras G12D, K-Ras G13D) protein bound to GDP and after release of the GDP, modulates the subsequent binding of GTP to the Ras bound to the compound.

In embodiments, the compound inhibits proliferation of cancer cells under nutrient deficient conditions relative to the absence of the compound. In embodiments, the compound inhibits growth of cancer cells under nutrient deficient conditions relative to the absence of the compound. In embodiments, the compound inhibits growth of cancer cells under nutrient deficient conditions relative to the absence of the compound. In embodiments, the compound inhibits growth of cancer cells under serum deprivation conditions relative to the absence of the compound. In embodiments, the compound inhibits proliferation of cancer cells under serum deprivation conditions relative to the absence of the compound. In embodiments, the compound inhibits growth of cancer cells under conditions (e.g. local cell environment in a patient) mimicking serum deprivation relative to the absence of the compound. In embodiments, the compound inhibits proliferation of cancer cells under conditions (e.g. local cell environment in a patient) mimicking serum deprivation relative to the absence of the compound.

In embodiments, the compound modulates the conformation of the amino acid corresponding to amino acid 60 in human K-Ras in a Ras protein. In embodiments, the compound modulates the distance between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras G12C, K-Ras G13C, K-Ras G12D, K-Ras G13D). In embodiments the compound increases the distance between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras G12C, K-Ras G13C, K-Ras G12D, K-Ras G13D). In embodiments the compound increases the distance (e.g. by about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0, or more angstroms) between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras G12C, K-Ras G13C, K-Ras G12D, K-Ras G13D) relative to the absence of the compound. In embodiments the compound increases the distance (e.g. by about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0, or more angstroms) between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras G12C, K-Ras G13C, K-Ras G12D, K-Ras G13D) when bound to GDP, relative to the absence of the compound. In embodiments the compound increases the distance (e.g. by about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0, or more angstroms) between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras G12C, K-Ras G13C, K-Ras G12D, K-Ras G13D) when bound to GTP, compared to the distance in the absence of the compound. In embodiments, upon binding to Ras (e.g. K-Ras, H-Ras, N-Ras, mutant Ras, K-Ras G12C, K-Ras G13C, K-Ras G12D, K-Ras G13D) the compound (e.g. a compound described herein, including embodiments and including a compound described in a table, example, or figure) modulates the distance between the alpha carbon of the amino acid corresponding to amino acid 12 in human K-Ras and the alpha carbon of the amino acid corresponding to amino acid 60 in human K-Ras, in the Ras protein (e.g. K-Ras, H-Ras, N-Ras, mutant Ras, K-Ras G12C, K-Ras G13C, K-Ras G12D, K-Ras G13D) to be about 4.9 angstoms or greater (e.g. about 5.0, 5.1, 5.2, 5.3, 5.4, 5.5, 5.6, 5.7, 5.8, 5.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0 angstroms, or greater). In embodiments, upon binding to Ras (e.g. K-Ras, H-Ras, N-Ras, mutant Ras, K-Ras G12C, K-Ras G13C, K-Ras G12D, K-Ras G13D) the compound (e.g. a compound described herein, including embodiments and including a compound described in a table, example, or figure) modulates the distance between the alpha carbon of the amino acid corresponding to amino acid 12 in human K-Ras and the alpha carbon of the amino acid corresponding to amino acid 60 in human K-Ras, in the Ras protein (e.g. K-Ras, H-Ras, N-Ras, mutant Ras, K-Ras G12C, K-Ras G13C, K-Ras G12D, K-Ras G13D) to be greater than about 4.9 angstroms (e.g. greater than about 5.0, 5.1, 5.2, 5.3, 5.4, 5.5, 5.6, 5.7, 5.8, 5.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0 angstroms, or greater). In embodiments, upon binding to Ras (e.g. K-Ras, H-Ras, N-Ras, mutant Ras, K-Ras G12C, K-Ras G13C, K-Ras G12D, K-Ras G13D) the compound (e.g. a compound described herein, including embodiments and including a compound described in a table, example, or figure) modulates the distance between the alpha carbon of the amino acid corresponding to amino acid 12 in human K-Ras and the alpha carbon of the amino acid corresponding to amino acid 60 in human K-Ras, in the Ras protein (e.g. K-Ras, H-Ras, N-Ras, mutant Ras, K-Ras G12C, K-Ras G13C, K-Ras G12D, K-Ras G13D) to be 4.9 angstoms or greater (e.g. 5.0, 5.1, 5.2, 5.3, 5.4, 5.5, 5.6, 5.7, 5.8, 5.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0 angstroms, or greater). In embodiments, upon binding to Ras (e.g. K-Ras, H-Ras, N-Ras, mutant Ras, K-Ras G12C, K-Ras G13C, K-Ras G12D, K-Ras G13D) the compound (e.g. a compound described herein, including embodiments and including a compound described in a table, example, or figure) modulates the distance between the alpha carbon of the amino acid corresponding to amino acid 12 in human K-Ras and the alpha carbon of the amino acid corresponding to amino acid 60 in human K-Ras, in the Ras protein (e.g. K-Ras, H-Ras, N-Ras, mutant Ras, K-Ras G12C, K-Ras G13C, K-Ras G12D, K-Ras G13D) to be greater than 4.9 angstroms (e.g. greater than 5.0, 5.1, 5.2, 5.3, 5.4, 5.5, 5.6, 5.7, 5.8, 5.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0 angstroms, or greater).

In embodiments, the compound increases the flexibility of Switch I relative to the absence of the compound. In embodiments, the compound increases the disorder of Switch I relative to the absence of the compound. In embodiments, the compound inhibits the binding of Ras ((e.g. K-Ras, H-Ras, N-Ras, mutant Ras, K-Ras G12C, K-Ras G13C, K-Ras G12D, K-Ras G13D) to another protein. In embodiments, the compound inhibits the binding of Ras ((e.g. K-Ras, H-Ras, N-Ras, mutant Ras, K-Ras G12C, K-Ras G13C, K-Ras G12D, K-Ras G13D) to another protein, wherein the binding is dependent on Ras binding to GTP. In embodiments, the compound inhibits the binding of Ras ((e.g. K-Ras, H-Ras, N-Ras, mutant Ras, K-Ras G12C, K-Ras G13C, K-Ras G12D, K-Ras G13D) to another protein, wherein the binding is dependent on Ras binding to GDP. In embodiments, the compound inhibits the binding of Ras ((e.g. K-Ras, H-Ras, N-Ras, mutant Ras, K-Ras G12C, K-Ras G13C, K-Ras G12D, K-Ras G13D) to Raf (e.g. Raf1). In embodiments, the compound inhibits the binding of Ras ((e.g. K-Ras, H-Ras, N-Ras, mutant Ras, K-Ras G12C, K-Ras G13C, K-Ras G12D, K-Ras G13D) to SOS. In embodiments, the compound inhibits the binding of Ras ((e.g. K-Ras, H-Ras, N-Ras, mutant Ras) to a GEF. In embodiments, the compound inhibits the binding of Ras ((e.g. K-Ras, H-Ras, N-Ras, mutant Ras, K-Ras G12C, K-Ras G13C, K-Ras G12D, K-Ras G13D) to PI3K. In embodiments, the compound modulates metal binding near the nucleotide binding site. In embodiments, the compound modulates the conformation of the Ras metal binding site near the nucleotide binding site. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid relative to the conformation in the absence of the compound, wherein the Ras amino acid conformation is also modulated by a Ras G60 mutation. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid relative to the conformation in the absence of the compound, wherein the Ras amino acid conformation is also modulated by a Ras G60A mutation. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid relative to the conformation in the absence of the compound, wherein the Ras amino acid conformation is also modulated by a Ras T35 mutation. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid relative to the conformation in the absence of the compound, wherein the Ras amino acid conformation is also modulated by a Ras T35S mutation. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid relative to the conformation in the absence of the compound, wherein the Ras amino acid conformation is also modulated by a mutation of the Ras amino acid corresponding to K-Ras G60. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid relative to the conformation in the absence of the compound, wherein the Ras amino acid conformation is also modulated by a mutation of the Ras amino acid corresponding to K-Ras T35.

The crystal structures of Hras and Kras bound to GTP show a contact between the gamma phosphate and the backbone amide of glycine-60 in switch II. This contact is known to be critical for orienting the switches for binding to downstream effectors. This conformation required for binding downstream effectors is called state 2. Mutation of glycine-60 to alanine (G60A) prevents proper rotation of residue-60 upon GTP binding, and induces an alternate conformation called state 1. In this conformation, the gamma phosphate of GTP forms a water-mediated hydrogen bond to alanine-60, which likely acts to maintain GTP affinity. Similarly, direct contacts between the gamma phosphate and switch I are replaced by water-mediated contacts. The complete loss of these contacts to the gamma phosphate would be likely to decrease the affinity of Ras for GTP, having less effect on the affinity for GDP.

The state 1 conformation can also be stabilized by mutating threonine-35 to serine (T35S), and the GTP-bound crystal structure of this mutant is known. A crystal structure of the wild-type protein in state 1 has also been solved. We noticed that the conformation of Ras (state 1 or state 2) could be predicted by measuring the distance between the alpha carbon of residue-60 and the alpha carbon of residue-12. If this distance is 3.9 Å or less, direct contacts between the gamma phosphate and the switches are possible and the protein adopts state 2. If this distance is 4.9 Å or greater, these direct contacts are no longer possible and the protein adopts state 1.

When bound to GDP, the conformation of the protein is unaffected by the G60A mutation or the T35S mutation. In both cases, as with the wild-type, the distance between position 12 and position 60 is approximately 8A. In crystal structures we have solved with our inhibitors (e.g. a compound selected from the compounds described herein) bound to KrasG12C, the structures show distances between residue-12 and residue-60 of more than 8 Å in the GDP-bound state. Unlike the wild-type, G60A and T35S, when our inhibitor (e.g. a compound selected from the compounds described herein) is bound this distance cannot decrease to below 5 Å upon GTP-binding due to a steric clash that would occur between our inhibitor and switch II. Therefore, our inhibitors (e.g. a compound selected from the compounds described herein) will prevent switch II from forming contacts with the gamma phosphate and, when they increase the distance between these two residues enough (>11 Å), even cause disordering of switch I.

Based on these observations, our compounds (e.g. a compound selected from the compounds described herein) are likely to have a deleterious effect on GTP binding. Due to the critical contacts from the gamma phosphate to switch II, some of our compounds (e.g. a compound selected from the compounds described herein) will have a greater effect on GTP binding than on GDP binding.

In some embodiments, the compound is any one of the compounds in Table 1, 2, 3, 4, or 5.

In some embodiments, a compound as described herein may include multiple instances of $R^3$, $R^7$, $R^8$, $R^9$, $R^{10}$, $R^{2A}$, $R^{7a}$, $R^{8a}$, $R^{9a}$, $R^{10a}$, $R^{2B}$, $R^{2C}$, $R^{7c}$, $R^{8C}$, $R^{9c}$, $R^{10c}$, X, $X^a$, $X^c$, m, n, v, m1, n1, v1, m3, n3, v3, and/or other variables. In such embodiments, each variable may optional be different and be appropriately labeled to distinguish each group for greater clarity. For example, where each $R^3$, $R^7$, $R^8$, $R^9$, $R^{10}$, $R^{2A}$, $R^{7a}$, $R^{8a}$, $R^{9a}$, $R^{10a}$, $R^{2B}$, $R^{2C}$, $R^{7c}$, $R^{8c}$, $R^{9c}$, $R^{10c}$, X, $X^a$, $X^c$, m, n, v, m1, n1, v1, m3, n3, and/or v3, is different, they may be referred to, for example, as $R^{3.1}$, $R^{3.2}$, $R^{3.3}$, $R^{3.4}$, $R^{3.5}$, $R^{3.6}$, $R^{3.7}$, $R^{7.1}$, $R^{7.2}$, $R^{7.3}$, $R^{74}$, $R^{7.5}$, $R^{7.6}$, $R^{7.7}$, $R^{8.1}$, $R^{8.2}$, $R^{8.3}$, $R^{8.4}$, $R^{8.5}$, $R^{8.6}$, $R^{8.7}$, $R^{9.1}$, $R^{9.2}$, $R^{9.3}$, $R^{9.4}$, $R^{9.5}$, $R^{9.6}$, $R^{9.7}$, $R^{10.1}$, $R^{10.2}$, $R^{10.3}$, $R^{10.4}$, $R^{10.5}$, $R^{10.6}$, $R^{10.7}$, $R^{2A.1}$, $R^{2A.2}$, $R^{2A.3}$, $R^{7a.1}$, $R^{7a.2}$, $R^{7a.3}$, $R^{7a.4}$, $R^{7a.5}$, $R^{7a.6}$, $R^{8a.1}$, $R^{8a.2}$, $R^{8a.3}$, $R^{8a.4}$, $R^{8a.5}$, $R^{8a.6}$, $R^{9a.1}$, $R^{9a.2}$, $R^{9a.3}$, $R^{9a.4}$, $R^{9a.5}$, $R^{9a.6}$, $R^{10a.1}$, $R^{10a.2}$, $R^{10a.3}$, $R^{10a.4}$, $R^{10a.5}$, $R^{10a.6}$, $R^{2B.1}$, $R^{2B.2}$, $R^{2B.3}$, $R^{2C.1}$, $R^{2C.2}$, $R^{2C.3}$, $R^{2C.4}$, $R^{2C.5}$, $R^{2C.6}$, $R^{2C.7}$, $R^{2C.8}$, $R^{2C.9}$, $R^{2C.10}$, $R^{2C.11}$, $R^{2C.12}$, $R^{2C.13}$, $R^{2C.14}$, $R^{2C.15}$, $R^{2C.16}$, $R^{2C.17}$, $R^{2C.18}$, $R^{2C.19}$, $R^{2C.20}$, $R^{2C.21}$, $R^{2C.22}$, $R^{2C.23}$, $R^{2C.24}$, $R^{2C.25}$, $R^{2C.26}$, $R^{2C.27}$, $R^{2C.28}$, $R^{2C.29}$, $R^{2C.30}$, $R^{2C.31}$, $R^{2C.32}$, $R^{2C.33}$, $R^{2C.34}$, $R^{2C.35}$, $R^{2C.36}$, $R^{2C.37}$, $R^{2C.38}$, $R^{2C.39}$, $R^{2C.40}$, $R^{2C.41}$, $R^{2C.42}$, $R^{7c.1}$, $R^{7c.2}$, $R^{7c.3}$, $R^{7c.4}$, $R^{7c.5}$, $R^{7c.6}$, $R^{7c.7}$, $R^{7c.8}$, $R^{7c.9}$, $R^{7c.10}$, $R^{7c.11}$, $R^{7c.12}$, $R^{7c.13}$, $R^{7c.14}$, $R^{7c.15}$, $R^{7c.16}$, $R^{7c.17}$, $R^{7c.18}$, $R^{7c.19}$, $R^{7c.20}$, $R^{7c.21}$, $R^{7c.22}$, $R^{7c.23}$, $R^{7c.24}$, $R^{7c.25}$, $R^{7c.26}$, $R^{7c.27}$, $R^{7c.28}$, $R^{7c.29}$, $R^{7c.30}$, $R^{7c.31}$, $R^{7c.32}$, $R^{7c.33}$, $R^{7c.34}$, $R^{7c.35}$, $R^{7c.36}$, $R^{7c.37}$, $R^{7c.38}$, $R^{7c.39}$, $R^{7c.40}$, $R^{7c.41}$, $R^{7c.42}$, $R^{8c.1}$, $R^{8c.2}$, $R^{8c.3}$, $R^{8c.4}$, $R^{8c.5}$, $R^{8c.6}$, $R^{8c.7}$, $R^{8c.8}$, $R^{8c.9}$, $R^{8c.10}$, $R^{8c.11}$, $R^{8c.12}$, $R^{8c.13}$, $R^{8c.14}$, $R^{8c.15}$, $R^{8c.16}$, $R^{8c.17}$, $R^{8c.18}$, $R^{8c.19}$, $R^{8c.20}$, $R^{8c.21}$, $R^{8c.22}$, $R^{8c.23}$, $R^{8c.24}$, $R^{8c.25}$, $R^{8c.26}$, $R^{8c.27}$, $R^{8c.28}$, $R^{8c.29}$, $R^{8c.30}$, $R^{8c.31}$, $R^{8c.32}$, $R^{8c.33}$, $R^{8c.34}$, $R^{8c.35}$, $R^{8c.36}$, $R^{8c.37}$, $R^{8c.38}$, $R^{8c.39}$, $R^{8c.40}$, $R^{8c.41}$, $R^{8c.42}$, $R^{9c.1}$, $R^{9c.2}$, $R^{9c.3}$, $R^{9c.4}$, $R^{9c.5}$, $R^{9c.6}$, $R^{9c.7}$, $R^{9c.8}$, $R^{9c.9}$, $R^{9c.10}$, $R^{9c.11}$, $R^{9c.12}$, $R^{9c.13}$, $R^{9c.14}$, $R^{9c.15}$, $R^{9c.16}$, $R^{9c.17}$, $R^{9c.18}$, $R^{9c.19}$, $R^{9c.20}$, $R^{9c.21}$, $R^{9c.22}$, $R^{9c.23}$, $R^{9c.24}$, $R^{9c.25}$, $R^{9c.26}$, $R^{9c.27}$, $R^{9c.28}$, $R^{9c.29}$, $R^{9c.30}$, $R^{9c.31}$, $R^{9c.32}$, $R^{9c.33}$, $R^{9c.34}$, $R^{9c.35}$, $R^{9c.36}$, $R^{9c.37}$, $R^{9c.38}$, $R^{9c.39}$, $R^{9c.40}$, $R^{9c.41}$, $R^{9c.42}$, $R^{10c.1}$, $R^{10c.2}$, $R^{10c.3}$, $R^{10c.4}$, $R^{10c.5}$, $R^{10c.6}$, $R^{10c.7}$, $R^{10c.8}$, $R^{10c.9}$, $R^{10c.10}$, $R^{10c.11}$, $R^{10c.12}$, $R^{10c.13}$, $R^{10c.14}$, $R^{10c.15}$, $R^{10c.16}$, $R^{10c.17}$, $R^{10c.18}$, $R^{10c.19}$, $R^{10c.20}$, $R^{10c.21}$, $R^{10c.22}$, $R^{10c.23}$, $R^{10c.24}$, $R^{10c.25}$, $R^{10c.26}$, $R^{10c.27}$, $R^{10c.28}$, $R^{10c.29}$, $R^{10c.30}$, $R^{10c.31}$, $R^{10c.32}$, $R^{10c.33}$, $R^{10c.34}$, $R^{10c.35}$, $R^{10c.36}$, $R^{10c.37}$, $R^{10c.38}$, $R^{10c.39}$, $R^{10c.40}$, $R^{10c.41}$, $R^{10c.42}$, $X^1$, $X^2$, $X^3$, $X^4$, $X^5$, $X^6$, $X^7$, $X^{a1}$, $X^{a2}$, $X^{a3}$, $X^{a4}$, $X^{a5}$, $X^{a6}$, $X^{c1}$, $X^{c2}$, $X^{c3}$, $X^{c4}$, $X^{c5}$, $X^{c6}$, $X^{c7}$, $X^{c8}$, $X^{c9}$, $X^{c10}$, $X^{c11}$, $X^{c12}$, $X^{c13}$, $X^{c14}$, $X^{c15}$, $X^{c16}$, $X^{c17}$, $X^{c18}$, $X^{c19}$, $X^{c20}$, $X^{c21}$, $X^{c22}$, $X^{c23}$, $X^{c24}$, $X^{c25}$, $X^{c26}$, $X^{c27}$, $X^{c28}$, $X^{c29}$, $X^{c30}$, $X^{c31}$, $X^{c32}$, $X^{c33}$, $X^{c34}$, $X^{c35}$, $X^{c36}$, $X^{c37}$, $X^{c38}$, $X^{c39}$, $X^{c40}$, $X^{c41}$, $X^{c42}$, $m^1$, $m^2$, $m^3$, $m^4$, $m^5$, $m^6$, $m^7$, $n^1$, $n^2$, $n^3$, $n^4$, $n^5$, $n^6$, $n^7$, $v^1$, $v^2$, $v^3$, $v^4$, $v^5$, $v^6$, $v^7$, $m1^1$, $m1^2$, $m1^3$, $m1^4$, $m1^5$, $m1^6$, $n1^1$, $n1^2$, $n1^3$, $n1^4$, $n1^5$, $n1^6$, $v1^1$, $v1^2$, $v1^3$, $v1^4$, $v1^5$, $v1^6$, $m3^1$, $m3^2$, $m3^3$, $m3^4$, $m3^5$, $m3^6$, $m3^7$, $m3^8$, $m3^9$, $m3^{10}$, $m3^{11}$, $m3^{12}$, $m3^{13}$, $m3^{14}$, $m3^{15}$, $m3^{16}$, $m3^{17}$, $m3^{18}$, $m3^{19}$, $m3^{20}$, $m3^{21}$, $m3^{22}$, $m3^{23}$, $m3^{24}$, $m3^{25}$, $m3^{26}$, $m3^{27}$, $m3^{28}$, $m3^{29}$, $m3^{30}$, $m3^{31}$, $m3^{32}$, $m3^{33}$, $m3^{34}$, $m3^{35}$, $m3^{36}$, $m3^{37}$, $m3^{38}$, $m3^{39}$, $m3^{40}$, $m3^{41}$, $m3^{42}$, $n3^1$, $n3^2$, $n3^3$, $n3^4$, $n3^5$, $n3^6$, $n3^7$, $n3^8$, $n3^9$, $n3^{10}$, $n3^{11}$, $n3^{12}$, $n3^{13}$, $n3^{14}$, $n3^{15}$, $n3^{16}$, $n3^{17}$, $n3^{18}$, $n3^{19}$, $n3^{20}$, $n3^{21}$, $n3^{22}$, $n3^{23}$, $n3^{24}$, $n3^{25}$, $n3^{26}$, $n3^{27}$, $n3^{28}$, $n3^{29}$, $n3^{30}$, $n3^{31}$, $n3^{32}$, $n3^{33}$, $n3^{34}$, $n3^{35}$, $n3^{36}$, $n3^{37}$, $n3^{38}$, $n3^{39}$, $n3^{40}$, $n3^{41}$, $n3^{42}$, $v3^1$, $v3^2$, $v3^3$, $v3^4$, $v3^5$, $v3^6$, $v3^7$, $v3^8$, $v3^9$, $v3^{10}$, $v3^{11}$, $v3^{12}$, $v3^{13}$, $v3^{14}$, $v3^{15}$, $v3^{16}$, $v3^{17}$, $v3^{18}$, $v3^{19}$, $v3^{20}$, $v3^{21}$, $v3^{22}$, $v3^{23}$, $v3^{24}$, $v3^{25}$, $v3^{26}$, $v3^{27}$, $v3^{28}$, $v3^{29}$, $v3^{30}$, $v3^{31}$, $v3^{32}$, $v3^{33}$, $v3^{34}$, $v3^{35}$, $v3^{36}$, $v3^{37}$, $v3^{38}$, $v3^{39}$, $v3^{40}$, $v3^{41}$, $v3^{42}$, respectively, wherein the definition of $R^3$ is assumed by $R^{3.1}$, $R^{3.2}$, $R^{3.3}$, $R^{3.4}$, $R^{3.5}$, $R^{3.6}$, $R^{3.7}$, the definition of $R^7$ is assumed by $R^{7.1}$, $R^{7.2}$, $R^{7.3}$, $R^{7.4}$, $R^{7.5}$, $R^{7.6}$, $R^{7.7}$, the definition of $R^8$ is assumed by $R^{8.1}$, $R^{8.2}$, $R^{8.3}$, $R^{8.4}$, $R^{8.5}$, $R^{8.6}$, $R^{8.7}$, the definition of $R^9$ is assumed by $R^{9.1}$, $R^{9.2}$, $R^{9.3}$, $R^{94}$, $R^{9.5}$, $R^{9.6}$, $R^{9.7}$, the definition of $R^{10}$ is assumed by $R^{10.1}$, $R^{10.2}$, $R^{10.3}$, $R^{10.4}$, $R^{10.5}$, $R^{10.6}$, $R^{10.7}$, the definition of $R^{2A}$ is assumed by $R^{2A.1}$, $R^{2A.2}$, $R^{2A.3}$, the definition of $R^{7a}$ is assumed by $R^{7a.1}$, $R^{7a.2}$, $R^{7a.3}$, $R^{7a.4}$, $R^{7a.5}$, $R^{7a.6}$, the definition of $R^{8a}$ is assumed by $R^{8a.1}$, $R^{8a.2}$, $R^{8a.3}$, $R^{8a.4}$, $R^{8a.5}$, $R^{8a.6}$, the definition of $R^{9a}$ is assumed by $R^{9a.1}$, $R^{9a.2}$, $R^{9a.3}$, $R^{9a.4}$, $R^{9a.5}$, $R^{9a.6}$, the definition of $R^{10a}$ is assumed by $R^{10a.1}$, $R^{10a.2}$, $R^{10a.3}$, $R^{10a.4}$, $R^{10a.5}$, $R^{10a.6}$, the definition of $R^{2B}$ is assumed by $R^{2B.1}$, $R^{2B.2}$, $R^{2B.3}$, the definition of $R^{2C}$ is assumed by $R^{2C.1}$, $R^{2C.2}$, $R^{2C.3}$, $R^{2C.4}$, $R^{2C.5}$, $R^{2C.6}$, $R^{2C.7}$, $R^{2C.8}$, $R^{2C.9}$, $R^{2C.10}$, $R^{2C.11}$, $R^{2C.12}$, $R^{2C.13}$, $R^{2C.14}$, $R^{2C.15}$, $R^{2C.16}$, $R^{2C.17}$, $R^{2C.18}$, $R^{2C.19}$, $R^{2C.20}$, $R^{2C.21}$, $R^{2C.22}$, $R^{2C.23}$, $R^{2C.24}$, $R^{2C.25}$, $R^{2C.26}$, $R^{2C.27}$, $R^{2C.28}$, $R^{2C.29}$, $R^{2C.30}$, $R^{2C.31}$, $R^{2C.32}$, $R^{2C.33}$, $R^{2C.34}$, $R^{2C.35}$, $R^{2C.36}$, $R^{2C.37}$, $R^{2C.38}$, $R^{2b.39}$, $R^{2C.40}$, $R^{2C.41.41}$, $R^{2C.42.42}$, the definition of $R^{7c}$ is assumed by $R^{7c.1}$, $R^{7c.2}$, $R^{7c.3}$, $R^{7c.4}$, $R^{7c.5}$, $R^{7c.6}$, $R^{7c.7}$, $R^{7c.8}$, $R^{7c.9}$, $R^{7c.10}$, $R^{7c.11}$, $R^{7c.12}$, $R^{7c.13}$, $R^{7c.14}$, $R^{7c.15}$, $R^{7c.16}$, $R^{7c.17}$, $R^{7c.18}$, $R^{7c.19}$, $R^{7c.20}$, $R^{7c.21}$, $R^{7c.22}$, $R^{7c.23}$, $R^{7c.24}$, $R^{7c.25}$, $R^{7c.26}$, $R^{7c.27}$, $R^{7c.28}$, $R^{7c.29}$, $R^{7c.30}$, $R^{7c.31}$, $R^{7c.32}$, $R^{7c.33}$, $R^{7c.34}$, $R^{7c.35}$, $R^{7c.36}$, $R^{7c.37}$, $R^{7c.38}$, $R^{7c.39}$, $R^{7c.40}$, $R^{7c.41}$, $R^{7c.42}$, the definition of $R^{8c}$ is assumed by $R^{8c.1}$, $R^{8c.2}$, $R^{8c.3}$, $R^{8c.4}$, $R^{8c.5}$, $R^{8c.6}$, $R^{8c.7}$, $R^{8c.8}$, $R^{8c.9}$, $R^{8c.10}$, $R^{8c.11}$, $R^{8c.12}$, $R^{8c.13}$, $R^{8c.14}$, $R^{8c.15}$, $R^{8c.16}$, $R^{8c.17}$, $R^{8c.18}$, $R^{8c.19}$, $R^{8c.20}$, $R^{8c.21}$, $R^{8c.22}$, $R^{8c.23}$, $R^{8c.24}$, $R^{8c.25}$, $R^{8c.26}$, $R^{8c.27}$, $R^{8c.28}$, $R^{8c.29}$, $R^{8c.30}$, $R^{8c.31}$, $R^{8c.32}$, $R^{8c.33}$, $R^{8c.34}$, $R^{8c.35}$, $R^{8c.36}$, $R^{8c.37}$, $R^{8c.38}$, $R^{8c.39}$, $R^{8c.40}$, $R^{8c.41}$, $R^{8c.42}$, the definition of $R^{9c}$ is assumed by $R^{9c.1}$, $R^{9c.2}$, $R^{9c.3}$, $R^{9c.4}$, $R^{9c.5}$, $R^{9c.6}$, $R^{9c.7}$, $R^{9c.8}$, $R^{9c.9}$, $R^{9c.10}$, $R^{9c.11}$, $R^{9c.12}$, $R^{9c.13}$, $R^{9c.14}$, $R^{9c.15}$, $R^{9c.16}$, $R^{9c.17}$, $R^{9c.18}$, $R^{9c.19}$, $R^{9c.20}$, $R^{9c.21}$, $R^{9c.22}$, $R^{9c.23}$, $R^{9c.24}$, $R^{9c.25}$, $R^{9c.26}$, $R^{9c.27}$, $R^{9c.28}$, $R^{9c.29}$, $R^{9c.30}$, $R^{9c.31}$, $R^{9c.32}$, $R^{9c.33}$, $R^{9c.34}$, $R^{9c.35}$, $R^{9c.36}$, $R^{9c.37}$, $R^{9c.38}$, $R^{9c.39}$, $R^{9c.40}$, $R^{9c.41}$, $R^{9c.42}$, the definition of $R^{10c}$ is assumed by $R^{10c.1}$, $R^{10c.2}$, $R^{10c.3}$, $R^{10c.4}$, $R^{10c.5}$, $R^{10c.6}$, $R^{10c.7}$, $R^{10c.8}$, $R^{10c.9}$, $R^{10c.10}$, $R^{10c.11}$, $R^{10c.12}$, $R^{10c.13}$, $R^{10c.14}$, $R^{10c.15}$, $R^{10c.16}$, $R^{10c.17}$, $R^{10c.18}$, $R^{10c.19}$, $R^{10c.20}$, $R^{10c.21}$, $R^{10c.22}$, $R^{10c.23}$, $R^{10c.24}$, $R^{10c.25}$, $R^{10c.26}$, $R^{10c.27}$, $R^{10c.28}$, $R^{10c.29}$, $R^{10c.30}$, $R^{10c.31}$, $R^{10c.32}$, $R^{10c.33}$, $R^{10c.34}$, $R^{10c.35}$, $R^{10c.36}$, $R^{10c.37}$, $R^{10c.38}$, $R^{10c.39}$, $R^{10c.40}$, $R^{10c.41}$, $R^{10c.42}$, the definition of X is assumed by $X^1$, $X^2$, $X^3$, $X^4$, $X^5$, $X^6$, $X^7$, the definition of $X^a$ is assumed by $X^{a1}$, $X^{a2}$, $X^{a3}$, $X^{a4}$, $X^{a5}$, $X^{a6}$, the definition of Xe is assumed by $X^{c1}$, Xe2, $X^{c3}$, $X^{c4}$, $X^{c5}$, $X^{c6}$, $X^{c7}$, $X^{c8}$, $X^{c9}$, $X^{c10}$, $X^{c11}$, $X^{c12}$, $X^{c13}$, $X^{c14}$, $X^{c15}$, $X^{c16}$, $X^{c17}$, $X^{c18}$, $X^{c19}$, $X^{c20}$, $X^{c21}$, $X^{c22}$, $X^{c23}$, $X^{c24}$, $X^{c25}$, $X^{c26}$, $X^{c27}$, $X^{c28}$, $X^{c29}$, $X^{c30}$, $X^{c31}$, $X^{c32}$, $X^{c34}$, $X^{c35}$, $X^{c36}$, $X^{c37}$, $X^{c38}$, $X^{c39}$, $X^{c40}$, $X^{c41}$, $X^{c42}$ the definition of m is assumed by $m^1$, $m^2$, m3, $m^4$, $m^5$, $m^6$, $m^7$, the definition of n is assumed by n', $n^2$, $n^3$, $n^4$, $n^5$, $n^6$, $n^7$, the definition of v is assumed by $v^1$, $v^2$, $v^3$, $v^4$, $v^5$, $v^6$, $v^7$, the definition of $m^1$ is assumed by $m1^1$, $m1^2$, $m1^3$, $m1^4$, $m1^5$, $m1^6$, the definition of $n^1$ is assumed by $n1^1$, $n1^2$, $n1^3$, $n1^4$, $n1^5$, $n1^6$, the definition of v1 is assumed by $v1^1$, $v1^2$, $v1^3$, $v1^4$, $v1^5$, $v1^6$, the definition of m3 is assumed by $m3^1$, $m3^2$, $m3^3$, $m3^4$, $m3^5$, $m3^6$, $m3^7$, $m3^8$, $m3^9$, $m3^{10}$, $m3^{11}$, $m3^{12}$, $m3^{13}$, $m3^{14}$, $m3^{15}$, $m3^{16}$, $m3^{17}$, $m3^{18}$, $m3^{19}$, $m3^{20}$, $m3^{21}$, $m3^{22}$, $m3^{23}$, $m3^{24}$, $m3^{25}$, $m3^{26}$, $m3^{27}$, $m3^{28}$, $m3^{29}$, $m3^{30}$, $m3^{31}$, $m3^{32}$, $m3^{33}$, $m3^{34}$, $m3^{35}$, $m3^{36}$, $m3^{37}$, $m3^{38}$, $m3^{39}$, $m3^{40}$, $m3^{41}$, $m3^{42}$, the definition of n3 is assumed by $n3^1$, $n3^2$, $n3^3$, $n3^4$, $n3^5$, $n3^6$, $n3^7$, $n3^8$, $n3^9$, $n3^{10}$, $n3^{11}$, $n3^{12}$, $n3^{13}$, $n3^{14}$, $n3^{15}$, $n3^{16}$, $n3^{17}$, $n3^{18}$, $n3^{19}$, $n3^{20}$, $n3^{21}$, $n3^{22}$, $n3^{23}$, $n3^{24}$, $n3^{25}$, $n3^{26}$, $n3^{27}$, $n3^{28}$, $n3^{29}$, $n3^{30}$, $n3^{31}$, $n3^{32}$, $n3^{33}$, $n3^{34}$, $n3^{35}$, $n3^{36}$, $n3^{37}$, $n3^{38}$, $n3^{39}$, $n3^{40}$, $n3^{41}$, $n3^{42}$, the definition of v3 is assumed by $v3^1$, $v3^2$, $v3^3$, $v3^4$, $v3^5$, $v3^6$, $v3^7$, $v3^8$, $v3^9$, $v3^{10}$, $v3^{11}$, $v3^{12}$, $v3^{13}$, $v3^{14}$, $v3^{15}$, $v3^{16}$, $v3^{17}$, $v3^{18}$, $v3^{19}$, $v3^{20}$, $v3^{21}$, $v3^{22}$, $v3^{23}$, $v3^{24}$, $v3^{25}$, $v3^{26}$, $v3^{27}$, $v3^{28}$, $v3^{29}$, $v3^{30}$, $v3^{31}$, $v3^{32}$, $v3^{33}$, $v3^{34}$, $v3^{35}$, $v3^{36}$, $v3^{37}$, $v3^{38}$, $v3^{39}$, $v3^{40}$, $v3^{41}$, $v3^{42}$.

The variables used within a definition of $R^3$, $R^7$, $R^8$, $R^9$, $R^{10}$, $R^{2A}$, $R^{7a}$, $R^{8a}$, $R^{9a}$, $R^{10a}$, $R^{2B}$, $R^{2C}$, $R^{7c}$, $R^{8C}$, $R^{9c}$, $R^{10c}$, X, $X^a$, $X^c$, m, n, v, $m^1$, $n^1$, v1, m3, n3, v3, and/or other variables that appear at multiple instances and are different may similarly be appropriately labeled to distinguish each group for greater clarity.

Pharmaceutical Compositions and Methods

In a second aspect, a pharmaceutical composition including a pharmaceutically acceptable excipient and a compound described herein (including embodiments, examples, and any compound in Table 1, 2, 3, 4, or 5) is provided.

In a third aspect, a method of treating a disease in a patient in need of such treatment is provided. The method including administering a therapeutically effective amount of a compound described herein (including embodiments, examples, and any compound in Table 1, 2, 3, 4, or 5) to the patient. In some embodiments, the disease is cancer. In some embodiments, the cancer is lung cancer, colorectal cancer, colon cancer, pancreatic cancer, breast cancer, or leukemia. In some embodiments, the cancer is lung cancer. In some embodiments, the cancer is non-small cell lung cancer. In some embodiments, the cancer is colon cancer. In some embodiments, the cancer is colorectal cancer. In some embodiments, the cancer is breast cancer. In some embodiments, the cancer is leukemia. In some embodiments, the cancer is pancreatic cancer. In some embodiments, the cancer is a cancer associated with aberrant K-Ras. In some embodiments, the cancer is a cancer associated with a mutant K-Ras. In some embodiments, the cancer is a cancer associated with K-Ras G12C. In some embodiments, the cancer is a cancer associated with K-Ras G12D. In some embodiments, the cancer is a cancer associated with K-Ras G13C. In some embodiments, the cancer is a cancer associated with K-Ras G13D.

In some embodiments, a method of treating a disorder in a subject in need thereof is provided, comprising a) determining the presence or absence of a mutation in a Ras protein (such as in a K-Ras, N-Ras, or H-Ras protein) in a malignant or neoplastic cell isolated from the subject and b) if the mutation is determined to be present in the subject, administering to the subject a therapeutically effective amount of a compound or pharmaceutically acceptable salt of the invention. In some embodiments, the disorder is cancer.

Various methods are suitable for determining the presence of absence of a mutation in a Ras protein in a cell isolated from a subject. As used herein, the term "mutation" is used to refer to deletions, insertions and/or substitutions as indicated. For example, assays can be performed to determine the presence of a nucleic acid sequence in the cell, where the nucleic acid sequence or a fragment thereof encodes the Ras protein. In some embodiments, nucleic acid detection comprises the use of a hybridization assay. Generally, a hybridization assay involves hybridization between complimentary sequences of one or more pairs of polynucleotides, such as between an oligonucleotide and an extracted or amplified genomic DNA. Non-limiting examples of hybridization assays for genotyping SNPs include polymerase chain reaction (PCR) assays, blotting assays, TaqMan assays (Life Technologies; Carlsbad, CA), mass spectroscopy assays, sequencing assays, gel electrophoresis, ELISA, MALDI-TOF mass spectrometry hybridization, primer extension, fluorescence detection, fluorescence resonance energy transfer (FRET), fluorescence polarization, microchannel electrophoresis, microarray, southern blot, northern blot, slot blot, dot blot, single primer linear nucleic acid amplification, as described in U.S. Pat. No. 6,251,639, SNP-IT, GeneChips (Affymetrix; Santa Clara, CA), HuSNP (Affymetrix; Santa Clara, CA), BeadArray (Illumina; San Diego, CA), Invader assay (Hologic; Bedford, MA), MassEXTEND (Sequenom; San Diego CA), MassCLEAVE (hMC) method (Sequenom; San Diego CA), and others. PCR assays include any assays utilizing a PCR amplification process. In some embodiments, the PCR assay comprises the use of oligonucleotide primers that hybridize only to the variant or wild type allele (e.g., to the region of polymorphism or mutation) of a diallelic SNP. PCR assays may also combine amplification with probe hybridization, such as in a TaqMan assay (see e.g., U.S. Pat. Nos. 5,962,233 and 5,538,848, each of which is herein incorporated by reference) where the assay is performed during a PCR reaction. Alternatively, detection of one or more mutations may utilize a SNP-IT primer extension assay (Orchid Cellmark, Burlington, NC.; See e.g., U.S. Pat. Nos. 5,952,174 and 5,919,626, each of which is herein incorporated by reference). In other embodiments, a mass spectroscopy-based assay is used, such as a MassARRAY system (Sequenom; San Diego CA). See for example U.S. Pat. Nos. 6,043,031; 5,777,324; and 5,605,798, incorporated herein by reference. Detection of one or more mutations may also utilize an array of probes (also referred to as a "DNA chip" assay, e.g. a GeneChip assay-Affymetrix, Santa Clara, CA). See e.g., U.S. Pat. Nos. 6,045,996; 5,925,525; and 5,858,659; each of which is herein incorporated by reference. In still other embodiments, a DNA microchip containing electronically captured probes is used (see e.g. U.S. Pat. Nos. 6,017,696; 6,068,818; and 6,051,380; each incorporated herein by reference). In yet other embodiments, detection of mutations is performed using a "bead array" (Illumina, San Diego, CA; See e.g., PCT Publications WO 99/67641 and WO 00/39587; each incorporated herein by reference). In other embodiments, a sample comprising nucleic acid obtained from a cell is sequenced to determine the presence of a mutation. Any method known in the art may be used, for instance as described in US 2011/0319290 and US 2009/0298075, each incorporated herein by reference. Sequencing may involve, for example, precipitation of the nucleic acid followed by resuspension and sequencing using Maxam-Gilbert sequencing, chain-termination sequencing, pyrosequencing, polony sequencing, or nanopore sequencing.

In some embodiments, a method of treating a disorder in a subject is provided, comprising determining the presence or absence of a Ras mutation (e.g. K-Ras mutation) in a malignant or neoplastic cell isolated from the subject, in connection with the prescription an effective amount of a compound or pharmaceutically acceptable salt of the invention, and, if the mutation is determined to be present in the subject, an alert is provided to a third party which may be, for example, a caregiver/care provider (e.g. a medical professional such as a physician, including an oncologist, a hospital, or clinic), care manager, other health professional, a third-party payor, an insurance company or a government office. For example, the third party is a caregiver who is a physician. The alert may comprise providing a report in any suitable form, such as in electronic or paper form. For example, providing the alert is performed with the aid of a processor, for example using a computer system executing instructions contained in computer-readable media. One or more steps of methods described here may be implemented and/or executed, in hardware or software. Software may be stored, for example, in memory or in any other computer readable medium and executed using a processor. Such processors may be associated with one or more controllers, calculation units, and/or other units of a computer system or implanted in firmware. Computer readable media and memory include RAM, ROM, flash memory, magnetic disks, laser disks, or other media. Software or alerts may be delivered to a computing device or between computing devices via any known delivery method, including, for example, a communication channel such as a telephone line, the internet, a wireless connection, or via a transportable medium such as a computer readable disk, flash drive etc. Computing devices include PCs, workstations, smartphones, tablets, PDAs or any other devices comprising processors.

Reports can comprise output from the detection method such as the presence and/or nature of the mutation. The alert may further comprise information regarding prognosis, resistance, or potential or suggested therapeutic options. The alert can comprise information on the likely effectiveness of a therapeutic option, the acceptability of a therapeutic option, or the advisability of applying the therapeutic option to a patient having a mutation identified in the test. The alert can include information, or a recommendation on, the administration of a drug, e.g., the administration at a preselected dosage or in a preselected treatment regimen, and/or in combination with other drugs, to the patient. In some embodiments, the subject is alerted if a subject is designated as having a cancer in which aberrant Ras (e.g. H-Ras, N-Ras, or K-Ras) expression or activity is involved. For example, a subject is alerted if the subject is determined to have a mutated version of Ras, e.g. K-Ras. In one embodiment, an alert is provided if the subject is determined to have a G12C mutation.

In a fourth aspect, a method of modulating the activity of a K-Ras protein is provided. The method including contacting the K-Ras protein with an effective amount of a compound described herein (including embodiments, examples, and any compound in Table 1, 2, 3, 4, or 5). In some embodiments, the activity of the K-Ras protein is it's GTPase activity, nucleotide exchange, differential GDP or GTP binding, effector protein binding, effector protein activation, guanine exchange factor (GEF) binding, GEF-facilitated nucleotide exchange, phosphate release, nucleotide release, nucleotide binding, K-Ras subcellular localization, K-Ras post-translational processing, K-Ras post-translational modifications, or a GTP bound K-Ras signaling pathway. In some embodiments, the activity of the K-Ras protein is its GTPase activity, nucleotide exchange, effector protein binding, effector protein activation, guanine exchange factor (GEF) binding, GEF-facilitated nucleotide exchange, phosphate release, nucleotide release, nucleotide binding, or the activity of a GTP bound K-Ras signaling pathway. In some embodiments, the modulating of the activity of the K-Ras protein includes modulating the binding affinity of K-Ras for GDP. In some embodiments, the modulating of the activity of the K-Ras protein includes the binding affinity of K-Ras for GTP. In some embodiments, the modulating of the activity of the K-Ras protein includes modulating the relative binding affinity of K-Ras for GTP vs. GDP. In some embodiments, the activity of the K-Ras protein is the activity of a signaling pathway activated by GTP bound K-Ras. In some embodiments, the modulating is increasing the activity of said K-Ras protein. In some embodiments, the modulating is reducing the activity of said K-Ras protein. In some embodiments, the K-Ras protein is a human K-Ras protein. In some embodiments, the human K-Ras protein contains a G12C mutation. In some embodiments, the human K-Ras protein contains a G12D mutation. In some embodiments, the human K-Ras protein contains a G13C mutation. In some embodiments, the human K-Ras protein contains a G13D mutation. In some embodiments, the K-Ras protein is a human K-Ras4A protein. In some embodiments, the K-Ras protein is a human K-Ras4B protein. In some embodiments, the K-Ras protein is a mutant K-Ras protein. In some embodiments, the K-Ras protein is an activated K-Ras protein. In some embodiments, the K-Ras protein is within a biological cell. In some embodiments, the biological cell forms part of an organism. In some embodiments of the method of modulating the activity of a K-Ras protein including contacting the K-Ras protein with an effective amount of a compound described herein (including embodiments, examples, and any compound in Table 1, 2, 3, 4, or 5), the compound is less effective at modulating the activity of an H-Ras protein. In some embodiments of the method, the compound modulates the activity of K-Ras at least two-fold more than it modulates the activity of H-Ras. In some embodiments of the method, the compound modulates the activity of K-Ras at least five-fold more than it modulates the activity of H-Ras. In some embodiments of the method, the compound modulates the activity of K-Ras at least ten-fold more than it modulates the activity of H-Ras. In some embodiments of the method, the compound modulates the activity of K-Ras at least fifty-fold more than it modulates the activity of H-Ras. In some embodiments of the method of modulating the activity of a K-Ras protein including contacting the K-Ras protein with an effective amount of a compound described herein (including embodiments, examples, and any compound in Table 1, 2, 3, 4, or 5), the compound is less effective at modulating the activity of an N-Ras protein. In some embodiments of the method, the compound modulates the activity of K-Ras at least two-fold more than it modulates the activity of N-Ras. In some embodiments of the method, the compound modulates the activity of K-Ras at least five-fold more than it modulates the activity of N-Ras. In some embodiments of the method, the compound modulates the activity of K-Ras at least ten-fold more than it modulates the activity of N-Ras. In some embodiments of the method, the compound modulates the activity of K-Ras at least fifty-fold more than it modulates the activity of N-Ras.

In a fifth aspect, a method of modulating a K-Ras protein is provided. The method including contacting the K-Ras protein with an effective amount of a compound described herein (including embodiments, examples, and in Table 1, 2, 3, 4, or 5). In some embodiments, the K-Ras protein is modulated in K-Ras subcellular localization, K-Ras post-translational processing, K-Ras post-translational modifications, or a GTP bound K-Ras signaling pathway. In some embodiments, the modulating is increasing the post-translational processing or modifications of the K-Ras protein. In some embodiments, the modulating is reducing the post-translational processing or modifications of the K-Ras protein. In some embodiments, the K-Ras protein is a human K-Ras protein. In some embodiments, the human K-Ras protein contains a G12C mutation. In some embodiments, the human K-Ras protein contains a G12D mutation. In some embodiments, the human K-Ras protein contains a G13C mutation. In some embodiments, the human K-Ras protein contains a G13D mutation. In some embodiments, the K-Ras protein is a human K-Ras4A protein. In some embodiments, the K-Ras protein is a human K-Ras4B protein. In some embodiments, the K-Ras protein is a mutant K-Ras protein. In some embodiments, the K-Ras protein is an activated K-Ras protein. In some embodiments, the K-Ras protein is within a biological cell. In some embodiments, the biological cell forms part of an organism.

In a sixth aspect, a K-Ras protein covalently bonded to a compound, for example a compound asdescribed herein (including modulators, inhibitors, embodiments, examples, and any compound in Table 1, 2, 3, 4, or 5), is provided. The compound is covalently bonded to a cysteine residue of the K-Ras protein. In some embodiments, the covalently modified K-Ras protein has a modulated activity relative to a control, wherein the activity is selected from GTPase activity, nucleotide exchange, effector protein binding, effector protein activation, guanine exchange factor (GEF) binding, GEF-facilitated nucleotide exchange, phosphate release, nucleotide release, nucleotide binding, K-Ras subcellular localization, K-Ras post-translational processing, and K-Ras post-translational modifications. In some embodiments, the covalently modified K-Ras protein is modulated in K-Ras subcellular localization, K-Ras post-translational processing, or K-Ras post-translational modifications. In some embodiments, the covalently modified K-Ras protein contains a G12C mutation. In some embodiments, the compound is covalently bonded to cysteine residue 12. In some embodiments, the covalently modified K-Ras protein contains a G13C mutation. In some embodiments, the compound is covalently bonded to cysteine residue 13. In some embodiments, the K-Ras protein is bonded to a K-Ras inhibitor, a mutant K-Ras inhibitor, a K-Ras G12C inhibitor, or a K-Ras G13C inhibitor. In some embodiments, the K-Ras protein is bonded to a K-Ras modulator, a mutant K-Ras modulator, a K-Ras G12C modulator, or a K-Ras G13C modulator.

In a seventh aspect, a K-Ras protein covalently bonded to a compound, for example a compound as described herein (including modulators, inhibitors, embodiments, examples, and in Table 1, 2, 3, 4, or 5), is provided. The compound is covalently bonded to an aspartate residue of the K-Ras protein. In some embodiments, the covalently modified K-Ras protein has a modulated activity relative to a control, wherein the activity is selected from GTPase activity, nucleotide exchange, effector protein binding, effector protein activation, guanine exchange factor (GEF) binding, GEF-facilitated nucleotide exchange, phosphate release, nucleotide release, nucleotide binding, K-Ras subcellular localization, K-Ras post-translational processing, and K-Ras post-translational modifications. In some embodiments, the covalently modified K-Ras protein is modulated in K-Ras subcellular localization, K-Ras post-translational processing, or K-Ras post-translational modifications. In some embodiments, the covalently modified K-Ras protein contains a G12D mutation. In some embodiments, the compound is covalently bonded to aspartate residue 12. In some embodiments, the covalently modified K-Ras protein contains a G13D mutation. In some embodiments, the compound is covalently bonded to aspartate residue 13. In some embodiments, the K-Ras protein is bonded to a K-Ras inhibitor, a mutant K-Ras inhibitor, a K-Ras G12D inhibitor, or a K-Ras G13D inhibitor. In some embodiments, the K-Ras protein is bonded to a K-Ras modulator, a mutant K-Ras modulator, a K-Ras G12D modulator, or a K-Ras G13D modulator.

In an eighth aspect, a method of identifying a covalent inhibitor of K-Ras protein is provided. The method including contacting a K-Ras protein with a K-Ras inhibitor test compound, allowing the K-Ras inhibitor test compound to covalently inhibit the K-Ras protein, detecting the level of covalent inhibition of the K-Ras protein, and thereby identifying a covalent inhibitor of K-Ras protein. In some embodiments of the method, the K-Ras inhibitor test compound is a Switch 2
  Binding Pocket covalent inhibitor test compound. In some embodiments, the K-Ras protein is a G12C mutant K-Ras protein. In some embodiments, the K-Ras protein is a G13C mutant K-Ras protein. In some embodiments, the K-Ras protein is a G12D mutant K-Ras protein. In some embodiments, the K-Ras protein is a G13D mutant K-Ras protein. In some embodiments of the method, wherein the K-Ras protein contacting the Switch 2—Binding Pocket covalent inhibitor test compound is a mutant K-Ras (e.g. K-Ras G12C, G12D, G13C, G13D), the method further includes contacting a wildtype K-Ras protein with the Switch 2—Binding Pocket covalent inhibitor test compound, allowing the Switch 2—Binding Pocket covalent inhibitor test compound to inhibit the wildtype K-Ras protein, detecting the level of inhibition of the wildtype K-Ras protein, comparing the level of inhibition of the wildtype K-Ras protein to the level of covalent inhibition of the mutant K-Ras protein (e.g. K-Ras G12C, G12D, G13C, G13D), wherein a higher level of covalent inhibition of the mutant K-Ras protein indicates the Switch 2—Binding Pocket covalent inhibitor test compound is specific for the mutant K-Ras protein. In some embodiments, the K-Ras inhibitor test compound is a Switch 2—Binding Pocket covalent inhibitor test compound and the K-Ras protein is a G12C mutant K-Ras protein. In some embodiments, the K-Ras inhibitor test compound is a Switch 2—Binding Pocket covalent inhibitor test compound and the K-Ras protein is a G12D mutant K-Ras protein. In some embodiments, the K-Ras inhibitor test compound is a Switch 2—Binding Pocket covalent inhibitor test compound and the K-Ras protein is a G13C mutant K-Ras protein. In some embodiments, the K-Ras inhibitor test compound is a Switch 2—Binding Pocket covalent inhibitor test compound and the K-Ras protein is a G13D mutant K-Ras protein. In some embodiments of the method, the Switch 2—Binding Pocket covalent test inhibitor compound does not covalently inhibit the wildtype K-Ras protein.

In some embodiments of the above aspects, the compound binds Ras (e.g. K-Ras, H-Ras, N-Ras, mutant Ras, K-Ras G12C, K-Ras G13C, K-Ras G12D, K-Ras G13D) behind Switch II. In embodiments, the compound modulates the conformation of Switch II. In embodiments, the compound modulates the conformation of Switch I. In embodiments, the compound modulates the conformation of Switch I and Switch II. In embodiments, the compound inhibits (e.g. by about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000, 10000 fold or more) Ras (e.g. K-Ras, H-Ras, N-Ras, mutant Ras, K-Ras G12C, K-Ras G13C, K-Ras G12D, K-Ras G13D) nucleotide exchange (e.g. GDP for GTP or GTP for GDP) relative to the absence of the compound. In embodiments, the compound inhibits release of GDP from Ras (e.g. K-Ras, H-Ras, N-Ras, mutant Ras, K-Ras G12C, K-Ras G13C, K-Ras G12D, K-Ras G13D) relative to the absence of the compound. In embodiments, the compound inhibits binding of GDP to Ras (e.g. K-Ras, H-Ras, N-Ras, mutant Ras, K-Ras G12C, K-Ras G13C, K-Ras G12D, K-Ras G13D) relative to the absence of the compound. In embodiments, the compound inhibits binding of GTP to Ras (e.g. K-Ras, H-Ras, N-Ras, mutant Ras, K-Ras G12C, K-Ras G13C, K-Ras G12D, K-Ras G13D) relative to the absence of the compound. In embodiments, the compound increases (e.g. by about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000, 10000 fold or more) Ras (e.g. K-Ras, H-Ras, N-Ras, mutant Ras, K-Ras G12C, K-Ras G13C, K-Ras G12D, K-Ras G13D) nucleotide exchange (e.g. GDP for GTP or GTP for GDP) relative to the absence of the compound. In embodiments, the compound increases release of GDP from Ras (e.g. K-Ras, H-Ras, N-Ras, mutant Ras, K-Ras G12C, K-Ras G13C, K-Ras G12D, K-Ras G13D) relative to the absence of the compound. In embodiments, the compound increases release of GTP from Ras (e.g. K-Ras, H-Ras, N-Ras, mutant Ras, K-Ras G12C, K-Ras G13C, K-Ras G12D, K-Ras G13D) relative to the absence of the compound. In embodiments, the compound increases binding of GDP to Ras (e.g. K-Ras, H-Ras, N-Ras, mutant Ras, K-Ras G12C, K-Ras G13C, K-Ras G12D, K-Ras G13D) relative to the absence of the compound. In embodiments, the compound inhibits binding of GTP to Ras (e.g. K-Ras, H-Ras, N-Ras, mutant Ras, K-Ras G12C, K-Ras G13C, K-Ras G12D, K-Ras G13D) relative to the absence of the compound. In embodiments, the compound inhibits binding of a GTP analog (e.g. mant-dGTP) to Ras (e.g. K-Ras, H-Ras, N-Ras, mutant Ras, K-Ras G12C, K-Ras G13C, K-Ras G12D, K-Ras G13D) relative to the absence of the compound. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid that contacts GTP in the absence of the compound. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid that contacts GDP in the absence of the compound. In embodiments, the compound modulates the conformation of a plurality of Ras (e.g. K-Ras, H-Ras, N-Ras, mutant Ras, K-Ras G12C, K-Ras G13C, K-Ras G12D, K-Ras G13D) amino acids that contact GTP in the absence of the compound. In embodiments, the compound modulates the conformation of a plurality of Ras (e.g. K-Ras, H-Ras, N-Ras, mutant Ras, K-Ras G12C, K-Ras G13C, K-Ras G12D, K-Ras G13D) amino acids that contact GDP in the absence of the compound. In embodiments, the compound modulates the binding of GTP and/or GDP to Ras (e.g. K-Ras, H-Ras, N-Ras, mutant Ras, K-Ras G12C, K-Ras G13C, K-Ras G12D, K-Ras G13D) compared to binding in the absence of the compound. In embodiments, the compound modulates the release of GTP and/or GDP from Ras (e.g. K-Ras, H-Ras, N-Ras, mutant Ras, K-Ras G12C, K-Ras G13C, K-Ras G12D, K-Ras G13D) compared to release in the absence of the compound. In embodiments, the compound modulates the ratio of the binding of GTP and GDP to Ras (e.g. K-Ras, H-Ras, N-Ras, mutant Ras, K-Ras G12C, K-Ras G13C, K-Ras G12D, K-Ras G13D) compared to the ratio in the absence of the compound. In embodiments, the compound modulates the ratio of the rate of release of GTP and GDP from Ras (e.g. K-Ras, H-Ras, N-Ras, mutant Ras, K-Ras G12C, K-Ras G13C, K-Ras G12D, K-Ras G13D) compared to the ratio in the absence of the compound. In embodiments, the compound modulates the conformation of a Ras amino acid that contacts the gamma phosphate of GTP when GTP is bound to Ras. In embodiments, the compound inhibits the binding of the gamma phosphate of GTP relative to the binding in the absence of the compound. In embodiments, the compound binds Ras (e.g. K-Ras, H-Ras, N-Ras, mutant Ras, K-Ras G12C, K-Ras G13C, K-Ras G12D, K-Ras G13D) protein bound to GDP and, after release of the GDP, modulates the subsequent binding of GDP or GTP to the Ras bound to the compound. In embodiments, the compound binds Ras (e.g. K-Ras, H-Ras, N-Ras, mutant Ras, K-Ras G12C, K-Ras G13C, K-Ras G12D, K-Ras G13D) protein bound to GDP and, after release of the GDP, modulates the subsequent binding of GDP to the Ras bound to the compound. In embodiments, the compound binds Ras (e.g. K-Ras, H-Ras, N-Ras, mutant Ras, K-Ras G12C, K-Ras G13C, K-Ras G12D, K-Ras G13D) protein bound to GDP and, after release of the GDP, modulates the subsequent binding of GTP to the Ras bound to the compound.

In embodiments, the compound inhibits proliferation of cancer cells under nutrient deficient conditions relative to the absence of the compound. In embodiments, the compound inhibits growth of cancer cells under nutrient deficient conditions relative to the absence of the compound. In embodiments, the compound inhibits growth of cancer cells under nutrient deficient conditions relative to the absence of the compound. In embodiments, the compound inhibits growth of cancer cells under serum deprivation conditions relative to the absence of the compound. In embodiments, the compound inhibits proliferation of cancer cells under serum deprivation conditions relative to the absence of the compound. In embodiments, the compound inhibits growth of cancer cells under conditions (e.g. local cell environment in a patient) mimicking serum deprivation relative to the absence of the compound. In embodiments, the compound inhibits proliferation of cancer cells under conditions (e.g. local cell environment in a patient) mimicking serum deprivation relative to the absence of the compound.

In embodiments, the compound modulates the conformation of the amino acid corresponding to amino acid 60 in human K-Ras in a Ras protein. In embodiments, the compound modulates the distance between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras G12C, K-Ras G13C, K-Ras G12D, K-Ras G13D). In embodiments the compound increases the distance between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras G12C, K-Ras G13C, K-Ras G12D, K-Ras G13D). In embodiments the compound increases the distance (e.g. by about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0, or more angstroms) between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras G12C, K-Ras G13C, K-Ras G12D, K-Ras G13D) when bound to GDP, relative to the absence of the compound. In embodiments the compound increases the distance (e.g. by about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0, or more angstroms) between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras G12C, K-Ras G13C, K-Ras G12D, K-Ras G13D) when bound to GTP, compared to the distance in the absence of the compound. In embodiments, upon binding to Ras (e.g. K-Ras, H-Ras, N-Ras, mutant Ras, K-Ras G12C, K-Ras G13C, K-Ras G12D, K-Ras G13D) the compound (e.g. a compound described herein, including embodiments and including a compound described in a table, example, or figure) modulates the distance between the alpha carbon of the amino acid corresponding to amino acid 12 in human K-Ras and the alpha carbon of the amino acid corresponding to amino acid 60 in human K-Ras, in the Ras protein (e.g. K-Ras, H-Ras, N-Ras, mutant Ras, K-Ras G12C, K-Ras G13C, K-Ras G12D, K-Ras G13D) to be about 4.9 angstoms or greater (e.g. about 5.0, 5.1, 5.2, 5.3, 5.4, 5.5, 5.6, 5.7, 5.8, 5.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0 angstroms, or greater). In embodiments, upon binding to Ras (e.g. K-Ras, H-Ras, N-Ras, mutant Ras, K-Ras G12C, K-Ras G13C, K-Ras G12D, K-Ras G13D) the compound (e.g. a compound described herein, including embodiments and including a compound described in a table, example, or figure) modulates the distance between the alpha carbon of the amino acid corresponding to amino acid 12 in human K-Ras and the alpha carbon of the amino acid corresponding to amino acid 60 in human K-Ras, in the Ras protein (e.g. K-Ras, H-Ras, N-Ras, mutant Ras, K-Ras G12C, K-Ras G13C, K-Ras G12D, K-Ras G13D) to be greater than about 4.9 angstroms (e.g. greater than about 5.0, 5.1, 5.2, 5.3, 5.4, 5.5, 5.6, 5.7, 5.8, 5.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0 angstroms, or greater). In embodiments, upon binding to Ras (e.g. K-Ras, H-Ras, N-Ras, mutant Ras, K-Ras G12C, K-Ras G13C, K-Ras G12D, K-Ras G13D) the compound (e.g. a compound described herein, including embodiments and including a compound described in a table, example, or figure) modulates the distance between the alpha carbon of the amino acid corresponding to amino acid 12 in human K-Ras and the alpha carbon of the amino acid corresponding to amino acid 60 in human K-Ras, in the Ras protein (e.g. K-Ras, H-Ras, N-Ras, mutant Ras, K-Ras G12C, K-Ras G13C, K-Ras G12D, K-Ras G13D) to be 4.9 angstoms or greater (e.g. 5.0, 5.1, 5.2, 5.3, 5.4, 5.5, 5.6, 5.7, 5.8, 5.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0 angstroms, or greater). In embodiments, upon binding to Ras (e.g. K-Ras, H-Ras, N-Ras, mutant Ras, K-Ras G12C, K-Ras G13C, K-Ras G12D, K-Ras G13D) the compound (e.g. a compound described herein, including embodiments and including a compound described in a table, example, or figure) modulates the distance between the alpha carbon of the amino acid corresponding to amino acid 12 in human K-Ras and the alpha carbon of the amino acid corresponding to amino acid 60 in human K-Ras, in the Ras protein (e.g. K-Ras, H-Ras, N-Ras, mutant Ras, K-Ras G12C, K-Ras G13C, K-Ras G12D, K-Ras G13D) to be greater than 4.9 angstroms (e.g. greater than 5.0, 5.1, 5.2, 5.3, 5.4, 5.5, 5.6, 5.7, 5.8, 5.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0 angstroms, or greater).

In embodiments, the compound increases the flexibility of Switch I relative to the absence of the compound. In embodiments, the compound increases the disorder of Switch I relative to the absence of the compound. In embodiments, the compound inhibits the binding of Ras ((e.g. K-Ras, H-Ras, N-Ras, mutant Ras, K-Ras G12C, K-Ras G13C, K-Ras G12D, K-Ras G13D) to another protein. In embodiments, the compound inhibits the binding of Ras ((e.g. K-Ras, H-Ras, N-Ras, mutant Ras, K-Ras G12C, K-Ras G13C, K-Ras G12D, K-Ras G13D) to another protein, wherein the binding is dependent on Ras binding to GTP. In embodiments, the compound inhibits the binding of Ras ((e.g. K-Ras, H-Ras, N-Ras, mutant Ras, K-Ras G12C, K-Ras G13C, K-Ras G12D, K-Ras G13D) to another protein, wherein the binding is dependent on Ras binding to GDP. In embodiments, the compound inhibits the binding of Ras ((e.g. K-Ras, H-Ras, N-Ras, mutant Ras, K-Ras G12C, K-Ras G13C, K-Ras G12D, K-Ras G13D) to Raf (e.g. Raf1). In embodiments, the compound inhibits the binding of Ras ((e.g. K-Ras, H-Ras, N-Ras, mutant Ras, K-Ras G12C, K-Ras G13C, K-Ras G12D, K-Ras G13D) to SOS. In embodiments, the compound inhibits the binding of Ras ((e.g. K-Ras, H-Ras, N-Ras, mutant Ras) to a GEF. In embodiments, the compound inhibits the binding of Ras ((e.g. K-Ras, H-Ras, N-Ras, mutant Ras, K-Ras G12C, K-Ras G13C, K-Ras G12D, K-Ras G13D) to PI3K. In embodiments, the compound modulates metal binding near the nucleotide binding site. In embodiments, the compound modulates the conformation of the Ras metal binding site near the nucleotide binding site. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid relative to the conformation in the absence of the compound, wherein the Ras amino acid conformation is also modulated by a Ras G60 mutation. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid relative to the conformation in the absence of the compound, wherein the Ras amino acid conformation is also modulated by a Ras G60A mutation. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid relative to the conformation in the absence of the compound, wherein the Ras amino acid conformation is also modulated by a Ras T35 mutation. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid relative to the conformation in the absence of the compound, wherein the Ras amino acid conformation is also modulated by a Ras T35S mutation. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid relative to the conformation in the absence of the compound, wherein the Ras amino acid conformation is also modulated by a mutation of the Ras amino acid corresponding to K-Ras G60. In embodiments, the compound modulates the conformation of a Ras (e.g. K-Ras, H-Ras, N-Ras, mutant Ras, K-Ras G12C, K-Ras G13C, K-Ras G12D, K-Ras G13D) amino acid relative to the conformation in the absence of the compound, wherein the Ras amino acid conformation is also modulated by a mutation of the Ras amino acid corresponding to K-Ras T35.

The pharmaceutical compositions include optical isomers, diastereomers, or pharmaceutically acceptable salts of the modulators disclosed herein. The compound included in the pharmaceutical composition may be covalently attached to a carrier moiety, as described above. Alternatively, the compound included in the pharmaceutical composition is not covalently linked to a carrier moiety.

In a ninth aspect, a Ras protein (e.g. K-Ras, N-Ras, H-Ras, or another Ras protein described herein) covalently bonded (e.g. reversibly or irreversibly) to a compound, for example a compound as described herein (including modulators, inhibitors, embodiments, examples, and any compound in Table 1, 2, 3, 4, or 5), is provided. In some embodiments, the compound is covalently bonded to a cysteine, aspartate, lysine, tyrosine or glutamate residue of the Ras protein (e.g. K-Ras, N-Ras, H-Ras, or another Ras protein described herein). In some embodiments, the compound is a modulator. In some embodiments, the compound is a modulator such as an inhibitor. In some embodiments, the compound is a Ras modulator. In some embodiments, the compound is a Ras inhibitor.

The compounds of the invention (i.e. compounds described herein, including embodiments, examples, compounds of Table 1, 2, 3, 4, or 5) can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, that may also act as diluents, flavoring agents, binders, preservatives, tablet disintegrating agents, or an encapsulating material.

In powders, the carrier is a finely divided solid in a mixture with the finely divided active component (e.g. a compound provided herein). In tablets, the active component is mixed with the carrier having the necessary binding properties in suitable proportions and compacted in the shape and size desired. The powders and tablets preferably contain from 5% to 70% of the active compound.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, PA) and WO 96/05309, the teachings of both of which are hereby incorporated by reference.

Aqueous solutions suitable for oral use can be prepared by dissolving the active component (e.g. compounds described herein, including embodiments, examples, compounds of Table 1, 2, 3, 4, or 5) in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present invention include compositions wherein the active ingredient (e.g. compounds described herein, including embodiments, examples, compounds of Table 1, 2, 3, 4, or 5) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. a Ras, K-Ras, K-Ras G12C, K-Ras G12D, K-Ras G13C, K-Ras G13D, a mutant K-Ras, an activated K-Ras), and/or reducing, eliminating, or slowing the progression of disease symptoms (e.g. cancer growth or metastasis). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. lung cancer, NSCL cancer, colon cancer, colorectal cancer, breast cancer, pancreatic cancer, leukemia), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The ratio between toxicity and therapeutic effect for a particular compound is its therapeutic index and can be expressed as the ratio between LD50 (the amount of compound lethal in 50% of the population) and ED50 (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the ED50 with little or no toxicity. The dosage may vary within this range depending upon the dosage form employed and the route of administration utilized. See, e.g. Fingl et al., In: THE PHARMACOLOGICAL BASIS OF THERAPEUTICS, Ch.1, p. 1, 1975. The exact formulation, route of administration and dosage can be chosen by the individual physician in view of the patient's condition and the particular method in which the compound is used.

Administration

The compositions of the present invention can be delivered by transdermally, by a topical route, formulated as applicator sticks, solutions, suspensions, emulsions, gels, creams, ointments, pastes, jellies, paints, powders, and aerosols. For therapeutic applications, the compounds or drugs of the present invention can be administered alone or co-administered in combination with conventional chemotherapy, radiotherapy, hormonal therapy, and/or immunotherapy.

The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical compositions of the present invention can be provided as a salt and can be formed with many acids, including but not limited to hydrochloric, sulfuric, acetic, lactic, tartaric, malic, succinic, etc. Pharmaceutical compositions described herein may be salts of a compound or composition which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compositions described herein or Ras inhibitor compounds of the present invention can exist in unsolvated forms as well as solvated forms, including hydrated forms. In general, the solvated forms are equivalent to unsolvated forms and are intended to be encompassed within the scope of the present invention. Certain Ras inhibitor compounds of the present invention may exist in multiple crystalline or amorphous forms. In general, all physical forms are equivalent for the uses contemplated by the present invention and are intended to be within the scope of the present invention.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

The compounds described herein can be used in combination with one another, with other active agents known to be useful in treating a disease associated with cells expressing a particular Ras, K-Ras, mutant K-Ras (e.g. cancer), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As a non-limiting example, the compounds described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), and the like.

The compounds described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds described herein can be co-administered with conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117}$msn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged compound or drug suspended in diluents, e.g., water, saline, or PEG 400; (b) capsules, sachets, or tablets, each containing a predetermined amount of a Ras inhibitor compound or drug, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a Ras inhibitor compound or drug in a flavor, e.g., sucrose, as well as pastilles comprising the Ras inhibitor compound in an inert base, such as gelatin and glycerin or sucrose and acacia emulsions, gels, and the like, containing, in addition to the Ras inhibitor, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which comprises an effective amount of a packaged Ras inhibitor compound or drug with a suppository base. Suitable suppository bases include natural or synthetic triglycerides or paraffin hydrocarbons. In addition, it is also possible to use gelatin rectal capsules which contain a combination of the Ras inhibitor compound or drug of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, orally, topically, intraperitoneally, intravesically, or intrathecally. Parenteral administration, oral administration, and intravenous administration are the preferred methods of administration. The formulations of compounds can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a Ras inhibitor compound. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of cancer, compound utilized in the pharmaceutical compositions of the present invention may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds described herein can be used in combination with one another, with other active agents known to be useful in treating cancer or with adjunctive agents that may not be effective alone, but may contribute to the efficacy of the active agent.

Kits/Articles of Manufacture

For use in the methods and/or applications (e.g. therapeutic applications) described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions may also be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label may be used to indicate that the contents are to be used for a specific therapeutic application. In addition, the label may indicate directions for use of the contents, such as in the methods described herein. In certain embodiments, the pharmaceutical compositions is presented in a pack or dispenser device which contains one or more unit dosage forms containing a compound provided herein. The pack for example contains metal or plastic foil, such as a blister pack. Or, the pack or dispenser device may be accompanied by instructions for administration. Or, the pack or dispenser may be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

ADDITIONAL EMBODIMENTS

1. A compound having the formula: $R^1$-$L^1$-$L^2$-$L^3$-E wherein, $R^1$ is a Switch 2—Binding Pocket binding moiety; $L^1$ is a bond or a divalent radical chemical linker; $L^2$ is a bond or a divalent radical chemical linker; $L^3$ is a bond or a divalent radical chemical linker; E is an electrophilic chemical moiety capable of forming a covalent bond with a K-Ras cysteine residue or a K-Ras aspartate residue.

2. The compound of embodiment 1, wherein $R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

3. The compound of embodiment 1, wherein $R^1$ is substituted or unsubstituted cycloalkyl, substituted or unsubstituted heterocycloalkyl, substituted or unsubstituted aryl, or substituted or unsubstituted heteroaryl.

4. The compound of embodiment 1, wherein $R^1$ is substituted or unsubstituted aryl or substituted or unsubstituted heteroaryl.

5. The compound of embodiment 1, wherein $R^1$ is substituted or unsubstituted fused ring aryl or substituted or unsubstituted fused ring heteroaryl.

6. The compound of embodiment 1, wherein $R^1$ is $R^3$-substituted or unsubstituted aryl or $R^3$-substituted or unsubstituted heteroaryl; wherein, $R^3$ is independently hydrogen, oxo, halogen, —$CX_3$, —CN, —$SO_2Cl$, —$SO_2R^{10}$, —$SOVNR^7R^8$, —$NHNH_2$, —$ONR^7R^8$, —NHC=(O) $NHNH_2$, —NHC=(O)$NR^7R^8$, —$N(O)_m$, —$NR^7R^8$, —C(O) $R^9$, —C(O)—$OR^9$, —C(O)$NR^7R^8$, —$OR^{10}$, —$NR^7SO_2R^{10}$, —$NR^7C$=(O) $R^9$, —$NR^{7c}$ (O)—$OR^9$, —$NR^7OR^9$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; Two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl. Two $R^3$ substituents bonded to the same atom may optionally be joined to form a substituted or unsubstituted cycloalkyl or substituted or unsubstituted heterocycloalkyl; $R^7$, $R^8$, $R^9$, and $R^{10}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC (O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; m and v are independently 1 or 2; n is independently an integer from 0 to 4; X is independently —Cl, —Br, —I, or —F.

7. The compound of embodiment 1, wherein $R^1$ is:

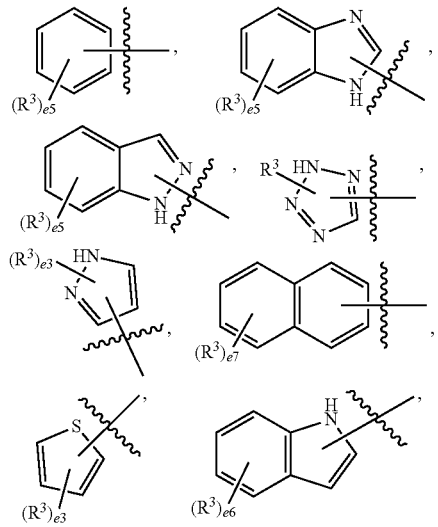

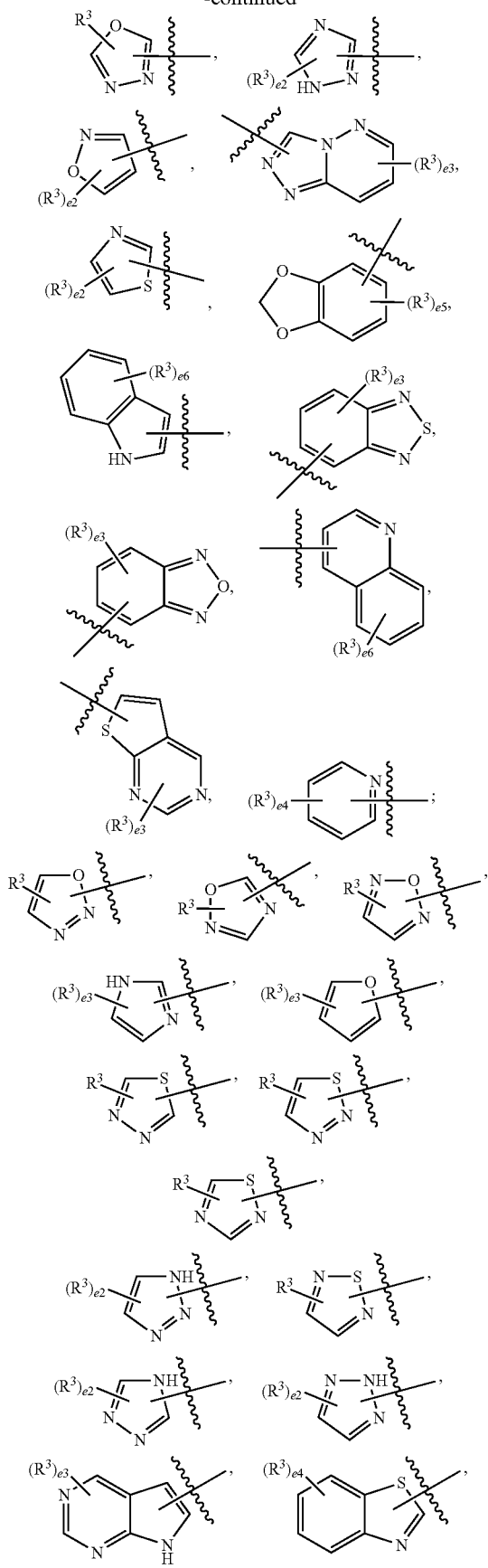
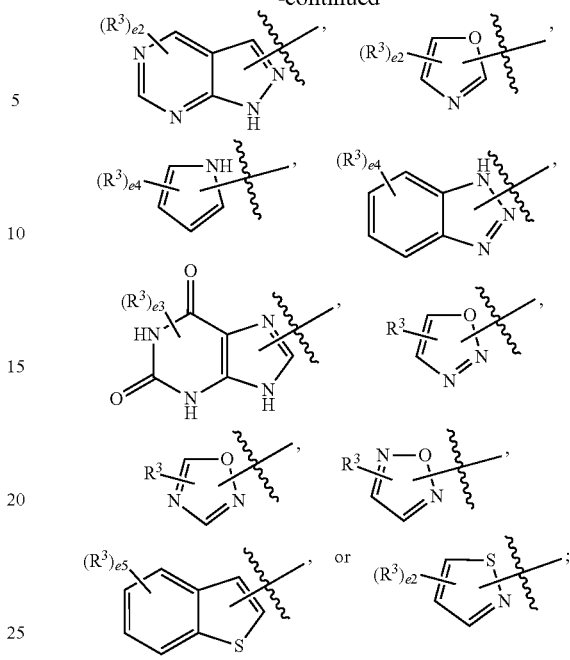

wherein, $R^3$ is independently hydrogen, oxo, halogen, —$CX_3$, —CN, —$SO_2Cl$, —$SO_2R^{10}$, —$SO_nNR^7R^8$, —$NHNH_2$, —$ONR^7R^8$, —NHC=(O)$NHNH_2$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, —$NR^7SO_2R^{10}$, —$NR^{7c}$=(O) $R^9$, —$NR^{7c}$ (O)—$OR^9$, —$NR^7OR^9$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; Two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl. Two $R^3$ substituents bonded to the same atom may optionally be joined to form a substituted or unsubstituted cycloalkyl or substituted or unsubstituted heterocycloalkyl; $R^7$, $R^8$, $R^9$, and $R^{10}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; m and v are independently 1 or 2; n is independently an integer from 0 to 4; X is independently —Cl, —Br, —I, or —F; e2 is independently an integer from 0 to 2; e3 is independently an integer from 0 to 3; e4 is independently an integer from 0 to 4; e5 is independently an integer from 0 to 5; e6 is independently an integer from 0 to 6; e7 is independently an integer from 0 to 7.

8. The compound of embodiment 1, wherein $R^1$ is $R^3$-substituted pyridinyl, $R^3$-substituted pyrimidinyl, $R^3$-substituted thiophenyl, $R^3$-substituted furanyl, $R^3$-substituted indolyl, $R^3$-substituted benzoxadiazolyl, $R^3$-substituted benzodioxolyl, $R^3$-substituted benzodioxanyl, $R^3$-substituted thianaphthanyl, $R^3$-substituted pyrrolopyridinyl, $R^3$-substituted indazolyl, $R^3$-substituted quinolinyl, $R^3$-substituted quinoxalinyl, $R^3$-substituted pyridopyrazinyl, $R^3$-substituted quinazolinonyl, $R^3$-substituted benzoisoxazolyl, $R^3$-substituted imidazopyridinyl, $R^3$-substituted benzofuranyl, $R^3$-substituted benzothiophenyl, $R^3$-substituted phenyl, $R^3$-substituted naphthyl, $R^3$-substituted biphenyl, $R^3$-substituted pyrrolyl, $R^3$-substituted pyrazolyl, $R^3$-substituted imidazolyl, $R^3$-substituted pyrazinyl, $R^3$-substituted oxazolyl, $R^3$-substituted isoxazolyl, $R^3$-substituted thiazolyl, $R^3$-substituted furylthienyl, $R^3$-substituted pyridyl, $R^3$-substituted pyrimidyl, $R^3$-substituted benzothiazolyl, $R^3$-substituted purinyl, $R^3$-substituted benzimidazolyl, $R^3$-substituted isoquinolyl, $R^3$-substituted thiadiazolyl, $R^3$-substituted oxadiazolyl, $R^3$-substituted pyrrolyl, $R^3$-substituted diazolyl, $R^3$-substituted triazolyl, $R^3$-substituted tetrazolyl, $R^3$-substituted benzothiadiazolyl, $R^3$-substituted isothiazolyl, $R^3$-substituted pyrazolopyrimidinyl, $R^3$-substituted pyrrolopyrimidinyl, $R^3$-substituted benzotriazolyl, or $R^3$-substituted quinolyl; $R^3$ is independently hydrogen, oxo, halogen, —$CX_3$, —CN, —$SO_2Cl$, —$SOIR10$, —$SOVNR^7R^8$, —$NHNH_2$, —$ONR^7R^8$, —NHC=(O)$NHNH_2$, —NHC=(O)$NR^7R^8$, —$N(O)_m$—, —$NR^7R^8$, —C(O)$R^9$, —C(O)—$OR^9$, —C(O)$NR^7R^8$, —$OR^{10}$, —$NR^7SO_2R^{10}$, —$NR^7C$=(O) $R^9$, —$NR^{7c}$ (O)—$OR^9$, —$NR^7OR^9$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; Two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl. Two $R^3$ substituents bonded to the same atom may optionally be joined to form a substituted or unsubstituted cycloalkyl or substituted or unsubstituted heterocycloalkyl; $R^7$, $R^8$, $R^9$, and $R^{10}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; m and v are independently 1 or 2; n is independently an integer from 0 to 4; X is independently —Cl, —Br, —I, or —F.

9. The compound of embodiment 1, wherein $R^1$ is unsubstituted pyridinyl, unsubstituted pyrimidinyl, unsubstituted thiophenyl, unsubstituted furanyl, unsubstituted indolyl, unsubstituted benzoxadiazolyl, unsubstituted benzodioxolyl, unsubstituted benzodioxanyl, unsubstituted thianaphthanyl, unsubstituted pyrrolopyridinyl, unsubstituted indazolyl, unsubstituted quinolinyl, unsubstituted quinoxalinyl, unsubstituted pyridopyrazinyl, unsubstituted quinazolinonyl, unsubstituted benzoisoxazolyl, unsubstituted imidazopyridinyl, unsubstituted benzofuranyl, unsubstituted benzothiophenyl, unsubstituted phenyl, unsubstituted naphthyl, unsubstituted biphenyl, unsubstituted pyrrolyl, unsubstituted pyrazolyl, unsubstituted imidazolyl, unsubstituted pyrazinyl, unsubstituted oxazolyl, unsubstituted isoxazolyl, unsubstituted thiazolyl, unsubstituted furylthienyl, unsubstituted pyridyl, unsubstituted pyrimidyl, unsubstituted benzothiazolyl, unsubstituted purinyl, unsubstituted benzimidazolyl, unsubstituted isoquinolyl, unsubstituted thiadiazolyl, unsubstituted oxadiazolyl, unsubstituted pyrrolyl, unsubstituted diazolyl, unsubstituted triazolyl, unsubstituted tetrazolyl, unsubstituted benzothiadiazolyl, unsubstituted isothiazolyl, unsubstituted pyrazolopyrimidinyl, unsubstituted pyrrolopyrimidinyl, unsubstituted benzotriazolyl, or unsubstituted quinolyl.

10. The compound of any one of embodiments 1 to 9, wherein $L^1$, $L^2$ and $L^3$ are independently a bond, —$NR^{2C}$—, —O—, —S—, —C(O)—, —S(O)—, —$S(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker; $R^{2C}$ is independently hydrogen, oxo, halogen, —$CX_{c3}$, —CN, —$SO_2Cl$, —$SO_{n3}R^{10c}$, —$SO_{v3}NR^{7c}R^{8c}C$, —$NHNH_2$, —$ONR^{7c}OR^{8c}$, —NHC=(O)$NHNH_2$, —NHC=(O)$NR^{7c}R^{8c}$, —$N(O)_{m3}$, —$NR^{7c}R^{8c}$, —C(O)$R^{9c}$, —C(O)—$OR^{9c}$, —C(O)$NR^{7c}R^{8c}$, —$OR^{10c}$, —$NR^{7c}SO_2R^{10c}$, —$NR^{7c}$=(O)$R^{9c}$, —$NR^{7c}$(O)—$OR^{9c}$, —$NR^{7c}OR^{8c}$, —$OCX^c_3$, —$OCHX^c_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; Two adjacent $R^{2C}$ substituents may optionally be joined to form a substituted or unsubstituted cycloalkyl, substituted or unsubstituted heterocycloalkyl, substituted or unsubstituted aryl, or substituted or unsubstituted heteroaryl; Two $R^{2C}$ substituents bonded to the same atom may optionally be joined to form a substituted or unsubstituted cycloalkyl or substituted or unsubstituted heterocycloalkyl; $R^{7c}$, $R^{8c}$, $R^{9c}$, and $R^{10c}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC—(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{7c}$ and $R^{8c}$ substituents bonded to the same nitrogen atom may optionally be joined to form a substituted or unsubstituted heterocycloalkyl or substituted or unsubstituted heteroaryl; $m^1$, m3, v1, and v3 are independently an integer from 1 to 2; $n^1$ and n3 are independently an integer from 0 to 4; Xe is independently —Cl, —Br, —I, or —F.

11. The compound of any one of embodiments 1 to 9, wherein $L^1$, $L^2$ and $L^3$ are indepedently —$CR^{2A}R^{2B}$—,

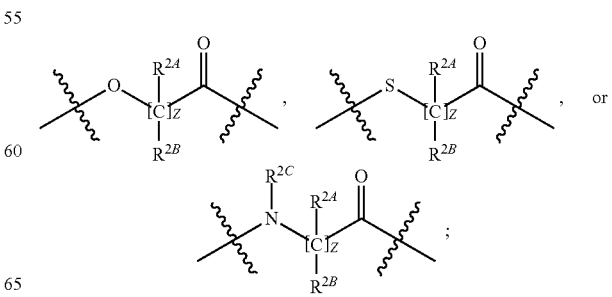

R$^{2A}$ and R$^{2B}$ are independently hydrogen, oxo, halogen, —CX$^a{}_3$, —CN, —SO$_2$Cl, —SO$_{a1}{}^{10a}$, —SO$_{v1}$NR$^{7a}$R$^{8a}$, —NHNH$_2$, —ONR$^{7a}$R$^{8a}$, —NHC═(O)NHNH$_2$, —NHC═(O)NR$^{7a}$R$^{8a}$, —NR$^{7a}$R$^{8a}$, —N(O)$_{m1}$, —C(O)R$^{9a}$, —C(O)—OR$^{9a}$, —C(O)NR$^{7a}$R$^{8a}$, —OR$^{10a}$, —NR$^{7a}$SO$_2$R$^{10a}$, —NR$^{7a}$C═(O) R$^{9a}$, —NR$^{7a}$C(O)—OR$^{9a}$, —NR$^{7a}$OR$^{9a}$, —OCX$^a{}_3$, —OCHX$^a{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{2A}$ and R$^{2B}$ substituent bonded to the same atom may optionally be joined to form a substituted or unsubstituted cycloalkyl or substituted or unsubstituted heterocycloalkyl; R$^{2C}$ is independently hydrogen, oxo, halogen, —CX$^c{}_3$, —CN, —SO$_2$Cl, —SO$_{n3}$R$^{10c}$, —SO$_{v3}$NR$^{7c}$R$^{8c}$, —NHNH$_2$, —ONR$^{7c}$R$^{8c}$, —NHC═(O)NHNH$_2$, —NHC═(O)NR$^{7c}$R$^{8c}$, —N(O)$_{m3}$, —NR$^{7c}$R$^{8c}$, —C(O)R$^c$, —C(O)—OR$^{9c}$, —C(O)NR$^{7c}$R$^{8c}$, —OR$^{10c}$, —NR$^{7c}$SO$_2$R$^{10c}$, —NR$^{7c}$═(O)R$^{9c}$, —NR$^{7c}$ (O)—OR$^{9c}$, —NR$^{7c}$OR$^{9c}$, —OCX$^c{}_3$, —OCHX$^c{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{7a}$, R$^{8a}$, R$^{9a}$ and R$^{10a}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{7a}$ and R$^{8a}$ substituents bonded to the same nitrogen atom may optionally be joined to form a substituted or unsubstituted heterocycloalkyl or substituted or unsubstituted heteroaryl; R$^{7c}$, R$^{8c}$, R$^{9c}$, and R$^{10c}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC—(O)NH$_2$, —NHSO$_2$H, —NHC═(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{7c}$ and R$^{8c}$ substituents bonded to the same nitrogen atom may optionally be joined to form a substituted or unsubstituted heterocycloalkyl or substituted or unsubstituted heteroaryl; z is independently an integer from 0 to 10; m$^1$, m3, v1, and v3 are independently an integer from 1 to 2; n$^1$ and n3 are independently an integer from 0 to 4; X$^a$ and X$^c$ are independently —Cl, —Br, —I, or —F.

12. The compound of embodiment 10, wherein L$^1$ is independently substituted or unsubstituted cycloalkylene, substituted or unsubstituted heterocycloalkylene, substituted or unsubstituted arylene, substituted or unsubstituted heteroarylene, or substituted or unsubstituted spirocyclic linker; or L$^2$ is independently substituted or unsubstituted cycloalkylene, substituted or unsubstituted heterocycloalkylene, substituted or unsubstituted arylene, substituted or unsubstituted heteroarylene, or substituted or unsubstituted spirocyclic linker; or L$^3$ is independently substituted or unsubstituted cycloalkylene, substituted or unsubstituted heterocycloalkylene, substituted or unsubstituted arylene, substituted or unsubstituted heteroarylene, or substituted or unsubstituted spirocyclic linker.

13. The compound of embodiment 10, wherein L$^1$ is independently R$^{2C}$-substituted or unsubstituted cycloalkylene, R$^{2C}$-substituted or unsubstituted heterocycloalkylene, R$^{2C}$-substituted or unsubstituted arylene, R$^{2C}$-substituted or unsubstituted heteroarylene, or R$^{2C}$-substituted or unsubstituted spirocyclic linker; or L$^2$ is independently R$^{2C}$-substituted or unsubstituted cycloalkylene, R$^{2C}$-substituted or unsubstituted heterocycloalkylene, R$^{2C}$-substituted or unsubstituted arylene, R$^{2C}$-substituted or unsubstituted heteroarylene, or R$^{2C}$-substituted or unsubstituted spirocyclic linker; or L$^3$ is independently R$^{2C}$-substituted or unsubstituted cycloalkylene, R$^{2C}$-substituted or unsubstituted heterocycloalkylene, R$^{2C}$-substituted or unsubstituted arylene, R$^{2C}$-substituted or unsubstituted heteroarylene, or R$^{2C}$-substituted or unsubstituted spirocyclic linker.

14. The compound of embodiment 10, wherein L$^1$ is independently

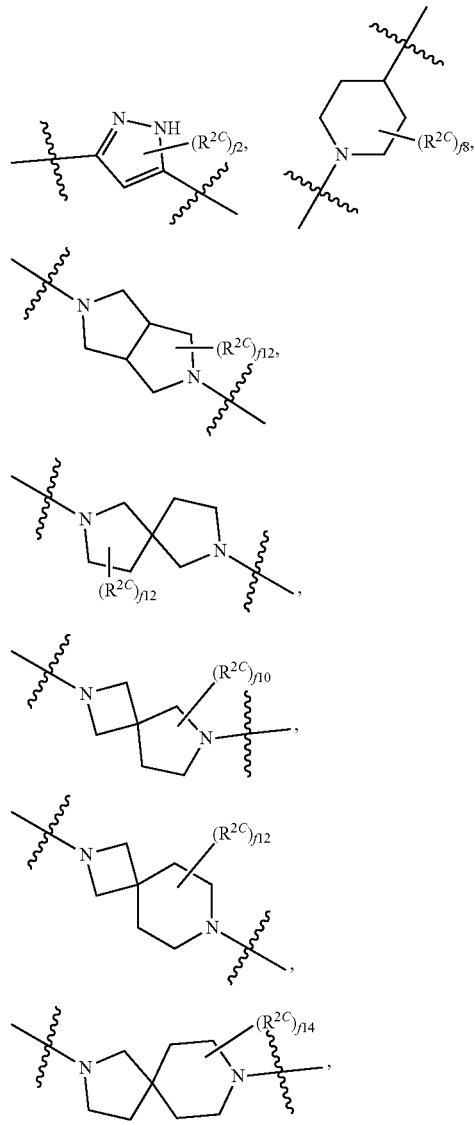

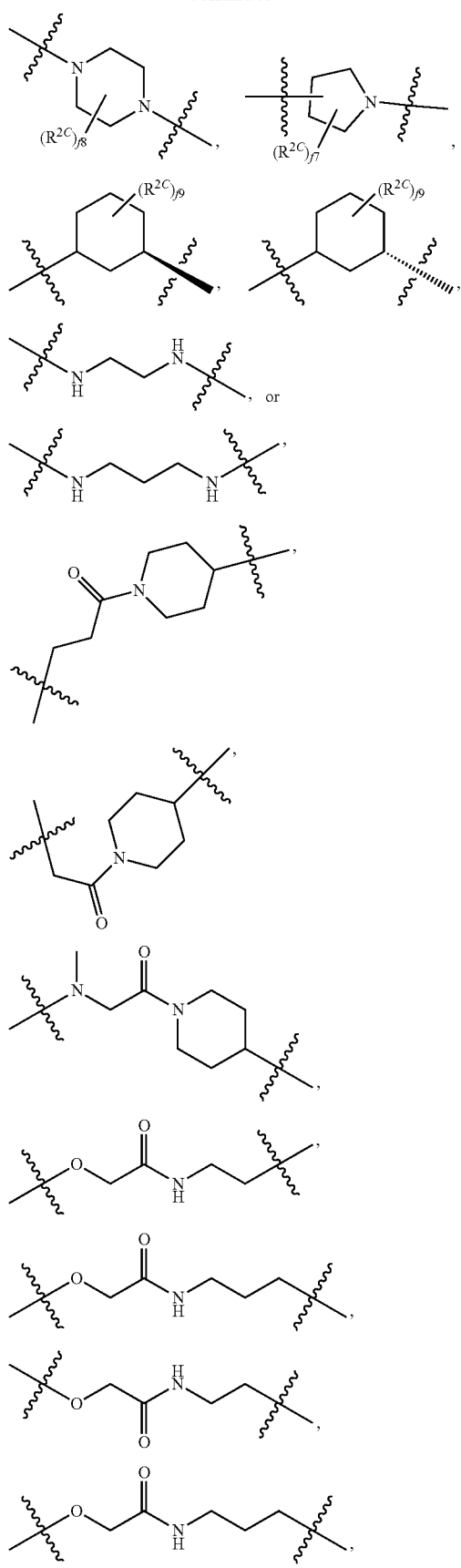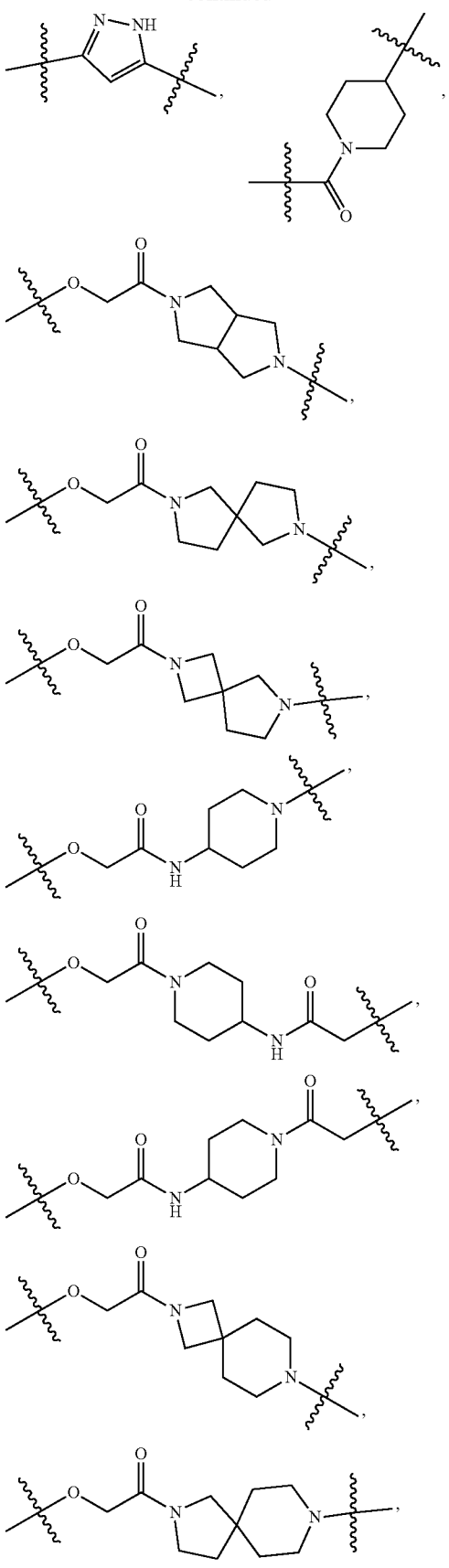

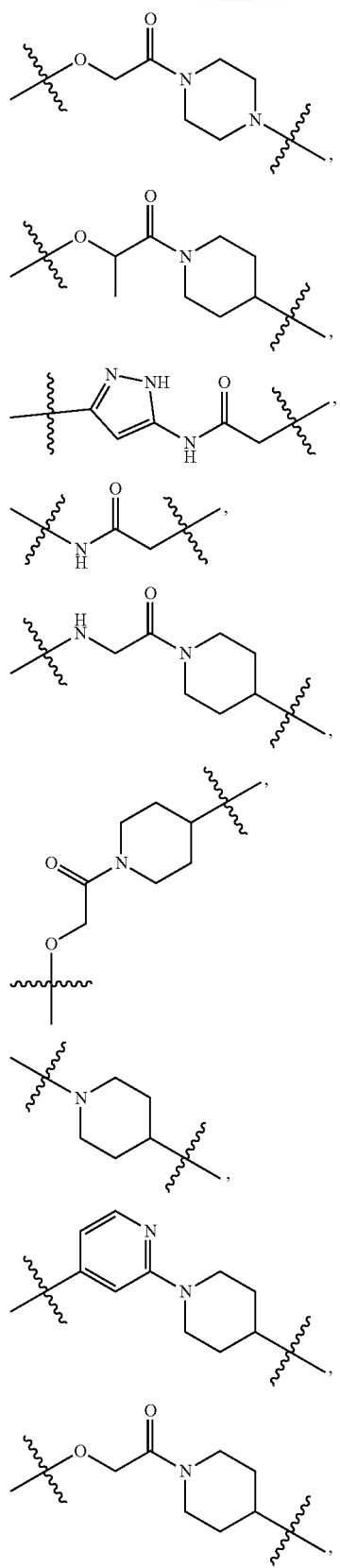
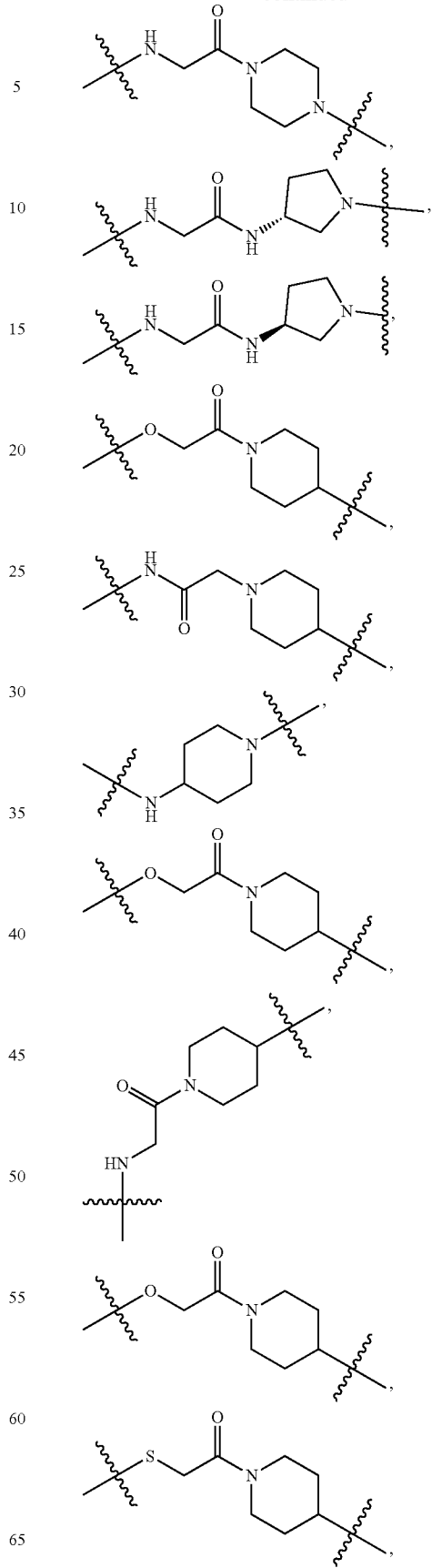

-continued
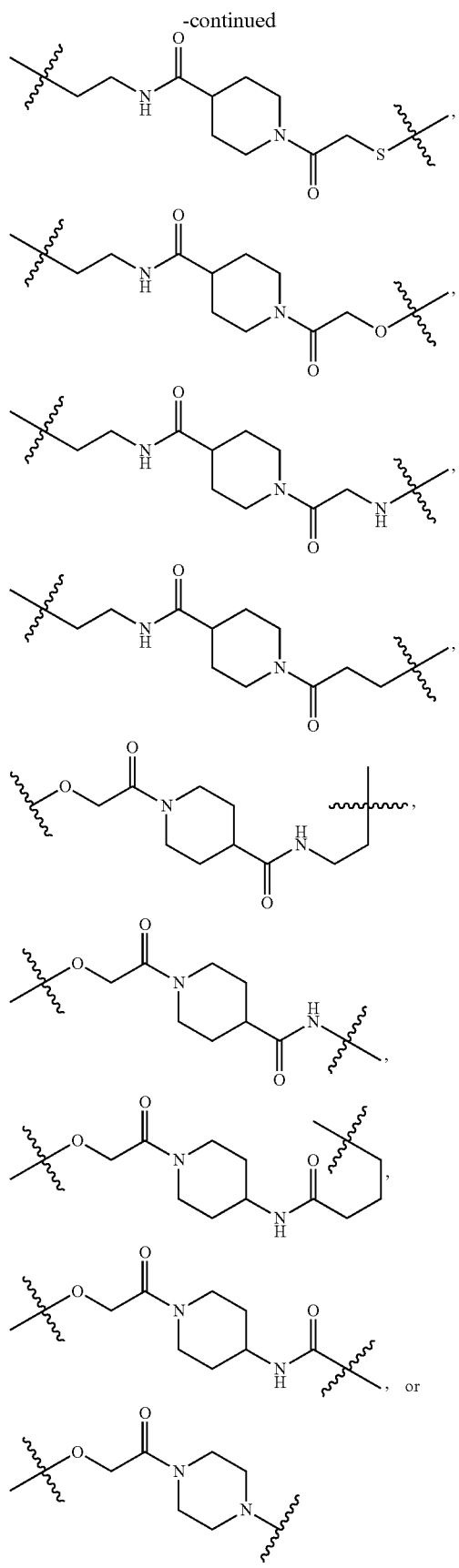
or L² is independently
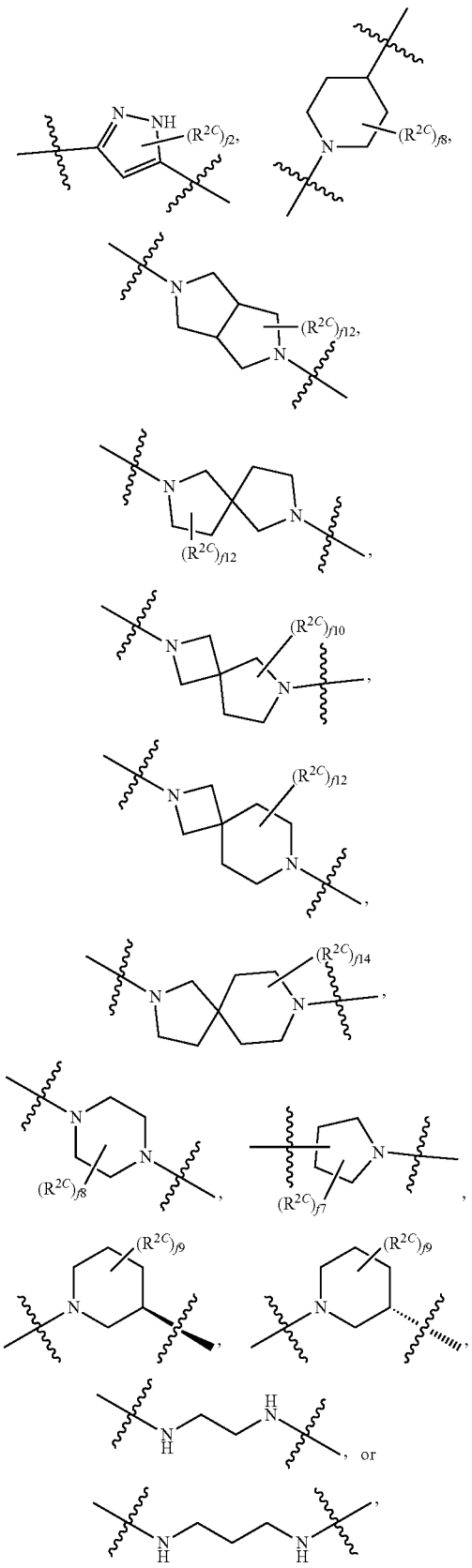

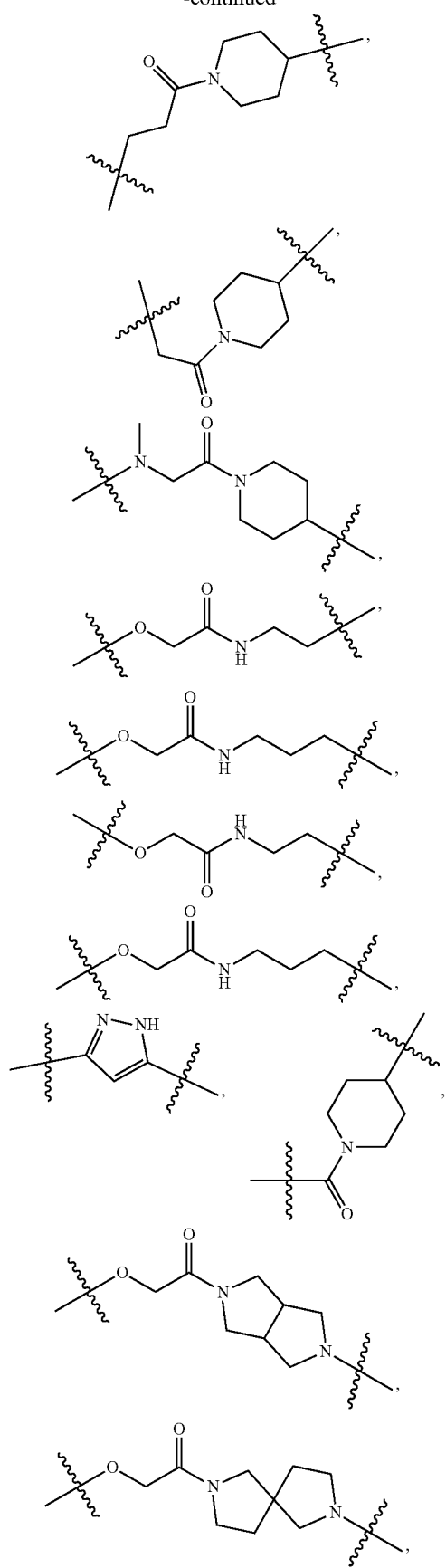
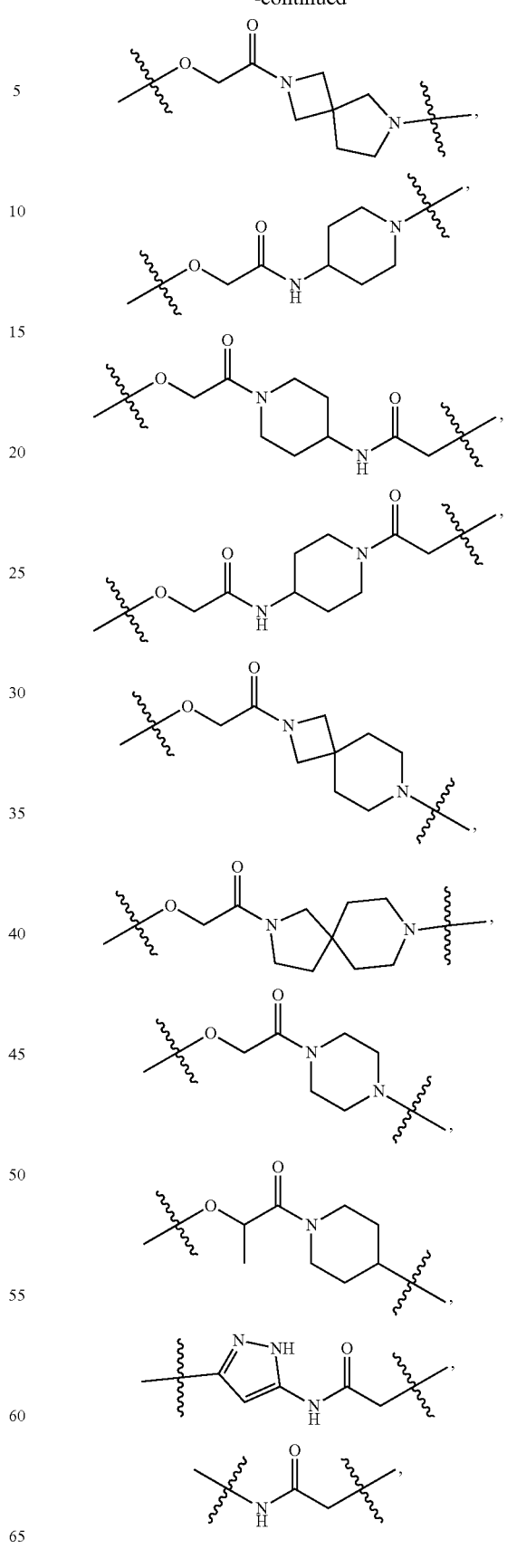

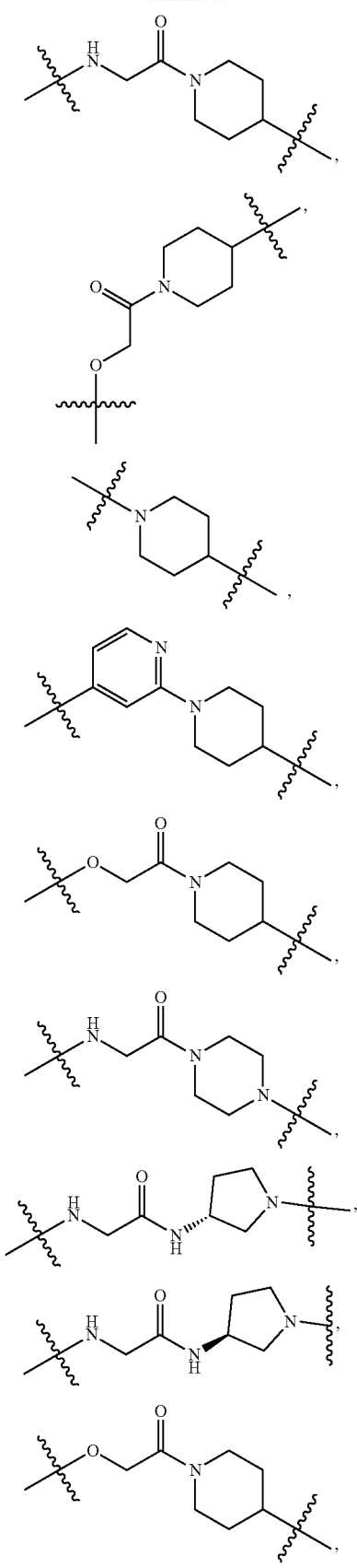
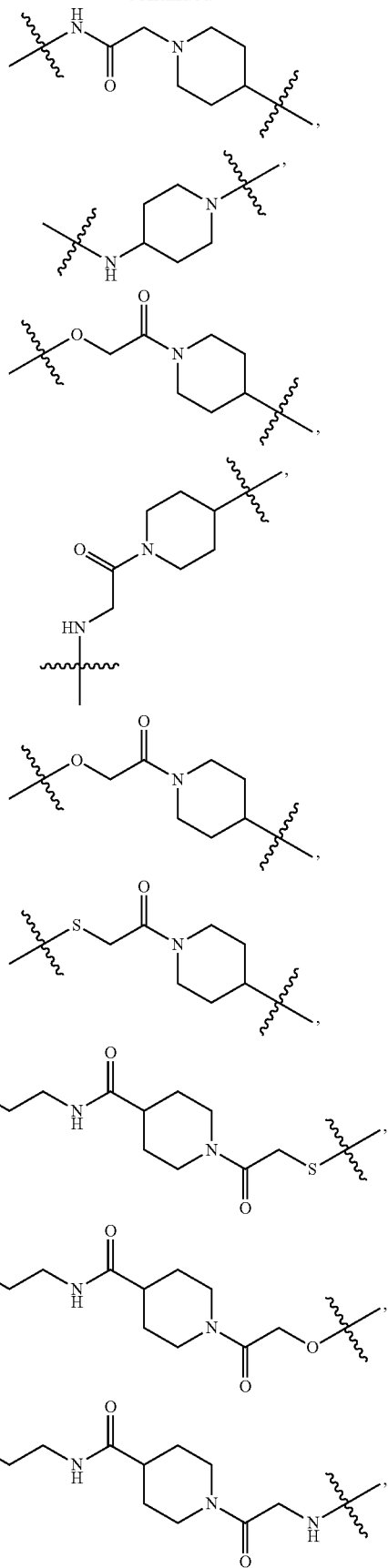

181
-continued
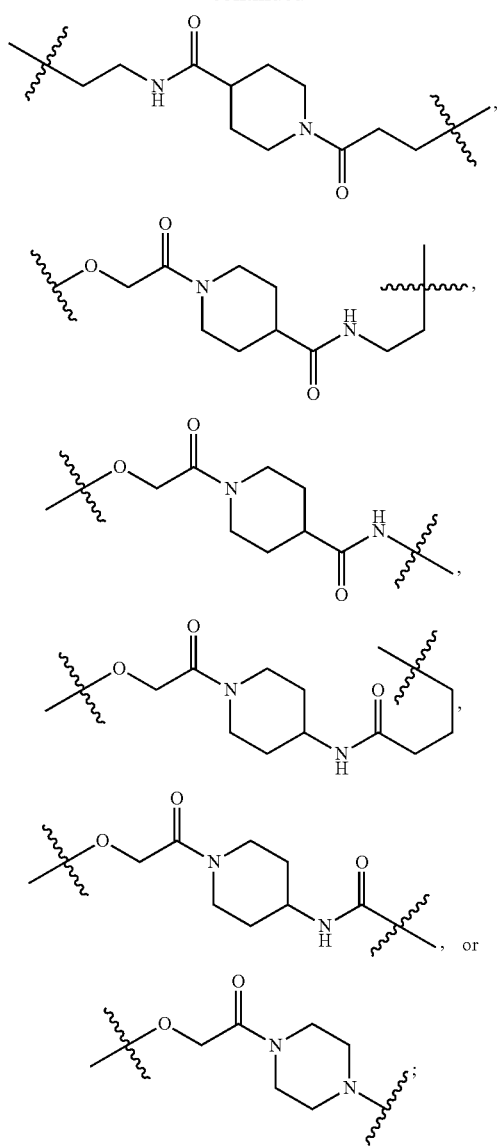 [SMILES: *CCNC(=O)C1CCN(C(=O)CC*)CC1 ; *CCNC(=O)C1CCN(C(=O)CO*)CC1 ; *NC(=O)C1CCN(C(=O)CO*)CC1 ; *CCCC(=O)NC1CCN(C(=O)CO*)CC1 ; *OCC(=O)N1CCC(NC(*)=O)CC1 ; *OCC(=O)N1CCN(*)CC1]
or L³ is independently
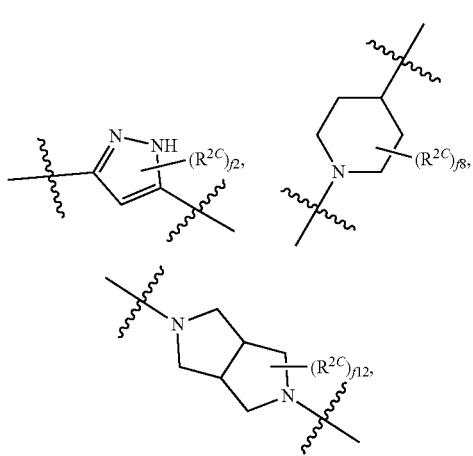
182
-continued
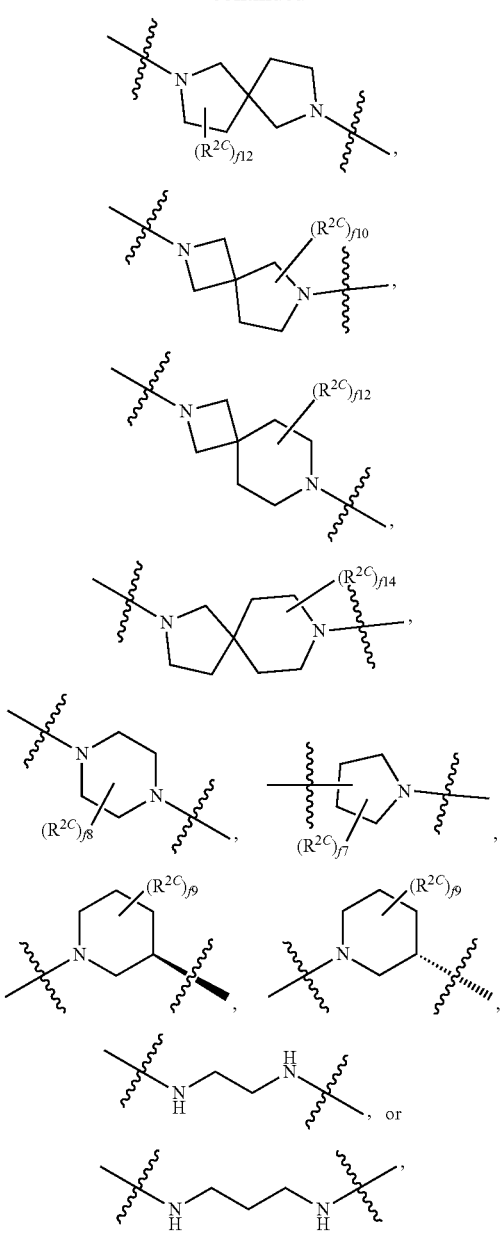
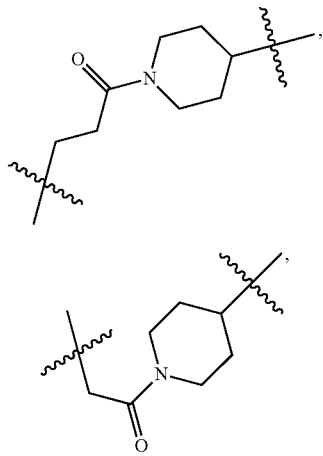

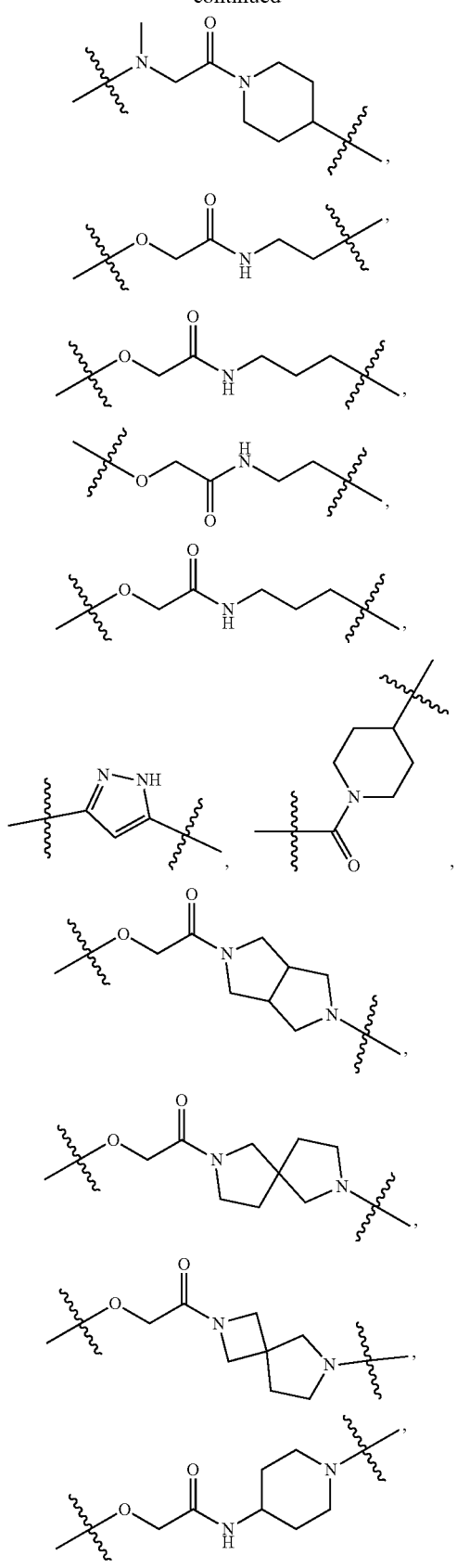
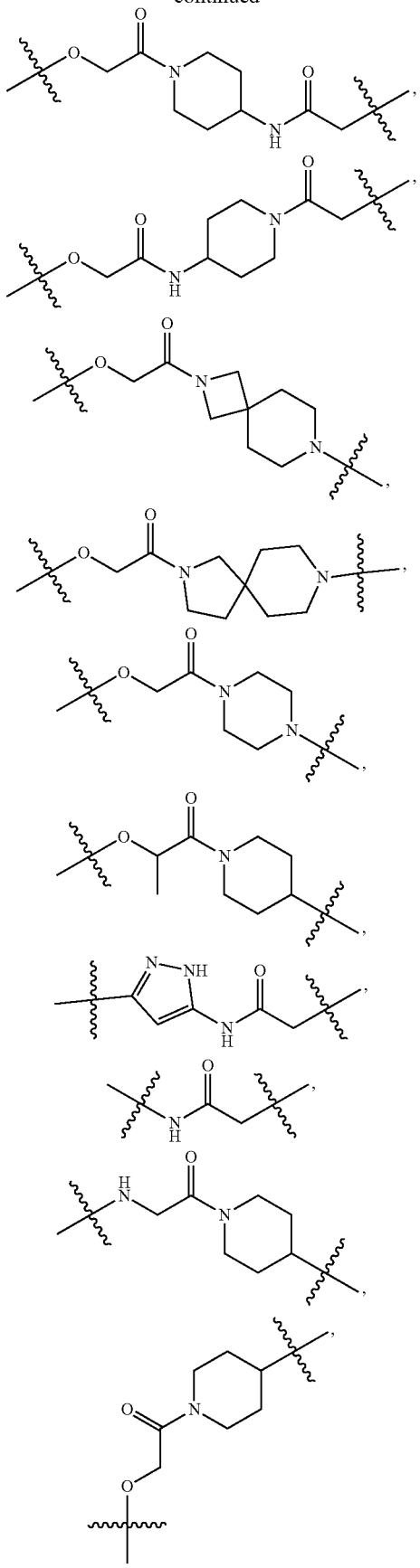

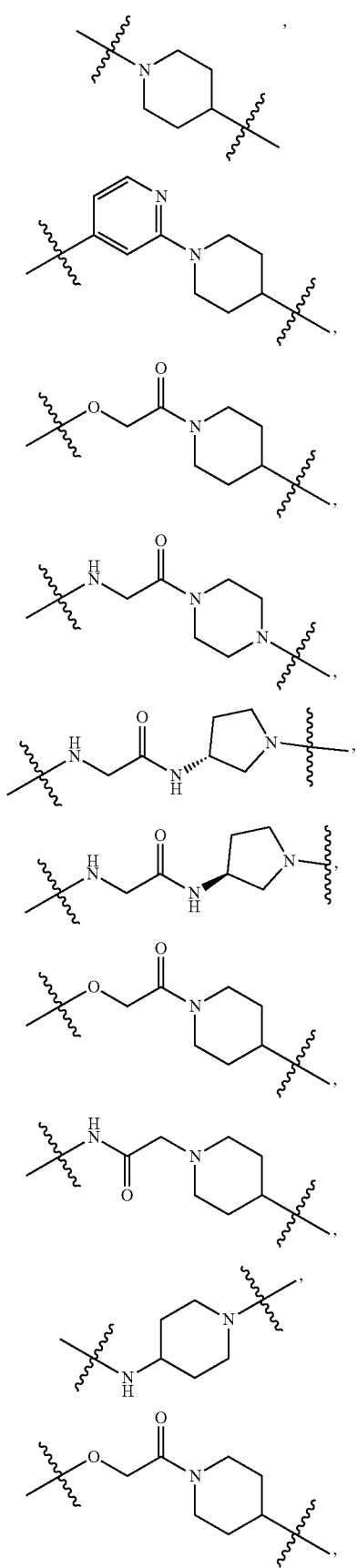
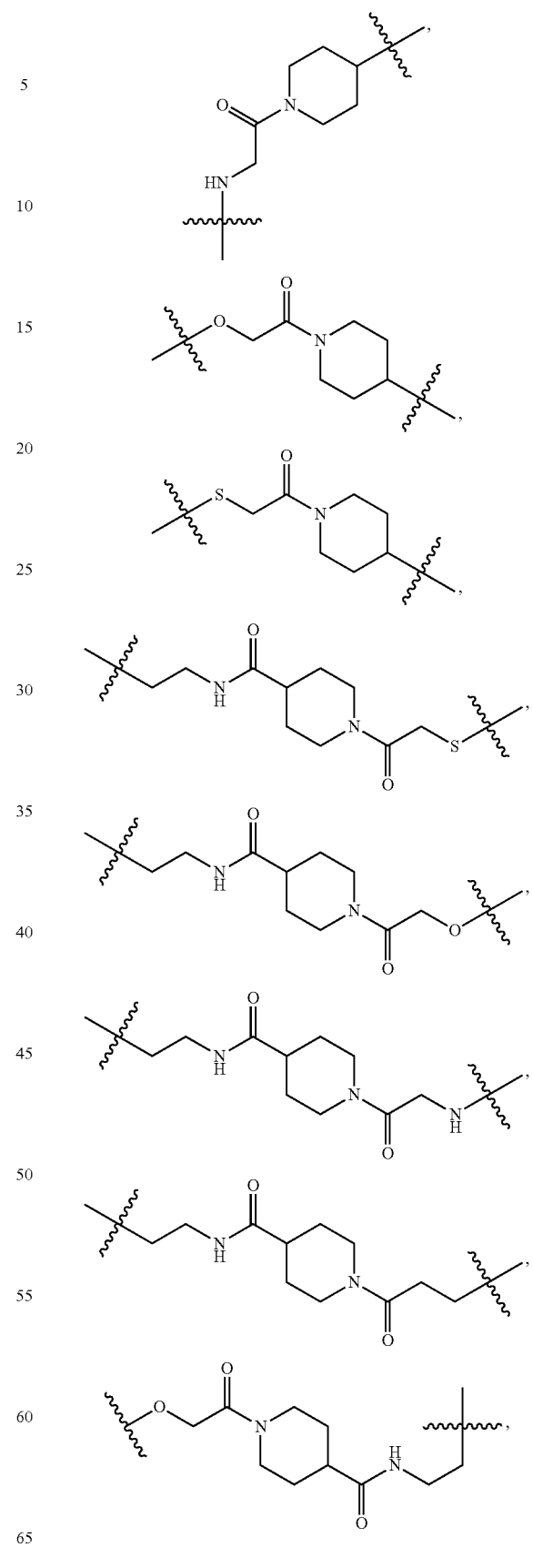

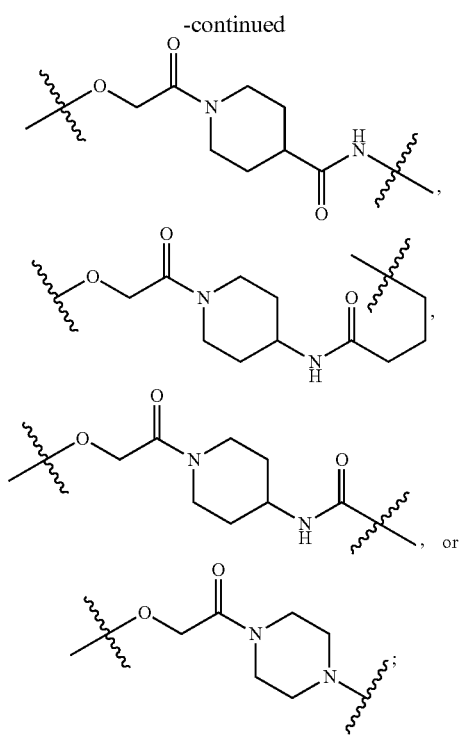

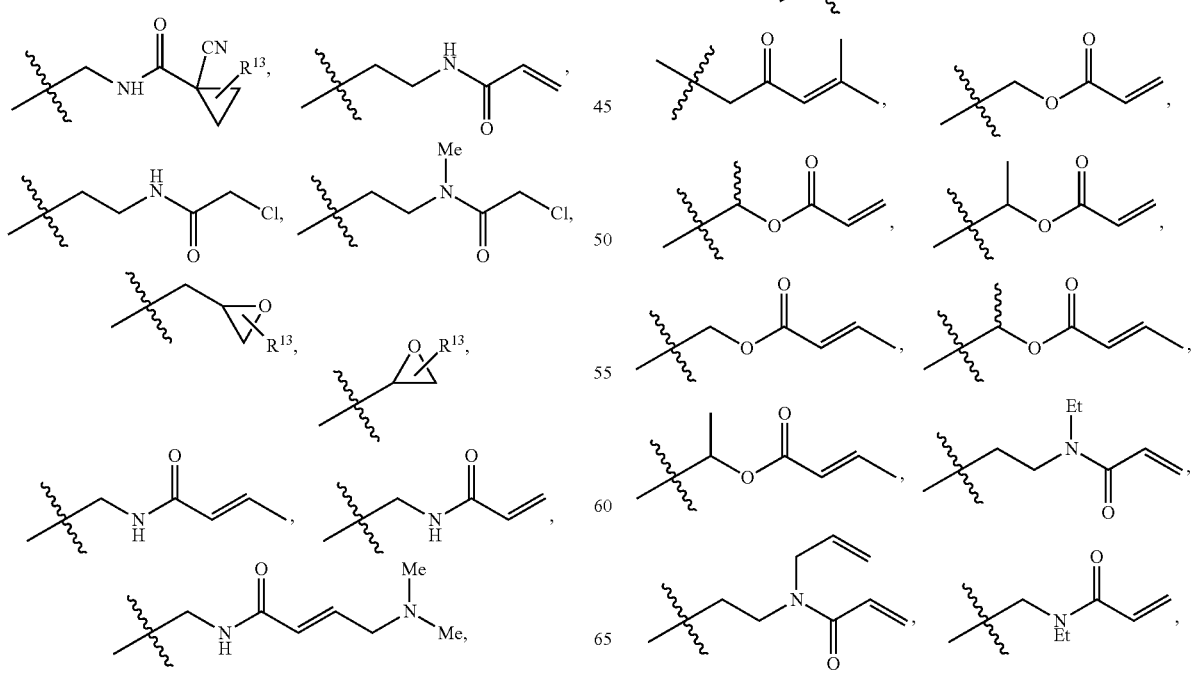

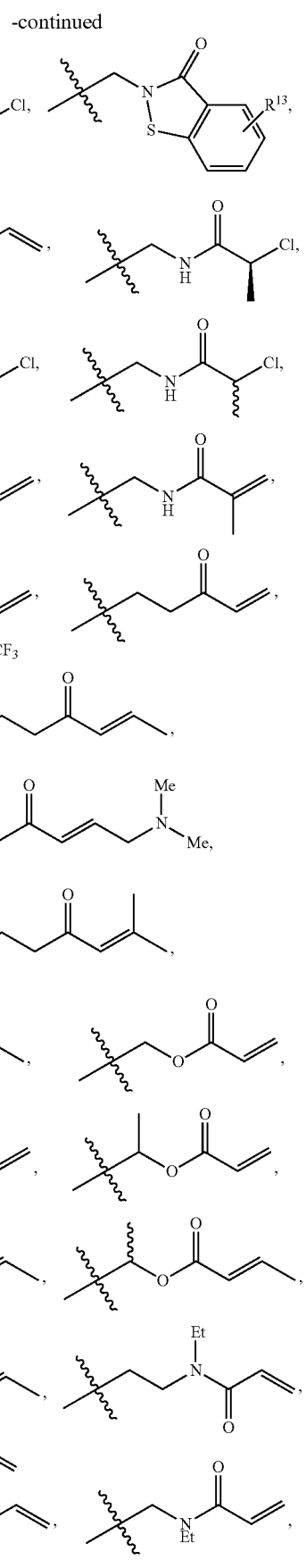

and wherein, f2 is independently an integer from 0 to 2; f6 is independently an integer from 0 to 6; f7 is independently an integer from 0 to 7; f8 is independently an integer from 0 to 8; f9 is independently an integer from 0 to 9; f10 is independently an integer from 0 to 10; f12 is independently an integer from 0 to 12; f14 is independently an integer from 0 to 14.

15. The compound of any one of embodiments 1 to 14, wherein E comprises

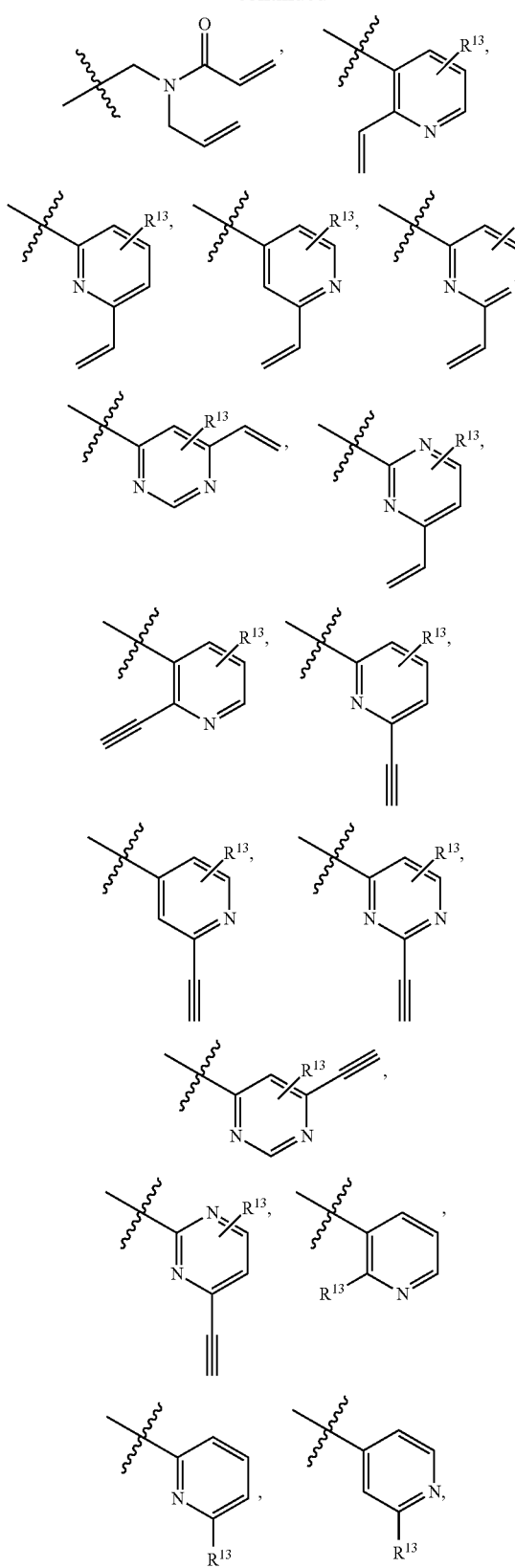
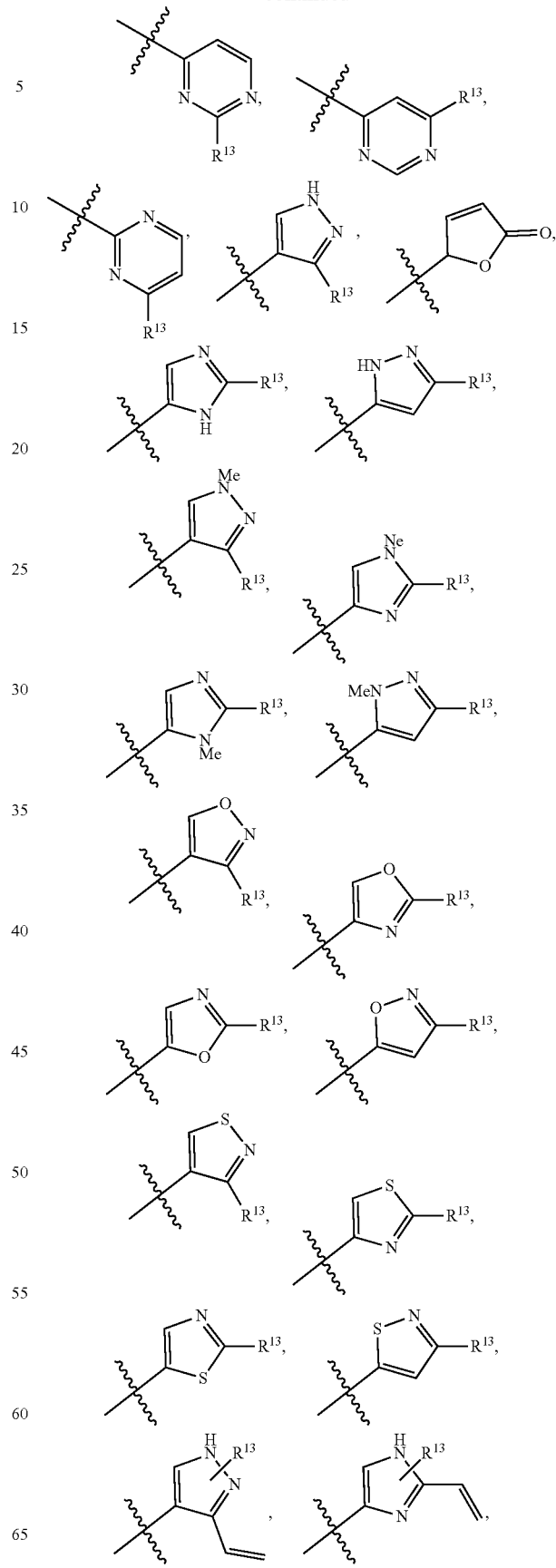

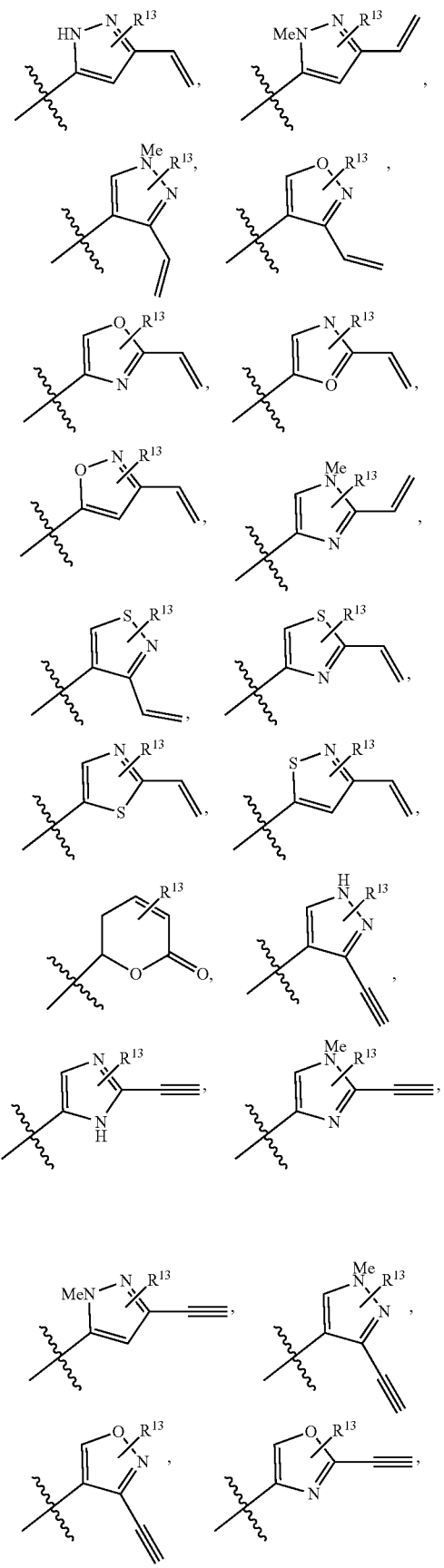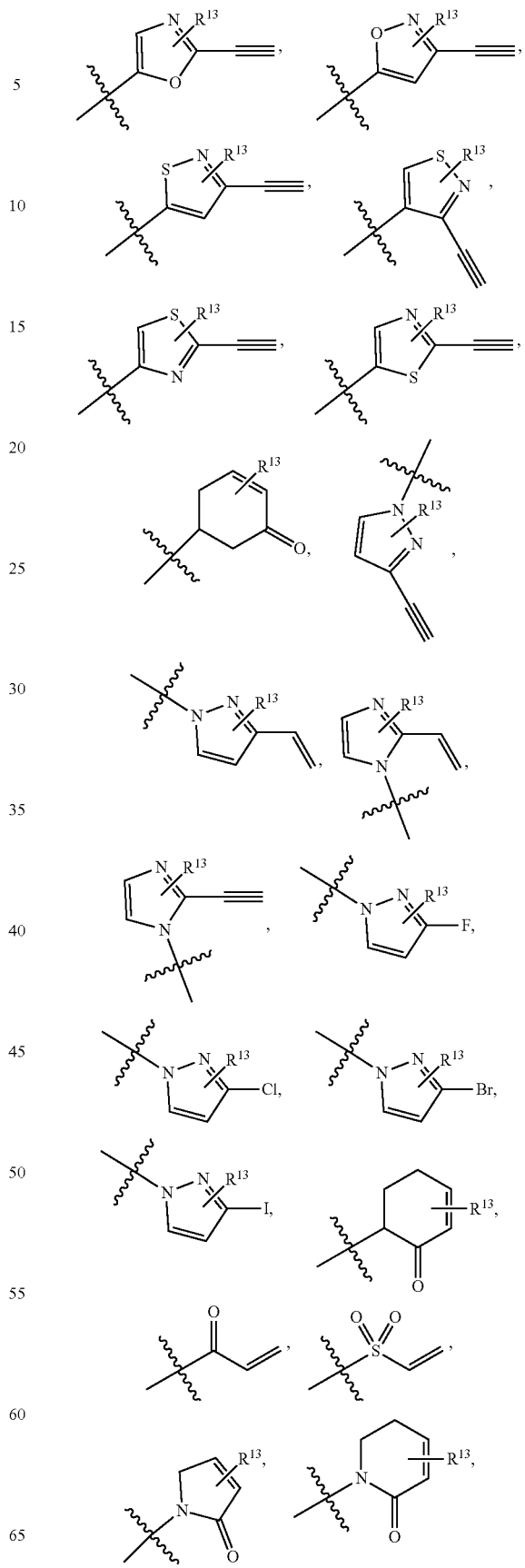

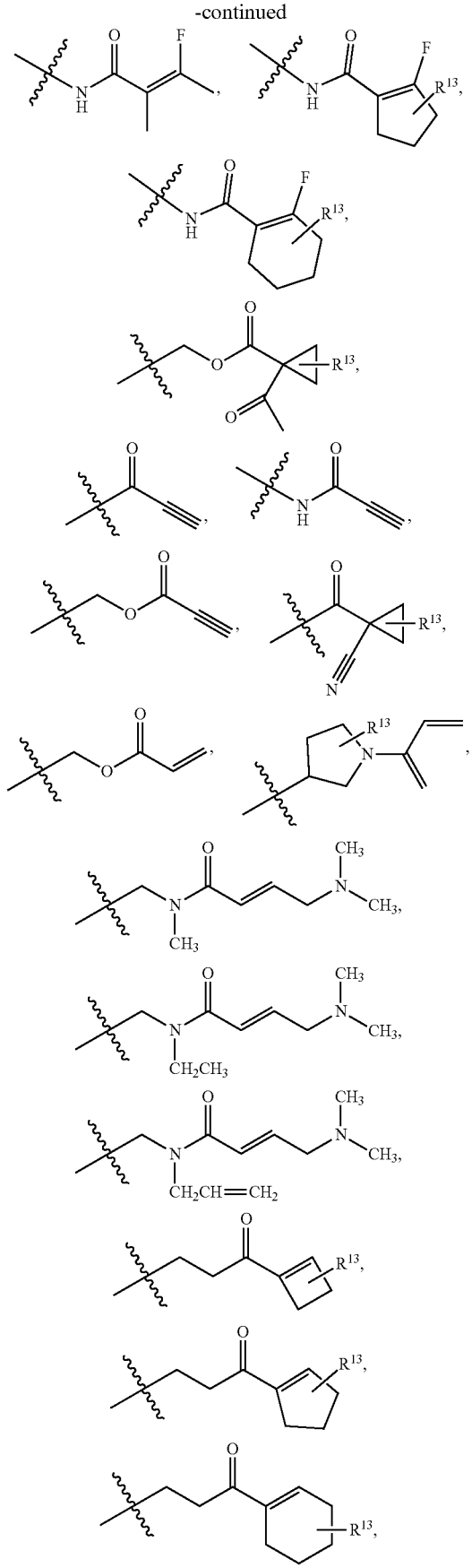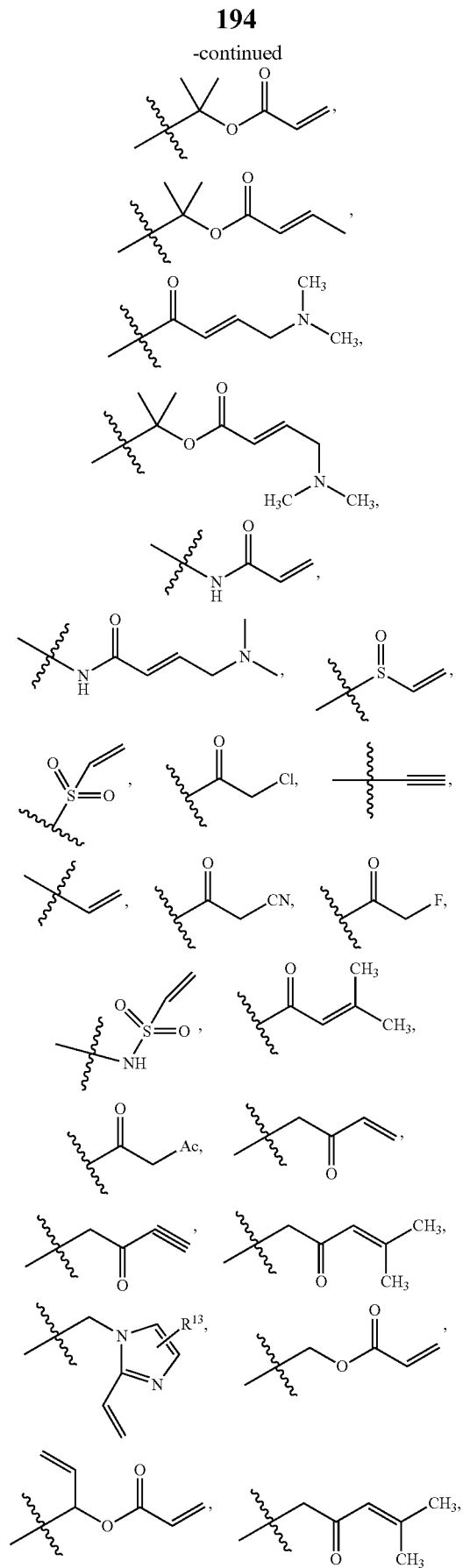

195
-continued
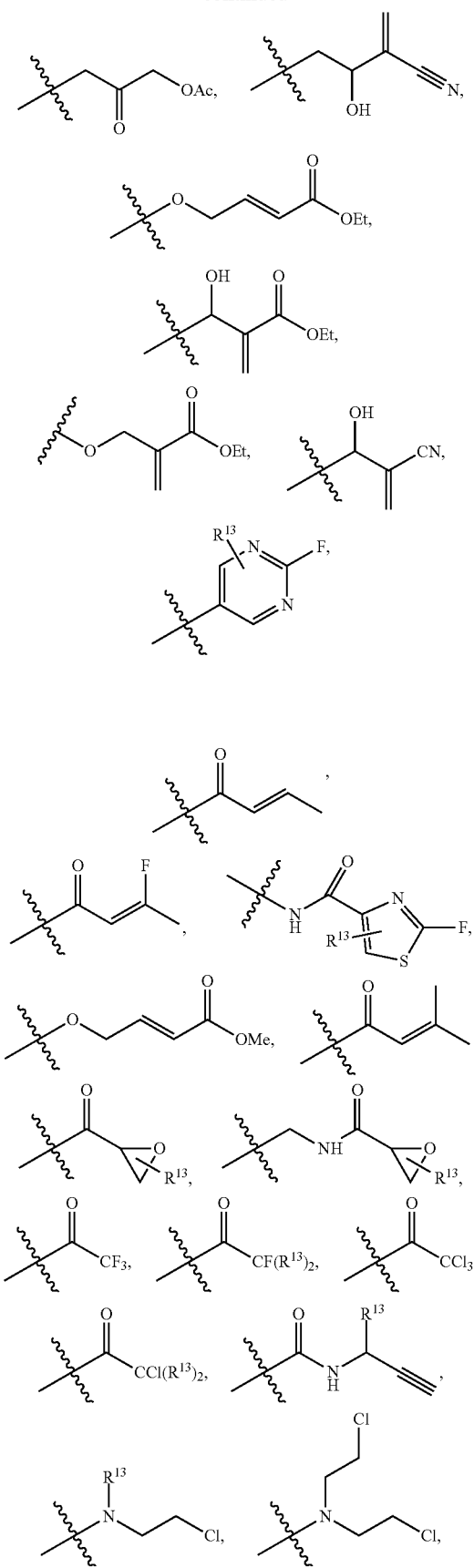
196
-continued
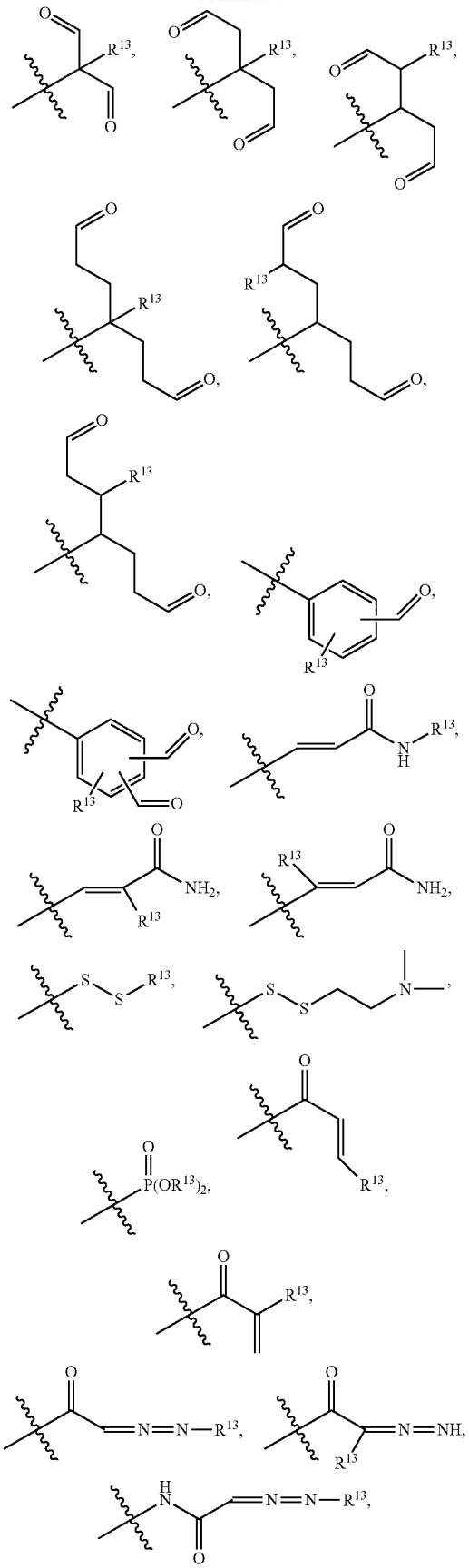

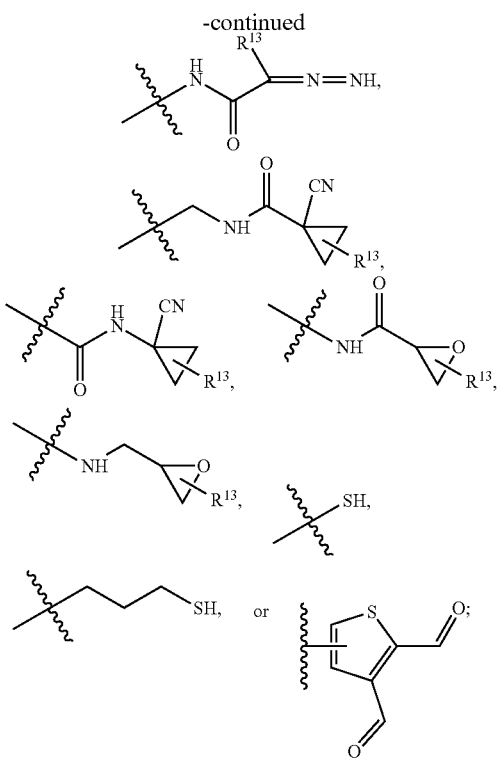

$R^{13}$ is independently hydrogen, oxo, halogen, —CX$^b_3$, —CN, —SO$_2$Cl, —SO$_r$R$^{17}$, —SO$_p$NR$^{14}$R$^{15}$, —NHNH$_2$, —ONR$^{14}$R$^{15}$, —NHC=(O)NHNH$_2$, —NHC=(O)NR$^{14}$R$^{15}$, —N(O) q, —NR$^{14}$R$^{15}$, —C(O)R$^{16}$, —C(O)—OR$^{16}$, —C(O)NR$^{14}$R$^{15}$, —OR$^{17}$, —NR$^{14}$SO$_2$R$^{17}$, —NR$^{14}$C=(O) R$^{16}$, —NR$^{14}$C(O)—OR$^{16}$, —NR$^{14}$OR$^{16}$, —OCX$^b_3$, —OCHX$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; Two adjacent R$^{13}$ substituents may optionally be joined to form a substituted or unsubstituted cycloalkyl, substituted or unsubstituted heterocycloalkyl, substituted or unsubstituted aryl, or substituted or unsubstituted heteroaryl; Two R$^{13}$ substituents bonded to the same atom may optionally be joined to form a substituted or unsubstituted cycloalkyl or substituted or unsubstituted heterocycloalkyl; R$^{14}$, R$^{15}$, R$^{16}$, and R$^{17}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{14}$ and R$^{15}$ substituents bonded to the same nitrogen atom may optionally be joined to form a substituted or unsubstituted heterocycloalkyl or substituted or unsubstituted heteroaryl; p is independently 1 or 2; q is independently an integer from 1 to 2; r is independently an integer from 0 to 4; X$^b$ is independently —Cl, —Br, —I, or —F.

16. The compound of any one of embodiments 1 to 14, wherein E comprises a substituted or unsubstituted vinyl sulfone moiety, substituted or unsubstituted vinyl sulfonamide moiety, substituted or unsubstituted fluoro (C$_1$-C$_4$) alkylketone moiety, substituted or unsubstituted chloro(C$_1$-C$_4$) alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety.

17. The compound of any one of embodiments 1 to 14, wherein E comprises an unsubstituted vinyl sulfone moiety, unsubstituted vinyl sulfonamide moiety, unsubstituted fluoro (C$_1$-C$_4$) alkylketone moiety, unsubstituted chloro(C$_1$-C$_4$) alkylketone moiety, unsubstituted acrylamide moiety, unsubstituted disulfide moiety, unsubstituted thiol moiety, unsubstituted phosphonate moiety, unsubstituted aldehyde moiety, unsubstituted enone moiety, unsubstituted diazomethylketone moiety, unsubstituted diazomethylamide moiety, unsubstituted cyanocyclopropyl carboxamide moiety, unsubstituted epoxide moiety, unsubstituted epoxyketone moiety, unsubstituted epoxyamide moiety, unsubstituted aryl aldehyde moiety, unsubstituted aryl dialdehyde moiety, unsubstituted dialdehyde moiety, unsubstituted nitrogen mustard moiety, unsubstituted propargyl moiety, or unsubstituted propargylamide moiety.

18. A pharmaceutical composition comprising a pharmaceutically acceptable excipient and a compound of any one of embodiments 1 to 17.

19. A method of treating a disease in a patient in need of such treatment, said method comprising administering a therapeutically effective amount of a compound of any one of embodiments 1 to 17 to said patient.

20. The method of embodiment 19, wherein said disease is cancer.

21. The method of embodiment 20, wherein said cancer is colon cancer, colorectal cancer, pancreatic cancer, breast cancer, or leukemia.

22. The method of embodiment 20, wherein said cancer is lung cancer.

23. The method of embodiment 22, wherein said lung cancer is non-small cell lung cancer.

24. A method of modulating the activity of a K-Ras protein, said method comprising contacting said K-Ras protein with an effective amount of a compound of any one of embodiments 1 to 17.

25. The method of embodiment 24, wherein said modulating of said activity comprises modulating GTPase activity, nucleotide exchange, differential GDP or GTP binding, effector protein binding, effector protein activation, guanine exchange factor (GEF) binding, GEF-facilitated nucleotide exchange, phosphate release, nucleotide release, nucleotide binding, K-Ras subcellular localization, K-Ras post-translational processing, or K-Ras post-translational modifications.

26. The method of embodiment 24, wherein said modulating is increasing the activity of said K-Ras protein.

27. The method of embodiment 24, wherein said modulating is reducing the activity of said K-Ras protein.

28. The method of embodiment 24, wherein said K-Ras protein is a human K-Ras protein.

29. The method of embodiment 28, wherein said human K-Ras protein contains a G12C, G12D, G13C, or G13D mutation.

30. The method of embodiment 28, wherein said human K-Ras protein contains a G12C mutation.

31. A method of modulating a K-Ras protein, said method comprising contacting said K-Ras protein with an effective amount of a compound of any one of embodiments 1 to 17.

32. The method of embodiment 31, wherein said modulating is of K-Ras subcellular localization, K-Ras post-translational processing, or a K-Ras post-translational modification.

33. The method of embodiment 31, wherein said K-Ras protein is a human K-Ras protein.

34. The method of embodiment 33, wherein said human K-Ras protein contains a G12C, G12D, G13C, or G13D mutation.

35. The method of embodiment 33, wherein said human K-Ras protein contains a G12C mutation.

36. The method of any one of embodiments 24 to 35, wherein said K-Ras protein is within a biological cell.

37. The method of embodiment 36, wherein said biological cell forms part of an organism.

38. A K-Ras protein covalently bound to a compound of any one of embodiments 1 to 17, wherein said compound is covalently bound to a cysteine residue of said K-Ras protein.

39. The covalently modified K-Ras protein of embodiment 38, wherein said compound is reversibly covalently bound to a cysteine residue of said K-Ras protein.

40. The covalently modified K-Ras protein of embodiment 38, wherein said compound is irreversibly covalently bound to a cysteine residue of said K-Ras protein.

41. The covalently modified K-Ras protein of any one of embodiments 38 to 40, wherein said covalently modified K-Ras protein has a modulated activity relative to a control, wherein said activity is selected from GTPase activity, nucleotide exchange, differential GDP or GTP binding, effector protein binding, effector protein activation, guanine exchange factor (GEF) binding, GEF-facilitated nucleotide exchange, phosphate release, nucleotide release, nucleotide binding, K-Ras subcellular localization, K-Ras post-translational processing, and K-Ras post-translational modifications.

42. The covalently modified K-Ras protein of any one of embodiments 38 to 40, wherein said covalently modified K-Ras protein is modulated in K-Ras subcellular localization, K-Ras post-translational processing, or K-Ras post-translational modification.

43. The covalently modified K-Ras protein of any one of embodiments 38 to 40, wherein said K-Ras protein contains a G12C mutation.

44. The covalently modified K-Ras protein of embodiment 43, wherein said compound is covalently bonded to cysteine residue 12.

45. The covalently modified K-Ras protein of any one of embodiments 38 to 40, wherein said K-Ras protein contains a G13C mutation.

46. The covalently modified K-Ras protein of embodiment 45, wherein said compound is covalently bonded to cysteine residue 13.

47. A K-Ras protein covalently bound to a compound of any one of embodiments 1 to 17, wherein said compound is covalently bound to an aspartate residue of said K-Ras protein.

48. The covalently modified K-Ras protein of embodiment 47, wherein said compound is reversibly covalently bound to an aspartate residue of said K-Ras protein.

49. The covalently modified K-Ras protein of embodiment 47, wherein said compound is irreversibly covalently bound to an aspartate residue of said K-Ras protein.

50. The covalently modified K-Ras protein of any one of embodiments 47 to 49, wherein said covalently modified K-Ras protein has a modulated activity relative to a control, wherein said activity is selected from GTPase activity, nucleotide exchange, differential GDP or GTP binding, effector protein binding, effector protein activation, guanine exchange factor (GEF) binding, GEF-facilitated nucleotide exchange, phosphate release, nucleotide release, nucleotide binding, K-Ras subcellular localization, K-Ras post-translational processing, and K-Ras post-translational modifications.

51. The covalently modified K-Ras protein of any one of embodiments 47 to 49, wherein said covalently modified K-Ras protein is modulated in K-Ras subcellular localization, K-Ras post-translational processing, or K-Ras post-translational modification.

52. The covalently modified K-Ras protein of any one of embodiments 47 to 49, wherein said K-Ras protein contains a G12D mutation.

53. The covalently modified K-Ras protein of embodiment 52, wherein said compound is covalently bonded aspartate residue 12.

54. The covalently modified K-Ras protein of any one of embodiments 47 to 49, wherein said K-Ras protein contains a G13D mutation.

55. The covalently modified K-Ras protein of embodiment 54, wherein said compound is covalently bonded to aspartate residue 13.

56. A method of identifying a covalent inhibitor of K-Ras protein comprising: contacting a K-Ras protein with a K-Ras inhibitor test compound; allowing said K-Ras inhibitor test compound to covalently inhibit said K-Ras protein; detecting the level of covalent inhibition of said K-Ras protein thereby identifying a covalent inhibitor of K-Ras protein.

57. The method of embodiment 56, wherein said K-Ras inhibitor test compound is a Switch 2—Binding Pocket covalent inhibitor test compound and said K-Ras protein is a G12C mutant K-Ras protein.

58. The method of embodiment 57 further comprising the steps of: contacting a wildtype K-Ras protein with said Switch 2—Binding Pocket covalent inhibitor test compound; allowing said Switch 2—Binding Pocket covalent inhibitor test compound to inhibit said wildtype K-Ras protein; detecting the level of inhibition of said wildtype K-Ras protein; comparing the level of inhibition of said wildtype K-Ras protein to the level of covalent inhibition of said G12C mutant K-Ras protein, wherein a higher level of covalent inhibition of said G12C mutant K-Ras indicates said Switch 2—Binding Pocket covalent inhibitor test compound is specific for said G12C mutant K-Ras protein.

59. The method of embodiment 56, wherein said K-Ras inhibitor test compound is a Switch 2—Binding Pocket covalent inhibitor test compound and said K-Ras protein is a G12D mutant K-Ras protein.

60. The method of embodiment 59 further comprising the steps of: contacting a wildtype K-Ras protein with said Switch 2—Binding Pocket covalent inhibitor test compound; allowing said Switch 2—Binding Pocket covalent inhibitor test compound to inhibit said wildtype K-Ras protein; detecting the level of inhibition of said wildtype K-Ras protein; comparing the level of inhibition of said wildtype K-Ras protein to the level of covalent inhibition of said G12D mutant K-Ras protein, wherein a higher level of covalent inhibition of said G12D mutant K-Ras indicates said Switch 2—Binding Pocket covalent inhibitor test compound is specific for said G12D mutant K-Ras protein.

61. The method of embodiment 56, wherein said K-Ras inhibitor test compound is a Switch 2—Binding Pocket covalent inhibitor test compound and said K-Ras protein is a G13C mutant K-Ras protein.

62. The method of embodiment 61 further comprising the steps of: contacting a wildtype K-Ras protein with said Switch 2—Binding Pocket covalent inhibitor test compound; allowing said Switch 2—Binding Pocket covalent inhibitor test compound to inhibit said wildtype K-Ras protein; detecting the level of inhibition of said wildtype K-Ras protein; comparing the level of inhibition of said wildtype K-Ras protein to the level of covalent inhibition of said G13C mutant K-Ras protein, wherein a higher level of covalent inhibition of said G13C mutant K-Ras indicates said Switch 2—Binding Pocket covalent inhibitor test compound is specific for said G13C mutant K-Ras protein.

63. The method of embodiment 56, wherein said K-Ras inhibitor test compound is a Switch 2—Binding Pocket covalent inhibitor test compound and said K-Ras protein is a G13D mutant K-Ras protein.

64. The method of embodiment 59 further comprising the steps of: contacting a wildtype K-Ras protein with said Switch 2—Binding Pocket covalent inhibitor test compound; allowing said Switch 2—Binding Pocket covalent inhibitor test compound to inhibit said wildtype K-Ras protein; detecting the level of inhibition of said wildtype K-Ras protein; comparing the level of inhibition of said wildtype K-Ras protein to the level of covalent inhibition of said G13D mutant K-Ras protein, wherein a higher level of covalent inhibition of said G13D mutant K-Ras indicates said Switch 2—Binding Pocket covalent inhibitor test compound is specific for said G13D mutant K-Ras protein.

65. A method of selectively modulating a Ras protein, said method comprising contacting said Ras protein with a compound which contacts at least one amino acid residue forming a Switch 2 binding pocket of said Ras protein, wherein said at least one amino acid residue is selected from valine-7, valine-9, glycine-10, proline-34, threonine-58, glycine-60, glutamine-61, glutamate-62, glutamate-63, arginine-68, tyrosine-71, methionine-72, tyrosine-96, glutamine-99 and isoleucine-100 of said Ras protein, and wherein said compound covalently reacts with an amino acid residue of said Ras protein.

66. The method of embodiment 65, wherein said compound binds to a K-Ras protein with a higher binding affinity as compared to a H-Ras protein.

67. The method of embodiment 65, wherein said compound interacts with at least one of glycine-60, glutamate-62, or glutamate-63.

68. The method of embodiment 65, wherein said interacting between said amino acid residue and said compound involves hydrogen bonding, van der Waals interaction, ionic bonding, covalent bonding, or hydrophobic interaction.

69. The method of embodiment 65, wherein said compound fills space within said Switch 2 binding pocket.

70. The method of embodiment 65, wherein said compound inhibits K-Ras as measured by the fraction of protein covalently labeled by the compound, wherein the compound is present in 50-fold excess and wherein the fraction of protein covalently labeled is determined by mass spectrometry.

71. The method of embodiment 65, wherein said compound covalently reacts with an amino acid residue of said K-ras protein.

72. The method of embodiment 71, wherein said amino acid residue is cysteine-12 of K-Ras G12C mutant protein.

73. A method of designing a compound which covalently binds to a Switch 2 binding pocket of a K-Ras protein, the method comprising the steps of: providing a structural model of a reference compound bound to the Switch 2 binding pocket of the K-Ras protein, wherein the reference compound is non-covalently bound to said Switch 2 binding pocket; identifying a cysteine, aspartate, lysine, tyrosine or glutamate residue located in proximity to said Switch 2 binding pocket when said reference compound is bound to said Switch 2 binding pocket; generating at least one additional structural model of a test compound bound to said Switch 2 binding pocket, wherein said test compound comprises an electrophilic moiety; and selecting said test compound if said electrophilic moiety is located within bonding distance of said cysteine residue when said test compound is bound to said Switch 2 binding pocket.

74. A compound having molecular dimensions compatible with the shape of a K-Ras Switch 2 binding pocket wherein the compound, when present in an aqueous solution comprising 200 μM of the compound and 4 μM K-Ras, covalently binds to at least 50% of K-Ras proteins present in solution after 24 hours.

75. A compound of Formula:

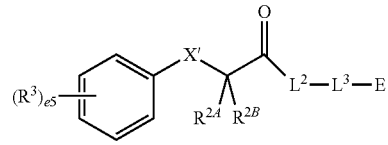

or a pharmaceutically acceptable salt thereof, wherein: e5 is an integer from 0 to 5; X' is —O—, —NH—, or —S—; $R^{2A}$ and $R^{2B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituent bonded to the same atom may optionally be joined to form a substituted or unsubstituted cycloalkyl or substituted or unsubstituted heterocycloalkyl; $R^3$ is independently hydrogen, oxo, halogen, —$CX_3$, —CN, —$SO_2Cl$, —$SO_nR^{10}$, —$SO_vNR^7R^8$, —$NHNH_2$, —$ONR^7R^8$, —NHC=(O)NHNH_2, —NHC=(O)NR^7R^8, —N(O)_m, —NR^7R^8, —C(O)R^9, —C(O)—OR^9, —C(O)NR^7R^8, —OR^{10}, —NR^7SO_2R^{10}, —NR^{7c}=(O) R^9, —NR^{7c} (O)—OR^9, —NR^7OR^9, —OCX_3, —OCHX_2, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^2$ is independently $R^{2C}$, substituted or unsubstituted cycloalkylene, $R^{2C}$-substituted or unsubstituted heterocycloalkylene, $R^{2C}$-substituted or unsubstituted arylene, $R^{2C}$-substituted or unsubstituted heteroarylene, or $R^{2C}$, substituted or unsubstituted spirocyclic linker; $L^3$ is independently $R^{2C}$-substituted or unsubstituted cycloalkylene, $R^{2C}$-substituted or unsubstituted heterocycloalkylene, $R^{2C}$-substituted or unsubstituted arylene, $R^{2C}$-substituted or unsubstituted heteroarylene, or $R^{2C}$-substituted or unsubstituted spirocyclic linker; E is an electrophilic chemical moiety capable of forming a covalent bond with a cysteine or aspartate residue; $R^{2C}$ is independently hydrogen, oxo, halogen, —$CX^c_3$, —CN, —$SO_2Cl$, —$SO_{n3}R^{10c}$, —$SO_{v3}NR^{7c}R^{8c}$, —$NHNH_2$, —$ONR^1CR^{8c}$, —NHC=(O)$NHNH_2$, —NHC=(O)$NR^7R^{8c}$, —N(O)$_{m3}$, —$NR^{7c}R^{8c}$, —C(O)$R^{9c}$, —C(O)—$OR^{9c}$, —C(O)$NR^{7c}R^{8c}$, —$OR^{10c}$, —$NR^{7c}SO_2R^{10c}$, —$NR^{7c}$=(O)$R^{9c}$, —$NR^{7c}$(O)—$OR^{9c}$, —$NR^{7c}OR^{9c}$, —$OCX^c_3$, —OCHX$^c_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^{2C}$ substituents may optionally be joined to form a substituted or unsubstituted cycloalkyl, substituted or unsubstituted heterocycloalkyl, substituted or unsubstituted aryl, or substituted or unsubstituted heteroaryl; two $R^{2C}$ substituents bonded to the same atom may optionally be joined to form a substituted or unsubstituted cycloalkyl or substituted or unsubstituted heterocycloalkyl; $R^7$, $R^8$, $R^9$, and $R^{10}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{7a}$, $R^{8a}$, $R^{9a}$ and $R^{10a}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC—(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{7a}$ and $R^{8a}$ substituents bonded to the same nitrogen atom may optionally be joined to form a substituted or unsubstituted heterocycloalkyl or substituted or unsubstituted heteroaryl; $R^{7c}$, $R^{8c}$, $R^{9c}$, and $R^{10c}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC—(O)$NHNH_2$, —NHC—(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; m, m$^1$, m3, v, v1, and v3 are independently 1 or 2; n, n$^1$, and n3 are independently an integer from 0 to 4; X, X$^a$ and X$^o$ are independently —Cl, —Br, —I, or —F.

76. The compound of embodiment 75, wherein E comprises a substituted or unsubstituted vinyl sulfone moiety, substituted or unsubstituted vinyl sulfonamide moiety, substituted or unsubstituted peroxide moiety, substituted or unsubstituted fluoro ($C_1$-$C_4$) alkylketone moiety, substituted or unsubstituted chloro($C_1$-$C_4$) alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety.

77. The compound or pharmaceutically acceptable salt of embodiment 75, wherein $L^2$ is independently $R^{2C}$-substituted or unsubstituted heterocycloalkylene or $R^{2C}$-substituted or unsubstituted spirocyclic linker and $L^3$ is a bond.

78. The compound or pharmaceutically acceptable salt of embodiment 75, wherein $L^2$ is monocyclic 4, 5, or 6-membered heterocycloalkylene.

79. The compound or pharmaceutically acceptable salt of embodiment 75, wherein $L^2$ is unsubstituted piperazino or unsubstituted piperidino.

80. The compound or pharmaceutically acceptable salt of embodiment 75, wherein $L^2$ is bicyclic fused heterocycloalkylene.

81. The compound or pharmaceutically acceptable salt of embodiment 75, wherein $L^2$ is an unsubstituted spirocyclic linker.

82. The compound or pharmaceutically acceptable salt of embodiment 75, wherein E is a substituted or unsubstituted vinyl sulfone moiety, substituted or unsubstituted vinyl sulfonamide moiety, or a substituted or unsubstituted acrylamide moiety.

83. The compound or pharmaceutically acceptable salt of embodiment 75, having the

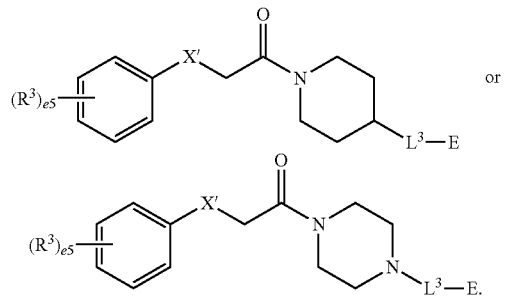

formula:

84. A method of treating a disorder in a subject in need thereof, comprising: determining the presence or absence of a K-Ras mutation in a malignant or neoplastic cell isolated from the subject; and if a K-Ras mutation is determined to be present in the subject, administering to the subject a therapeutically effective amount of a compound or pharmaceutically acceptable salt of any one of embodiments 1-17 and 74-83.

85. A method of treating a disorder in a subject in need thereof, comprising: determining the presence or absence of a K-Ras mutation in a malignant or neoplastic cell isolated from the subject, in connection with the prescription of an effective amount of a compound or pharmaceutically acceptable salt of any one of embodiments 1-17 and 74-83 to said subject; and if a K-Ras mutation is determined to be present in the subject, providing an alert to a caregiver of said subject.

86. The method of embodiment 84 or 85, wherein the disorder is cancer.

87. A method of treating cancer in a human subject in need thereof, comprising administering to said subject at least one compound or pharmaceutically acceptable salt of any one of embodiments 1-17 and 74-83, wherein said subject has a K-Ras mutation.

88. The method of any one of embodiments 84 to 87, wherein the K-Ras mutation is selected from the group consisting of G12C, G13C, G12D, and G13D.

89. The method of embodiment 88, wherein the K-Ras mutation is G12C.

90. The compound, or a pharmaceutically acceptable salt thereof, of any one of embodiments 1-17 and 74-83, wherein said compound modulates the binding of GDP or GTP to a K-Ras protein.

91. The compound, or a pharmaceutically acceptable salt thereof, of any one of embodiments 1-17 and 74-83, wherein said compound inhibits the binding of GDP or GTP to a K-Ras protein.

92. The compound, or a pharmaceutically acceptable salt thereof, of any one of embodiments 1-17 and 74-83, wherein said compound increases the binding of GDP or GTP to a K-Ras protein.

93. The compound, or a pharmaceutically acceptable salt thereof, of any one of embodiments 1-17 and 74-83, wherein said compound inhibits the binding of GTP to a K-Ras protein.

94. The compound, or a pharmaceutically acceptable salt thereof, of any one of embodiments 1-17 and 74-83, wherein said compound increases the binding of GDP to a K-Ras protein.

95. The compound, or a pharmaceutically acceptable salt thereof, of any one of embodiments 1-17 and 74-83, wherein said compound inhibits the release of GDP from a K-Ras protein.

96. The compound, or a pharmaceutically acceptable salt thereof, of any one of embodiments 1-17 and 74-83, wherein said compound increases the release of GDP or GTP from a K-Ras protein.

97. The compound, or a pharmaceutically acceptable salt thereof, of any one of embodiments 1-17 and 74-83, wherein said compound increases the release of GDP from a K-Ras protein.

98. The compound, or a pharmaceutically acceptable salt thereof, of any one of embodiments 1-17 and 74-83, wherein said compound increases the release of GTP from a K-Ras protein.

99. The compound, or a pharmaceutically acceptable salt thereof, of any one of embodiments 1-17 and 74-83, wherein said compound modulates the binding of a K-Ras protein to Raf.

100. The compound, or a pharmaceutically acceptable salt thereof, of any one of embodiments 1-17 and 74-83, wherein said compound inhibits the binding of a K-Ras protein to Raf.

101. The method of any one of embodiments 19-37, 65-72, and 84-89, wherein said compound modulates the binding of GDP or GTP to a K-Ras protein.

102. The method of any one of embodiments 19-37, 65-72, and 84-89, wherein said compound inhibits the binding of GDP or GTP to a K-Ras protein.

103. The method of any one of embodiments 19-37, 65-72, and 84-89, wherein said compound increases the binding of GDP or GTP to a K-Ras protein.

104. The method of any one of embodiments 19-37, 65-72, and 84-89, wherein said compound inhibits the binding of GTP to a K-Ras protein.

105. The method of any one of embodiments 19-37, 65-72, and 84-89, wherein said compound increases the binding of GDP to a K-Ras protein.

106. The method of any one of embodiments 19-37, 65-72, and 84-89, wherein said compound inhibits the release of GDP from a K-Ras protein.

107. The method of any one of embodiments 19-37, 65-72, and 84-89, wherein said compound increases the release of GDP or GTP from a K-Ras protein.

108. The method of any one of embodiments 19-37, 65-72, and 84-89, w herein said compound increases the release of GDP from a K-Ras protein.

109. The method of any one of embodiments 19-37, 65-72, and 84-89, wherein said compound increases the release of GTP from a K-Ras protein.

110. The method of any one of embodiments 19-37, 65-72, and 84-89, wherein said compound modulates the binding of a K-Ras protein to Raf.

111. The method of any one of embodiments 19-37, 65-72, and 84-89, wherein said compound inhibits the binding of a K-Ras protein to Raf.

112. The method of any one of embodiments 19-37, 65-72, 84-89, and 101-111, wherein said compound binds a GDP bound K-Ras protein.

113. The compound of any one of embodiments 1-17, 74-83, and 90-100, wherein said compound binds a GDP bound K-Ras protein.

114. A pharmaceutical composition comprising a pharmaceutically acceptable excipient and a compound of any one of embodiments 74-83, 90-100, and 113.

EXAMPLES

The following examples are meant to illustrate certain embodiments of the invention and not to limit the scope of the invention described herein. Activating mutations in K-Ras are among the most common lesions found in human cancer, and such mutations are generally associated with poor prognosis. Despite numerous efforts in academia and industry, small molecule inhibitors that directly target K-Ras remain elusive. Even more highly desired are molecules that selectively target mutant K-Ras while sparing the wild type protein. We have used a fragment-based screen to discover oncogenic mutant-specific inhibitors of K-Ras. Crystallographic studies with multiple inhibitors in complex with K-Ras reveal that the compounds bind in a novel hydrophobic pocket that is not apparent in any published crystal structure of Ras. These inhibitors disrupt the conformations of Switch I and Switch II, domains that are essential for the association and activation of downstream signaling partners. Our medicinal chemistry effort has greatly improved potency, showing that this pocket is particularly amenable to chemical optimization. In vitro biochemical characterization of these inhibitors confirms that they block Ras function. Our discovery of a new druggable pocket in K-Ras, and a set of inhibitors that bind to it in a mutant-specific fashion, provides a promising new avenue for the direct pharmacological inhibition of oncogenic Ras. In embodiments, inhibitors bind to an allosteric pocket behind Switch II, selectively bind to GDP-bound state and not to GTP-bound state, the structure of inhibitor-Ras complex suggests potential to block formation of proper GTP-bound conformation and impair effector activation, and/or inhibitors slow GEF-catalyzed nucleotide exchange, suggesting they might trap Ras in the inactive state.

Compound Binding to K-Ras

In some embodiments, compounds described herein are divided into three distinct parts: a terminal portion (e.g. $R^1$ above), a linker portion (e.g. $L^1$-$L^2$-$L^3$-above) and a chemically reactive portion (e.g. E above). In some embodiments, the terminal portion is a hydrophobic moiety and may comprise a phenyl ring. In some further embodiments the hydrophobic moiety is substituted with at least one halogen atom. In some embodiments the linker portion is a flexible linker portion. The linker portion may include a substituted or unsubstituted saturated heterocycloalkylene. In some embodiments, the chemically reactive portion forms a covalent bond with a thiol of the oncogenic G12C mutant of K-Ras.

In some embodiments of the compounds described herein, the hydrophobic terminal portion (e.g. $R^1$) binds the K-Ras protein in a deep pocket that is not apparent in structures of the protein without a compound. In some embodiments, the deep pocket is formed by compound binding. As shown in ligand interaction maps (FIGS. 7 and 8), this binding pocket includes the following amino acids: valine-7, valine-9, threonine-58, arginine-68, tyrosine-71, methionine-72, tyrosine-96. In some embodiments of the compounds, having a hydrophobic terminal portion, the pocket may form a hydrophobic counterpart to the compounds. In some embodiments, several of the interacting amino acids (e.g. residues contacting a compound) are integral parts of Switch-2, a flexible region of K-Ras involved in effector binding and downstream signaling. In some embodiments of K-Ras bound to a compound as disclosed herein, Switch 2 looks distinct from the active conformation of Switch 2 in GTP-bound K-Ras. In some embodiments, the changes in Switch-2 upon compound binding may be how the compounds described herein (including embodiments) modulate K-Ras, K-Ras activity, and/or K-Ras function (e.g. decreasing the binding affinity of compound bound K-Ras for a signaling pathway interacting protein (e.g. PI3K)).

In some embodiments, the linker portion of compounds described herein (e.g. $L^1$, $L^2$, and $L^3$) shows interactions with the K-Ras protein. In some embodiments of the compounds described herein, the linker portion is more solvent exposed than the terminal portion. In some embodiments, the linker portion of the compounds described herein contacts amino acid residues of Switch-2. In some embodiments, a Switch 2 residue contacted by the linker portion is glycine-60, glutamate-62 or glutamate-63. In some embodiments, the linker portion contacts all three residues. In some embodiments, contact between the compound linker portion and K-Ras provides stabilization of the unusual protein conformation that may be induced by compound binding. In some embodiments of the compounds described herein, the linker portion of the compounds described herein have flexibility in regard to chemical composition, while still providing modulation of K-Ras.

In some embodiments of the compounds, several groups have been found to be effective as the reactive portion of the compounds (e.g. E, the electrophilic moiety, thiol reactive, aspartate reactive). In some embodiments, the compounds are disulfide based compounds to link the compound to K-Ras cysteine-12. X-ray crystal structures (e.g. JO-01-189cbut) show clear electron density for the disulfide linkage. Due to the possible instability of disulfide linkages in the reducing environment of cells we developed compounds with different reactive portions (e.g. electrophilic moieties) that can covalently (e.g. reversibly, irreversibly) bind to cysteine and aspartate. In some embodiments, the electrophilic moiety E is selected from vinyl sulfones, acrylamides and epoxides. In some embodiments, crystal structures for compounds containing the electrophilic moiety vinyl sulfone show interactions of the sulfone oxygens with either the protein directly or with ordered water molecules. In some embodiments of the compounds, compounds containing sulfones are sterically more demanding than disulfide containing compounds. In some embodiments, the electrophilic moiety E (e.g. vinyl sulfones) can modulate the conformation of Switch-1. In some embodiments, the modulation of Switch 1 by compound binding may modulate K-Ras activity or function (e.g. effector binding, for example Raf or PI3K). In some embodiments, the compound binding to K-Ras may modulate K-Ras metal binding by modulating Switch 1 structure or function (e.g. partially disordering Switch-1 relative to the Switch 1 conformation in K-Ras that is not bound to a compound as described herein). In some embodiments, the electrophilic group E contributes to the binding of compound to K-Ras by contacting K-Ras residues. In some embodiments, the electrophilic group E contributes to the binding of compound to K-Ras by covalently bonding to K-Ras through a cysteine or aspartate at residues 12 or 13. The right balance between chemically reactivity, sterical demands and favorable interactions with the protein needs to be achieved for the best reactive group to link the compound to oncogenic cysteine-12.

In some embodiments, the compounds described herein (including embodiments, examples and compounds of Table 1, 2, 3, 4, or 5) provide interactions with K-Ras through a novel complementary pocket and the terminal portion including $R^1$, that leads to a previously unknown conformation of Switch-2, and a covalent link of the compound to the oncogenic mutant K-Ras (e.g. G12C, G12D, G13C, G13D), through the reactive portion containing E. In some embodiments, E can contribute to K-Ras binding through interactions beyond the covalent bond formation and can modulate Switch-1 conformation and stability. In some embodiments, by utilizing both features with the described compounds, K-Ras G12C or G12D or G13C or G13D can be selectively targeted.

Structure-Activity Relationships of Compound Examples

In some embodiments, where the the terminal portion includes a phenyl (e.g. $R^1$ includes a phenyl ring), a hydrophobic group is preferred in the 2-position on the phenyl ring, ortho to the O, S, or N linking to the rest of the molecule (e.g. $L^1$, $L^2$, or $L^3$). In some embodiments, the terminal portion includes a phenyl substituted with a larger halogen. In some embodiments, $R^1$ is a phenyl substituted with a substituted or unsubstituted aryl or substituted or unsubstituted heteroaryl at the ortho position to the bond to the linker portion. In some embodiments, $R^1$ is a phenyl substituted with a substituted or unsubstituted fused ring aryl or substituted or unsubstituted fused ring heteroaryl at the ortho position to the bond to the linker portion. In some embodiments, these hydrophobic substituents (e.g. substituted or unsubstituted aryl or substituted or unsubstituted heteroaryl) on $R^1$ (e.g. phenyl ring) ortho to the bond to the linker portion, point toward the same affinity pocket in K-Ras. In some embodiments, bulky substituents are well tolerated at the 5-position of phenyl relative to the bond to the linker portion. In some embodiments, this position may accommodate bulky groups such as a propargyl group, without compromising affinity. In some embodiments, the 6 position on an $R^1$ phenyl group (relative to the ortho at the 2 position described previously in this paragraph) is a non-hydrophobic group. In some embodiments, the terminal portion includes a fused ring such as a fused ring aryl or fused ring heteroaryl.

In some embodiments of the compounds, the linker portion is bonded to the S2BP moiety through a secondary amine. In some embodiments of the compounds linker portion is bonded to the S2BP moiety through an ether or thioether. In some embodiments, the linker portion is not a rigid moiety. In some embodiments, the linker includes a ring (e.g, substituted or unsubstituted heterocycloalkylene, substituted or unsubstituted cycloalkylene, substituted or unsubstituted arylene, substituted or unsubstituted heteroarylene substituted or unsubstituted fused rings, substituted or unsubstituted spirocyclic rings). In some embodiments, the linker portion includes a diamine. In some embodiments the linker portion positions the S2BP binding moiety $R^1$ and the electrophilic moiety E for optimal contact with the S2BP and a cysteine or asparate respectively.

In some embodiments, the electrophilic moiety E may have flexibility. In some embodiments, optimization of the electrophile positioning and angle of attack may provide compounds with greater binding and potency.

The Switch 2—Binding Pocket

In some embodiments, the S2BP binding moiety or S2BP binding compound interact with one or more of amino acid residues V7, V9, G10, P34, T58, G60, Q61, E62, E63, $R^{68}$, Y71, M72, Y96, Q99, and I100 of K-Ras or the equivalent (i.e. corresponding) amino acids present in mutants or homologs of K-Ras. In some embodiments, the S2BP binding moiety or S2BP binding compound displace one or more amino acids in Switch 2 of K-Ras that interact, in the GTP bound form, with one or more of the amino acids of the Switch 2 Binding Region of K-Ras, or the equivalent (i.e. corresponding) amino acids present in mutants or homologs of K-Ras. In some embodiments, the S2BP binding moiety or S2BP binding compound displace one or more amino acids in the Switch 2 Binding Region of K-Ras that interact, in the GTP bound form, with one or more of the Switch 2 residues of K-Ras, or the equivalent (i.e. corresponding) amino acids present in mutants or homologs of K-Ras.

In some embodiments, the Switch 2—Binding Pocket binding moiety additionally interacts (e.g. bonds) with an amino acid that forms part of the Switch 2—Binding Pocket. In some related embodiments, the interaction is a hydrogen bond, van der Waals interaction, ionic bond, covalent bond (e.g. disulfide bond) or hydrophobic interaction.

Switch 2—Binding Pocket Binding Moieties That Interact with the Switch 2—Binding Pocket In some embodiments, to determine whether the Switch 2—Binding Pocket binding moiety or Switch 2—Binding Pocket binding compound contacts and/or fills space within the Switch 2—Binding Pocket, computer modeling techniques are employed. In some embodiments, a query Switch 2—Binding Pocket binding compound (i.e. a test or reference compound) is fit into a structural model, such as a computer image, of Ras (e.g. K-Ras). In some embodiments, the structural model is derived from one or more of the solved co-crystal structures of human K-Ras bound to a compound as described herein. The PyMOL Molecular Graphics System may be employed to generate the image. Examples are presented in FIG. 7 or 8, wherein two compounds are built into the computer image of K-Ras, derived from their respective co-crystal structures with K-Ras.

The computer models are typically analyzed to prevent any gross steric clashes and to satisfy key hydrogen bonds between the query Switch 2—Binding Pocket binding compound and the K-Ras protein. In some embodiments, energy minimization calculations are performed to optimize binding energy. Using these techniques, one skilled in the art can easily determine whether a query Switch 2—Binding Pocket binding compound includes a Switch 2—Binding Pocket binding moiety that fills space within the Switch 2—Binding Pocket.

In some embodiments, the query Switch 2—Binding Pocket binding compound is analyzed to determine whether at least one bond (e.g. a hydrogen bond) is formed between the query Switch 2—Binding Pocket binding compound and an amino acid that forms part of the Switch 2—Binding Pocket. In some embodiments, using a computer modeling technique as described above, the distance between one or more amino acids that form part of the Switch 2—Binding Pocket and a potential contact point on the Switch 2—Binding Pocket binding moiety is determined. In some embodiments, based on this distance, one skilled in the art may determine whether at least one bond is formed between one or more amino acids that form part of the Switch 2—Binding Pocket and a Switch 2—Binding Pocket binding moiety.

Identification of Covalent K-Ras Inhibitors

The invention further provides a method of designing a compound which covalently binds to a Switch 2 binding pocket of a K-Ras protein, the method comprising the steps of: a) providing a structural model of a reference compound bound to the Switch 2 binding pocket of the K-Ras protein, wherein the reference compound is covalently or non-covalently bound to said Switch 2 binding pocket; b) identifying a cysteine, aspartate, lysine, tyrosine or glutamate residue located in proximity to said Switch 2 binding pocket when said reference compound is bound to said Switch 2 binding pocket; c) generating at least one additional structural model of a test compound bound to said Switch 2 binding pocket, wherein said test compound comprises an electrophilic moiety; and d) selecting said test compound if said electrophilic moiety is located within bonding distance of said cysteine, aspartate, lysine, tyrosine or glutamate residue when said test compound is bound to said Switch 2 binding pocket.

A structural model of a reference compound bound to a Switch 2 binding pocket of a Ras protein (such as K-Ras, N-Ras, or H-Ras) may be provided as described above. Any suitable structural model of a reference compound bound covalently or non-covalently to the Ras protein can be used. For example, a three-dimensional computer model or a representation thereof (e.g. a computer image) is used. In some embodiments, an X-Ray crystal structure is used. For example, one of the solved co-crystal structures of human K-Ras can be used. In some embodiments, a structural model of a Switch 2 binding pocket of a K-Ras protein is used. Structural models can be obtained from public databases, including but not limited to the RCSB Protein Data Bank, available online at pdb.org and rcsb.orb. Alternatively, structural models can also be obtained and manipulated by computer modeling, including homology modeling and folding studies.

Suitable reactive amino acid residues can be identified by analyzing the sequence of the protein in conjunction with the structural model to which the reference compound is bound. Putative reactive amino acid residues which are cysteine, aspartate, lysine, tyrosine or glutamate may be identified in proximity to the reference compound. For example, cysteine residues in proximity to the reference compound are identified. Once an amino acid residue in the structural model has been identified, the intermolecular distance between the reference compound and the putative reactive amino acid may be noted. In some embodiments, the distance between the putative reactive amino acid and at least one atom of the reactive compound is less than or equal to 15, 12, 10, 8, 6, or 4 angstroms.

Test compounds comprising an electrophilic moiety may subsequently used to generate additional structural models in which the position of the electrophilic moiety relative to one or more of the identified putative reactive amino acid residues is noted. The bonding distance between the test compound and one of such residues may be calculated based on the structural model, and a determination may be made regarding the potential bonding distance between the test compound (e.g. the electrophilic moiety) and the putative reactive residue. Test compounds which appear to provide a suitable bonding distance likely to result in the formation of a covalent bond may then be chosen for further development. When making such determinations, factors such as steric hindrance and orientation of each chemical moiety may be taken into account. Test compounds which are initially rejected may also be further modified in order to improve the likelihood that they will form a covalent bond with the target protein.

In some embodiments, the compounds described herein target a mutant of K-Ras, glycine-12 to cysteine (G12C). This is the most common Ras mutation in lung cancer (Forbes et al. 2006 *Br J Cancer*) and the only known transforming mutation found in a recent comparative sequencing study of a human lung tumor (Lee et al. 2010 Nature). 100% of K-Ras mutations in MYH-associated polyposis (familial colon cancer syndrome) are K-RasG12C (Jones, S., Lambert, S., Williams, G. T., Best, J. M., Sampson, J. R., & Cheadle, J. P. (2004). Increased frequency of the k-ras G12C mutation in MYH polyposis colorectal adenomas. *British Journal of Cancer*, 90 (8), 1591-1593. doi: 10.1038/sj.bjc.6601747) G12C places a nucleophilic sulfhydryl group between the nucleotide-binding site and the allosteric site. Since the regions surrounding both sites are involved in interactions with effectors and GEFs, binding of compounds (e.g. antagonists, inhibitors, small molecules) at either site has the potential to disrupt downstream signaling. In some embodiments, the location and nucleophilicity of this mutant residue allows development of covalent (e.g. reversible, irreversible) inhibitors of oncogenic K-Ras that bind in either the active site or the cleft behind Switch 2 or the Switch 2—Binding Pocket.

In some embodiments, a library of disulfide compounds may be screened against a cysteine-containing protein in the presence of a reducing agent such as β-mercaptoethanol (βME). Compounds with complementary binding interactions with a region of the protein near the cysteine may shift the disulfide exchange equilibrium away from βME modification of the cysteine thiol and enhance the ratio of the hit ligand bound to the cysteine (see FIG. 3). The resulting mass change of the protein can be readily detected by mass spectrometry, and the percentage of modified protein can be used as a measure of potency. Compounds which exchange with the cysteine without conferring affinity should exchange with reducing agent equally well and will not shift the equilibrium toward protein modification. The potency of various compounds at a given concentration of βME may be compared by calculating the dose-response 50 (DR50), which is the concentration of compound at which the protein becomes 50% modified.

In some embodiments, screening is for inhibitors of K-Ras G12C, a naturally occurring, oncogenic form of the target does not require removal of the mutant cysteine residue.

The crystal structure of the complex between H-Ras and SOS (Margarit et al. 2003 *Cell*) shows that a deep nucleotide pocket has been pried open, and the interface between Ras and SOS creates two new clefts on either side of Ras residue 12.

Figure 1:
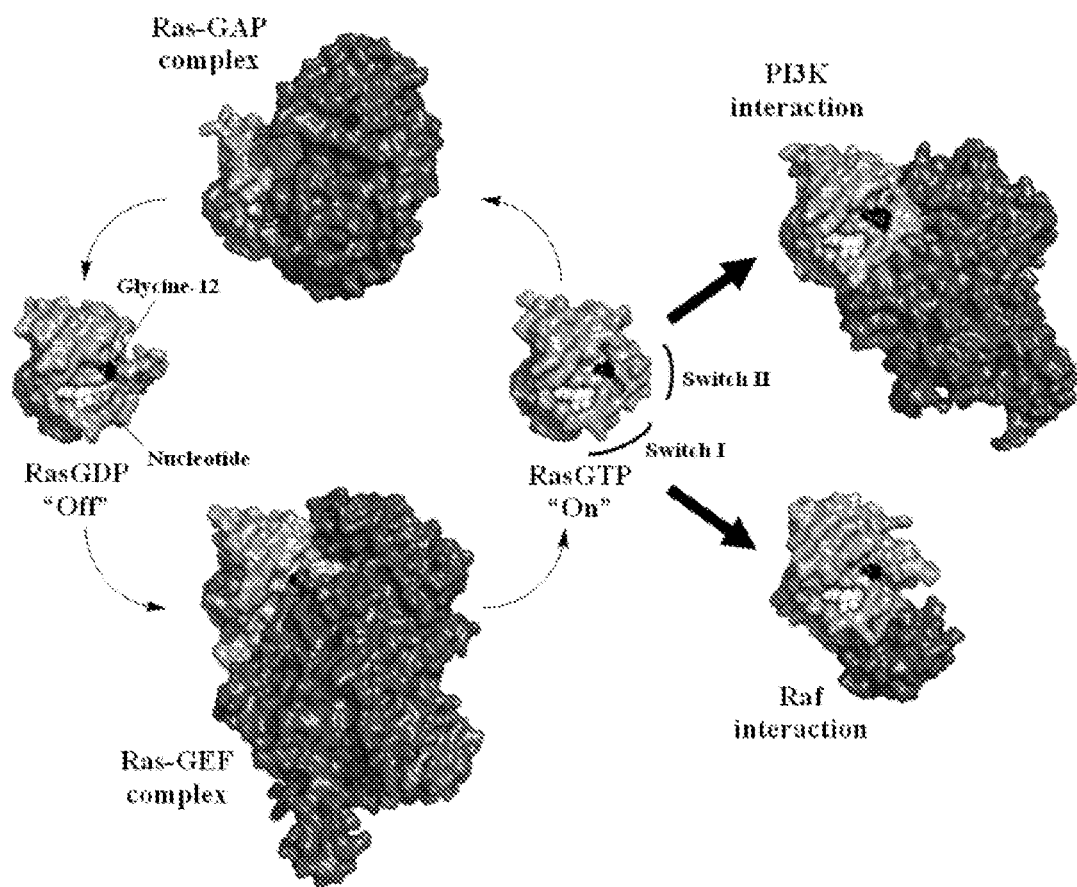
FIG. 1. Ras cycles from inactive GDP-bound state to active GTP-bound state. In the active conformation, Ras may interact with downstream effector proteins. PI3K is unusual amongst effectors in that it makes critical contacts with the Switch 2 region of Ras. Structural data suggest that other effectors, including Raf, only make direct contacts with the Switch 1 region.

The Switch 1 and Switch 2 areas of Ras show significant structural differences between the GDP- and GTP-bound states. Moreover, these regions are involved in interactions with all known Ras binding partners, including effectors, GEFs and GAPs (See FIG. 1). In some embodiments, the compounds described herein covalently modify cysteine-12 thereby altering the conformation of either switch region affecting GEF binding or effector protein binding. Multiple modes of compound (e.g. small molecule, antagonist, inhibitor) interruption of Ras function can be employed.

In some embodiments, the compounds provided herein effect the Ras binding to Raf or PI3K. In some embodiments, binding of the compounds provided herein to K-Ras modulates K-Ras binding to Raf. In some embodiments, binding of the compounds provided herein to K-Ras modulates K-Ras binding to PI3K. In some embodiments, binding of the compounds provided herein to K-Ras modulates K-Ras binding to PI3K but not K-Ras binding to Raf. In some embodiments, binding of the compounds provided herein to K-Ras reduces K-Ras binding to PI3K but not K-Ras binding to Raf. In some embodiments, binding of the compounds provided herein to K-Ras modulates K-Ras binding to Raf but not K-Ras binding to PI3K. In some embodiments, binding of the compounds provided herein to K-Ras reduces K-Ras binding to Raf but not K-Ras binding to PI3K. In other embodiments, the compounds provided herein alter intrinsic or GEF-enhanced nucleotide exchange. In other embodiments, the compounds provided herein alter Ras binding to SOS. In other embodiments, the compounds provided herein modulate SOS-enhanced nucleotide exchange. In some embodiments, the compounds provided herein increase the intrinsic or GAP-stimulated rate of GTP hydrolysis. In some embodiments, the compounds provided herein decrease the intrinsic affinity of K-Ras for nucleotide. In some embodiments, the compounds provided herein decrease the intrinsic affinity of K-Ras for GTP. In some embodiments, the compounds provided herein decrease the intrinsic affinity of K-Ras for GDP.

Residue 12 of K-Ras lies between the nucleotide-binding site and an allosteric pocket. In some embodiments, the compounds provided herein bind to either site or both sites. In some embodiments, compound binding to the allosteric pocket alters K-Ras-effector interactions. In some embodiments, compound binding to the S2BP alters K-Ras-effector interactions. In some embodiments, compound binding to the nucleotide-binding site alters K-Ras-effector interactions. In some embodiments, simultaneous compound binding to the allosteric pocket and the nucleotide-binding site alters K-Ras-effector interactions. In some embodiments, simultaneous compound binding to the S2BP and the nucleotide-binding site alters K-Ras-effector interactions. In some embodiments, compound binding to the allosteric pocket, S2BP, and/or nucleotide-binding site alters the activity of the K-Ras protein, it's GTPase activity, nucleotide exchange, effector protein binding, effector protein activation, guanine exchange factor (GEF) binding, GEF-facilitated nucleotide exchange, phosphate release, nucleotide release, nucleotide binding, K-Ras subcellular localization, K-Ras post-translational processing, K-Ras post-translational modifications, or GTP bound K-Ras signaling pathway.

In some embodiments, the compounds described herein afford a covalent yet reversible handle.

Determining Intrinsic and GEF Mediated Nucleotide Exchange Rates for Compound-Bound K-RasG12C GEF-mediated nucleotide exchange assays were carried out using full-length recombinant human K-Ras G12C and WT containing an N-terminal hexahistidine tag and the catalytic domain of SOS (residues 566-1049), also containing a hexahistidine tag, in the presence of $\alpha$-$^{32}$P-labeled GTP. K-Ras WT and G12C were treated with 250 µM inhibitor overnight at 4 C in the following buffer: 20 mM HEPES [pH 7.5], 150 mM NaCl, 10 mM EDTA. The percent modification was determined by mass spectrometry (Waters Acquity TQD). The proteins were then run over NAP-5 columns, eluting with Buffer A (20 mM HEPES [pH 7.5], 150 mM NaCl, 20 mM $MgCl_2$), following the manufacturer's instructions. Reaction mixes were prepared containing 4 µM K-Ras and 1 µM SOS in Buffer A with 1 mg/mL BSA. Separately, a solution of [$\alpha$-$^{32}$P] GTP (160 pCi/mL, 2 µM total GTP) was prepared. The reactions were initiated by adding 25 µL GTP solution to 25 µL of each reaction mixture. Exchange was measured by blotting the reaction onto nitrocellulose, washing with Buffer A, then visualizing by phosphorimager.

Recombinant Protein Expression of K-Ras

Hexahistidine-tagged recombinant human K-Ras (isoform 2, residues 1-169, based on construct used for pdb entry 3GFT) was transformed into *Escherichia coli* (BL21 (DE)). After the bacterial growth to an OD (600) of 0.4-0.6 in Terrific Broth containing 30 mg/L kanamycin at 37 C, induction was carried out at 18 C using 0.5 mM IPTG and growth was continued at 18° C. for about 18 h. The bacteria were harvested by centrifugation and the obtained pellet either stored at −80 C or used freshly for the subsequent steps.

The pellet was resuspended in lysis buffer (500 mM NaCl, 20 mM TRIS pH=8, 5 mM imidazole) containing protease inhibitor cocktail (Roche complete EDTA free), the bacteria were lysed by microfluidizer, 2 mM βME (final) was added and cell debris was removed by ultracentrifugation. The supernatant was incubated for 1 h with Co-affinity beads (Clontech, ~2 mL bed volume per 1 L initial culture), the loaded beads then washed with lysis buffer containing 2 mM βME and the protein eluded with buffer containing 125-250 mM imidazole. The hexahistidine tag was then cleaved using Hexahistidine-tagged TEV-protease (1 mg recombinant TEV per 25 mg crude K-Ras, 1 mg GDP added per 20 mg crude K-Ras) while dialyzing against a buffer containing 300 mM NaCl, 20 mM TRIS pH=8, 5 mM imidazole, 1 mM DTT, 0.5 mM EDTA. The cleaved protein was then diluted 5-fold with low salt buffer (50 mM NaCl, 20 mM TRIS pH=8), incubated with Ni-agarose beads (Qiagen) to remove uncleaved protein and protease, and 5 mM $MgCl_2$ and GDP was added to fully load the metal and nucleotide site of K-Ras.

The crude protein was then purified by ion exchange chromatography (HiTrap Q HP column, salt gradient from 50 to 500 mM NaCl) to give the partially purified protein, commonly in following buffer (~230 mM NaCl, 20 mM TRIS pH=8, small amounts of GDP).

At this point the partially purified protein was either fully labeled with the desired compound (incubation overnight with an excess of compound at 4 C, labeling checked by massspec analysis), frozen down and stored at −80 C, or used for further purification.

The last purification step for the labeled or unlabeled protein was gel-filtration using a Superdex 200 column (10/300 GL) with the following buffer: 20 mM HEPES pH=7.5, 150 mM NaCl and 1 mM DTT (for the unlabeled proteins). The freshly prepared and purified protein was then concentrated to 5-20 mg/mL and used for the X-ray crystallography trays.

X-Ray Crystallography

Sequences for the different K-Ras constructs were generally codon-optimized and synthesized by DNA2.0 using the pJexpress411 vector. For the X-ray structures of compound labeled K-Ras G12C a special cysteine-light mutant was used (G12C, C51S, C80L, C118S) to enable more uniformly labeled species.

For X-ray crystallography 1 mM magnesium chloride and 40 microM GDP (final) were added to the freshly purified protein. After high speed centrifugation hanging drop crystallization conditions were set up by mixing 1:1 protein and precipitation solutions. Common successful reservoir conditions were: 28-32% PEG3000, 200 mM NaCl, 100 mM Tris pH=7; 1.8-2.2M 2:3 NaH2PO4: K2HPO4, 0.1M NaAc; 28-32% PEG4000, 200 mM $NH_4CH_3COO$, 100 mM Na-citrate pH=5.6; 18-22% PEG8000, 100 mM CaCl2, 100 mM Tris pH=7.5; 18-22% PEG3350, 0.2M CaCl2, pH=7.5. After a varying amount of time, commonly several days, at 20 C three dimensional crystals were observed. If necessary crystals were cryoprotected in the crystallization solution supplemented with glycerol, flash frozen and stored in liquid nitrogen prior to obtaining diffraction data at beamlines 8.2.1/8.2.2 (100 K nitrogen stream) at the Berkeley Lab Advanced Light Source. Data was initially processed with HKL2000 (HKL Research, Inc., scaling) and then solved by molecular replacement and refined to the indicated statistics using Phenix (Adams et al.).

Mass Spectrometric Screen for Extent of Covalent Labeling

Un-tagged recombinant K-Ras G12C (1-169) at 4 µM in Buffer A was reacted with inhibitors at 200 µM or 10 µM (2% DMSO final). At 2, 6, and 24 hrs, 10 µL aliquots were removed and the reactions were stopped by addition of 1 µL 2% formic acid. The extent of modification was determined by mass spectrometry.

Disulfide Library Screen

We screened a library of disulfide compounds for covalent modification of K-RasG12C (1-169) as determined by mass spectrometry. Hit compounds will be defined as those causing >50% modification of Ras at a concentration of 100 µM while in the presence of 100 µM βME. It has been shown previously that EDTA increases the nucleotide exchange rate of both H-Ras (Hattori et al. 1987 Mol Cell Biol) and K-Ras (Hara et al. 1988 Oncogene Res). The EDTA chelates $Mg^{2+}$ and destabilizes the nucleotide bound state of Ras. To enhance the possibility of finding molecules which bind to the GTP site. The screen was carried out in the presence of EDTA. Once hits have been identified, compound titrations will be carried out in the presence of 200 µM βME to determine their DR50. These compounds will also be counter-screened against wild-type K-Ras to verify that they modify the mutant cysteine and not one of the three cysteines already present in the wild-type sequence. While treatment of Ras with EDTA increases the rate of nucleotide exchange by two orders of magnitude, nucleotide exchange factors can increase the rate by a factor of 105. With a higher rate of exchange, we may be more likely to identify compounds binding in the GTP site.

We have screened a library of 480 tethering compounds at 100 µM each against K-RasG12C (1-169) in the presence of 100 µM βME and 10 mM EDTA. From this screen we have identified 17 molecules which reach >50% modification of Ras. A disulfide containing hit (6H05) reached 95% modification, and titration experiments gave a DR50 of 31 µM. None of our hit compounds from this library screen caused greater than 10% modification of wild-type K-Ras, suggesting they are specifically tethering to the mutant cysteine. When the entire library was screened against H-RasG12C only 6H05 exhibited greater than 50% modification (see FIG. 5).

All disulfide hit compounds identified in this screen were less potent in the absence of EDTA, including 6H05. However, when GDP and non-hydrolyzable GTP (GMPPNP) were each titrated up to 0.8 mM in the presence of EDTA, there was no detectable effect on modification. This result strongly suggests that 6H05 does not share a binding site with nucleotide.

To begin understanding the structure-activity relationship of 6H05, we designed and synthesized a family of 10 analogues (see FIG. 6). One of these analogues, JO-148A, showed slightly increased potency over 6H05 with a DR50 of 27 μM in the presence of EDTA. In addition, this analogue retained a DR50 of 63 μM in the presence of 10 mM $MgCl_2$ and 100 μM GMPPNP. Under these conditions, over the course of the experiment essentially no nucleotide exchange is expected to occur.

Determining Intrinsic GTPase and GAP Mediated Activity of Compound-Bound K-Ras G12C The assays will be carried out as described previously (Schubbert et al., Mol. Cell Biol. 2007, 7765-70). 200 nM of each recombinant K-Ras protein (G12C, compound loaded G12C, G12D, WT) that had been preloaded with [γ-$^{32}$P]GTP is incubated without (intrinsic GTPase activity assay) or with (GAP assays) GAP-related domain (GRD) proteins (neurofibromin or p120 GAP) at room temperature. The hydrolyzed and released radioactive phosphate is extracted and detected by liquid scintillation counting at defined time points. Recombinant K-Ras and GRD proteins are produced in *Escherichia coli*.

Determining Occupancy of the Pocket by Click Chemistry

Lysate from Calu-1 (G12C), NCI H-1792 (G12C), or HEK cells is treated with 10 μM inhibitor or DMSO for 24 hrs at 4° C. Ras is then immunoprecipitated with anti-Ras antibody on magnetic beads. Immobilized Ras is then treated with 200 μM Ras-069 (propargyl) for 24 hrs at 4 C. Rhodamine-azide or biotin-azide is then attached to the propargyl group of Ras-069 by Cu-catalyzed click reaction. Following elution of the proteins, the extent of modification by Ras-069 is visualized by Western blot (biotin) or fluorescence imager (rhodamine), and reveals the extent of K-RasG12C with an unoccupied allosteric pocket after inhibitor treatment. Thus, the extent of inhibitor modification is anti-correlated with Western or fluorescence signal.

Initial Stop Flow Experiments

Conditions: 1 micM protein, buffer: 20 mM HEPES pH=7.5, 150 mM NaCl, 1 mM DTT, 2 mM unlabeled GDP if indicated, 1 micM SOS if indicated, 2.5 mM EDTA if indicated, no added free Mg in buffer, protein loaded with mant-dGDP, (1 h r.t. incubation with 2 mM EDTA, NAP-5 purification), protein pre-labeled with compounds and frozen, experiment at 20 C. Results: fast intrinsic bleaching/exchange, larger drop in fluorescence due to EDTA treatment with compound, acceleration of exchange in presence of SOS.

Continued Stop Flow Experiments

Conditions: 1 micM protein (same), buffer (changed): 40 mM HEPES pH=7.5, 10 mM $MgCl_2$, 1 mM DTT, 0.1 mM unlabeled GDP if indicated (changed), 0.1 mM unlabeled GTP if indicated (new), 1 micM SOS if indicated (same concentration), 15 mM EDTA if indicated (changed), now contains free Mg in buffer (s.a.), protein loaded with mant-dGDP. (1 h r.t. incubation with 2 mM EDTA, NAP-5 purification), protein pre-labeled with compounds and frozen, experiment at 20 C. Results: lowered intrinsic exchange, less effect of EDTA, initial drop (may need more?), basically no SOS acceleration. Ongoing experiments comparing GDP vs. GTP. Crystallization screen Carried out screen for ~500 conditions with labeled protein loaded with either nucleotide. Found large number (>10 conditions) that showed crystallization with either form, more for GDP, some overlap in conditions. Followed up on conditions: 9 for GDP, 6 for GppNp (same for all 3 compounds). Reproduced fairly well (about ½ of conditions)

Compound Binding Perturbs Nucleotide Binding (GTP vs. GDP)

More than 15 co-crystal structures confirm novel pocket behind Switch II with strong SAR. Inhibitors block nucleotide exchange and decrease Raf binding. It is possible to specifically inhibit proliferation of KrasG12C-driven cancer cell lines by treating under serum deprivation. Experiments being conducted to obtain more complete signaling data, including for control compound. FIGS. 12, 13, and 15 to 19 show modulation of K-ras conformation by compound binding, which modulates nucleotide binding site (e.g. GTP binding) and show novel binding pocket.

Compound Binding to K-Ras Alters Affinities for GTP and GppNp (GNP), (See FIGS. 34 to 36 and Tables 6 to 8)

The corresponding recombinantly expressed, full-length K-Ras protein (wild type, G12C-mutant, G12C-mutant labeled fully with either compound 055 (Ras-055) or 083 (Ras-083)) at about 10 micM (micromolar) concentration was incubated with 200 micM mant-d-GDP in the presence of 2.5 M EDTA. After one hour at room temperature $MgCl_2$ to a final concentration of 10 mM was added. The protein was then run through a NAP-5 column to remove free nucleotide. The concentration of the obtained protein was determined by Bradford assay and the protein was then used in the described plate-based assay. For the assay 10 micL of the prepared protein in reaction buffer (20 mM HEPES pH=7.5, 150 mM NaCl, 1 mM DTT, 1 mM $MgCl_2$) was added to a well of a low volume black bottom plate (Corning, #3676). The fluorescence intensity was measured on a spectramax M5 plate reader (Molecular devices, 360 nm excitation, 440 nm emission) to provide a value used in later normalization. Then 5 micL of an EDTA solution with the indicated nucleotide (GDP, GTP, or GppNp) was added to each well and the reaction mix was allowed to equilibrate for two hours at room temperature. Measurement of the fluorescent intensity at this time provided the end point. Samples were measured in duplicates for each experiment. In the final mix the concentrations were the following: protein (1 micM), EDTA (5 mM), nucleotide (as indicated, titrated in 2.5-fold dilution series, 15-points). Curves show results from one representative experiment, the column-graph shows the averaged data from three experiments with standard deviation shown as error. For the determination of IC50 for each nucleotide a sigmoidal curve fit was used (Prism-software).

Compound binding to K-Ras reduces SOS-mediated exchange (dissociaton of mant-d-GDP monitored). The corresponding recombinantly expressed, full-length K-Ras protein (wild type, G12C-mutant, G12C-mutant labeled fully with either compound 055 or 083) at about 10 micM concentration was incubated with 200 micM mant-d-GDP in the presence of 2.5 M EDTA. After one hour at room temperature $MgCl_2$ to a final concentration of 10 mM was added. The protein was then run through a NAP-5 column to remove free nucleotide. The concentration of the obtained protein was determined by Bradford assay and the protein was then used in the described plate-based assay. Concentration of recombinantly expressed SOS-protein was determined by Bradford assay as well. For the assay 10 micL of the prepared protein in reaction buffer (20 mM HEPES pH=7.5, 150 mM NaCl, 1 mM DTT, 1 mM $MgCl_2$) was added to a well of a low volume black bottom plate (Corning, #3676). Then 5 micL of either buffer (for intrinsic rate), SOS-solution, or EDTA-solution containing the indicated nucleotide (GDP, GTP, or GppNp) was added to each well. The fluorescence intensity of each reaction was followed on a spectramax M5 plate reader (Molecular devices, 360 nm excitation, 440 nm emission) over five hours (18000 seconds) at one minute intervals. Samples were measured in triplicate for each experiment. In the final mix the concentrations were the following: protein (1 micM), EDTA (if present: 5 mM), SOS (if present: 1 micM), nucleotide (as indicated: ~200 micM, excess). Curves show results from one representative experiment, the table shows the averaged data from three experiments with standard deviation shown as error. For the determination of half-lives a one-phase exponential decay model was used (Prism-software).

Compound binding to K-Ras reduces SOS-mediated exchange (association of mant-d-GDP or mant-d-GppNp monitored). Protein concentrations of freshly thawed, recombinantly expressed, GDP-loaded full-length K-Ras protein (wild type, G12C-mutant, G12C-mutant labeled fully with either compound 055 or 083) and SOS were determined by Bradford assay. Then a K-Ras solution containing varying amount of SOS in reaction buffer (20 mM HEPES pH=7.5, 150 mM NaCl, 1 mM DTT, 1 mM $MgCl_2$) was prepared and 10 micL were added to each well of a low volume black bottom plate (Corning, #3676). The exchange reaction was started by addition of either 5 micL of a mant-d-GDP or mant-d-GppNp solution in reaction buffer. The fluorescence intensity of each reaction was followed on a spectramax M5 plate reader (Molecular devices, 360 nm excitation, 440 nm emission) over five hours (18000 seconds) at one minute intervals. Samples were measured in triplicate for each experiment. In the final mix the concentrations were the following: K-Ras (1 micM), SOS (0 (intrinsic), 0.25-4 micM, 2-fold dilution series), mant-d-GDP/mant-d-GppNp (1 micM). Curves show results from one representative experiment, the table shows the averaged data from three experiments with standard deviation shown as error. For the determination of half-lives a one-phase association model was used (Prism software).

TABLE 1

Obtained structures (Electrophiles) ordered by increasing potency: Labeling percentage + <= 5%, 5% < ++ <= 20%, 20% < +++ <= 40%, 40% < ++++ <= 60%, 60% < +++++

| Structure | Compound | Labeling % (10 micM) 24 h | Resolution/ Space group Unit cell | R-free/R-work |
|---|---|---|---|---|
| JO-02-112D | 2,4-dichlorophenoxyacetyl-piperazine-N-sulfonyl-vinyl | +++ (plate) | 3 sets 1.35A 1.35A 1.40A C121 (72, 40, 55A) (90, 105, 90) | 0.1806/ 0.1504 0.1809/ 0.1577 0.1937/ 0.1537 |
| JO-02-172 | 2,4-dichlorophenoxyacetyl-piperazine-N-acryloyl | + (plate) | 2.09 A C121 (71, 83, 87A) (90, 109, 90) Diff. orient. | 0.2285/ 0.1897 |
| JO-02-31A | 2,4-dichlorophenoxyacetyl-piperidine-4-NH-sulfonyl-vinyl | ++ (plate) | 1.70 A C121 (68, 83, 85A) (90, 111, 90) | 0.2106/ 0.1763 |
| JO-02-56A | 2,4-dichlorophenoxyacetyl-piperidine-4-NH-glycyl-sulfonyl-vinyl | ++++ (plate) | 2.30 A P22121 (93, 108, 121A) (90, 90, 90) | 0.2218/ 0.1809 |

TABLE 1-continued

Obtained structures (Electrophiles) ordered by increasing potency: Labeling percentage + <= 5%, 5% < ++ <= 20%, 20% < +++ <= 40%, 40% < ++++ <= 60%, 60% < +++++

| Structure | Compound | Labeling % (10 micM) 24 h | Resolution/ Space group Unit cell | R-free/R-work |
|---|---|---|---|---|
| Ras-028 | | +++ (plate) | 1.55 A C121 (68, 84, 86A) (90, 111, 90) | 0.1966/ 0.1814 |
| Ras-055 (C2) | | +++++ (plate) | 1.57 A C121 (68, 84, 87A) (90, 111, 90) | 0.1931/ 0.1584 |
| Ras-055 (P1) | | +++++ (plate) | 1.49 A P1 (33, 40, 62A) (77, 82, 78) | 0.2122/ 0.1752 |
| Ras-059 | | +++++ (single) | 1.58A C121 (68, 84, 87A) (90, 111, 90) | 0.1913/ 0.1740 |
| Ras-062 | | +++ (single) | 1.94A C121 (68, 84, 87A) (90, 111, 90) | 0.2351/ 0.1948 |
| UP-I-177C | | ++++ (plate) | 1.57 A C121 (68, 84, 86A) (90, 111, 90) | 0.2087/ 0.1837 |
| UP-I-185a | | +++++ (single) | 1.81A C121 (68, 84, 87A) (90, 111, 90) | 0.2038/ 0.1801 |

Obtained structures (Disulfides) ordered by increasing potency: Labeling percentage + <= 5 micromolar, 5 micromolar < ++ <= 20 micromolar, 20 micromolar < +++ <= 40 micromolar, 40 micromolar < ++++ <= 60 micromolar, 60 micromolar < +++++

| Structure | Compound | Potency/ Labeling | Resolution/ Space group Unit cell | R-free/R-work |
|---|---|---|---|---|
| JO-01-148 | [2,4-dichlorophenoxyacetyl-piperidine-4-carboxamide-N-ethyl-S-] | (EC50 at 200 micM BME) Tethering | 1.50 A P1 (33, 39, 63A) (77, 81, 77) | 0.1977/ 0.1639 |
| JO-01-189 Cbut | [2,4-dichlorophenoxyacetyl-piperidine-4-amino-butanamide-S-] | ++ (EC50 at 200 micM BME) Tethering | 1.29 A P1 (33, 39, 62A) (78, 82, 78) | 0.1723/ 0.1591 |

TABLE 3

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| [2,4-dichlorophenoxyacetyl-piperidine-4-carboxamide-N-(1-cyanocyclopropyl)] | Ras-001 | 396.268 | + | + | + |
| [2,4,6-trichlorophenoxyacetyl-piperidine-4-acrylamide] | Ras-002 | 391.677 | + | + | + |
| [benzimidazole-N-acetyl-piperidine-4-acrylamide] | Ras-003 | 312.366 | + | + | + |
| [indazole-N-acetyl-piperidine-4-acrylamide] | Ras-004 | 312.366 | + | + | + |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
| --- | --- | --- | --- | --- | --- |
| 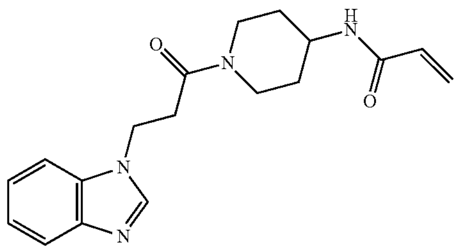 [SMILES: C=CC(=O)NC1CCN(C(=O)CCn2cnc3ccccc32)CC1] | Ras-005 | 326.393 | + | + | + |
| 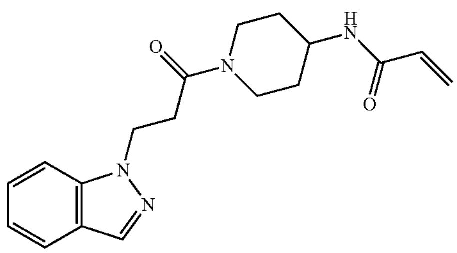 [SMILES: C=CC(=O)NC1CCN(C(=O)CCn2ncc3ccccc32)CC1] | Ras-006 | 326.393 | + | + | + |
| 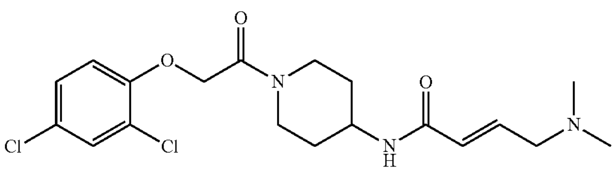 [SMILES: CN(C)C/C=C/C(=O)NC1CCN(C(=O)COc2ccc(Cl)cc2Cl)CC1] | Ras-007 | 414.326 | + | + | + |
| 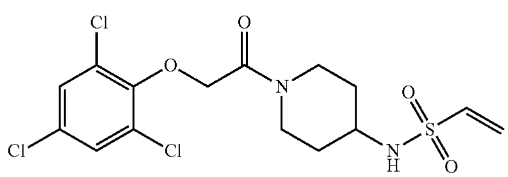 [SMILES: C=CS(=O)(=O)NC1CCN(C(=O)COc2c(Cl)cc(Cl)cc2Cl)CC1] | Ras-008 | 427.73 | + | + | + |
| 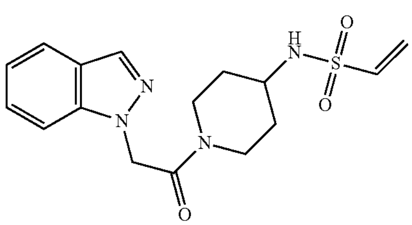 [SMILES: C=CS(=O)(=O)NC1CCN(C(=O)Cn2ncc3ccccc32)CC1] | Ras-009 | 348.42 | + | + | + |
| 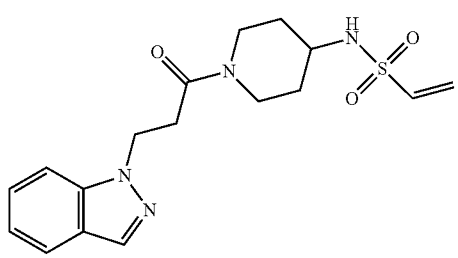 [SMILES: C=CS(=O)(=O)NC1CCN(C(=O)CCn2ncc3ccccc32)CC1] | Ras-010 | 362.447 | + | + | + |
| 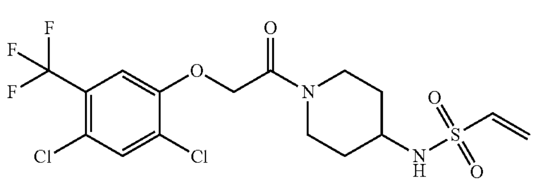 [SMILES: C=CS(=O)(=O)NC1CCN(C(=O)COc2cc(C(F)(F)F)c(Cl)cc2Cl)CC1] | Ras-011 | 461.283 | + | + | +++ |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 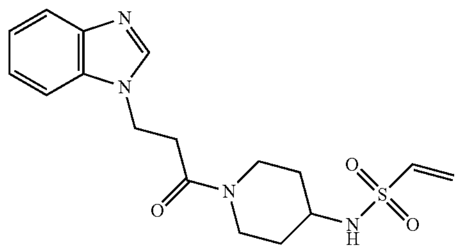 [SMILES: C=CS(=O)(=O)NC1CCN(C(=O)CCn2cnc3ccccc32)CC1] | Ras-012 | 362.447 | + | + | + |
| 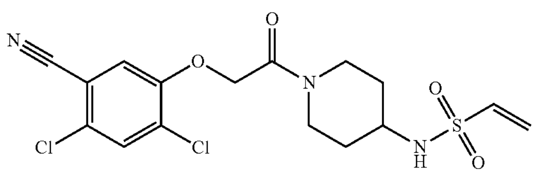 [SMILES: C=CS(=O)(=O)NC1CCN(C(=O)COc2cc(C#N)c(Cl)cc2Cl)CC1] | Ras-013 | 418.295 | + | + | ++ |
| 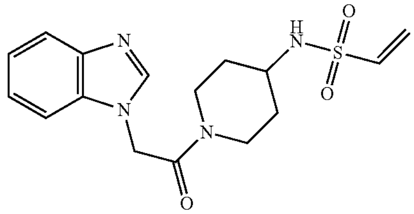 [SMILES: C=CS(=O)(=O)NC1CCN(C(=O)Cn2cnc3ccccc32)CC1] | Ras-014 | 348.42 | + | + | + |
| 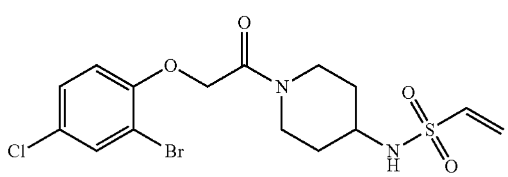 [SMILES: C=CS(=O)(=O)NC1CCN(C(=O)COc2ccc(Cl)cc2Br)CC1] | Ras-015 | 437.736 | + | + | +++ |
| 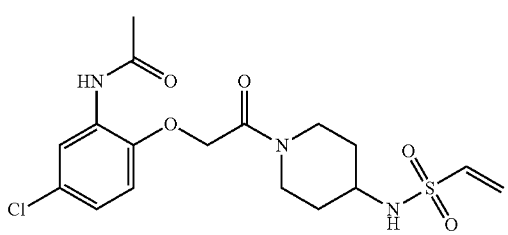 [SMILES: C=CS(=O)(=O)NC1CCN(C(=O)COc2ccc(Cl)cc2NC(C)=O)CC1] | Ras-016 | 415.892 | + | + | + |
| 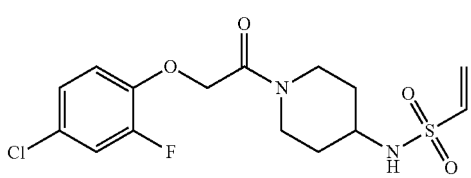 [SMILES: C=CS(=O)(=O)NC1CCN(C(=O)COc2ccc(Cl)cc2F)CC1] | Ras-017 | 376.831 | + | + | + |
| 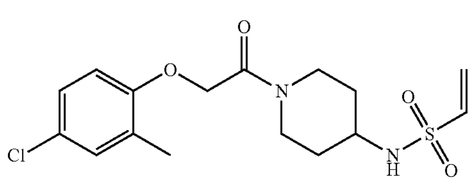 [SMILES: C=CS(=O)(=O)NC1CCN(C(=O)COc2ccc(Cl)cc2C)CC1] | Ras-018 | 372.867 | + | + | +++ |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 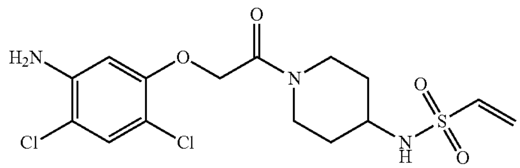 [SMILES: C=CS(=O)(=O)NC1CCN(C(=O)COc2cc(N)c(Cl)cc2Cl)CC1] | Ras-019 | 408.3 | + | + | ++ |
| 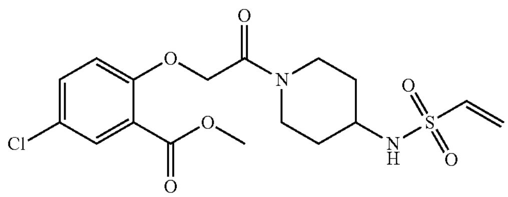 [SMILES: C=CS(=O)(=O)NC1CCN(C(=O)COc2ccc(Cl)cc2C(=O)OC)CC1] | Ras-020 | 416.876 | + | + | + |
| 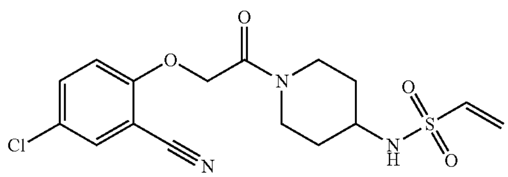 [SMILES: C=CS(=O)(=O)NC1CCN(C(=O)COc2ccc(Cl)cc2C#N)CC1] | Ras-021 | 383.85 | + | + | + |
| 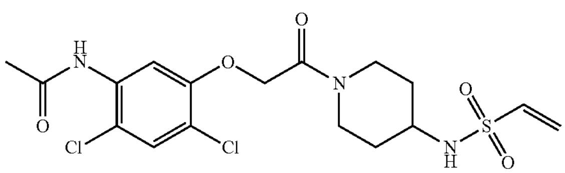 [SMILES: C=CS(=O)(=O)NC1CCN(C(=O)COc2cc(NC(C)=O)c(Cl)cc2Cl)CC1] | Ras-022 | 450.337 | + | + | + |
| 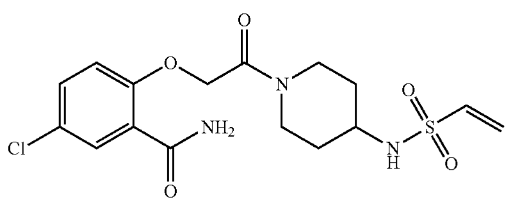 [SMILES: C=CS(=O)(=O)NC1CCN(C(=O)COc2ccc(Cl)cc2C(N)=O)CC1] | Ras-023 | 401.865 | + | + | + |
| 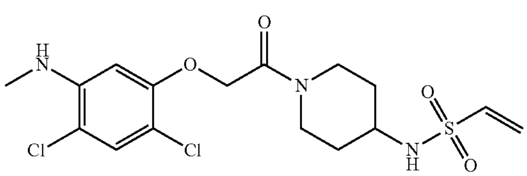 [SMILES: C=CS(=O)(=O)NC1CCN(C(=O)COc2cc(NC)c(Cl)cc2Cl)CC1] | Ras-024 | 422.327 | + | + | + |
| 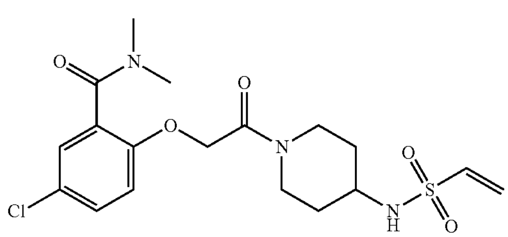 [SMILES: C=CS(=O)(=O)NC1CCN(C(=O)COc2ccc(Cl)cc2C(=O)N(C)C)CC1] | Ras-025 | 429.918 | + | + | + |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 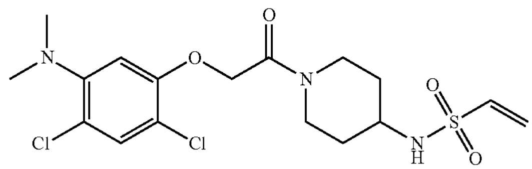 [SMILES: C=CS(=O)(=O)NC1CCN(C(=O)COc2cc(N(C)C)c(Cl)cc2Cl)CC1] | Ras-026 | 436.353 | + | + | ++ |
| 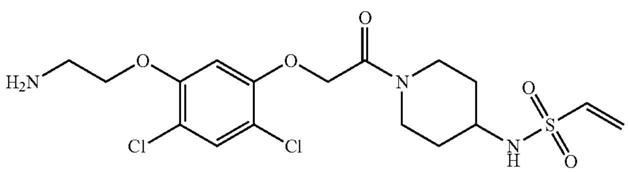 [SMILES: C=CS(=O)(=O)NC1CCN(C(=O)COc2cc(OCCN)c(Cl)cc2Cl)CC1] | Ras-027 | 452.353 | + | + | + |
| 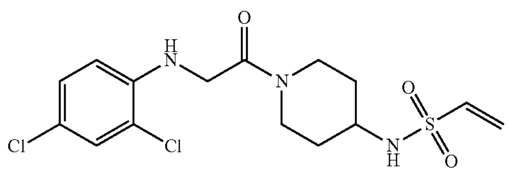 [SMILES: C=CS(=O)(=O)NC1CCN(C(=O)CNc2ccc(Cl)cc2Cl)CC1] | Ras-028 | 392.301 | + | + | +++ |
| 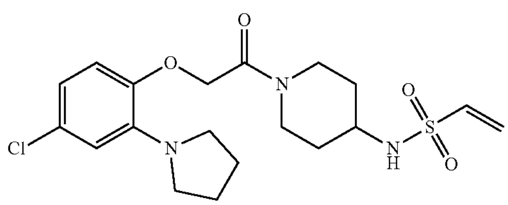 [SMILES: C=CS(=O)(=O)NC1CCN(C(=O)COc2ccc(Cl)cc2N2CCCC2)CC1] | Ras-029 | 427.945 | + | + | + |
| 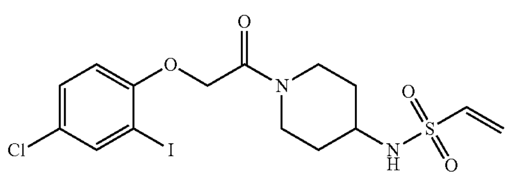 [SMILES: C=CS(=O)(=O)NC1CCN(C(=O)COc2ccc(Cl)cc2I)CC1] | Ras-030 | 484.737 | + | + | ++++ |
| 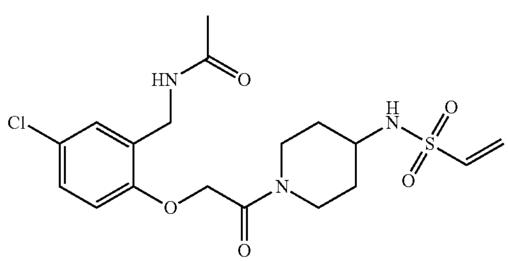 [SMILES: C=CS(=O)(=O)NC1CCN(C(=O)COc2ccc(Cl)cc2CNC(C)=O)CC1] | Ras-031 | 429.918 | + | + | + |
| 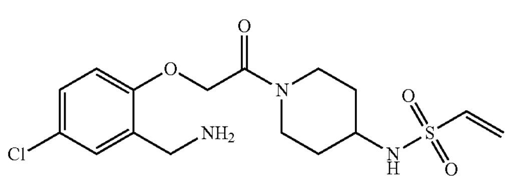 [SMILES: C=CS(=O)(=O)NC1CCN(C(=O)COc2ccc(Cl)cc2CN)CC1] | Ras-032 | 387.882 | + | + | + |
| 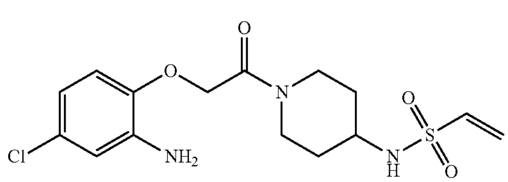 [SMILES: C=CS(=O)(=O)NC1CCN(C(=O)COc2ccc(Cl)cc2N)CC1] | Ras-033 | 373.855 | + | + | + |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 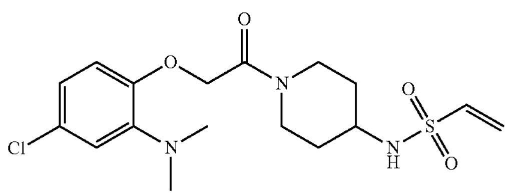 [SMILES: C=CS(=O)(=O)NC1CCN(C(=O)COc2ccc(Cl)cc2N(C)C)CC1] | Ras-034 | 401.908 | + | + | + |
| 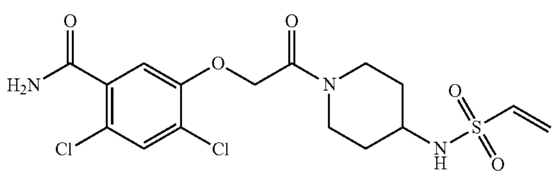 [SMILES: C=CS(=O)(=O)NC1CCN(C(=O)COc2cc(C(N)=O)c(Cl)cc2Cl)CC1] | Ras-035 | 436.31 | + | + | + |
| 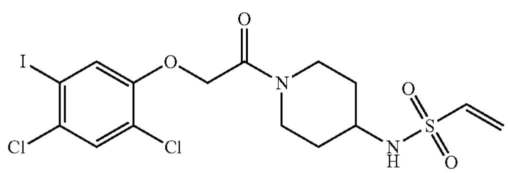 [SMILES: C=CS(=O)(=O)NC1CCN(C(=O)COc2cc(I)c(Cl)cc2Cl)CC1] | Ras-036 | 519.182 | + | ++ | ++++ |
| 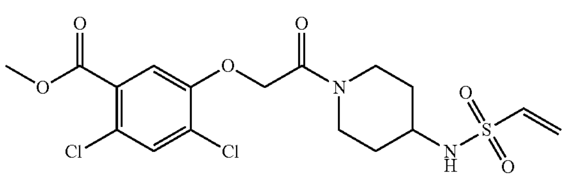 [SMILES: C=CS(=O)(=O)NC1CCN(C(=O)COc2cc(C(=O)OC)c(Cl)cc2Cl)CC1] | Ras-037 | 451.321 | + | + | ++ |
| 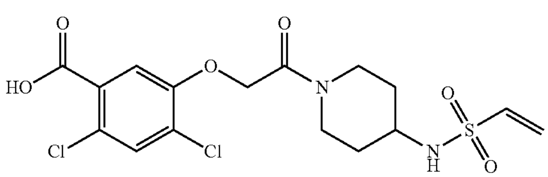 [SMILES: C=CS(=O)(=O)NC1CCN(C(=O)COc2cc(C(=O)O)c(Cl)cc2Cl)CC1] | Ras-038 | 437.295 | + | + | + |
| 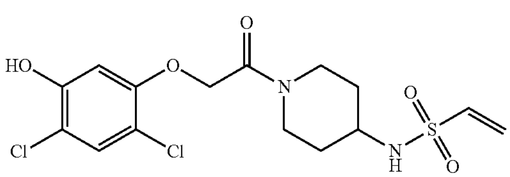 [SMILES: C=CS(=O)(=O)NC1CCN(C(=O)COc2cc(O)c(Cl)cc2Cl)CC1] | Ras-039 | 409.285 | + | + | ++ |
| 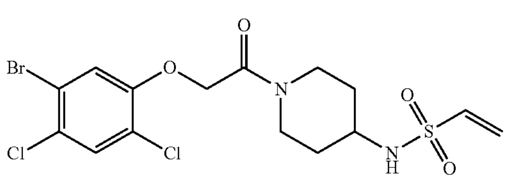 [SMILES: C=CS(=O)(=O)NC1CCN(C(=O)COc2cc(Br)c(Cl)cc2Cl)CC1] | Ras-040 | 472.181 | + | + | +++ |
| 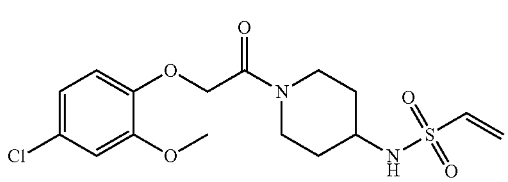 [SMILES: C=CS(=O)(=O)NC1CCN(C(=O)COc2ccc(Cl)cc2OC)CC1] | Ras-041 | 388.866 | + | + | ++ |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 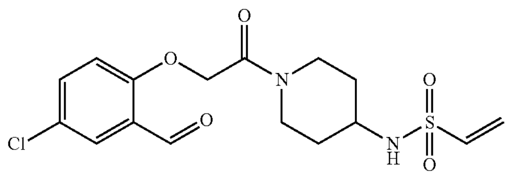 [SMILES: C=CS(=O)(=O)NC1CCN(C(=O)COc2ccc(Cl)cc2C=O)CC1] | Ras-042 | 386.85 | + | + | ++ |
| 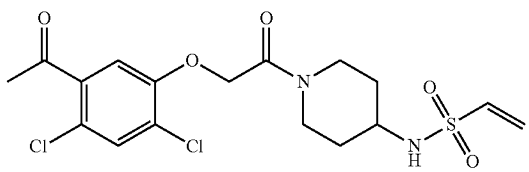 [SMILES: C=CS(=O)(=O)NC1CCN(C(=O)COc2cc(C(C)=O)c(Cl)cc2Cl)CC1] | Ras-043 | 435.322 | + | + | + |
| 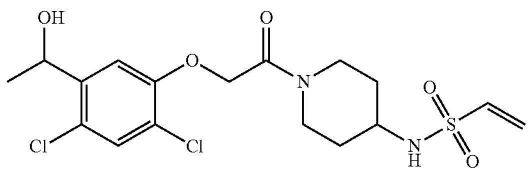 [SMILES: C=CS(=O)(=O)NC1CCN(C(=O)COc2cc(C(C)O)c(Cl)cc2Cl)CC1] | Ras-044 | 437.338 | + | + | ++ |
| 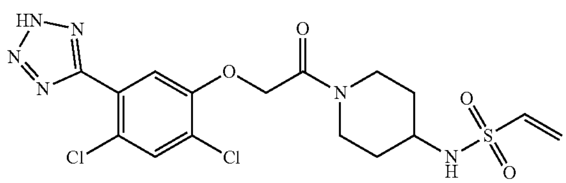 [SMILES: C=CS(=O)(=O)NC1CCN(C(=O)COc2cc(-c3nn[nH]n3)c(Cl)cc2Cl)CC1] | Ras-045 | 461.323 | + | + | + |
| 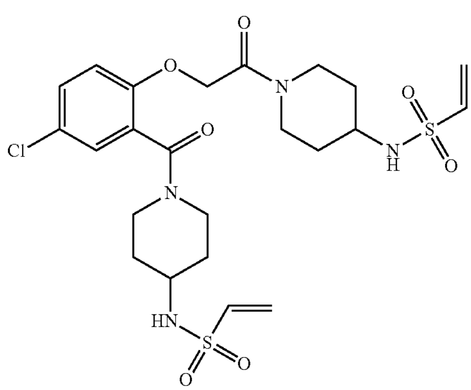 [SMILES: C=CS(=O)(=O)NC1CCN(C(=O)COc2ccc(Cl)cc2C(=O)N2CCC(NS(=O)(=O)C=C)CC2)CC1] | Ras-046 | 575.098 | + | + | + |
| 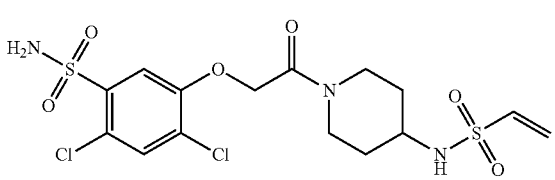 [SMILES: C=CS(=O)(=O)NC1CCN(C(=O)COc2cc(S(N)(=O)=O)c(Cl)cc2Cl)CC1] | Ras-047 | 472.364 | + | + | + |
| 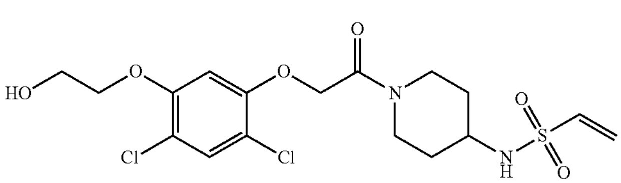 [SMILES: C=CS(=O)(=O)NC1CCN(C(=O)COc2cc(OCCO)c(Cl)cc2Cl)CC1] | Ras-048 | 453.337 | + | + | ++ |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 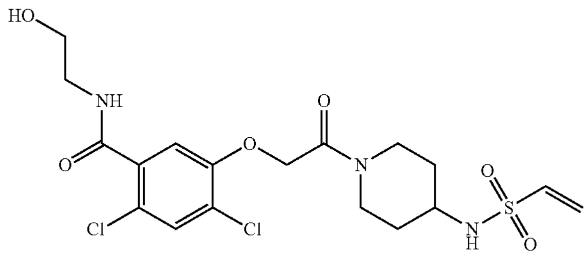 [SMILES: C=CS(=O)(=O)NC1CCN(C(=O)COc2cc(C(=O)NCCO)c(Cl)cc2Cl)CC1] | Ras-049 | 480.363 | + | + | + |
| 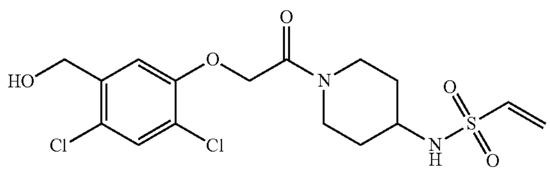 [SMILES: C=CS(=O)(=O)NC1CCN(C(=O)COc2cc(CO)c(Cl)cc2Cl)CC1] | Ras-050 | 423.311 | + | + | ++ |
| 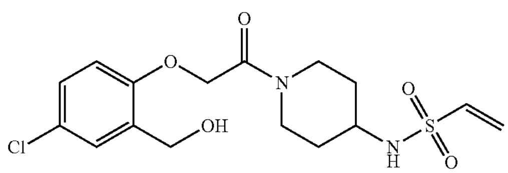 [SMILES: C=CS(=O)(=O)NC1CCN(C(=O)COc2ccc(Cl)cc2CO)CC1] | Ras-051 | 388.866 | + | + | ++ |
| 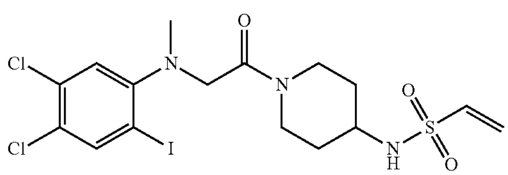 [SMILES: C=CS(=O)(=O)NC1CCN(C(=O)CN(C)c2cc(Cl)c(Cl)cc2I)CC1] | Ras-052 | 532.224 | + | + | ++ |
| 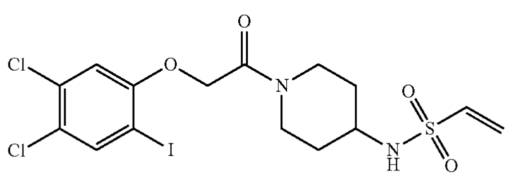 [SMILES: C=CS(=O)(=O)NC1CCN(C(=O)COc2cc(Cl)c(Cl)cc2I)CC1] | Ras-053 | 519.182 | + | ++ | ++++ |
| 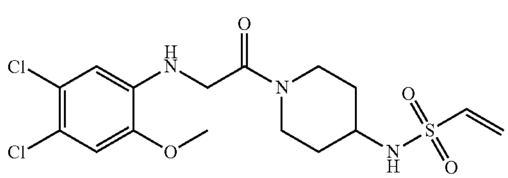 [SMILES: C=CS(=O)(=O)NC1CCN(C(=O)CNc2cc(Cl)c(Cl)cc2OC)CC1] | Ras-054 | 422.327 | + | +++ | +++++ |
| 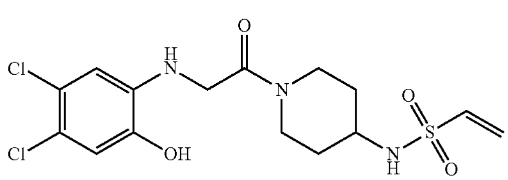 [SMILES: C=CS(=O)(=O)NC1CCN(C(=O)CNc2cc(Cl)c(Cl)cc2O)CC1] | Ras-055 | 408.3 | ++ | +++ | +++++ |
| 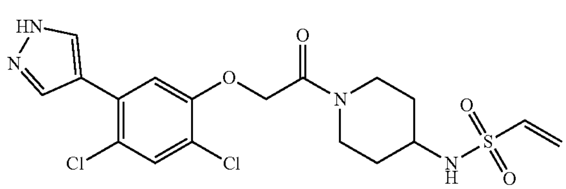 [SMILES: C=CS(=O)(=O)NC1CCN(C(=O)COc2cc(-c3cn[nH]c3)c(Cl)cc2Cl)CC1] | Ras-056 | 459.347 | + | + | + |

TABLE 3-continued
Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.
| Structure | Name | Mol Weight | 2 hrs | 6 hrs | 24 hrs |
|---|---|---|---|---|---|
| 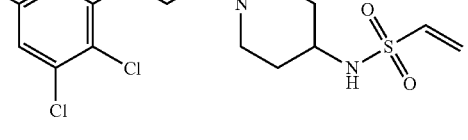 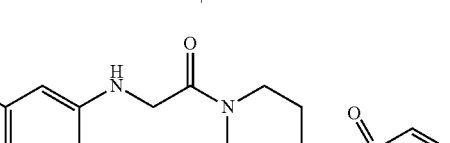 2:1 ratio | Ras-057 | 920.597 | + | ++ | ++++ |
| 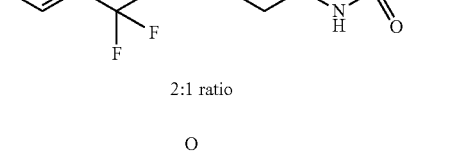 | JO-01-171 | 357.232 | + | + | + |
| 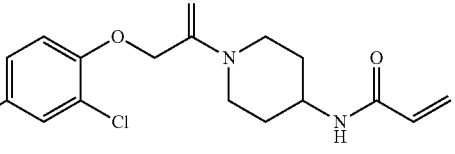 | JO-01-172 | 343.205 | + | + | + |
| 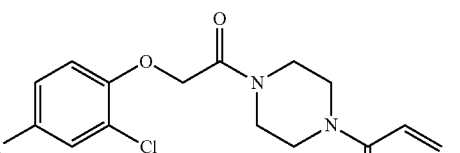 | JO-02-26 | 409.351 | + | + | ++ |
| 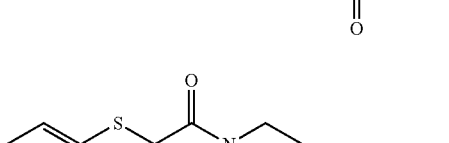 | JO-02-31A | 393.285 | + | + | ++ |
| 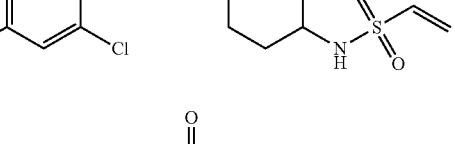 | JO-02-31B | 388.933 | + | + | ++ |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 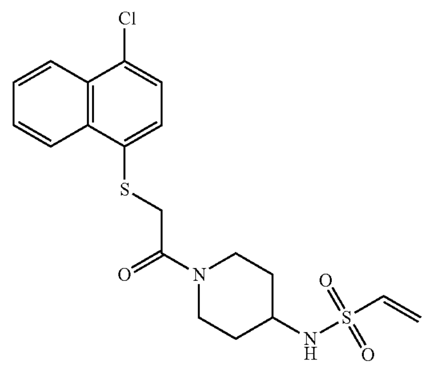 [SMILES: C=CS(=O)(=O)NC1CCN(C(=O)CSc2ccc(Cl)c3ccccc23)CC1] | JO-02-31C | 424.965 | + | + | +++ |
| 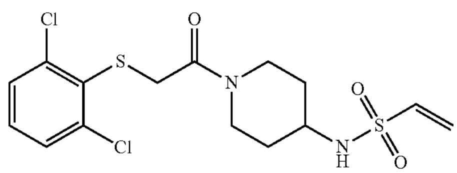 [SMILES: C=CS(=O)(=O)NC1CCN(C(=O)CSc2c(Cl)cccc2Cl)CC1] | JO-02-31D | 409.351 | + | + | + |
| 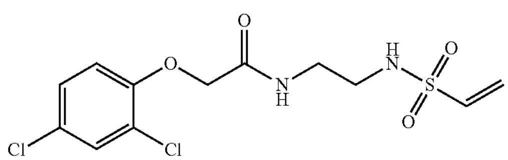 [SMILES: C=CS(=O)(=O)NCCNC(=O)COc1ccc(Cl)cc1Cl] | JO-02-36A | 353.222 | + | + | + |
| 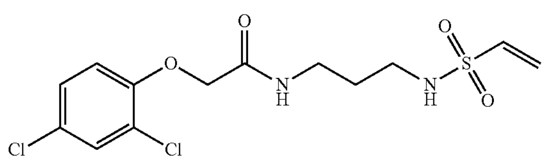 [SMILES: C=CS(=O)(=O)NCCCNC(=O)COc1ccc(Cl)cc1Cl] | JO-02-36B | 367.248 | + | + | + |
| 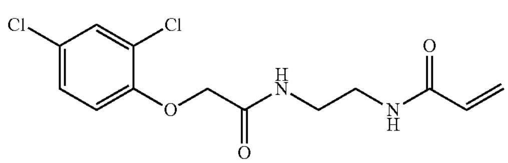 [SMILES: C=CC(=O)NCCNC(=O)COc1ccc(Cl)cc1Cl] | JO-02-37A | 317.168 | + | + | + |
| 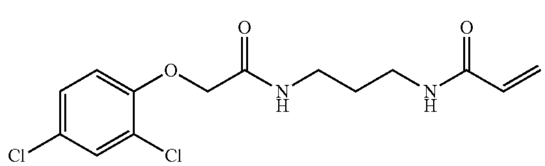 [SMILES: C=CC(=O)NCCCNC(=O)COc1ccc(Cl)cc1Cl] | JO-02-37B | 331.194 | + | + | + |
| 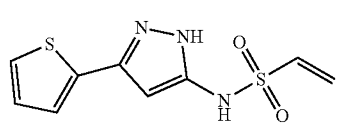 [SMILES: C=CS(=O)(=O)Nc1cc(-c2cccs2)n[nH]1] | JO-02-38B | 255.317 | + | + | + |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 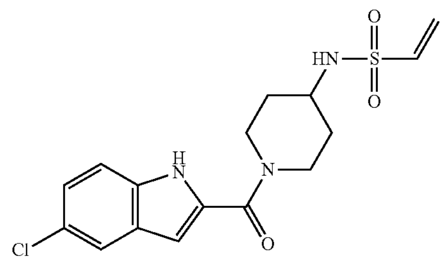 [SMILES: C=CS(=O)(=O)NC1CCN(C(=O)c2cc3cc(Cl)ccc3[nH]2)CC1] | JO-02-49A | 367.85 | + | + | + |
| 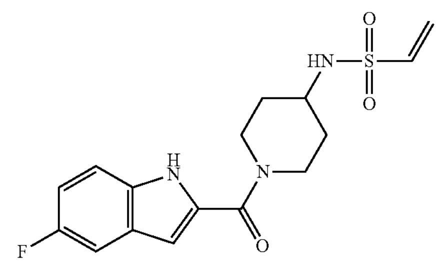 [SMILES: C=CS(=O)(=O)NC1CCN(C(=O)c2cc3cc(F)ccc3[nH]2)CC1] | JO-02-49B | 351.396 | + | + | + |
| 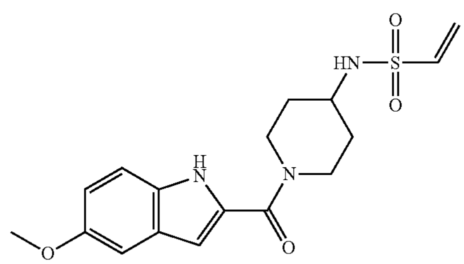 [SMILES: C=CS(=O)(=O)NC1CCN(C(=O)c2cc3cc(OC)ccc3[nH]2)CC1] | JO-02-49C | 363.431 | + | + | + |
| 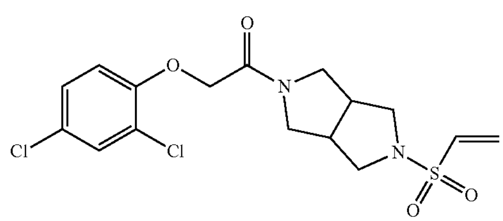 [SMILES: C=CS(=O)(=O)N1CC2CN(C(=O)COc3ccc(Cl)cc3Cl)CC2C1] | JO-02-74A | 405.296 | + | + | +++ |
| 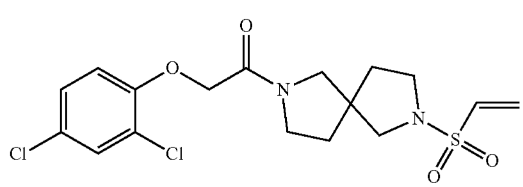 [SMILES: C=CS(=O)(=O)N1CCC2(CCN(C(=O)COc3ccc(Cl)cc3Cl)C2)C1] | JO-02-74B | 419.323 | + | + | ++ |
| 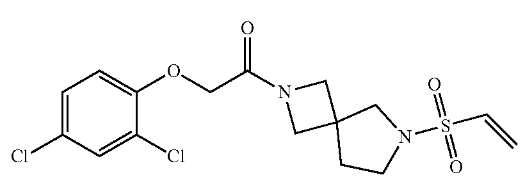 [SMILES: C=CS(=O)(=O)N1CCC2(CN(C(=O)COc3ccc(Cl)cc3Cl)C2)C1] | JO-02-74C | 405.296 | + | + | ++ |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 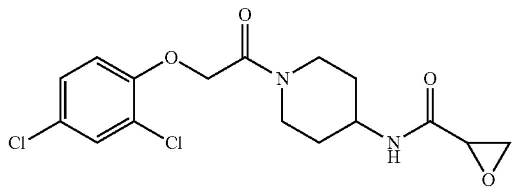 [SMILES: O=C(NC1CCN(C(=O)COc2ccc(Cl)cc2Cl)CC1)C1CO1] | JO-02-72 | 373.231 | + | + | + |
| 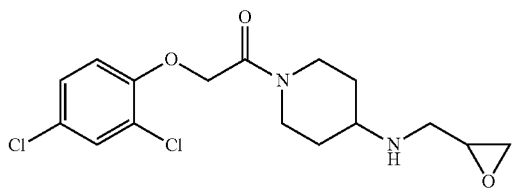 [SMILES: O=C(COc1ccc(Cl)cc1Cl)N1CCC(NCC2CO2)CC1] | JO-02-77A | 359.248 | + | + | + |
| 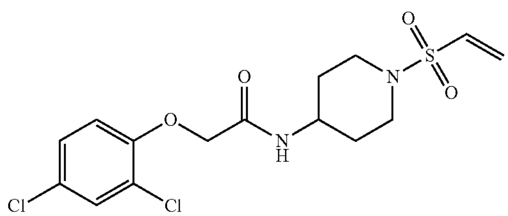 [SMILES: C=CS(=O)(=O)N1CCC(NC(=O)COc2ccc(Cl)cc2Cl)CC1] | JO-02-55 | 393.285 | + | + | ++ |
| 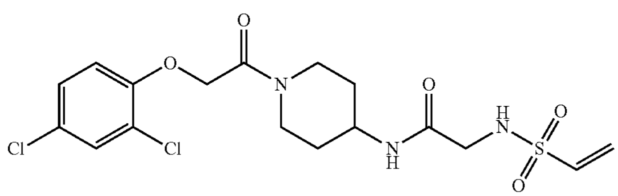 [SMILES: C=CS(=O)(=O)NCC(=O)NC1CCN(C(=O)COc2ccc(Cl)cc2Cl)CC1] | JO-02-56A | 450.337 | + | + | ++++ |
| 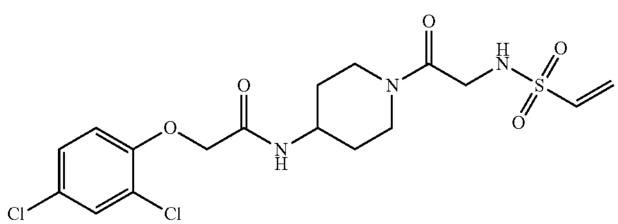 [SMILES: C=CS(=O)(=O)NCC(=O)N1CCC(NC(=O)COc2ccc(Cl)cc2Cl)CC1] | JO-02-56B | 450.337 | + | + | ++ |
| 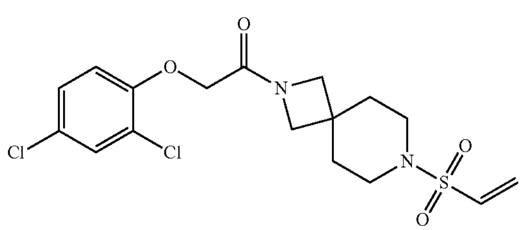 [SMILES: C=CS(=O)(=O)N1CCC2(CC1)CN(C(=O)COc1ccc(Cl)cc1Cl)C2] | JO-02-112A | 419.323 | + | + | ++ |
| 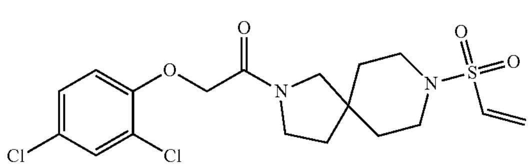 [SMILES: C=CS(=O)(=O)N1CCC2(CCN(C(=O)COc3ccc(Cl)cc3Cl)C2)CC1] | JO-02-112B | 433.349 | + | + | ++ |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 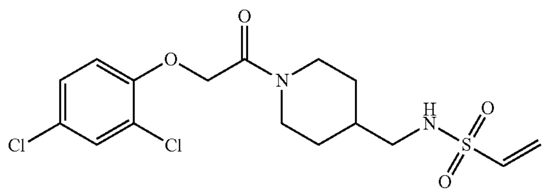 [SMILES: C=CS(=O)(=O)NCC1CCN(C(=O)COc2ccc(Cl)cc2Cl)CC1] | JO-02-112C | 407.312 | + | + | + |
| 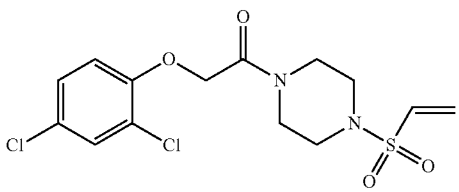 [SMILES: C=CS(=O)(=O)N1CCN(C(=O)COc2ccc(Cl)cc2Cl)CC1] | JO-02-112D | 379.259 | + | + | +++ |
| 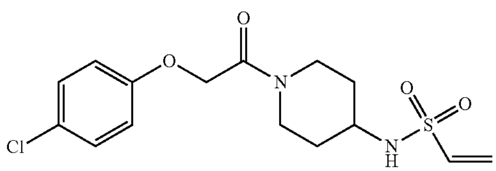 [SMILES: C=CS(=O)(=O)NC1CCN(C(=O)COc2ccc(Cl)cc2)CC1] | JO-02-115A | 358.84 | + | + | + |
| 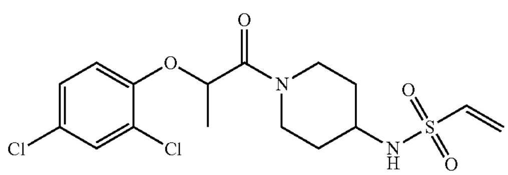 [SMILES: C=CS(=O)(=O)NC1CCN(C(=O)C(C)Oc2ccc(Cl)cc2Cl)CC1] | JO-02-115B | 407.312 | + | + | + |
| 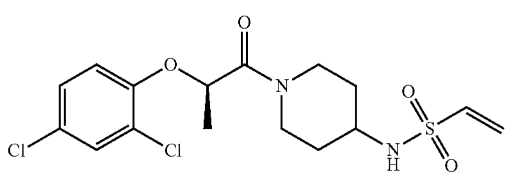 [SMILES: C=CS(=O)(=O)NC1CCN(C(=O)[C@@H](C)Oc2ccc(Cl)cc2Cl)CC1] | JO-02-115C | 407.312 | + | + | + |
| 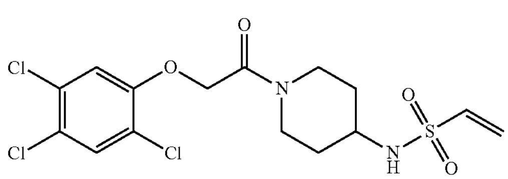 | JO-02-115D | 427.73 | + | + | +++ |
| 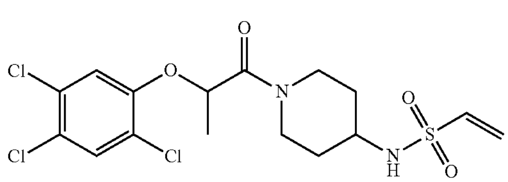 [SMILES: C=CS(=O)(=O)NC1CCN(C(=O)C(C)Oc2cc(Cl)c(Cl)cc2Cl)CC1] | JO-02-116A | 441.757 | + | + | + |
| 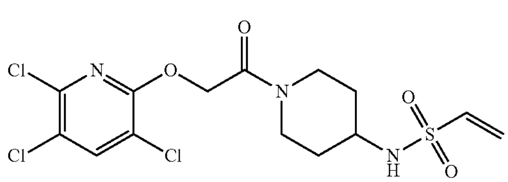 [SMILES: C=CS(=O)(=O)NC1CCN(C(=O)COc2nc(Cl)c(Cl)cc2Cl)CC1] | JO-02-116B | 428.719 | + | + | + |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 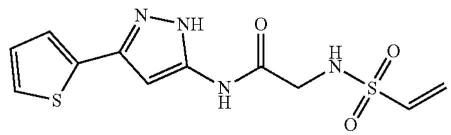 [SMILES: C=CS(=O)(=O)NCC(=O)Nc1cc(-c2cccs2)n[nH]1] | JO-02-125 | 312.368 | + | + | +++ |
| 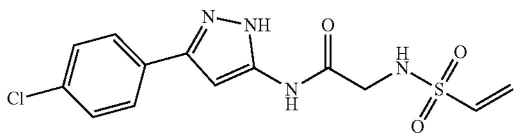 [SMILES: C=CS(=O)(=O)NCC(=O)Nc1cc(-c2ccc(Cl)cc2)n[nH]1] | JO-02-139E | 340.785 | + | + | + |
| 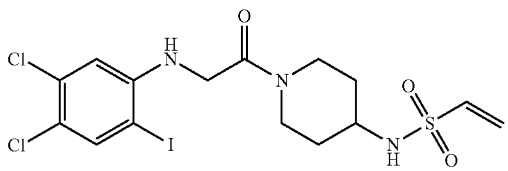 [SMILES: C=CS(=O)(=O)NC1CCN(C(=O)CNc2cc(Cl)c(Cl)cc2I)CC1] | JO-02-144 | 518.197 | + | ++ | +++++ |
| 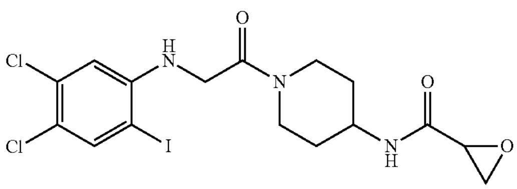 [SMILES: O=C(NC1CCN(C(=O)CNc2cc(Cl)c(Cl)cc2I)CC1)C1CO1] | JO-02-152 | 498.143 | + | + | +++ |
| 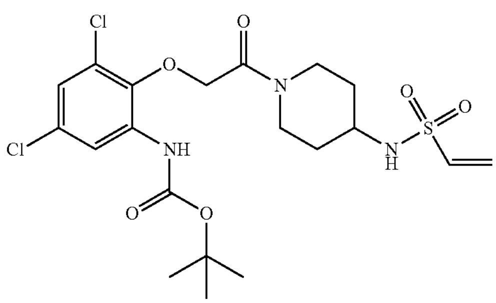 [SMILES: C=CS(=O)(=O)NC1CCN(C(=O)COc2c(Cl)cc(Cl)cc2NC(=O)OC(C)(C)C)CC1] | UP-I-162B | 508.416 | + | + | + |
| 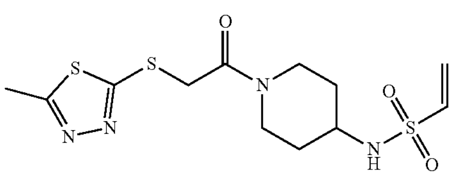 [SMILES: C=CS(=O)(=O)NC1CCN(C(=O)CSc2nnc(C)o2)CC1] | UP-I-164A | 362.491 | + | + | + |
| 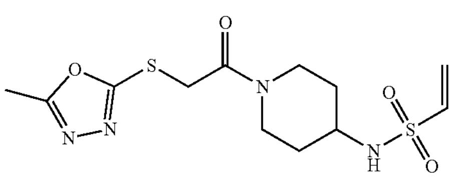 | UP-I-164B | 346.426 | + | + | + |
| 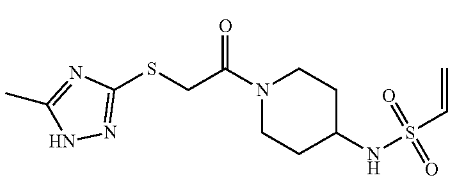 [SMILES: C=CS(=O)(=O)NC1CCN(C(=O)CSc2n[nH]c(C)n2)CC1] | UP-I-164C | 345.441 | + | + | + |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 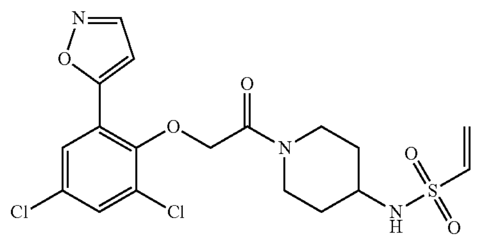 [SMILES: C=CS(=O)(=O)NC1CCN(C(=O)COc2c(Cl)cc(Cl)cc2-c2ccno2)CC1] | UP-I-165B | 460.332 | + | + | + |
| 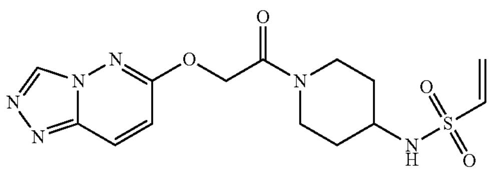 [SMILES: C=CS(=O)(=O)NC1CCN(C(=O)COc2ccc3nncn3n2)CC1] | UP-I-165C | 366.396 | + | + | + |
| 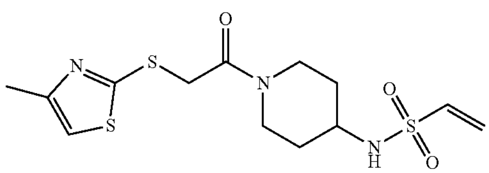 [SMILES: C=CS(=O)(=O)NC1CCN(C(=O)CSc2nc(C)cs2)CC1] | UP-I-165D | 361.503 | + | + | + |
| 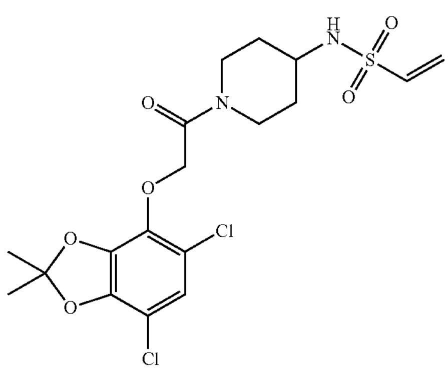 [SMILES: C=CS(=O)(=O)NC1CCN(C(=O)COc2c(Cl)cc(Cl)c3c2OC(C)(C)O3)CC1] | UP-I-177C | 465.348 | + | ++ | ++++ |
| 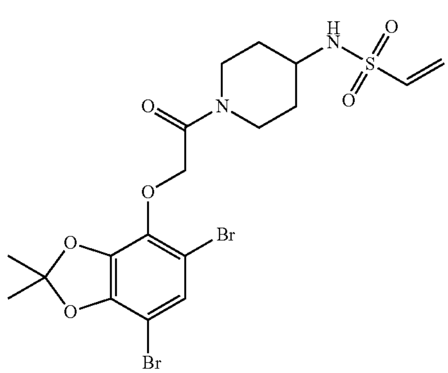 [SMILES: C=CS(=O)(=O)NC1CCN(C(=O)COc2c(Br)cc(Br)c3c2OC(C)(C)O3)CC1] | UP-I-177D | 554.25 | + | + | +++++ |

TABLE 3-continued
Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.
| Structure | Name | Mol Weight | 2 hrs | 6 hrs | 24 hrs |
|---|---|---|---|---|---|
| 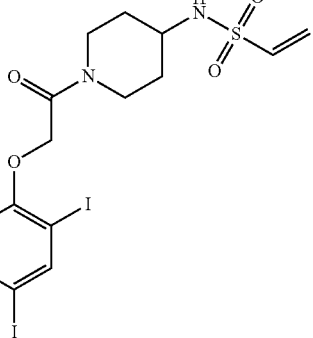 | UP-I-177E | 648.251 | + | + | +++++ |
| 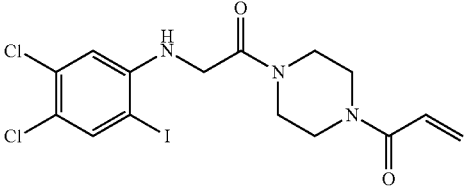 [SMILES: C=CC(=O)N1CCN(C(=O)CNc2cc(Cl)c(Cl)cc2I)CC1] | JO-02-155 | 468.117 | + | ++ | ++++ |
| 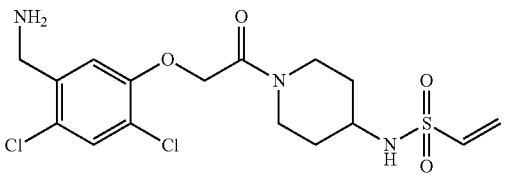 [SMILES: C=CS(=O)(=O)NC1CCN(C(=O)COc2cc(CN)c(Cl)cc2Cl)CC1] | Ras-058 | 422.327 | + | + | + |
| 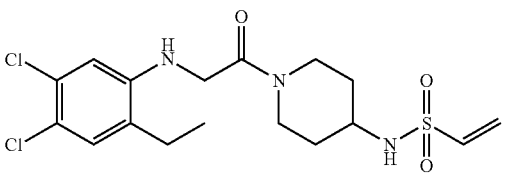 [SMILES: C=CS(=O)(=O)NC1CCN(C(=O)CNc2cc(Cl)c(Cl)cc2CC)CC1] | Ras-059 | 420.354 | + | ++ | +++++ |
| 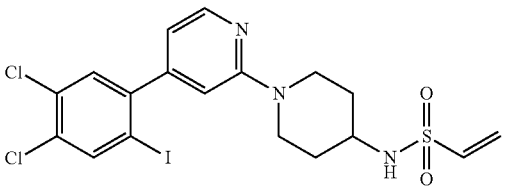 [SMILES: C=CS(=O)(=O)NC1CCN(c2cc(-c3cc(Cl)c(Cl)cc3I)ccn2)CC1] | Ras-060 | 538.23 | + | + | + |
| 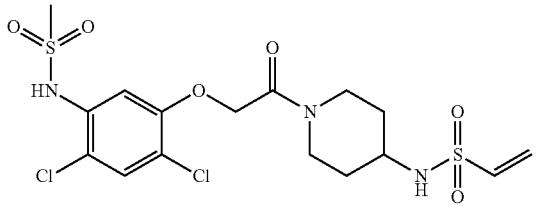 [SMILES: C=CS(=O)(=O)NC1CCN(C(=O)COc2cc(NS(C)(=O)=O)c(Cl)cc2Cl)CC1] | Ras-061 | 486.39 | + | + | + |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 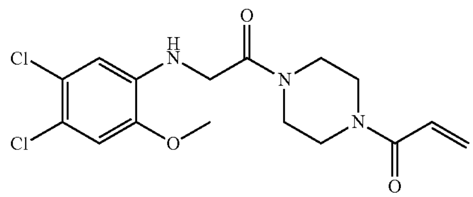 | Ras-062 | 372.246 | + | + | +++ |
| 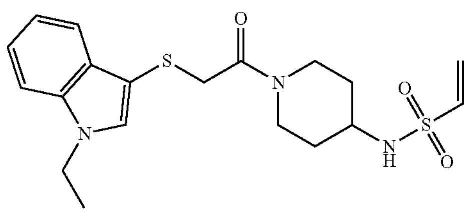 [SMILES: C=CS(=O)(=O)NC1CCN(C(=O)CSc2cn(CC)c3ccccc23)CC1] | UP-I-154B | 407.55 | + | + | + |
| 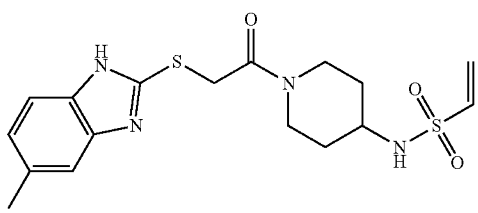 [SMILES: C=CS(=O)(=O)NC1CCN(C(=O)CSc2nc3cc(C)ccc3[nH]2)CC1] | UP-I-160B | 394.512 | + | + | + |
| 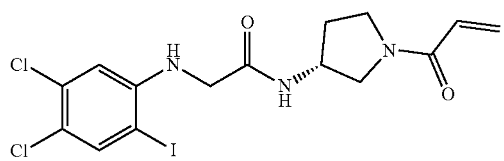 [SMILES: C=CC(=O)N1CC[C@@H](NC(=O)CNc2cc(Cl)c(Cl)cc2I)C1] | JO-02-157A (R) | 468.117 | + | + | + |
| 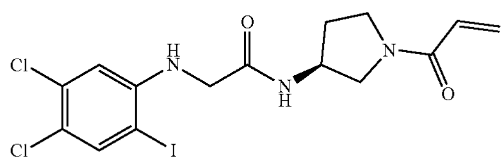 [SMILES: C=CC(=O)N1CC[C@H](NC(=O)CNc2cc(Cl)c(Cl)cc2I)C1] | JO-02-157B (S) | 468.117 | + | + | ++ |
| 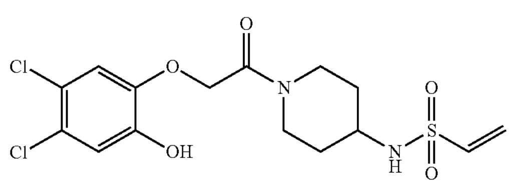 [SMILES: C=CS(=O)(=O)NC1CCN(C(=O)COc2cc(Cl)c(Cl)cc2O)CC1] | Ras-063 | 409.285 | + | ++ | +++ |
| 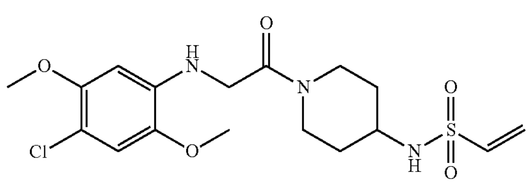 [SMILES: C=CS(=O)(=O)NC1CCN(C(=O)CNc2cc(OC)c(Cl)cc2OC)CC1] | Ras-064 | 417.908 | + | + | +++ |
| 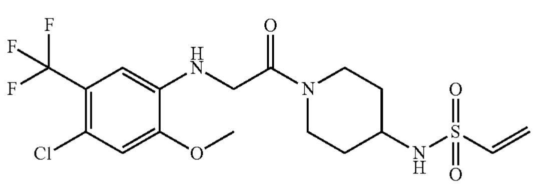 [SMILES: C=CS(=O)(=O)NC1CCN(C(=O)CNc2cc(C(F)(F)F)c(Cl)cc2OC)CC1] | Ras-065 | 455.88 | + | ++ | +++ |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 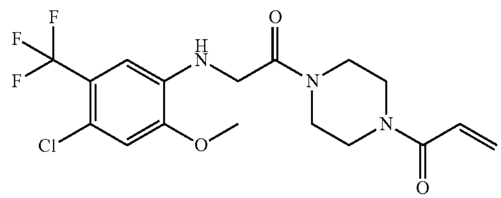 [SMILES: C=CC(=O)N1CCN(C(=O)CNc2cc(C(F)(F)F)c(Cl)cc2OC)CC1] | Ras-066 | 405.799 | + | + | ++ |
| 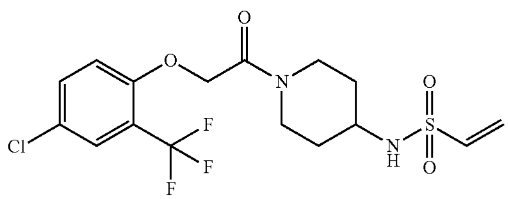 [SMILES: C=CS(=O)(=O)NC1CCN(C(=O)COc2ccc(Cl)cc2C(F)(F)F)CC1] | Ras-067 | 426.838 | + | + | ++ |
| 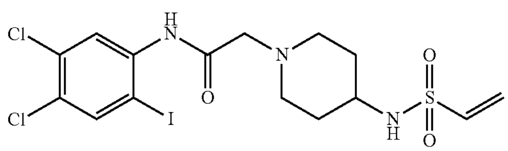 [SMILES: C=CS(=O)(=O)NC1CCN(CC(=O)Nc2cc(Cl)c(Cl)cc2I)CC1] | Ras-068 | 518.197 | + | + | + |
| 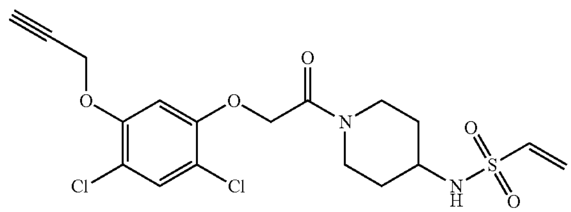 [SMILES: C#CCOc1cc(OCC(=O)N2CCC(NS(=O)(=O)C=C)CC2)c(Cl)cc1Cl] | Ras-069 | 447.333 | + | ++ | +++++ |
| 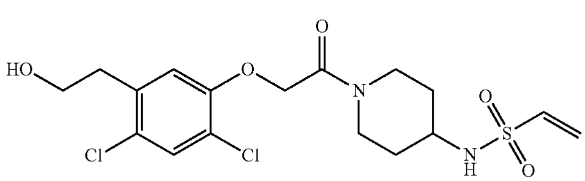 [SMILES: C=CS(=O)(=O)NC1CCN(C(=O)COc2cc(CCO)c(Cl)cc2Cl)CC1] | Ras-070 | 437.338 | + | + | +++ |
| 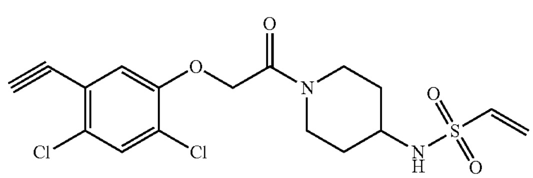 [SMILES: C#Cc1cc(OCC(=O)N2CCC(NS(=O)(=O)C=C)CC2)c(Cl)cc1Cl] | Ras-071 | 417.307 | + | + | ++++ |
| 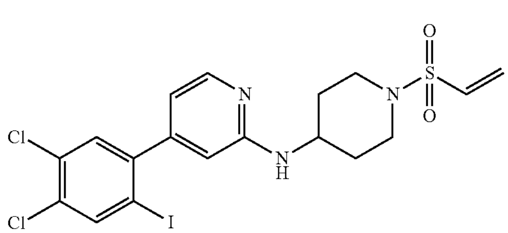 [SMILES: C=CS(=O)(=O)N1CCC(Nc2cc(-c3cc(Cl)c(Cl)cc3I)ccn2)CC1] | Ras-072 | 538.23 | + | + | + |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 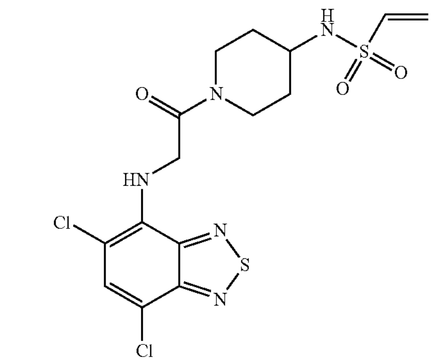 [SMILES: C=CS(=O)(=O)NC1CCN(C(=O)CNc2c(Cl)cc(Cl)c3nsnc23)CC1] | UP-I-185a | 450.363 | ++ | +++ | +++++ |
| 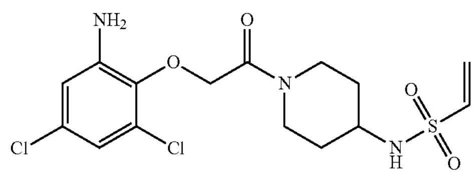 [SMILES: C=CS(=O)(=O)NC1CCN(C(=O)COc2c(N)cc(Cl)cc2Cl)CC1] | UP-I-185b | 408.3 | + | + | ++ |
| 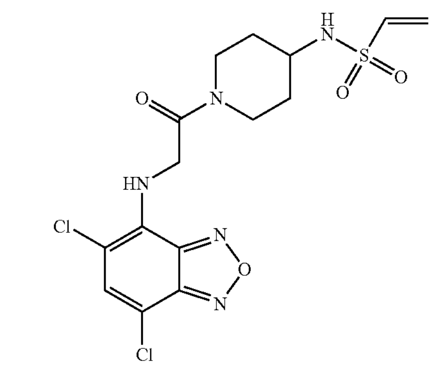 [SMILES: C=CS(=O)(=O)NC1CCN(C(=O)CNc2c(Cl)cc(Cl)c3nonc23)CC1] | UP-I-187 | 434.298 | + | + | +++ |
| 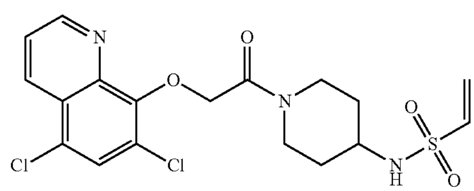 [SMILES: C=CS(=O)(=O)NC1CCN(C(=O)COc2c(Cl)cc(Cl)c3cccnc23)CC1] | UP-I-154A | 444.332 | + | + | + |
| 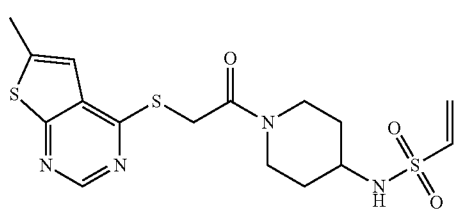 [SMILES: C=CS(=O)(=O)NC1CCN(C(=O)CSc2ncnc3sc(C)cc23)CC1] | UP-I-154K | 412.55 | + | + | + |
| 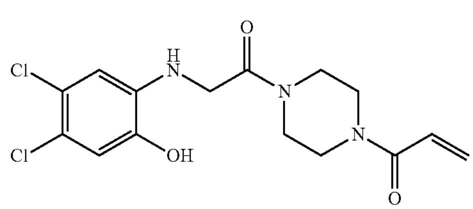 [SMILES: C=CC(=O)N1CCN(C(=O)CNc2cc(Cl)c(Cl)cc2O)CC1] | Ras-073 | | | +++ | +++++ |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 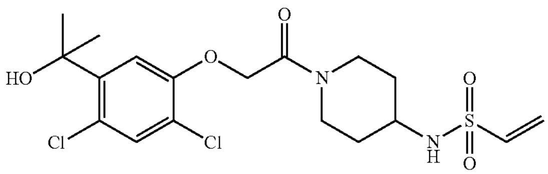 [SMILES: C=CS(=O)(=O)NC1CCN(C(=O)COc2cc(C(C)(C)O)c(Cl)cc2Cl)CC1] | Ras-074 | | | | ++++ |
| 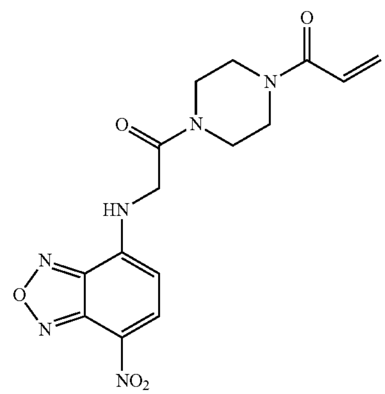 [SMILES: C=CC(=O)N1CCN(C(=O)CNc2ccc([N+](=O)[O-])c3nonc23)CC1] | Ras-075 | | | | − |
| 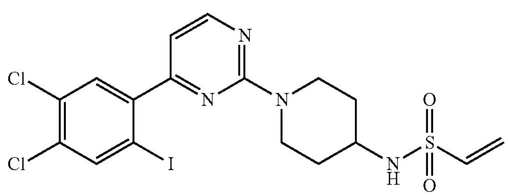 [SMILES: C=CS(=O)(=O)NC1CCN(c2nccc(-c3cc(Cl)c(Cl)cc3I)n2)CC1] | Ras-076 | | | | − |
| 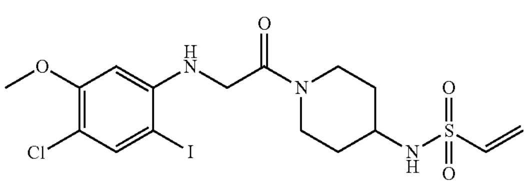 [SMILES: C=CS(=O)(=O)NC1CCN(C(=O)CNc2cc(OC)c(Cl)cc2I)CC1] | Ras-077 | | | ++ | +++++ |
| 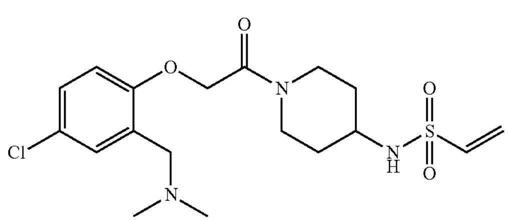 [SMILES: C=CS(=O)(=O)NC1CCN(C(=O)COc2ccc(Cl)cc2CN(C)C)CC1] | Ras-078 | | | | − |
| 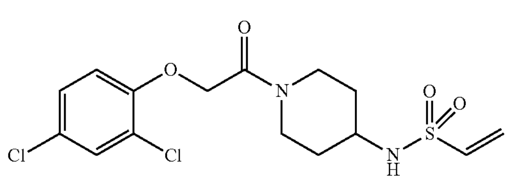 [SMILES: C=CS(=O)(=O)NC1CCN(C(=O)COc2ccc(Cl)cc2Cl)CC1] | JO-02-31A | | | | +++ |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 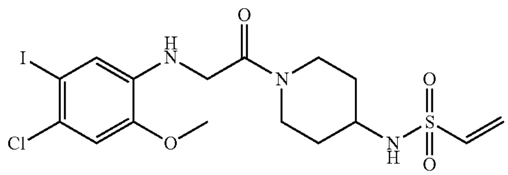 [SMILES: C=CS(=O)(=O)NC1CCN(C(=O)CNc2cc(I)c(Cl)cc2OC)CC1] | Ras-079 | | +++ | +++++ | +++++ |
| 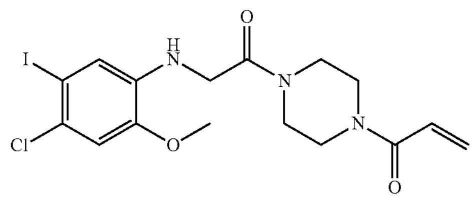 | Ras-080 | | | | +++ |
| 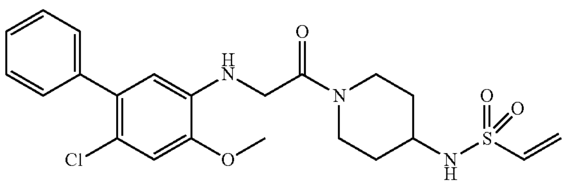 [SMILES: C=CS(=O)(=O)NC1CCN(C(=O)CNc2cc(-c3ccccc3)c(Cl)cc2OC)CC1] | Ras-081 | | +++ | ++++ | +++++ |
| 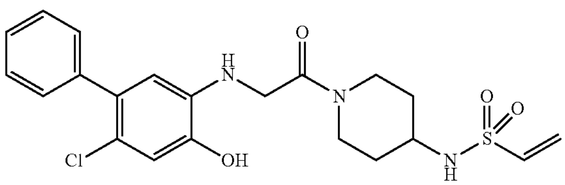 [SMILES: C=CS(=O)(=O)NC1CCN(C(=O)CNc2cc(-c3ccccc3)c(Cl)cc2O)CC1] | Ras-082 | | | +++ | +++++ |
| 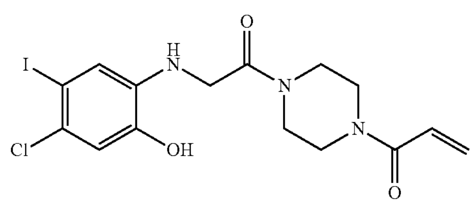 [SMILES: C=CC(=O)N1CCN(C(=O)CNc2cc(I)c(Cl)cc2O)CC1] | Ras-083 | | | +++ | +++++ |
| 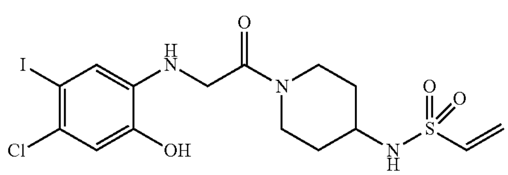 [SMILES: C=CS(=O)(=O)NC1CCN(C(=O)CNc2cc(I)c(Cl)cc2O)CC1] | Ras-084 | | +++ | +++++ | +++++ |
| 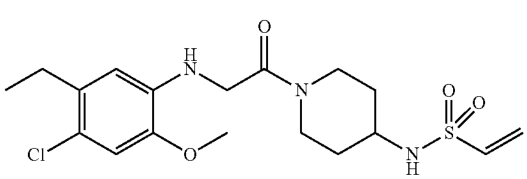 [SMILES: C=CS(=O)(=O)NC1CCN(C(=O)CNc2cc(CC)c(Cl)cc2OC)CC1] | Ras-085 | | ++ | +++ | +++++ |
| 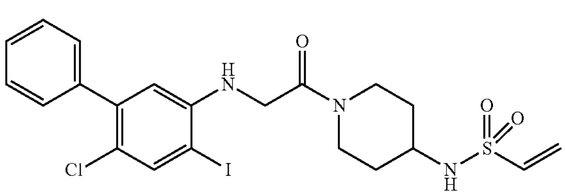 [SMILES: C=CS(=O)(=O)NC1CCN(C(=O)CNc2cc(-c3ccccc3)c(Cl)cc2I)CC1] | Ras-086 | | | | ++++ |

TABLE 3-continued

Eletrophilic K-Ras Modulators (e.g. covalent S2BP binding compounds). Percent reduction in activity of compound at 10 micromolar relative to control (no compound): + <= 5%, 5% < ++ <= 20%, 20% < +++ <= 40%, 40% < ++++ <= 60%, 60% < +++++.

| Structure | Name | Mol Weight | 2 hrs | 6 hrs | 24 hrs |
|---|---|---|---|---|---|
| 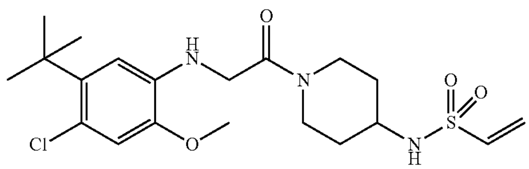 [SMILES: C=CS(=O)(=O)NC1CCN(C(=O)CNc2cc(C(C)(C)C)c(Cl)cc2OC)CC1] | Ras-087 |  |  |  |  |

TABLE 4

Modulation of Ras by compound binding.

| | 12Cα to 60Cα distance (Å) | Switch I | Metal ion |
|---|---|---|---|
| GDP-bound | | | |
| WT | 8 | | Mg |
| Hras G60A (1XJ0) | 8.1 | | Mg |
| JO-02-172 | 8.3 | | Mg |
| JO-02-112D | 8.4 | | Mg |
| JO-02-56A Chain D | 8.5 | | Mg |
| JO-02-56A Chain E | 8.6 | | Mg |
| JO-01-148 | 9 | | Ca |
| JO-01-189 | 9.1 | | Ca |
| Ras-055_P1 (Ras-055 in P1) | 9.5 | | Ca |
| Ras-028 | 11.1 | disordered | — |
| JO-02-56A Chain C | 11.2 | disordered | Mg |
| JO-02-31A | 11.6 | disordered | — |
| JO-02-56A Chain A | 11.7 | disordered | — |
| Ras-055_C2 (Ras-055 in C2) | 11.9 | disordered | — |
| UP-I-185a | 12 | disordered | — |
| Ras-059 | 12.6 | disordered | — |
| UP-I-177C | 12.8 | disordered | — |
| JO-02-56A Chain B | no density | disordered | — |
| Ras-062 | no density | disordered | — |
| GTP-bound | | | |
| Hras G12C | 3.8 | | Mg |
| Kras WT state state 2 (3GFT) | 3.9 | | Mg |
| Rap1A (RafRBD) (1C1Y) | 3.9 | | Mg |
| Hras T35S state 2 (2KKM) | 3.9 | | Mg |
| Hras T35S state 1 (3KKN) | 4.9 | low affinity state | Mg |
| Kras WT state 1 (4EFL) | 4.9 | low affinity state | Mg |
| Hras G60A (1XCM) | 5.2 | low affinity state | Mg |

TABLE 5

| Structure | Compound | Labeling % (10 micM) 24 h | Resolution/ Space group Unit cell | R-free/R-work |
|---|---|---|---|---|
| JO-02-112D |  | +++ (plate) | 3 sets 1.35A 1.35A 1.40A C121 (72, 40, 55A) (90, 105, 90) | 0.1806/ 0.1504 0.1809/ 0.1577 0.1937/ 0.1537 |
| JO-02-172 |  | + (plate) | 2.09 A C121 (71, 83, 87A) (90, 109, 90) Diff. orient. | 0.2285/ 0.1897 |

TABLE 5-continued

| Structure | Compound | Labeling % (10 micM) 24 h | Resolution/ Space group Unit cell | R-free/R-work |
|---|---|---|---|---|
| JO-02-31A | | ++ (plate) | 1.70 A C121 (68, 83, 85A) (90, 111, 90) | 0.2106/ 0.1763 |
| JO-02-56A | | ++++ (plate) | 2.30 A P22121 (93, 108, 121A) (90, 90, 90) | 0.2218/ 0.1809 |
| Ras-028 | | +++ (plate) | 1.55 A C121 (68, 84, 86A) (90, 111, 90) | 0.1966/ 0.1814 |
| Ras-055 (C2) | | +++++ (plate) | 1.57 A C121 (68, 84, 87A) (90, 111, 90) | 0.1931/ 0.1584 |
| Ras-055 (P1) | | +++++ (plate) | 1.49 A P1 (33, 40, 62A) (77, 82, 78) | 0.2122/ 0.1752 |
| Ras-059 | | +++++ (single) | 1.58A C121 (68, 84, 87A) (90, 111, 90) | 0.1913/ 0.1740 |
| Ras-062 | | +++ (single) | 1.94A C121 (68, 84, 87A) (90, 111, 90) | 0.2351/ 0.1948 |

TABLE 5-continued

| Structure | Compound | Labeling % (10 micM) 24 h | Resolution/ Space group Unit cell | R-free/R-work |
|---|---|---|---|---|
| UP-I-177C | | ++++ (plate) | 1.57 A C121 (68, 84, 86A) (90, 111, 90) | 0.2087/ 0.1837 |
| UP-I-185a | | +++++ (single) | 1.81A C121 (68, 84, 87A) (90, 111, 90) | 0.2038/ 0.1801 |
| UP-I-185a (update, delete the old one) | | +++++ (single) | 1.49A C121 (68, 84, 86A) (90, 111, 90) | 0.1908/ 0.1689 |
| Ras-069 | | +++ (single) | 1.74A C121 (69, 85, 87A) (90, 111, 90) | 0.2098/ 0.1849 |
| Ras-079 (C2) | | +++++ (single) | 1.37A C121 (68, 84, 84A) (90, 111, 90) | 0.1918/ 0.1652 |
| Ras-079 (P212121) | | +++++ (single) | 1.93A P212121 (39, 43, 88A) (90, 90, 90) | 0.2086/ 0.1736 |
| Ras-081 | | +++++ (single) | 2.04A C121 (68, 84, 86A) (90, 110, 90) | 0.2169/ 0.1836 |

TABLE 5-continued

| Structure | Compound | Labeling % (10 micM) 24 h | Resolution/ Space group Unit cell | R-free/R-work |
|---|---|---|---|---|
| UP-I-177E | | ++++ (plate) | 2.27 A C121 (68, 85, 86A) (90, 111, 90) | 0.2340/ 0.1857 |
| UP-I-187 | | +++ (single) | 1.59A C121 (68, 84, 87A) (90, 111, 90) | 0.2004/ 0.1753 |

TABLE 6

Calculated/estimated half-lives from experiments in FIG. 34.
mant-dGDP
Calculated/Estimated Half-lives

| | mant-dGDP | | | | | |
|---|---|---|---|---|---|---|
| | intrinsic | SOS, 4 µM | SOS, 2 µM | SOS, 1 µM | SOS, 0.5 µM | SOS, 0.25 µM |
| WT | >18000 s | 350 ± 40 s | 420 ± 40 s | 1030 ± 130 s | 1850 ± 200 s | 4500 ± 800 s |
| G12C | >18000 s | 580 ± 70 s | 810 ± 80 s | 2100 ± 400 s | 3700 ± 300 s | 10700 ± 3000 s |
| G12C-055 | >18000 s | 11300 ± 2500 s | 10500 ± 4200 s | >18000 s | >18000 s | >18000 s |
| G12C-083 | >18000 s | 8200 ± 2400 s | >18000 s | >18000 s | >18000 s | >18000 s |

TABLE 7

Calculated/estimated half-lives from experiments in FIG. 35.
mant-dGppNp
Calculated/Estimated Half-Lives

| | mant-dGppNp | | | | | |
|---|---|---|---|---|---|---|
| | intrinsic | SOS, 4 µM | SOS, 2 µM | SOS, 1 µM | SOS, 0.5 µM | SOS, 0.25 µM |
| WT | >18000 s | 610 ± 70 s | 940 ± 100 s | 2000 ± 150 s | 3300 ± 140 s | 7000 ± 500 s |
| G12C | >18000 s | 1160 ± 70 s | 1780 ± 70 s | 3860 ± 730 s | 4480 ± 80 s | 16300 ± 1500 s |
| G12C-055 | | | | no reliable data obtained | | |
| G12C-083 | | | | no reliable data obtained | | |

TABLE 8
Calculated/estimated half-lives from experiments in FIG. 36.
Calculated/Estimated Half-lives
|  | SOS/GDP | SOS/GTP | SOS/GppNp | EDTA/GDP | EDTA/GTP | EDTA/GppNp |
| --- | --- | --- | --- | --- | --- | --- |
| WT | 2080 ± 140 s | 1010 ± 50 s | 1120 ± 70 s | 117 ± 6 s | 112 ± 3 s | 107 ± 2 s |
| G12C | 3640 ± 340 s | 1560 ± 320 s | 1640 ± 160 s | 157 ± 5 s | 151 ± 4 s | 143 ± 5 s |
| G12C-055 | >18000 s | >18000 s | >18000 s | 247 ± 14 s | 232 ± 13 s | 197 ± 10 s |
| G12C-083 | >18000 s | >18000 s | >18000 s | 370 ± 7 s | 334 ± 7 s | 304 ± 11 s |
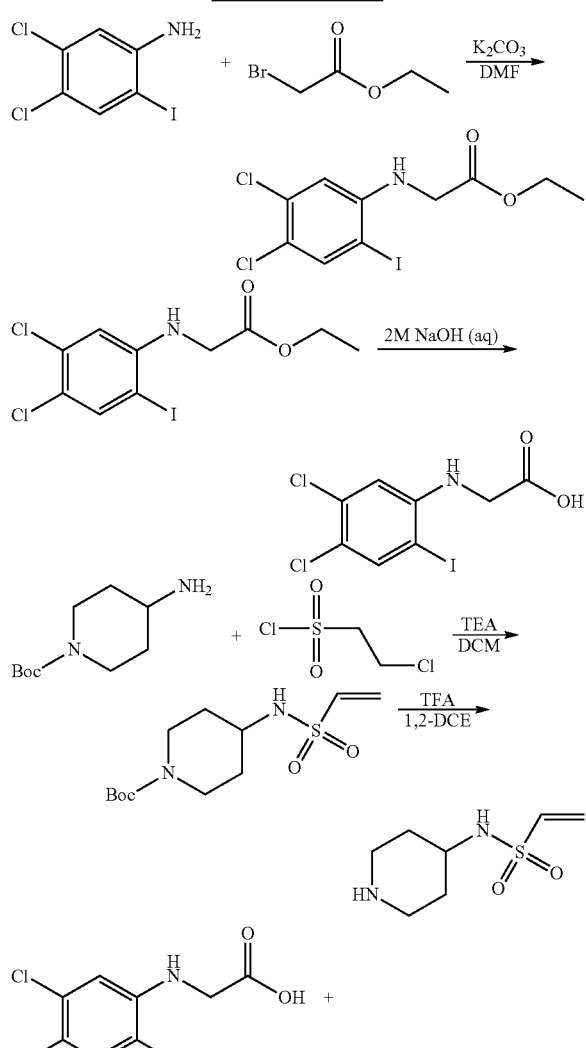
Scheme for JO-02-144
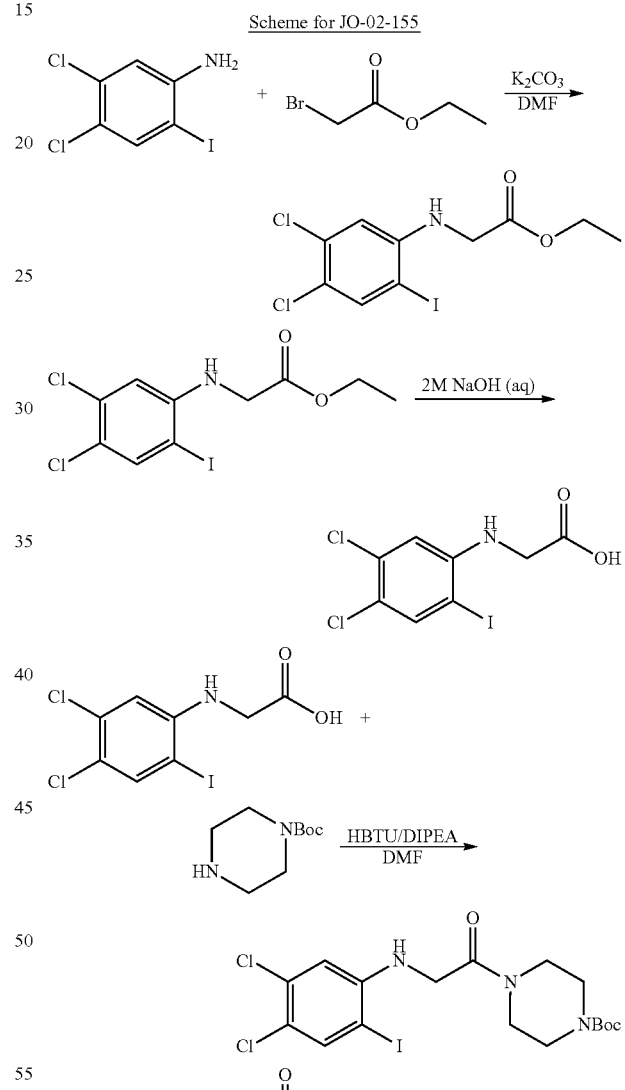
Scheme for JO-02-155

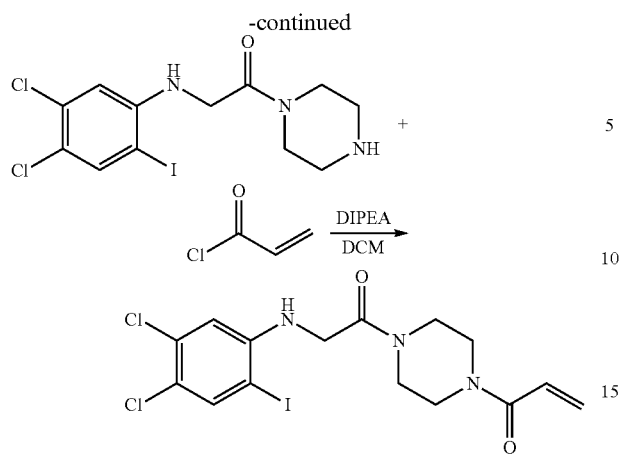

REFERENCES

Arkin M R, Randal M, DeLano W L, Hyde J, Luong T N, Oslob J D, Raphael D R, Taylor L, Wang J, McDowell R S, Wells J A, Braisted A C. PNAS 2003, 100 (4): 1603-8. Choong I C, Lew W, Lee D, Pham P, Burdett M T, Lam J W, Wiesmann C, Luong T N, Fahr B, DeLano W L, McDowell R S, Allen D A, Erlanson D A, Gordon E M, O'Brien T. J Med Chem 2002, 45 (23): 5005-22. Erlanson D A, Braisted A C, Raphael D R, Randal M, Stroud R M, Gordon E M, Wells J A. PNAS 2000, 97 (17): 9367-72. Forbes S, Clements J, Dawson E, Bamford S, Webb T, Dogan A, Flanagan A, Teague J, Wooster R, Futreal P A, Stratton M R. Br J Cancer 2006, 94 (2): 318-22. Hall A and Self A J. JBC 1986, 261 (24): 10963-5. Hara M, Tamaoki T, Nakano H. Oncogene Res 1988, 2 (4): 325-33. Hardy J A, Lam J, Nguyen J T, O'Brien T, Wells J A. PNAS 2004, 101 (34): 12461-6. Hattori S, Clanton D J, Satoh T, Nakamura S, Kaziro Y, Kawakita M, Shih T Y. Mol Cell Biol 1987, 7 (5): 1999-2002. Ito Y, Yamasaki K, Iwahara J, Terada T, Kamiya A, Shirouzu M, Muto Y, Kawai G, Yokoyama S, Laue E D, Wälchli M, Shibata T, Nishimura S, Miyazawa T. Biochemistry 1997, 36 (30): 9109-19. Kraulis P J, Domaille P J, Campbell-Burk S L, Van Aken T, Laue E D. Biochemistry 1994, 33 (12): 3515-31. Lee W, Jiang Z, Liu J, Haverty P M, Guan Y, Stinson J, Yue P, Zhang Y, Pant K P, Bhatt D, Ha C, Johnson S, Kennemer M I, Mohan S, Nazarenko I, Watanabe C, Sparks A B, Shames D S, Gentleman R, de Sauvage F J, Stern H, Pandita A, Ballinger D G, Drmanac R, Modrusan Z, Seshagiri S, Zhang Z. Nature 2010, 465 (7297): 473-7. Lenzen C, Cool R H, Wittinghofer A. Methods Enzymol. 1995 255:95-109. Margarit S M, Sondermann H, Hall B E, Nagar B, Hoelz A, Pirruccello M, Bar-Sagi D, Kuriyan J. Cell 2003, 112 (5): 685-95. Milburn M V, Tong L, de Vos A M, Brünger A, Yamaizumi Z, Nishimura S, Kim S H. Science 1990, 247 (4945): 939-45. Pacold M E, Suire S, Perisic O, Lara-Gonzalez S, Davis C T, Walker E H, Hawkins P T, Stephens L, Eccleston J F, Williams R L. Cell 2000, 103 (6): 931-43. Palmioli A, Sacco E, Abraham S, Thomas C J, Di Domizio A, De Gioia L, Gaponenko V, Vanoni M, Peri F. Bioorg Med Chem Lett 2009, 19 (15): 4217-22. Rensland H, John J, Linke R, Simon I, Schlichting I, Wittinghofer A, Goody R S. Biochemistry 1995, 34 (2): 593-9. Sydor J R, Engelhard M, Wittinghofer A, Goody R S, Herrmann C. Biochemistry 1998, 37 (40): 14292-9. Taveras A G, Remiszewski S W, Doll R J, Cesarz D, Huang E C, Kirschmeier P, Pramanik B N, Snow M E, Wang Y S, del Rosario J D, Vibulbhan B, Bauer B B, Brown J E, Carr D, Catino J, Evans C A, Girijavallabhan V, Heimark L, James L, Liberles S, Nash C, Perkins L, Senior M M, Tsarbopoulos A, Webber S E, et al. Bioorg Med Chem 1997, 5 (1): 125-33. Vetter I R, Wittinghofer A. Science 2001, 294 (5545): 1299-304. Yang W, Fucini R V, Fahr B T, Randal M, Lind K E, Lam M B, Lu W, Lu Y, Cary D R, Romanowski M J, Colussi D, Pietrak B, Allison T J, Munshi S K, Penny D M, Pham P, Sun J, Thomas A E, Wilkinson J M, Jacobs J W, McDowell R S, Ballinger M D. Biochemistry 2009, 48 (21): 4488-96.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A human K-Ras protein having a cysteine at residue 12, wherein said cysteine is covalently bonded to a compound, wherein said compound has the formula $R^1\text{-}L^1\text{-}L^2\text{-}L^3\text{-}E$, wherein
$R^1$ is a substituted or unsubstituted heteroaryl;
$L^1$ is substituted or unsubstituted heteroarylene;
$L^2$ is a bond;
$L^3$ is

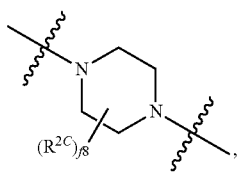

wherein
f8 is an integer from 0 to 8;
each $R^{2C}$ is independently oxo, halogen, —$CX^c_3$, —CN, —$SO_2Cl$, —$SO_{n3}R^{10c}$, —$SO_{v3}NR^{7c}R^{8c}$, —$NHNH_2$, —$ONR^{7c}R^{8c}$, —NHC═(O)$NHNH_2$, —NHC═(O)$NR^{7c}R^{8c}$, —N(O)$_{m3}$, —$NR^{7c}R^{8c}$, —C(O)$R^{9c}$, —C(O)—$OR^{9c}$, C(O)$NR^{7c}R^{8c}$, —$OR^{10c}$, —$NR^{7c}SO_2R^{10c}$, —$NR^{7c}$═(O)$R^{9c}$, —$NR^{7c}C(O)$—$OR^{9c}$, —$NR^{7c}OR^{9c}$, —$OCX^c_3$, —$OCHX^c_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
wherein
two adjacent $R^{2C}$ substituents are optionally joined to form a substituted or unsubstituted cycloalkyl, substituted or unsubstituted heterocycloalkyl, substituted or unsubstituted aryl, or substituted or unsubstituted heteroaryl;
each $R^{7c}$, $R^{8c}$, $R^{10c}$ and $R^{10c}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O) $NHNH_2$, —NHC═(O)$NH_2$, —$NHSO_2H$, —NHC═(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{7c}$ and $R^{8c}$ are optionally joined to form a substituted or unsubstituted heterocycloalkyl or substituted or unsubstituted heteroaryl;
m3 and v3 are independently an integer from 1 to 2;
n3 is an integer from 0 to 4;
$X^c$ is independently —Cl, —Br, —I, or —F; and, prior to covalently bonding to the cysteine 12,
E is

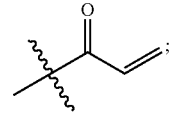 [SMILES: *C(=O)C=C]

wherein each substituted alkyl, substituted heteroalkyl, substituted cycloalkyl, substituted heterocycloalkyl, substituted heteroaryl, substituted aryl is independently substituted with a substituent group.

2. The human K-Ras protein of claim 1, wherein $R^1$ is substituted monocyclic heteroaryl or substituted 6,5-fused ring heteroaryl or substituted 6,6-fused ring heteroaryl.

3. The human K-Ras protein of claim 1, wherein $R^1$ is substituted 6,5-fused ring heteroaryl.

4. The human K-Ras protein of claim 1, wherein $R^1$ is selected from 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, each independently substituted.

5. The human K-Ras protein of claim 2, wherein each substituent group on the $R^1$ is independently selected from oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O) H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, and unsubstituted heteroaryl.

6. The human K-Ras protein of claim 5, wherein each substituent group on the $R^1$ is independently selected from halogen, —$CF_3$, —CN, —OH, —$NH_2$, —COOH, —$CONH_2$, —$CH_3$, and —$CH_2CH_3$.

7. The human K-Ras protein of claim 3, wherein each substituent group on the $R^1$ is independently selected from halogen, —$CF_3$, —CN, —OH, —$NH_2$, —COOH, —$CONH_2$, —$CH_3$, and —$CH_2CH_3$.

8. The human K-Ras protein of claim 4, wherein each substituent group on the $R^1$ is independently selected from halogen, —$CF_3$, —CN, —OH, —$NH_2$, —COOH, —$CONH_2$, —$CH_3$, and —$CH_2CH_3$.

9. The human K-Ras protein of claim 6, wherein
f8 is 1 and $R^{2C}$ is methyl, trifluoromethyl, phenyl, or oxo; or
f8 is 2 and $R^{2C}$ is methyl.

10. The human K-Ras protein of claim 6, wherein f8 is 1 and $R^{2C}$ is methyl.

11. The human K-Ras protein of claim 8, wherein
f8 is 1 and $R^{2C}$ is methyl, trifluoromethyl, phenyl, or oxo; or
f8 is 2 and $R^{2C}$ is methyl.

12. The human K-Ras protein of claim 8, wherein f8 is 1 and $R^{2C}$ is methyl.

13. The human K-Ras protein of claim 7, wherein f8 is 2 and $R^{2C}$ is methyl.

14. The human K-Ras protein of claim 1, wherein $R^1$ is substituted pyridinyl, substituted pyrimidinyl, substituted thiophenyl, substituted furanyl, substituted indolyl, substituted benzoxadiazolyl, substituted benzodioxolyl, substituted benzodioxanyl, substituted thianaphthanyl, substituted pyrrolopyridinyl, substituted indazolyl, substituted quinolinyl, substituted quinoxalinyl, substituted pyridopyrazinyl, substituted quinazolinonyl, substituted benzoisoxazolyl, substituted imidazopyridinyl, substituted benzofuranyl, substituted benzothiophenyl, substituted phenyl, substituted naphthyl, substituted biphenyl, substituted pyrrolyl, substituted pyrazolyl, substituted imidazolyl, substituted pyrazinyl, substituted oxazolyl, substituted isoxazolyl, substituted thiazolyl, substituted furylthienyl, substituted pyridyl, substituted pyrimidyl, substituted benzothiazolyl, substituted purinyl, substituted benzimidazolyl, substituted isoquinolyl, substituted thiadiazolyl, substituted oxadiazolyl, substituted pyrrolyl, substituted diazolyl, substituted triazolyl, substituted tetrazolyl, substituted benzothiadiazolyl, substituted isothiazolyl, substituted pyrazolopyrimidinyl, substituted pyrrolopyrimidinyl, substituted benzotriazolyl, or substituted quinolyl.

15. The human K-Ras protein of claim 14, wherein each substituent group on the $R^1$ is independently selected from oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O) H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, and unsubstituted heteroaryl.

16. The human K-Ras protein of claim 14, wherein each substituent group on the $R^1$ is independently selected from halogen, —$CF_3$, —CN, —OH, —$NH_2$, —COOH, —$CONH_2$, —$CH_3$, and —$CH_2CH_3$.

17. The human K-Ras protein of claim 16, wherein $R^1$ is substituted pyridinyl.

18. The human K-Ras protein of claim 1, wherein $R^1$ is $R^3$-substituted pyridinyl, $R^3$-substituted pyrimidinyl, $R^3$-substituted thiophenyl, $R^3$-substituted furanyl, $R^3$-substituted indolyl, $R^3$-substituted benzoxadiazolyl, $R^3$-substituted benzodioxolyl, $R^3$-substituted benzodioxanyl, $R^3$-substituted thianaphthanyl, $R^3$-substituted pyrrolopyridinyl, $R^3$-substituted indazolyl, $R^3$-substituted quinolinyl, $R^3$-substituted quinoxalinyl, $R^3$-substituted pyridopyrazinyl, $R^3$-substituted quinazolinonyl, $R^3$-substituted benzoisoxazolyl, $R^3$-substituted imidazopyridinyl, $R^3$-substituted benzofuranyl, $R^3$-substituted benzothiophenyl, $R^3$-substituted phenyl, $R^3$-substituted naphthyl, $R^3$-substituted biphenyl, $R^3$-substituted pyrrolyl, $R^3$-substituted pyrazolyl, $R^3$-substituted imidazolyl, $R^3$-substituted pyrazinyl, $R^3$-substituted oxazolyl, $R^3$-substituted isoxazolyl, $R^3$-substituted thiazolyl, $R^3$-substituted furylthienyl, $R^3$-substituted pyridyl, $R^3$-substituted pyrimidyl, $R^3$-substituted benzothiazolyl, $R^3$-substituted purinyl, $R^3$-substituted benzimidazolyl, $R^3$-substituted isoquinolyl, $R^3$-substituted thiadiazolyl, $R^3$-substituted oxadiazolyl, $R^3$-substituted pyrrolyl, $R^3$-substituted diazolyl, $R^3$-substituted triazolyl, $R^3$-substituted tetrazolyl, $R^3$-substituted benzothiadiazolyl, $R^3$-substituted isothiazolyl, $R^3$-substituted pyrazolopyrimidinyl, $R^3$-substituted pyrrolopyrimidinyl, $R^3$-substituted benzotriazolyl, or $R^3$-substituted quinolyl, where each $R^3$ substituent is independently methyl, —Cl, —$NH_2$, —I, —CCH, —$CH_2CH_2OH$, —$OCH_2CCH$, —$CF_3$, —$OCH_3$, —OH, —$CH_2CH_3$, —$NHS(O)_2CH_3$, —$CH_2NH_2$, —Br, isoxazolyl, —$NHC(O)OC(CH_3)_3$, p-chlorophenyl, thiophenyl, —F, pyrazolyl, —$CH_2OH$, —C(O) $NHCH_2CH_2OH$, —$OCH_2CH_2OH$, —$S(O)_2NH_2$, tetrazolyl, —$CHCH_3OH$, —$C(O)CH_3$, —C(O) H, —C(O) OH, —$C(O)OCH_3$, —C(O)$NH_2$, —$N(CH_3)_2$, —$CH_2NH_2$, —$CH_2NHC(O)CH_3$, pyrrolidinyl, —$OCH_2CH_2NH_2$, —C(O) $N(CH_3)_2$, $NHCH_3$, —$NHC(O)CH_3$, —CN, or

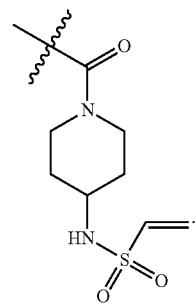 [SMILES: *C(=O)N1CCC(NS(=O)(=O)C=C)CC1]

19. The human K-Ras protein of claim 18, wherein each $R^3$ substituent is independently methyl, —Cl, —NH$_2$, —I, —CF$_3$, —OH, —CH$_2$CH$_3$, —Br, —F, —CH$_2$OH, —OCH$_3$, or —CN.

20. The human K-Ras protein of claim 19, wherein $R^1$ is $R^3$-substituted pyridinyl.

21. The human K-Ras protein of claim 19, wherein $R^1$ is $R^3$-substituted benzothiophenyl.

22. The human K-Ras protein of claim 16, wherein f8 is 1 and $R^{2C}$ is methyl.

23. The human K-Ras protein of claim 18, wherein f8 is 1 and $R^{2C}$ is methyl.

24. The human K-Ras protein of claim 19, wherein f8 is 1 and $R^{2C}$ is methyl.

25. The human K-Ras protein of claim 9, wherein $L^1$ is fused ring heteroarylene substituted with at least one substituent group.

26. The human K-Ras protein of claim 9, wherein $L^1$ is 6,6-fused ring heteroarylene substituted with at least one substituent group.

27. The human K-Ras protein of claim 25, wherein each substituent group on the $L^1$ is independently selected from the group consisting of oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O) H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

28. The human K-Ras protein of claim 27, wherein each substituent group on the $L^1$ is independently selected from the group consisting of halogen, —CF$_3$, —CN, —OH, —NH$_2$, —NO$_2$, —OCF$_3$, —OCHF$_2$, substituted or unsubstituted alkyl, and substituted or unsubstituted heteroalkyl.

29. The human K-Ras protein of claim 10, wherein $L^1$ is 6,6-fused ring heteroarylene substituted with at least one substituent group.

30. The human K-Ras protein of claim 12, wherein $L^1$ is 6,6-fused ring heteroarylene substituted with at least one substituent group.

* * * * *